(12) United States Patent
Boyden et al.

(10) Patent No.: US 8,163,003 B2
(45) Date of Patent: *Apr. 24, 2012

(54) ACTIVE BLOOD VESSEL SLEEVE METHODS AND SYSTEMS

(75) Inventors: Edward S. Boyden, Cambridge, MA (US); Ralph G. Dacey, Jr., St. Louis, MO (US); Colin P. Derdeyn, St. Louis, MO (US); Joshua L. Dowling, Webster Groves, MO (US); Roderick A. Hyde, Redmond, WA (US); Muriel Y. Ishikawa, Livermore, CA (US); Eric C. Leuthardt, St. Louis, MO (US); Nathan P. Myhrvold, Medina, WA (US); Clarence T. Tegreene, Bellevue, WA (US); Lowell L. Wood, Jr., Bellevue, WA (US); Victoria Y. H. Wood, Livermore, CA (US); Gregory J. Zipfel, St. Louis, MO (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1010 days.

This patent is subject to a terminal disclaimer.

(21) Appl. No.: 11/901,693

(22) Filed: Sep. 17, 2007

(65) Prior Publication Data

US 2008/0262341 A1    Oct. 23, 2008

Related U.S. Application Data

(63) Continuation-in-part of application No. 11/645,357, filed on Dec. 21, 2006, and a continuation-in-part of application No. 11/454,343, filed on Jun. 16, 2006, and a continuation-in-part of application No. 11/455,010, filed on Jun. 16, 2006, and a continuation-in-part of application No. 11/526,089, filed on Sep. 22, 2006, and a continuation-in-part of application No. 11/526,144, filed on Sep. 22, 2006, and a continuation-in-part of application No. 11/526,201, filed on Sep. 22, 2006, and a continuation-in-part of application No. 11/526,203, filed on Sep. 22, 2006, now Pat. No. 7,769,603, and a continuation-in-part of application No. 11/541,377, filed on Sep. 29, 2006, and a continuation-in-part of application No.

(Continued)

(51) Int. Cl.
*A61F 2/06* (2006.01)
*G06Q 10/00* (2006.01)
*G06Q 50/00* (2006.01)
*A61M 29/00* (2006.01)

(52) U.S. Cl. .............. 623/1.13; 705/2; 705/3; 623/1.15; 623/1.16; 606/200

(58) Field of Classification Search .................. 705/2–4; 623/1.15–1.16, 1.13; 606/200
See application file for complete search history.

(56) References Cited

U.S. PATENT DOCUMENTS 3,391,697 A    7/1968  Greatbatch (Continued)

OTHER PUBLICATIONS

Rothenberg, Robert S., et al., Sleeve Keeps Blockages At Bay, February 1998, USA Today Magazine, vol. 126, Issue 2633, p. 3.*

(Continued)

*Primary Examiner* — Jason Dunham
*Assistant Examiner* — Amber Altschul

(57) ABSTRACT

Methods, apparatuses, computer program products, devices and systems are described that include accepting one or more blood vessel sleeve dimensions based on blood vessel data from an individual; and making a rapid-prototyped blood vessel sleeve at least partly based on the one or more blood vessel sleeve dimensions.

21 Claims, 67 Drawing Sheets

Related U.S. Application Data

11/541,378, filed on Sep. 29, 2006, and a continuation-in-part of application No. 11/541,448, filed on Sep. 29, 2006, and a continuation-in-part of application No. 11/541,452, filed on Sep. 29, 2006, and a continuation-in-part of application No. 11/541,492, filed on Sep. 29, 2006, and a continuation-in-part of application No. 11/879,751, filed on Jul. 17, 2007, and a continuation-in-part of application No. 11/880,434, filed on Jul. 19, 2007, and a continuation-in-part of application No. 11/888,623, filed on Jul. 31, 2007, and a continuation-in-part of application No. 11/894,563, filed on Aug. 20, 2007, now Pat. No. 7,818,084.

(56) References Cited

U.S. PATENT DOCUMENTS

| | | |
|---|---|---|
| 3,821,469 A | 6/1974 | Whetstone et al. |
| 3,941,127 A | 3/1976 | Froning |
| 3,983,474 A | 9/1976 | Kuipers |
| 4,054,881 A | 10/1977 | Raab |
| 4,119,900 A | 10/1978 | Kremnitz |
| 4,202,349 A | 5/1980 | Jones |
| 4,262,306 A | 4/1981 | Renner |
| 4,314,251 A | 2/1982 | Raab |
| 4,317,078 A | 2/1982 | Weed et al. |
| 4,339,953 A | 7/1982 | Iwasaki |
| 4,396,885 A | 8/1983 | Constant |
| 4,403,321 A | 9/1983 | Krüger |
| 4,418,422 A | 11/1983 | Richter et al. |
| 4,431,005 A | 2/1984 | McCormick |
| 4,460,642 A | 7/1984 | Errede et al. |
| 4,496,535 A | 1/1985 | Gould et al. |
| 4,575,805 A | 3/1986 | Moermann et al. |
| 4,638,798 A | 1/1987 | Shelden et al. |
| 4,642,786 A | 2/1987 | Hansen |
| 4,651,732 A | 3/1987 | Frederick |
| 4,658,214 A | 4/1987 | Petersen |
| 4,733,661 A | 3/1988 | Palestrant |
| 4,805,615 A | 2/1989 | Carol |
| 4,872,867 A | 10/1989 | Joh |
| 4,889,526 A | 12/1989 | Rauscher et al. |
| 4,943,296 A | 7/1990 | Funakubo et al. |
| 4,962,453 A | 10/1990 | Pong et al. |
| 5,031,109 A | 7/1991 | Gloton |
| 5,051,906 A | 9/1991 | Evans, Jr. et al. |
| 5,078,140 A | 1/1992 | Kwoh |
| 5,086,401 A | 2/1992 | Glassman et al. |
| 5,163,007 A | 11/1992 | Slilaty |
| 5,163,952 A | 11/1992 | Froix |
| 5,165,064 A | 11/1992 | Mattaboni |
| 5,188,111 A | 2/1993 | Yates et al. |
| 5,204,814 A | 4/1993 | Noonan et al. |
| 5,258,020 A | 11/1993 | Froix |
| 5,313,835 A | 5/1994 | Dunn |
| 5,321,614 A | 6/1994 | Ashworth |
| 5,381,786 A | 1/1995 | Spears |
| 5,398,670 A | 3/1995 | Ortiz et al. |
| 5,407,431 A | 4/1995 | Botich et al. |
| 5,502,638 A | 3/1996 | Takenaka |
| 5,507,287 A | 4/1996 | Palcic et al. |
| 5,554,180 A | 9/1996 | Turk |
| 5,589,932 A | 12/1996 | Garcia-Rubio et al. |
| 5,683,449 A | 11/1997 | Marcade |
| 5,702,432 A | 12/1997 | Chen et al. |
| 5,733,868 A | 3/1998 | Peterson et al. |
| 5,758,298 A | 5/1998 | Guldner |
| 5,823,948 A | 10/1998 | Ross, Jr. et al. |
| 5,850,222 A | 12/1998 | Cone |
| 5,954,701 A | 9/1999 | Matalon |
| 5,966,693 A | 10/1999 | Burgess |
| 5,966,963 A | 10/1999 | Kovalaske |
| 6,053,873 A | 4/2000 | Govari et al. |
| 6,108,597 A | 8/2000 | Kirchner et al. |
| 6,149,433 A | 11/2000 | Ziegler et al. |
| 6,175,757 B1 | 1/2001 | Watkins et al. |
| 6,221,447 B1 | 4/2001 | Munn et al. |
| 6,231,514 B1 | 5/2001 | Lowe et al. |
| 6,240,312 B1 | 5/2001 | Alfano et al. |
| 6,255,361 B1 | 7/2001 | Rajagopalan et al. |
| 6,255,793 B1 | 7/2001 | Peless et al. |
| 6,263,245 B1 | 7/2001 | Snell |
| 6,289,270 B1 | 9/2001 | Baumgarten |
| 6,398,280 B1 | 6/2002 | Parker et al. |
| 6,417,641 B2 | 7/2002 | Peless et al. |
| 6,458,153 B1 * | 10/2002 | Bailey et al. ............... 623/1.24 |
| 6,464,687 B1 * | 10/2002 | Ishikawa et al. ........... 604/891.1 |
| 6,481,262 B2 | 11/2002 | Ching et al. |
| 6,493,607 B1 | 12/2002 | Bourne et al. |
| 6,532,964 B2 * | 3/2003 | Aboul-Hosn et al. ........ 128/898 |
| 6,547,723 B1 | 4/2003 | Ouchi |
| 6,569,104 B2 | 5/2003 | Ono et al. |
| 6,592,565 B2 | 7/2003 | Twardowski |
| 6,592,605 B2 | 7/2003 | Lenker et al. |
| 6,612,982 B1 | 9/2003 | Ouchi |
| 6,663,765 B2 | 12/2003 | Cherkes |
| 6,673,363 B2 | 1/2004 | Luo et al. |
| 6,685,738 B2 * | 2/2004 | Chouinard et al. ........ 623/1.15 |
| 6,711,423 B2 | 3/2004 | Colvin, Jr. |
| 6,719,684 B2 | 4/2004 | Kim et al. |
| 6,726,696 B1 | 4/2004 | Houser et al. |
| 6,726,923 B2 | 4/2004 | Iyer et al. |
| 6,754,357 B2 | 6/2004 | McIntosh et al. |
| 6,754,536 B2 | 6/2004 | Swoyer et al. |
| 6,776,165 B2 | 8/2004 | Jin |
| 6,780,510 B2 | 8/2004 | Ogle et al. |
| 6,793,668 B1 | 9/2004 | Fisher |
| 6,816,632 B1 | 11/2004 | Slice |
| 6,824,508 B2 | 11/2004 | Kim et al. |
| 6,834,118 B2 | 12/2004 | Kim |
| 6,866,626 B2 | 3/2005 | Long et al. |
| 6,911,004 B2 | 6/2005 | Kim et al. |
| 6,939,290 B2 | 9/2005 | Iddan |
| 6,951,053 B2 | 10/2005 | Padilla et al. |
| 6,958,034 B2 | 10/2005 | Iddan |
| 6,984,205 B2 | 1/2006 | Gazdzinski |
| 6,984,952 B2 | 1/2006 | Peless et al. |
| 6,996,245 B2 | 2/2006 | Hanna |
| 7,020,231 B1 | 3/2006 | Frey et al. |
| 7,027,134 B1 | 4/2006 | Garcia-Rubio et al. |
| 7,039,453 B2 | 5/2006 | Mullick et al. |
| RE39,133 E | 6/2006 | Clayton et al. |
| 7,083,578 B2 | 8/2006 | Lewkowicz et al. |
| 7,118,531 B2 | 10/2006 | Krill |
| 7,171,285 B2 | 1/2007 | Kim et al. |
| 7,212,110 B1 | 5/2007 | Martin et |
| 7,214,182 B2 | 5/2007 | Shimizu et al. |
| 7,245,954 B2 | 7/2007 | Glukhovsky |
| 7,326,240 B1 | 2/2008 | Caro et al. |
| 7,365,614 B2 | 4/2008 | McCorquodale et al. |
| 7,371,067 B2 | 5/2008 | Anderson et al. |
| 7,398,734 B1 | 7/2008 | Jean |
| 7,451,537 B2 | 11/2008 | Liu et al. |
| 7,486,967 B2 | 2/2009 | Pan et al. |
| 7,596,403 B2 | 9/2009 | Horn |
| 7,625,338 B2 | 12/2009 | Gilad et al. |
| 7,684,840 B2 | 3/2010 | Palti |
| 7,736,300 B2 | 6/2010 | Ziegler et al. |
| 7,804,991 B2 * | 9/2010 | Abovitz et al. ............... 382/128 |
| 2001/0025131 A1 | 9/2001 | Edwin et al. |
| 2001/0039504 A1 | 11/2001 | Linberg et al. |
| 2001/0051766 A1 | 12/2001 | Gazdzinski |
| 2002/0006401 A1 | 1/2002 | Rogers et al. |
| 2002/0023843 A1 * | 2/2002 | Cherkes ........................ 205/75 |
| 2002/0026944 A1 * | 3/2002 | Aboul-Hosn et al. ........ 128/898 |
| 2002/0035555 A1 | 3/2002 | Wheeler et al. |
| 2002/0068968 A1 | 6/2002 | Hupp |
| 2002/0103417 A1 | 8/2002 | Gazdzinski |
| 2002/0183628 A1 | 12/2002 | Reich et al. |
| 2002/0198470 A1 | 12/2002 | Imran et al. |
| 2002/0198587 A1 | 12/2002 | Greenberg et al. |
| 2003/0018294 A1 | 1/2003 | Cox |
| 2003/0060782 A1 | 3/2003 | Bose et al. |

| | | |
|---|---|---|
| 2003/0065250 A1 | 4/2003 | Chiel et al. |
| 2003/0093031 A1 | 5/2003 | Long et al. |
| 2003/0149335 A1 | 8/2003 | Silverman et al. |
| 2003/0151524 A1 | 8/2003 | Clark |
| 2003/0153866 A1 | 8/2003 | Long et al. |
| 2003/0191430 A1 | 10/2003 | D'Andrea et al. |
| 2003/0200120 A1 | 10/2003 | Binkert |
| 2003/0214580 A1 | 11/2003 | Iddan |
| 2004/0024443 A1 | 2/2004 | Dwyer et al. |
| 2004/0093105 A1 | 5/2004 | Holloway et al. |
| 2004/0111019 A1 | 6/2004 | Long |
| 2004/0149294 A1 | 8/2004 | Gianchandani et al. |
| 2004/0152988 A1 | 8/2004 | Weirich |
| 2004/0162469 A1 | 8/2004 | Imran |
| 2004/0162501 A1 | 8/2004 | Imran |
| 2004/0176664 A1 | 9/2004 | Iddan |
| 2004/0193010 A1 | 9/2004 | Fujimori et al. |
| 2004/0204751 A1 | 10/2004 | Fischell et al. |
| 2004/0230131 A1 | 11/2004 | Kassab et al. |
| 2004/0267240 A1 | 12/2004 | Gross et al. |
| 2005/0004474 A1 | 1/2005 | Iddan |
| 2005/0037133 A1 | 2/2005 | Halleriet et al. |
| 2005/0038342 A1* | 2/2005 | Mozayeni et al. ............ 600/454 |
| 2005/0043583 A1 | 2/2005 | Killmann et al. |
| 2005/0049691 A1 | 3/2005 | Mericle et al. |
| 2005/0058701 A1 | 3/2005 | Gross et al. |
| 2005/0061336 A1 | 3/2005 | Goetz et al. |
| 2005/0062562 A1 | 3/2005 | Ries |
| 2005/0096498 A1 | 5/2005 | Houser et al. |
| 2005/0107817 A1 | 5/2005 | White et al. |
| 2005/0107867 A1 | 5/2005 | Taheri |
| 2005/0171418 A1 | 8/2005 | Lin |
| 2005/0171434 A1 | 8/2005 | Madden et al. |
| 2005/0203457 A1 | 9/2005 | Smego |
| 2005/0215911 A1 | 9/2005 | Alfano et al. |
| 2005/0251183 A1 | 11/2005 | Buckman et al. |
| 2005/0267569 A1 | 12/2005 | Barrett et al. |
| 2005/0272974 A1 | 12/2005 | Iddan |
| 2005/0273157 A1 | 12/2005 | Pinchasik |
| 2005/0288763 A1 | 12/2005 | Andreas et al. |
| 2006/0058638 A1 | 3/2006 | Boese et al. |
| 2006/0069426 A1 | 3/2006 | Weinberger |
| 2006/0079740 A1 | 4/2006 | Silver et al. |
| 2006/0122697 A1 | 6/2006 | Shanley et al. |
| 2006/0129228 A1 | 6/2006 | Golesworthy et al. |
| 2006/0152309 A1 | 7/2006 | Mintchev et al. |
| 2006/0167339 A1 | 7/2006 | Gilad et al. |
| 2006/0169294 A1 | 8/2006 | Kaler et al. |
| 2006/0178551 A1 | 8/2006 | Melvin |
| 2006/0206038 A1 | 9/2006 | Jenkins et al. |
| 2006/0235275 A1 | 10/2006 | Rabinovitz et al. |
| 2006/0252987 A1 | 11/2006 | Hasegawa et al. |
| 2006/0280351 A1 | 12/2006 | Luping et al. |
| 2007/0021816 A1 | 1/2007 | Rudin |
| 2007/0051366 A1 | 3/2007 | Hansmann et al. |
| 2007/0083258 A1 | 4/2007 | Falotico et al. |
| 2007/0112581 A1 | 5/2007 | Smith et al. |
| 2007/0118243 A1 | 5/2007 | Schroeder et al. |
| 2007/0156211 A1 | 7/2007 | Ferren et al. |
| 2008/0015677 A1 | 1/2008 | Glossop et al. |
| 2008/0030497 A1 | 2/2008 | Hu et al. |
| 2008/0063703 A1 | 3/2008 | Gross et al. |
| 2008/0121054 A1 | 5/2008 | Goldenberg et al. |
| 2008/0234831 A1 | 9/2008 | Clarke et al. |
| 2008/0241847 A1 | 10/2008 | Hoon et al. |
| 2008/0243284 A1 | 10/2008 | Grishaber et al. |
| 2008/0266106 A1 | 10/2008 | Lim et al. |
| 2009/0062646 A1 | 3/2009 | Creighton, IV et al. |
| 2009/0069821 A1 | 3/2009 | Farritor et al. |
| 2009/0082652 A1 | 3/2009 | Koh et al. |
| 2009/0099652 A1 | 4/2009 | Granada et al. |
| 2009/0182388 A1 | 7/2009 | Von Arx et al. |

OTHER PUBLICATIONS

U.S. Appl. No. 12/804,897, Edward K.Y. Jung et al.
PCT International Search Report; International App. No. PCT/US2008/008813; Jan. 9, 2009; pp. 1-2.
UK Intellectual Property Office Examination Report under Section 18(3); App. No. GB0821521.2; Jan. 12, 2011 (received by our agent on Jan. 13, 2011); pp. 1-4.
Arkin, Ronald C.; "Towards the Unification of Navigational Planning and Reactive Control"; Working Notes of the AAAI Spring Symposium on Robot Navigation; bearing dates of Mar. 20-28, 1989; pp. 1-6.
Arleo et al.; "Spatial Cognition and Neuro-Mimetic Navigation: A Model of Hippocampal Place Cell Activity"; bearing a date of Oct. 28, 1999; pp. 1-13.
Balakrishnan et al.; "Spatial Learning and Localization in Rodents: A Computational Model of the Hippocampus and its Implications for Mobile Robots"; Adaptive Behavior; bearing a date of 1999; pp. 173-216 plus cover page; vol. 7, No. 2; SAGE Publications.
Bellin et al.; "Polymeric triple-shape materials"; PNAS; bearing dates of Nov. 18, 2006 and 2006; pp. 18043-18047; vol. 103, No. 48; The National Academy of Sciences of the USA; located at www.pnas.org/cgi/doi/10.1073/pnas.0608586103.
Berman et al.; "Decentralized Autonomous AGV System for Material Handling"; iFirst; bearing a date of Oct. 2002; pp. 3995-4006 (Only the Abstract is being provided); vol. 40, No. 15; located at: http://www.informaworld.com/smpp/content~content=a713846479~db=ai; printed on Apr. 24, 2007.
Bianco et al.; "Carbon Nanotube-based Vectors for Delivering Immunotherapeutics and Drugs"; Nanotechnologies for the Live Sciences: Nanomaterials for Medical Diagnosis and Therapy; bearing a date of 2007; Chapter 3; pp. 85-142.; vol. 10; WILEY-VCH Verlag GmbH & Co. KGaA; Weinheim.
Breslin et al.; "Autofluorescence and Diffuse Reflectance Properties Malignant and Benign Breast Tissues"; Annals of Surgical Oncology; bearing dates of 2003 and 2004; pp. 65-70; vol. 11, No. 1; Lippincott Williams & Wilkin.
Bright et al.; "Automated Pipe Inspection Robot"; Industrial Robot: An International Journal; bearing a date of Aug. 1997; pp. 285-289 (Only the Abstract is being provided); vol. 24, No. 4; located at: http://www.emeraldinsight.com/10.1108/01439919710176372; printed on Apr. 23, 2007.
Brinn, David; "A incredible journey from an Israeli robotics team"; ISRAEL21c: A Focus Beyond; bearing a date of Nov. 12, 2006; pp. 1-3; ISRAEL21c.org.
Brown et al.; "Performance Test Results of an Integrated GPS/MEMS Inertial Navigation Package"; Proceedings of ION GNSS 2004, bearing a date of Sep. 2004; pp. 1-8.
Budgett et al.; "Novel technology for the provision of power to implantable physiological devices"; Journal of Applied Physiology; bearing dates of Jan. 27, 2006, Jan. 5, 2007, and 2007; pp. 1658-1663; vol. 102; The American Physiological Society.
Bullitt et al.; "Analysis of Time-Varying Images Using 3D Vascular Models"; Proceedings 30th Applied Imagery Pattern Recognition Workshop; bearing a date of Apr. 2001; pp. 9-14; IEEE Computer Society; Piscataway, NJ.
Burke et al.; "Towards a single-chip, implantable RFID system: is a single-cell radio possible?"; Biomed Microdevices; bearing a date of 2009; pp. 1-8; Springer.
Cady et al.; "Optimized linkage and quenching strategies for quantum dot molecular beacons"; Molecular and Cellular Probes; bearing dates of Jul. 5, 2006, Sep. 7, 2006, Sep. 17, 2006, 2006, and 2007; pp. 116-124; vol. 21; Elsevier Ltd.
Cavalcanti et al.; "Autonomous Multi-Robot Sensor-Based Cooperation for Nanomedicine"; Nanotechnology Special Edition; bearing a date of Aug. 2002; pp. 1-4; International Journal of Nonlinear Science and Numerical Stimulation.
Chen et al.; "Review on the Achievements in Simultaneous Localization and Map Building for Mobile Robot" CSA Illumina; bearing a date of Jun. 2005; pp. 455-460 (Only the Abstract is being provided); vol. 22, No. 3; ProQuest-CSA LLC; located at: http://md1.csa.com/partners/viewrecord.php?requester=gs&collection=TRD&recid=A056354818AH&recid=2005134422784EA&q=Review+on+the+Achievements+in+Simultaneous+Localization+and+Map+Building+for+Mobile+Robot&uid=790366044&setcookie=yes.
Chiyo et al.; "Effective detection of bronchial preinvasive lesions by a new autofluorescence imaging bronchovideoscope system"; Lung Cancer; bearing dates of May 12, 2004, Nov. 17, 2004, Nov. 23, 2004, 2004, and 2005; pp. 307-313; vol. 48; Elsevier Ireland Ltd.

Chung et al.; "Advanced Optical Imaging Requiring No Contrast Agents—A New Armamentarium for Medicine and Surgery"; Current Surgery; bearing dates of May/Jun. 2005 and 2005; pp. 365-370; vol. 62, No. 3; Elsevier Inc.

Dacosta et al.; "Autofluorescence characterisation of isolated whole crypts and primary cultured human epithelial cells from normal, hyperplastic, and adenomatous colonic mucosa"; Journal of Clinical Pathology; bearing dates of 2004 and 2005; pp. 766-774; vol. 58.

Degani et al.; "Minimalistic, Dynamic, Tube Climbing Robot"; 2010 IEEE International Conference on Robotics and Automation; bearing dates of May 3-8, 2010 and 2010; pp. 1100-1101; IEEE.

Desouza et al.; "Vision for Mobile Robot Navigation: A Survey"; IEEE Transactions on Pattern Analysis and Machine Intelligence; bearing a date of Feb. 2002; pp. 237-267 (Only the Abstract is being provided); vol. 24, No. 2; located at: http://csdl2.computer.org/persagen/DLAbsToc.jsp?resourcePath =/dl/trans/tp/&toc=comp/trans/tp/2002/02/i2toc.xml&DOI=10.1109/34.982903; printed on Apr. 23, 2007.

Diard et al.; "A theoretical comparison of probabilistic and biomimetic models of mobile robot navigation"; Proceedings of the 2004 IEEE International Conference on Robotics & Automation; bearing dates of Apr. 2004 and 2004; pp. 933-938; IEEE.

Dweik et al.; "Exhaled breath analysis: the new frontier in medical testing"; Journal of Breath Research; bearing a date of 2008; pp. 1-3; vol. 2; IOP Publishing Ltd; UK.

Edwards, Lin; "Spider pill to seek out disease"; PhysOrg.com; bearing dates of Oct. 16, 2009 and 2009; p. 1.

Eker et al.; "Clinical spectral characterisation of colonic mucosal lesions using autofluorescence and δ aminolevulinic acid sensitization"; Gut; bearing dates of 1998 and 1999; pp. 511-518; vol. 44.

Eulenstein et al.; "Ultrasound-Based Navigation System Incorporating Preoperative Planning for Liver Surgery"; International Congress Series CARS 2004—Computer Assisted Radiology and Surgery, Proceedings of the 18$^{th}$ International Congress and Exhibition; bearing a date of 2004; pp. 758-763; vol. 1268.

Filliat et al.; "Map Based Navigation in Mobile Robots: I. A Review of Localization Strategies"; Science Direct-Cognitive Systems Research; bearing dates of Feb. 12, 2003 and Dec. 2003; pp. 1-58; vol. 4, No. 4; Elsevier Science.

Foxlin et al.; "Miniature 6-DOF inertial system for tracking HMDs"; Helmet and Head-Mounted Displays III, AeroSense 98; bearing dates of Apr. 13-14, 1998; pp. 1-15; vol. 3362; SPIE.

Gabrecht et al.; "Detection of early bronchial cancer by autofluorescence: results in patients with H&N cancer"; Diagnostic Optical Spectroscopy in Biomedicine IV, Proc. SPIE-OSA Biomedical Optics; bearing a date of 2007; pp. 1-8; vol. 6628; SPIE-OSA.

Gao et al., "A Micro Sensing Probe for Detecting Individual Biological Cells"; Proceedings of the 25$^{th}$ Annual International Conference of the IEEE EMBS; bearing dates of Sep. 17-21, 2003 and 2003; pp. 3348-3351; IEEE.

Gillenwater et al.; "Noninvasive Diagnosis of Oral Neoplasia Based on Fluorescence Spectroscopy and Native Tissue Autofluorescence"; Archives of Otolaryngology-Head & Neck Surgery; bearing a date of Nov. 1998 and 1998; pp. 1251-1258; vol. 124.

Grifantini, Kristina; "Voyage of the Bacteria Bots"; Technology Review; bearing a date of Oct. 31, 2008; pp. 1-4; Technology Review.

Groothuis et al.; "The entry of antiviral and antiretroviral drugs into the central nervous system"; Journal of NeuroVirology; bearing a date of 1997; pp. 387-400; vol. 3; Journal of NeuroVirology, Inc.

"Guessing Robots Predict Their Environments, Navigate Better"; PhysOrg.com; printed on Sep. 16, 2008; pp. 1-2; original story found at www.phyorg.com/news100887209.html.

Gur, Amir; "The Nanobots are Coming"; TFOT; bearing a date of Jul. 9, 2007; pp. 1-2; The Future of Things.

Hattori, Kevin; "Robot Can Crawl Through Human Body"; American Technion Society; bearing a date of Jul. 7, 2009; pp. 1-2; American Technion Society; located at http://www.ats.org/site/News2?page=NewsArticle&id=6063&news_iv_ctrl=1161&printer_friendly=1.

Herth et al.; "Successful Bronchoscopic Placement of Tracheobronchial Stents Without Fluoroscopy*"; Chest; bearing a date of Jun. 2001; pp. 1910-1912; vol. 119, No. 6; American College of Chest Physicians.

Hertzberg et al.; "Landmark-Based Autonomous Navigation in Sewerage Pipes"; Proceedings of EUROBOT; bearing a date of 1996; pp. 68-73; IEEE.

Hirsch et al.; "A new device with PZT ultrasonic transducers in MEMS technology"; Journal of Physics: Conference Series 34, International MEMS Conference 2006; bearing a date of 2006; pp. 475-480; IOP Publishing Ltd.

Hollings et al.; "Diagnostic imaging of lung cancer"; European Respiratory Journal; bearing a date of 2002, pp. 722-742; vol. 19; ERS Journals Ltd.

Hornyak, Tim; "RFID Powder"; Scientific American Magazine; bearing dates of Feb. 2008 and 2008; pp. 68-71; Scientific American, Inc.

Hosseini-Khayat, Saied; "A Lightweight Security Protocol for Ultralow Power ASIC Implementation for Wireless Implantable Medical Devices"; 2011 Symposium on Medical Information and Communication Technology (ISMICT); bearing dates of 2011 and Mar. 27-30, 2011; pp. 6-9; IEEE.

Howell et al.; "Practical Mobile Robot Self-Localization"; Proceedings of the IEEE International Conference on Robotics and Automation, 2000; bearing dates of Apr. 24-28, 2000; pp. 3485-3492; vol. 4.

Jaiswal et al.; "Long-term multiple color imaging of live cells using quantum dot bioconjugates"; Nature Biotechnology; bearing dates of Jan. 2003 and 2003; pp. 47-51; vol. 21; Nature Publishing Group.

Jovanov et al.; "A wireless body area network of intelligent motion sensors for computer assisted physical rehabilitation"; Journal of NeuroEngineering and Rehabilitation; bearing dates of Mar. 1, 2005, Jan. 28, 2005, Mar. 1, 2005, and 2005; pp. 1-10; vol. 2, No. 6; BioMed Central Ltd.

Karino et al.; "Flow Patterns in Vessels of Simple and Complex Geometries$^a$"; Annals of the New York Academy of Sciences; bearing a date of 1987; pp. 422-441; vol. 516.

Kawaguchi et al.; "Internal Pipe Inspection Robot"; IEEE Xplore; bearing dates of May 21, 1995-May 27, 1995 and 2005; pp. 857-862 (Only the Abstract is being provided); vol. 1; IEEE; located at: http://ieeexplore.ieee.org/xpls/abs_all.jsp?rnumber=525390; printed on Apr. 23, 2007.

Kharitonov et al.; "Exhaled Markers of Pulmonary Disease"; American Journal of Respiratory and Critical Care Medicine; bearing dates of Sep. 5, 2000, Jan. 24, 2001, and 2001; pp. 1693-1722; vol. 163.

Kim et al.; "Inchworm-Like Microbot for Capsule Endoscope"; Proceedings of the 2004 IEEE International Conference on Robotics and Biomimetics; bearing dates of Aug. 22-26, 2004 and 2004; pp. 458-463; IEEE.

Kim et al.; "Ultrasensitive carbon nanotube-based biosensors using antibody-binding fragments"; Analytical Biochemistry; bearing a date of 2008; pp. 193-198; vol. 381; Elsevier Inc.

Kirchner et al.; "A Prototype Study of an Autonomous Robot Platform for Sewerage System Maintenance"; Autonomous Robots; bearing a date of 1997; pp. 319-331; vol. 4; Kluwer Academic Publishers.

Kitaoka et al.; "A three-dimensional model of the human airway tree"; Journal of Applied Physiology; bearing a date of 1999; pp. 2207-2217; vol. 87; The American Physiological Society.

Kitching, John; "Time for a Better Receiver: Chip-Scale Atomic Frequency References"; GPS World; bearing a date of Nov. 2007; pp. 52-57.

Knappe, Svenja; "Emerging Topics: MEMS Atomic Clocks"; Comprehensive Microsystems; bearing a date of 2007; pp. 571-612; vol. 3; Elsevier B.V.; Netherlands.

Koenig et al.; "Laser-Induced Autofluorescence for Medical Diagnosis"; Journal of Fluorescence; bearing a date of 1994, pp. 17-40; vol. 4, No. 1; Plenum Publishing Corporation.

Kuipers et al.; "A Robot Exploration and Mapping Strategy Based on a Semantic Hierarchy of Spatial Representations"; Robotics and Autonomous Systems; bearing a date of 1981; pp. 47-63; vol. 8; Elsevier Science Publishers B.V.

Kuntze et al.; "Experiences With the Development of a Robot for Smart Multisensoricpipe Inspection"; IEEE Xplore; bearing dates of May 16, 1998-May 20, 1998 and 2005; pp. 1773-1778 (Only the Abstract is being provided); vol. 2; IEEE; located at: http://ieeexplore.ieee.org/xpls/abs_all.jsp?rnumber=677423; printed on Apr. 23, 2007.

Latombe, Jean-Claude; "Chapter 1: Introduction and Overview"; Robot Motion Planning; bearing a date of 1991; 11 pages total, pp. 12-20; Kluwer Academic Publishers.

Laumond et al.; "Robot Motion Planning and Control"; bearing a date of 1998; pp. 1-343 plus cover page, foreword and table of contents (353 total pages); Springer.

Leong et al.; "Tetherless thermobiochemically actuated microgrippers"; PNAS; bearing dates of Jan. 20, 2009 and 2009; pp. 703-708; vol. 106, No. 3; The National Academy of Sciences of the USA; located at www.pnas.org_cgi_doi_10.1073_pnas.0807698106.

Luckevich, Mark, "MEMS microvalves: the new valve world"; Valve-World; bearing a date of May 2007; pp. 79-83.

Lynch et al.; "Design of Piezoresistive MEMS-Based Accelerometer for Integration with Wireless Sensing Unit for Structural Monitoring"; Journal of Aerospace Engineering; bearing a date of Jul. 2003; pp. 108-114; vol. 3; ASCE.

Machado et al., "Detection of Lung Cancer by Sensor Array Analyses of Exhaled Breath"; American Journal of Respiratory and Critical Care Medicine; bearing a date of 2005; pp. 1286-1291; vol. 171.

Marcu et al.; "In vivo detection of macrophages in a rabbit atherosclerotic model by time-resolved laser-induced fluorescence spectroscopy"; Atherosclerosis; bearing a date of 2005, pp. 295-303; vol. 181; Elsevier Ireland Ltd.

Martel, Sylvain; "Fundamental Principles and Issues of High-speed Piezoactuated Three-legged Motion for Miniature Robots Designed for Nanometer-scale Operations"; The International Journal of Robotics Research; bearing dates of Jul. 2005 and 2005; pp. 575-588; vol. 24, No. 7; Sage Publications.

Mataric, Maja J.; "Integration of Representation into Goal-Driven Behavior-Based Robots"; IEEE Transactions on Robotics and Automation; bearing dates of Jun. 1992 and 1992; pp. 304-312; vol. 8, No. 3; IEEE.

Mattley et al.; "Blood Characterization using uv/vis Spectroscopy"; Advances in Fluorescence Sensing Technology II (Proceedings Volume); bearing a date of 1995; pp. 462-470; vol. 2388; SPIE.

Mehmood et al.; "Autonomous Navigation of Mobile Agents Using RFID-Enabled Space Partitions"; ACMGIS '08; bearing dates of Nov. 5-7, 2008 and 2008; pp. 1-10; ACM.

Menciassi et al.; "Towards Active Capsular Endoscopy: Preliminary Results on a Legged Platform"; Proceedings of the 28th IEEE EMBS Annual International Conference; bearing dates Aug. 30, 2006-Sep. 3, 2006 and 2006; pp. 2215-2218; IEEE.

Meyer et al.; "Map-Based Navigation in Mobile Robots: II. A Review of Map-Learning and Path-Learning Strategies"; Science Direct-Cognitive Systems Research; bearing dates of Feb. 12, 2003 and Dec. 4, 2003; pp. 1-51; vol. 4, No. 4; Elsevier Science.

Mohan et al., "Bokode: Imperceptible Visual tags for Camera Based Interaction from a Distance"; ACM Transactions on Graphics (Proceedings of SIGGRAPH 2009); bearing dates of Aug. 3-7, 2009; pp. 1-8.

Mok et al.; "Recent Progress in Nucleic Acid Aptamer-Based Biosensors and Bioassays"; Sensors; bearing a date of 2008; pp. 7050-7084; vol. 8.

Morrison et al., "Clinical Applications of Micro- and Nanoscale Biosensors"; Biomedical Nanostructures; bearing a date of 2008; Chapter 17; pp. 433-454; John Wiley & Sons, Inc.

Motomiya et al.; "Flow Patterns in the Human Carotid Artery Bifurcation"; Stroke; bearing dates of Jan.-Feb. 1984; pp. 50-56; vol. 15, No. 1.

Nehmzow et al.; "Robot Navigation in the Real World: Experiments with Manchester's *FortyTwo* in Unmodified, Large Environments"; Robotics and Autonomous Systems; bearing a date of 2000; pp. 223-242; vol. 33; Elsevier Science B.V.

Nguyen, Clark T.-C.; "MEMS Technology for Timing and Frequency Control"; IEEE Transactions on Ultrasonics, Ferroelectrics, and Frequency Controls; bearing dates of Feb. 2007 and 2007; pp. 251-270; vol. 54, No. 2; IEEE.

Nordstrom et al.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.

Nowinski et al.; "Three-dimensional Atlas of the Brain Anatomy and Vasculature[1]"; RadioGraphics; bearing dates of Jan.-Feb. 2005 and 2005; pp. 263-271; vol. 25, No. 1; RSNA.

Pan et al.; "A magnetically driven PDMS micropump with ball check-valves"; Journal of Micromechanics and Microengineering; bearing a date of 2005, pp. 1021-1026; vol. 15; IOP Publishing Ltd.

Pavlidis, N.; "The diagnostic and therapeutic management of leptomeningeal carcinomatosis"; Annals of Oncology; bearing a date of 2004; pp. iv285-iv291; vol. 15 (Supp. 4); European Society for Medical Oncology.

Peng et al.; "Ultraviolet light-emitting diodes operating in the 340 nm wavelength range and application to time-resolved fluorescence spectroscopy"; Applied Physics Letters; bearing dates of Aug. 23, 2004 and 2004; pp. 1436-1438; vol. 85, No. 8; American Institute of Physics.

Pfister et al.; "Weighted Line Fitting Algorithms for Mobile Robot Map Building and Efficient Data Representation"; Proceedings of the 2003 IEEE International Conference on Robotics and Automation; bearing a date of Sep. 14-19, 2003; pp. 1-8.

"Philips develops "intelligent pill""; Reuters; bearing a date of Nov. 11, 2008; p. 1; Thomson Reuters.

"Philips' intelligent pill targets drug development and treatment for digestive tract diseases"; PhysOrg.com; bearing a date of Nov. 11, 2008; pp. 1-3; located at http://www.physorg.com/news145640874.html.

Phillips et al.; "Detection of Lung Cancer With Volatile Markers in the Breath*"; Chest; bearing dates of Jun. 2003 and 2003; pp. 2115-2123; vol. 123, No. 6; American College of Chest Physicians.

Pisupati et al.; "A Central Axis Algorithm for 3D Bronchial Tree Structures"; Proceedings of the International Symposium on Computer Vision; bearing a date of 1995; pp. 259-264; IEEE.

Psathakis et al.; "8-Isoprostane, a Marker of Oxidative Stress, Is Increased in the Expired Breath Condensate of Patients With Pulmonary Sarcoidosis*"; Chest; bearing dates of Mar. 2004 and 2004, pp. 1005-1011; vol. 125, No. 3; American College of Chest Physicians.

Quaglia et al.; "An endoscopic capsule robot: a meso-scale engineering case study"; Journal of Micromechanics and Microengineering; bearing a date of 2009; pp. 1-11; vol. 19; IOP Publishing Ltd.

Quirini et al.; "Design of a Pill-Sized 12-legged Endoscopic Capsule Robot"; 2007 IEEE International Conference on Robotics and Automation; bearing dates of Apr. 10-14, 2007 and 2007; pp. 1856-1862; IEEE.

Raman et al.; "In Vivo Atherosclerotic Plaque Characterization Using Magnetic Susceptibility Distinguishes Symptom-Producing Plaques"; JACC: Cardiovascular Imaging; bearing dates of Jan. 2008 and 2008; pp. 49-57; vol. 1, No. 1; Elsevier.

Rasmussen et al.; "Proximity-based Access Control for Implantable Medical Devices"; CCS '09, Proceedings of the 16th ACM Conference on Computer and Communications Security; bearing dates of Nov. 9-13, 2009 and 2009; pp. 1-10.

"Remote-controlled capsule endoscope safely examines the stomach"; PhysOrg.com; bearing a date of Jan. 18, 2011; pp. 1-2; located at http://www.physorg.com/news-2011-01-remote-controlled-capsule-endoscope-safely-stomach.html.

"Researchers Create Tiny, Self-Propelled Devices"; PhysOrg.com; printed on Feb. 12, 2007; pp. 1-3; located at: http://www.physorg.com/printnews.php?newsid=90521279.

Roh et al.; "Strategy for Navigation Inside Pipelines With Differential-Driveinpipe Robot"; IEEE Xplore; 2002 and 2005; pp. 2575-2580 (Only the Abstract is being provided); vol. 3; IEEE; located at: http://ieeexplore.ieee.org/xpls/abs_all.jsp?arnumber=1013619; printed on Apr. 23, 2007.

Roh et al.; "Actively Steerable In-Pipe Inspection Robots for Underground Urban Gas Pipelines"; IEEE Xplore; bearing dates of 2001 and 2005; pp. 761-766 (Only the Abstract is being provided); vol. 1; IEEE; located at: http://ieeexplore.ieee.org/xpls/abs_all.jsp?arnumber=932642; printed on Apr. 23, 2007.

Rolfe, Brigitte; "Toward Nanometer-Scale Sensing Systems: Natural and Artificial Noses as Models for Ultra-Small, Ultra-Dense Sensing Systems"; Advances in Computers; bearing dates of Nov. 2004, 2004, and 2007; pp. 11-46; vol. 71; Elsevier, B.V.

Schertler et al.; "Effects of ECG Gating and Postprocessing Techniques on 3D MDCT of the Bronchial Tree"; AJR; bearing a date of Jul. 2004; pp. 83-89; vol. 183; American Roentgen Ray Society.

Schnakenberg et al.; "Intravascular pressure monitoring system"; Sensors and Actuators A: Physical; bearing a date of 2004; pp. 61-67; vol. 110; Elsevier B.V.

Schwartz, John; "In the Lab: Robots That Slink and Squirm"; The New York Times: Science; bearing a date of Mar. 27, 2007; pp. 1-4; The New York Times Company; located at: http://www.nytimes.com/2007/03/27/science/27robo.html?ex=1332648000&en=d4541141c174b454&ei=5124&partner=digg&exprod=digg; printed on Mar. 27, 2007.

"Spider pill to seek out diseases"; PhysOrg.com; bearing a date of Oct. 16, 2009 and 2009; p. 1; located at http://www.physorg.com/news174893082.html.

Sun et al.; "A Miniature RF Communication System for Micro Gastrointestinal Robots"; Journal of Medical Engineering & Technology; bearing a date of 2003; pp. 160-163; vol. 27.

Suzumori et al.; "Micro Inspection Robot for 1-in Pipes"; IEEE/ASME Transactions on Mechatronics; bearing dates of Sep. 1999 and 1999; pp. 286-292; vol. 4, No. 3; IEEE.

Tang et al.; "Cerebral Vascular Tree Matching of 3D-RA Data Based on Tree Edit Distance"; Medical Imaging and Augmented Reality; bearing a date of 2006; pp. 116-123.

The Biomedical Engineering Handbook, Second Edition; bearing a date of 2000; pp. IV-1-43-31; vol. I; CRC Press LLC.

The Biomedical Engineering Handbook, Second Edition; bearing a date of 2000; pp. V-1-51-9; vol. I; CRC Press LLC.

Thrun, Sebastian; "Learning Metric-Topological Maps for Indoor Mobile Robot Navigation"; Artificial Intelligence; bearing a date of 1998; pp. 21-71; vol. 99; Elsevier Science B.V.

Thrun, Sebastian; "Probabilistic Algorithms in Robotics"; AI Magazine; bearing dates of Winter 2000 and 2000; pp. 93-109; vol. 21, No. 4; American Association for Artificial Intelligence.

Thrun, Sebastian; "Robotic Mapping: A Survey"; Exploring Artificial Intelligence in the New Millenium; bearing a date of Feb. 2002; pp. 1-29 (31 total pages); Morgan Kaufmann.

Thrun et al.; "A Real-Time Algorithm for Mobile Robot Mapping With Applications to Multi-Robot and 3D Mapping"; IEEE International Conference on Robotics and Automation; bearing a date of Apr. 2000; pp. 1-8.

Tomatis et al.; "Simultaneous Localization and Map Building: A Global Topological Model with Local Metric Maps"; Robotics Autonomous Systems; bearing a date of 2003; pp. 1-6; vol. 44.

Tsuruta et al.; "Control Circuit in an In-Pipe Wireless Micro Inspection Robot"; IEEE Xplore; bearing dates of 2000 and 2005; pp. 59-64 (Only the Abstract is being provided); IEEE; located at: http://ieeexplore.ieee.org/xpls/abs_all.jsp?arnumber=903290; printed on Apr. 23, 2007.

Ulrich et al.; "Appearance-Based Place Recognition for Topological Localization"; IEEE International Conference on Robotics and Automation; bearing a date of Apr. 2000; pp. 1023-1029.

Verheye et al.; "Selective Clearance of Macrophages in Atherosclerotic Plaques by Autophagy"; Journal of the American College of Cardiology; bearing dates of Feb. 13, 2007 and 2007; pp. 706-715; vol. 49, No. 6; Elsevier Inc.

Wacharasindhu et al.; "Radioisotope microbattery based on liquid semiconductor"; Applied Physics Letters; bearing dates of Dec. 11, 2008, Jun. 9, 2009, Jul. 6, 2009, Dec. 8, 2009 and 2009; pp. 014103-1-014103-3; vol. 95; American Institute of Physics.

Wakimoto et al.; "A Micro Snake-Like Robot for Small Pipe Inspection"; International Symposium on Micromechatronics and Human Science; bearing a date of 2003; pp. 303-308; IEEE.

Wang et al.; "A MEMS-based Air Flow Sensor with a Free-standing Micro-cantilever Structure"; Sensors; bearing dates of Aug. 27, 2007, Oct. 10, 2007, Oct. 17, 2007, and 2007; pp. 2389-2401; vol. 7; MDPI.

Watson et al.; "Piezoelectric ultrasonic resonant motor with stator diameter less than 250 μm: the *Proteus* motor"; Journal of Micromechanics and Microengineering; bearing dates of Sep. 25, 2008, Nov. 18, 2008, Jan. 20, 2009, and 2009; pp. 1-5; vol. 19; IOP Publishing Ltd.

Weingandt et al.; "Autofluorescence spectroscopy for the diagnosis of cervical intraepithelial neoplasia"; BJOG: an International Journal of Obstetrics and Gynaecology; bearing dates of Aug. 2002 and 2002; pp. 947-951; vol. 109; RCOG.

Xi et al.; "Self-assembled microdevices driven by muscle"; Nature Materials; bearing dates of Feb. 2005 and 2005; pp. 180-184 (10 pages total); vol. 4; Nature Publishing Group.

Yang et al.; "Power generation with laterally packaged piezoelectric fine wires"; Nature Nanotechnology; bearing dates of Nov. 9, 2008, Jan. 2009, and 2009; pp. 34-39; vol. 4; Macmillan Publishers Limited.

Yang et al.; "Converting Biomechanical Energy into Electricity by a Muscle-Movement-Driven Nanogenerator"; Nano Letters; bearing dates of Dec. 25, 2008, Jan. 31, 2009, and 2009; pp. 1201-1205; vol. 9, No. 3; American Chemical Society.

Yu et al.; "System for the analysis and visualization of large 3D anatomical trees"; Computers in Biology and Medicine; bearing dates of Oct. 6, 2006, May 31, 2007, Jun. 4, 2007, and 2007; pp. 1802-1820; vol. 37; Elsevier Ltd.

Zhao et al.; "Physicist Develops Natural Motor Technique"; PhysOrg.com; bearing dates of Apr. 21, 2007 and 2007; 1 page; United Press International; located at: http://www.physorg.com/news96357975.html; printed on Apr. 23, 2007.

Zheng et al.; "Design and Fabrication of a Micro Coulter Counter with Thin Film Electronics"; Proceedings of 2006 International Conference on Microtechnologies in Medicine and Biology; bearing dates of May 9-12, 2006 and 2006; pp. 16-19; IEEE.

Zhu et al.; "Flattening Maps for the Visualization of Multibranched Vessels"; IEEE Transactions on Medical Imaging; bearing dates of Feb. 10, 2004, Sep. 27, 2004, Feb. 2005, and 2005; pp. 191-198; vol. 24, No. 2; IEEE.

Zrimec et al.; "3D Modelling and Visualization of the Human Lung"; Proceedings of the 2nd International Symposium on 3D Data Processing, Visualization, and Transmission (3DPVT'04); bearing a date of 2004; pp. 110-115; IEEE.

Zyga, Lisa; "Microswimmer Propels Itself With Near-Zero Friction"; PhysOrg.com; bearing dates of Jun. 4, 2007 and 2007; pp. 1-2; PhyOrg.com; located at: http://www.physorg.com/news100176842.html; printed on Jun. 6, 2007.

U.S. Appl. No. 13/135,437, Jung et al.
U.S. Appl. No. 11/541,492, Jung et al.
U.S. Appl. No. 11/541,452, Jung et al.
U.S. Appl. No. 11/541,448, Jung et al.
U.S. Appl. No. 11/541,378, Jung et al.
U.S. Appl. No. 11/541,377, Jung et al.
U.S. Appl. No. 11/526,203, Jung et al.
U.S. Appl. No. 11/526,201, Jung et al.
U.S. Appl. No. 11/526,144, Jung et al.
U.S. Appl. No. 11/526,089, Jung et al.
U.S. Appl. No. 11/455,010, Jung et al.
U.S. Appl. No. 11/454,343, Jung et al.

Billinger, M.; Buddeberg, F.; Hubbell, J. A.; Elbert, D. L.; Schaffner, T.; Mettler, D.; Windecker, S.; Meier, B.; Hess O. M.; "Polymer Stent Coating for Prevention of Neointimal Hyperplasia"; The Journal of Invasive Cardiology; bearing a date of Sep. 2006; printed on Jul. 16, 2007; pp. 423-426; vol. 18; No. 9.

"Human Arterial Tree Project"; Jun. 5, 2007; pp. 1-16; located at http://www.cfm.brown.edu/crunch/ATREE/.

"Intellectual Property"; Patent Disclosure Form; bearing a date of Sep. 2, 2003; pp. 1-9; Case #CHFT-MRI-01.

Istook, Cynthia L.; "Rapid Prototyping in the Textile & Apparel Industry: A Pilot Project"; Journal of Textile and Apparel, Technology and Management; Sep. 2000; pp. 1-14; vol. 1, No. 1; NC State University.

Kaufman, John A.; Brewster, David C.; Geller, Stuart C.; Fan, Chieh-Min; Cambria, Richard P.; Abbott, William A.; Waltman, Arthur C.; "Custom Bifurcated Stent-Graft for Abdominal Aortic Aneurysms: Initial Experience"; Journal of Vascular and Interventional Radiology; 1999; pp. 1099-1106; vol. 10; No. 8; Society of Cardiovascular and Interventional Radiology.

Lee, Haeshin; Lee, Bruce P.; Messersmith; Phillip B.; "A Reversible Wet/Dry Adhesive Inspired by Mussels and Geckos"; Nature; bearing a date of Jul. 19, 2007; pp. 338-341; vol. 448; Nature Publishing Group.

"Press Release: SurModics Provides Hydrophilic Coating on Xtent's Drug-Eluting Stent Delivery System"; Business Wire: Financial News; bearing a date of May 15, 2006; pp. 1-2; Yahoo! Inc.

"Rapid Protyping Technology"; DRM Associates; printed on Jun. 26, 2007; pp. 1-2; located at http://www.npd-solutions.com/rp.html.

"'Sleeve' Keeps Blockages At Bay—Research Shows Gortex Sleeves Wrapped Around Arteries Can Prevent Plaque Formations From Forming—Brief Article"; USA Today (Society for the Advancement of Education); Feb. 1998; pp. 1; located at http://findarticles.com/p/articles/mi_m1272/is_n2633_v126/ai_20305717.

"Switchable Adhesive"; pp. 1-2; PhysOrg.com; located at: http://www.physorg.com/printnews.php?newsid=104488044.

"Tracking Acute Myocardial Infarction: The First Step in Treating Ischemic CHF"; CHFT Proposal; bearing a date of 1999; pp. 1-4; American College of Cardiology and American Heart Association, Inc.

Tropea, Bradford I.; Schwarzacher, Severin P.; Chang, Albert; Asvar, Chris; Huie, Phil; Sibley, Richard K.; Zarins, Christopher K.; "Reduction of Aortic Wall Motion Inhibits Hypertension-Mediated Experimental Atherosclerosis"; Journal of the American Heart Association; 2000; pp. 2127-2133; vol. 20; American Heart Association.

Twardowski, Z.J.; Haynie, J.D.; "Measurements of Hemodialysis Catheter Blood Flow in Vivo"; The International Journal of Artificial Organs; bearing a date of 2002; pp. 276-280; vol. 25, No. 4; Wichtig Editore.

Twardowski, Z.J.; Seger, R.M.; "Dimensions of Central Venous Structures in Humans Measured in Vivo Using Magnetic Resonance Imaging: Implications for Central-Vein Catheter Dimensions"; The International Journal of Artificial Organs; bearing a date of 2002; pp. 107-123; vol. 25, No. 2; Wichtig Editore.

Van Der Giessen, Willem J., PhD., MD; Van Beusekom, Heleen M.M.; Larsson, Rolf; Serruys, Patrick W., PhD., MD; "Heparin-Coated Coronary Stents"; Current Interventional Cardiology Reports; bearing a date of 1999; pp. 234-240; vol. 1; Current Science Inc.

Waugh, Alice C.; "Multidisciplinary Science May Yield New Drug Therapy"; MIT Tech Talk; bearing a date of May 18, 1994; printed on Jun. 4, 2007; pp. 1-2; vol. 38; No. 33; Massachusetts Institute of Technology.

Winder, R. J.; Sun, Z.; Kelly, B.; Ellis, P. K.; Hirst, D.; "Abdominal Aortic Aneurysm and Stent Graft Phantom Manufactured by Medical Rapid Prototyping"; Journal of Medical Engineering & Technology; Mar./Apr. 2002; pp. 75-78; vol. 26; No. 2; Taylor & Francis Health Sciences.

"Xtent Custom I Trial Shows Zero Restenosis, Favorable Late Loss Results at Eight Months"; Healthcare Sales & Marketing Network NewsFeed; bearing a date of May 16, 2006; pp. 1-2.

"Xtent Customized Stent System Achieves Two Coronary Firsts: Single Catheter Delivers Multiple Stents and Longest Stent Ever Placed"; News & Information About Minimally Invasive Medicine; bearing dates of 1996-2006 and Jan. 5, 2006; pp. 1-2; Venture Digital LLC.

* cited by examiner

FIG. 3
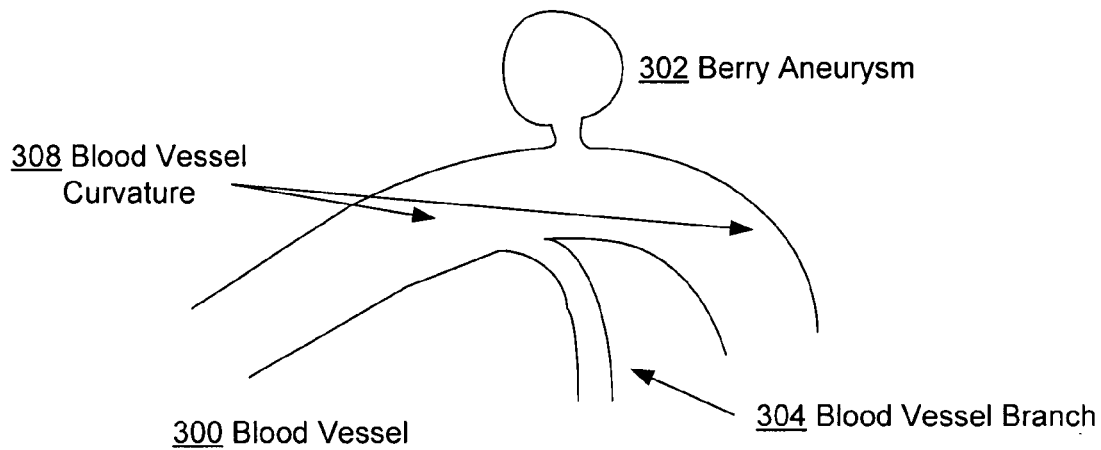
FIG. 3A
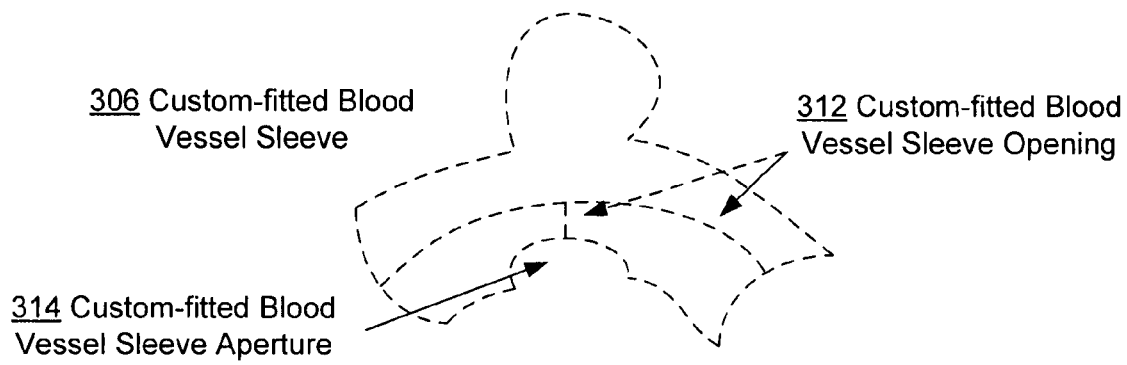
FIG. 3B
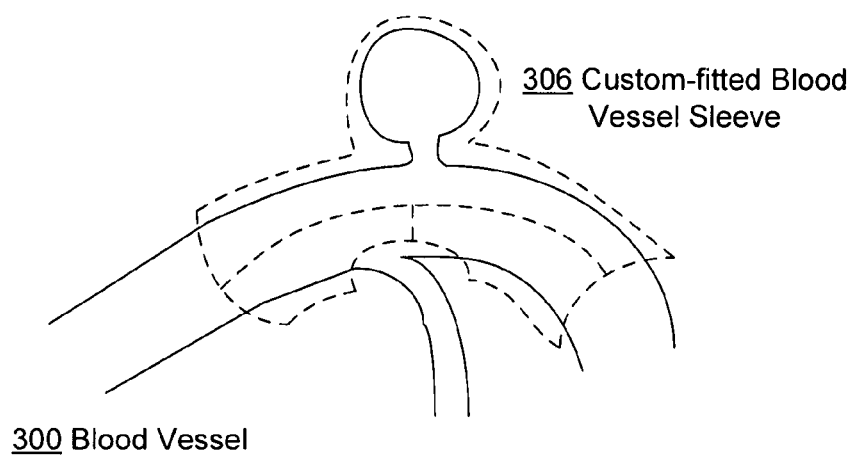
FIG. 3C

FIG. 4
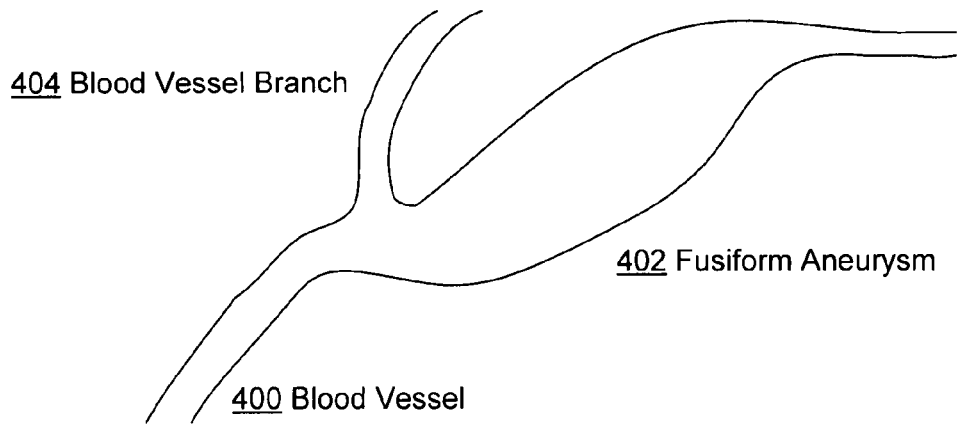
404 Blood Vessel Branch
402 Fusiform Aneurysm
400 Blood Vessel
FIG. 4A
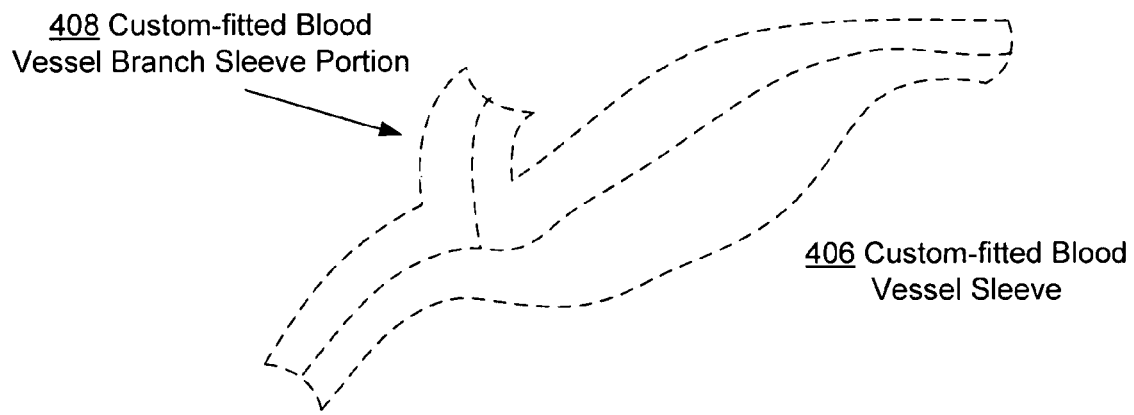
408 Custom-fitted Blood Vessel Branch Sleeve Portion
406 Custom-fitted Blood Vessel Sleeve
FIG. 4B
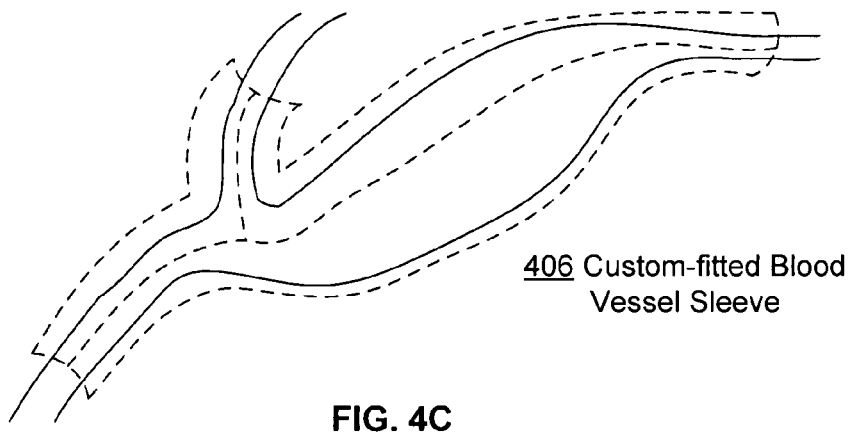
406 Custom-fitted Blood Vessel Sleeve
FIG. 4C
400 Blood Vessel

FIG. 5
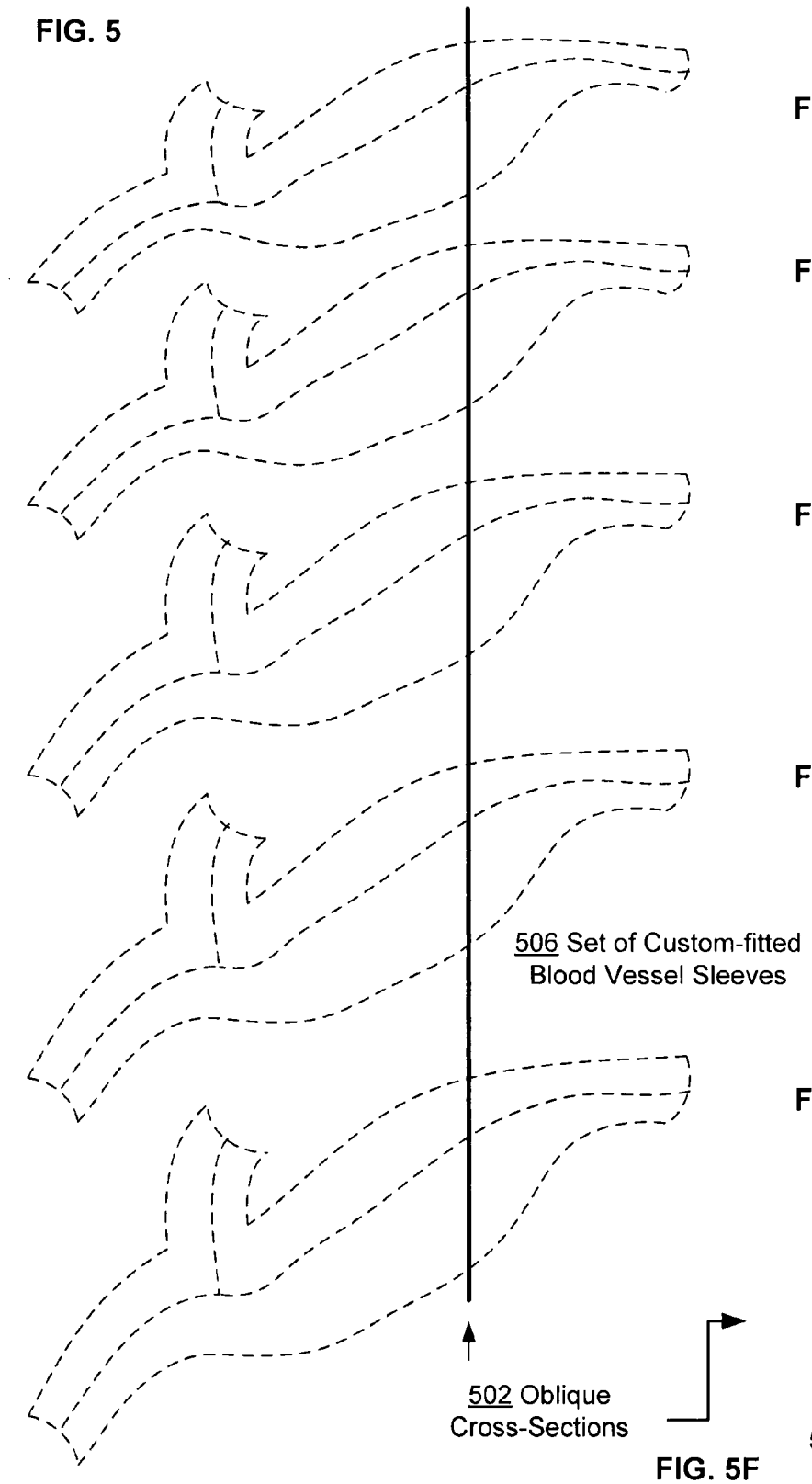
FIG. 5A
FIG. 5B
FIG. 5C
FIG. 5D
506 Set of Custom-fitted Blood Vessel Sleeves
FIG. 5E
502 Oblique Cross-Sections
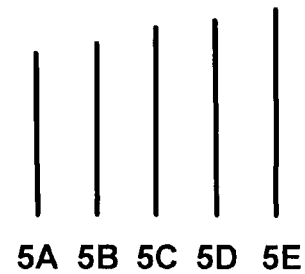
5A 5B 5C 5D 5E
FIG. 5F

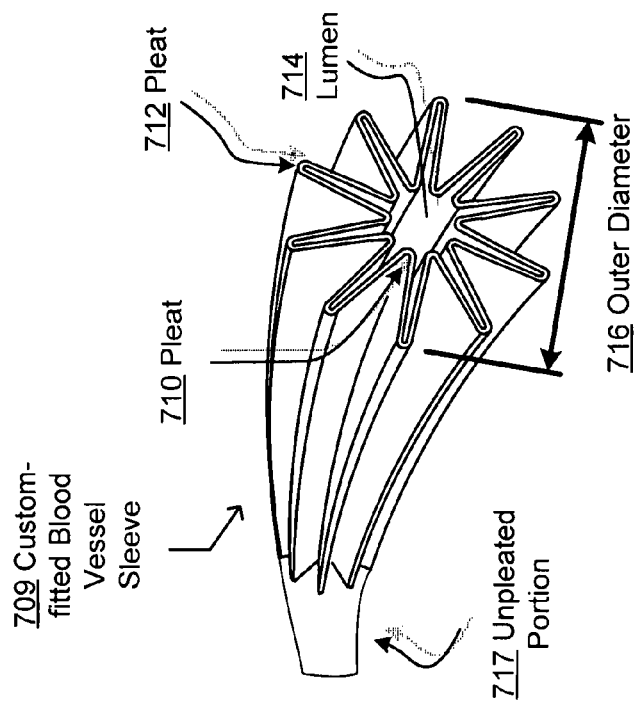
FIG. 7B
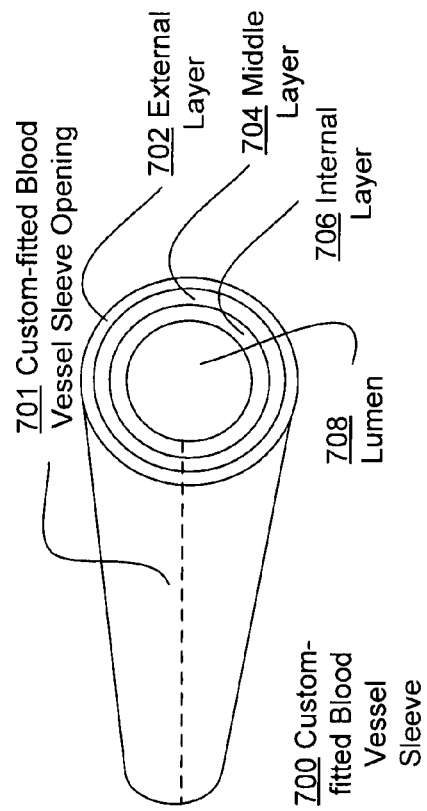
FIG. 7A
FIG. 7

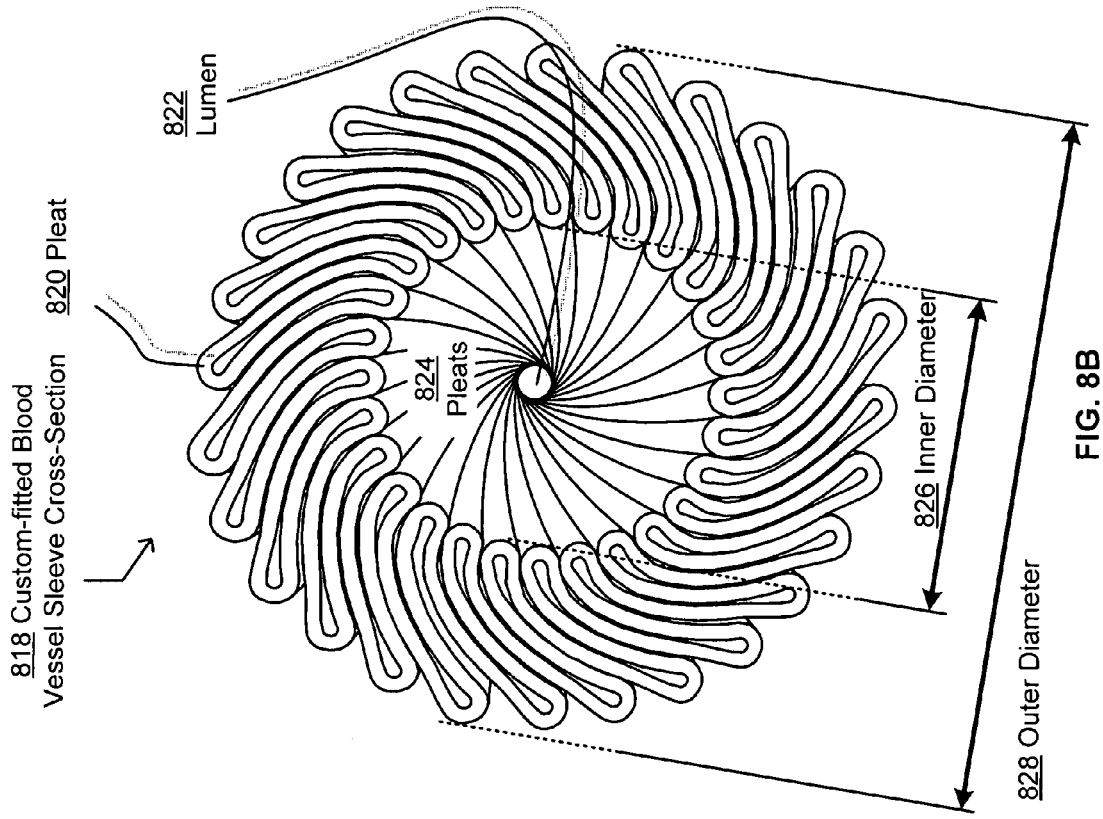
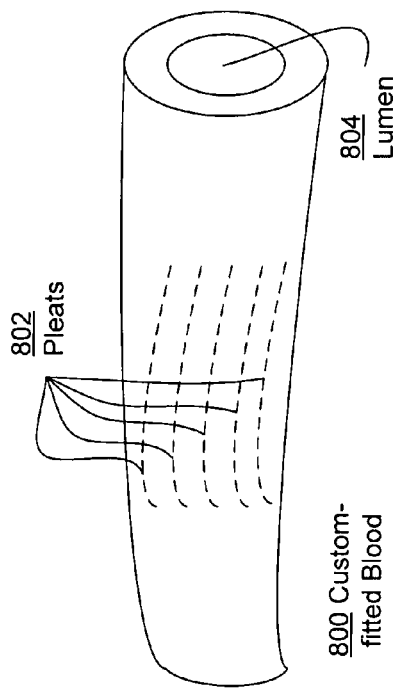
FIG. 8

FIG. 32

3200 Computing System Environment

3204 Device (e.g., a workstation or other desktop computing device)

3202 Computing device

3208 Storage medium

3210 Computer-executable instructions operable to:

(a) accept three-dimensional blood vessel data;

(b) apply a sleeve-fitting algorithm to the three-dimensional blood vessel data; and (c) present a sleeve-fitting algorithm output in response to said applying the sleeve-fitting algorithm to the three-dimensional blood vessel data

3206

3204 Device

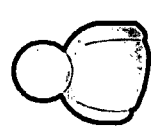

222 Health Care Provider

FIG. 34

3400 Computing System Environment

3404 Device (e.g., a workstation or other desktop computing device)

3402 Computing device

3408 Storage medium

3410 Computer-executable instructions operable to:

(a) obtain blood vessel data pertaining to an individual;

(b) convert the blood vessel data pertaining to the individual into a three-dimensional model;

(c) apply a sleeve-fitting algorithm to the three-dimensional model; and (d) present a sleeve-fitting algorithm output in response to said applying the sleeve-fitting algorithm to the three-dimensional model

3406

3404 Device

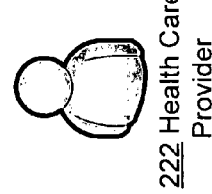

222 Health Care Provider

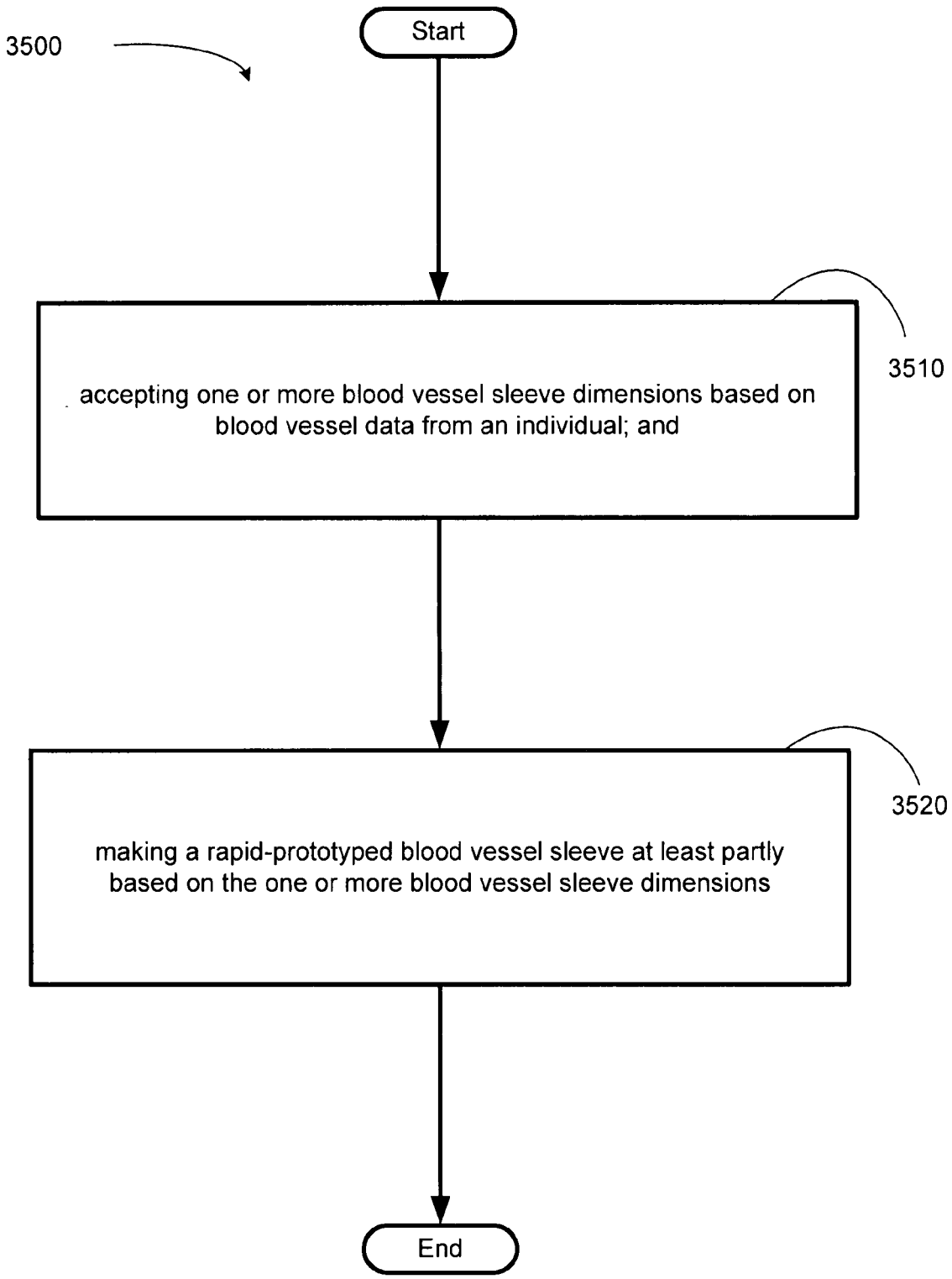

FIG. 50

5000 Computing System Environment

5004 Device (e.g., a workstation or other desktop computing device)

5002 Computing device

5008 Storage medium

5010 Computer-executable instructions operable to:

(a) accept one or more blood vessel sleeve dimensions based on blood vessel data from an individual; and (b) make a rapid-prototyped blood vessel sleeve at least partly based on the one or more blood vessel sleeve dimensions 5012 Sleeve-making Device

5006

5004 Device

222 Health Care Provider

FIG. 53
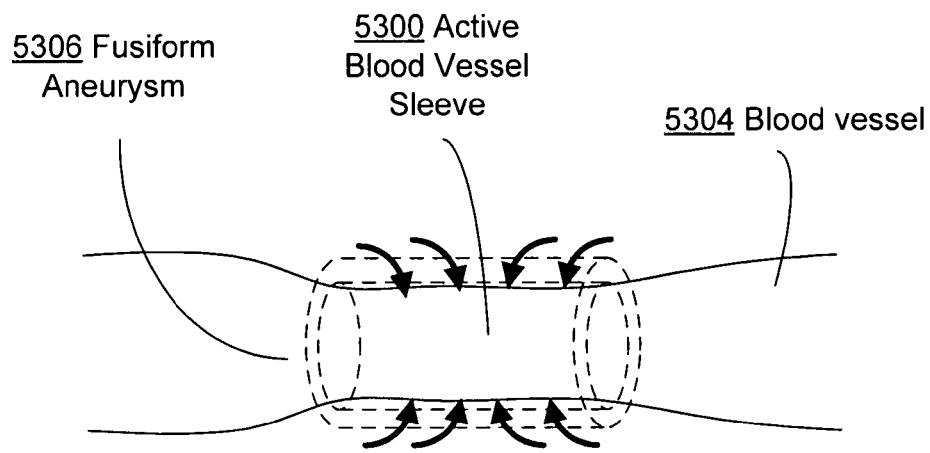
FIG. 53A
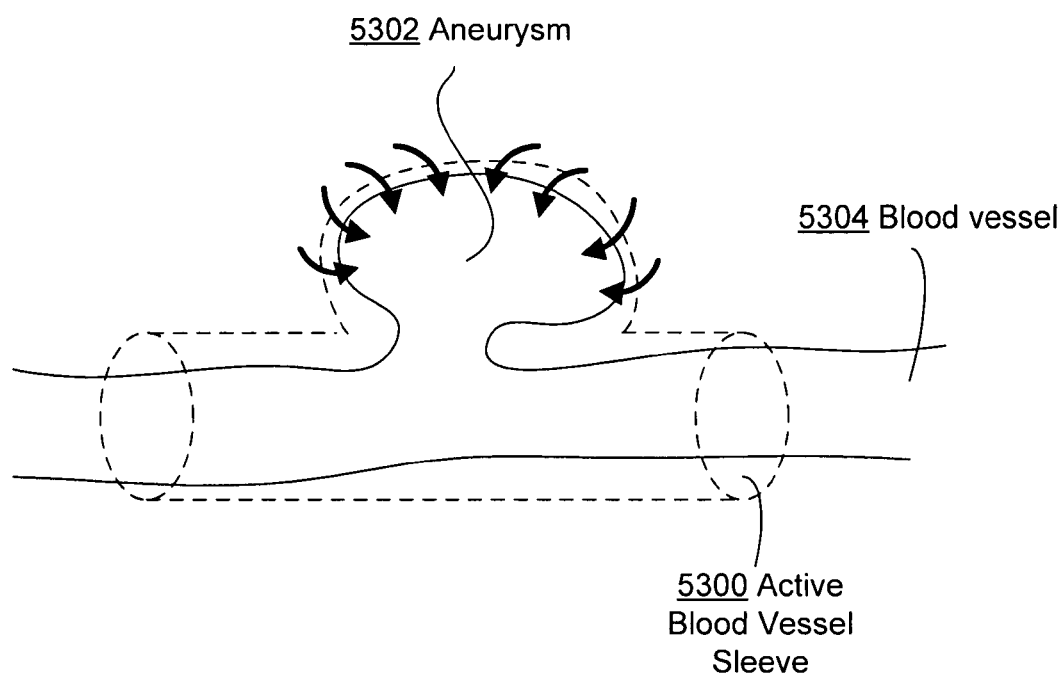
FIG. 53B

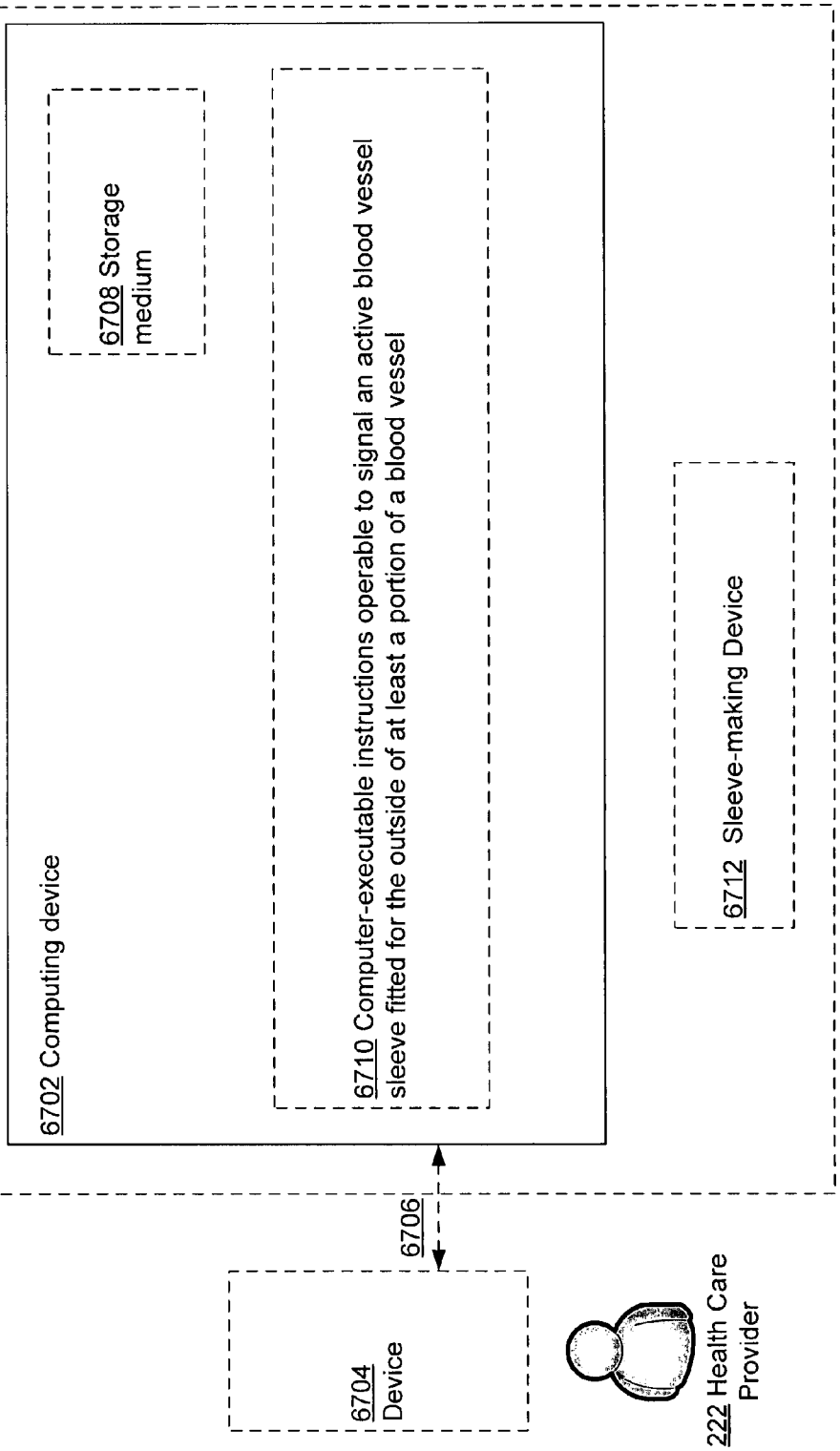

ACTIVE BLOOD VESSEL SLEEVE METHODS AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/645,357, entitled LUMEN-TRAVELING DEVICE, naming Bran Ferren, W. Daniel Hillis, Roderick A. Hyde, Muriel Y. Ishikawa, Edward K. Y. Jung, Eric C. Leuthardt, Nathan P. Myhrvold, Elizabeth A. Sweeney, Clarence T. Tegreene, Lowell L. Wood, Jr. and Victoria Y. H. Wood as inventors, filed 21 Dec. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/454,343, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 16 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/455,010, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 16 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,089, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,144, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,201, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006 now U.S. Pat. No. 7,769,603, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,203, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006 now U.S. Pat. No. 7,769,603, which is currently, or is an application of which a currently co-pending application is entitled to the benefit of the filing date.

For purposes of the USPTO extra-statutory requirements, the present application constitutes a continuation-in-part of U.S. patent application Ser. No. 11/541,377, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date. For purposes of the USPTO extra-statutory requirements, the present application constitutes a continuation-in-part of U.S. patent application Ser. No. 11/541,378, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,448, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,452, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,492, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/879,751, entitled CUSTOM-FITTED BLOOD VESSEL SLEEVE, naming Edward S. Boyden, Ralph G. Dacey, Jr., Colin P. Derdeyn, Joshua L. Dowling, Roderick A. Hyde, Muriel Y. Ishikawa, Eric C. Leuthardt, Nathan P. Myhrvold, Clarence T. Tegreene, Lowell L. Wood, Jr., Victoria Y. H. Wood, and Gregory J. Zipfel as inventors, filed 17 Jul. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/880,434, entitled RAPID-PROTOTYPED CUSTOM-FITTED BLOOD VESSEL SLEEVE, naming Edward S. Boyden, Ralph G. Dacey, Jr., Colin P. Derdeyn, Joshua L. Dowling, Roderick A. Hyde, Muriel Y. Ishikawa, Eric C. Leuthardt, Nathan P. Myhrvold, Clarence T. Tegreene, Lowell L. Wood, Jr., Victoria Y. H. Wood, and Gregory J. Zipfel as inventors, filed 19 Jul. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/888,623, entitled METHODS AND SYSTEMS FOR SPECIFYING A BLOOD VESSEL SLEEVE, naming Edward S. Boyden, Ralph G. Dacey, Jr., Colin P. Derdeyn, Joshua L. Dowling, Roderick A. Hyde, Muriel Y. Ishikawa, Eric C. Leuthardt, Nathan P. Myhrvold, Clarence T. Tegreene, Lowell L. Wood, Jr., Victoria Y. H. Wood, and Gregory J. Zipfel as inventors, filed 31 Jul. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/894,563, entitled METHODS AND SYSTEMS FOR MAKING A BLOOD VESSEL SLEEVE, naming Edward S. Boyden, Ralph G. Dacey, Jr., Colin P. Derdeyn, Joshua L. Dowling, Roderick A. Hyde, Muriel Y. Ishikawa, Eric C. Leuthardt, Nathan P. Myhrvold, Clarence T. Tegreene, Lowell L. Wood, Jr., Victoria Y. H. Wood, and Gregory J. Zipfel as inventors, filed 20 Aug. 2007 now U.S. Pat. No. 7,818,084, which is currently, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, Applicant entity understands that the USPTO's computer programs have certain data entry requirements, and hence Applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to an active blood vessel sleeve methods and systems.

SUMMARY

An embodiment provides a method. In one implementation, the method includes but is not limited to signaling an active blood vessel sleeve fitted for the outside of at least a portion of a blood vessel. In addition to the foregoing, other aspects are described in the claims, drawings, and text forming a part of the present disclosure.

An embodiment provides a method. In one implementation, the method includes but is not limited to detecting in an individual an active blood vessel sleeve fitted for the outside of at least a portion of a blood vessel; and signaling the active blood vessel sleeve fitted for the outside of at least a portion of the blood vessel. In addition to the foregoing, other aspects are described in the claims, drawings, and text forming a part of the present disclosure.

An embodiment provides a computer program product. In one implementation, the system includes but is not limited to a signal-bearing medium bearing one or more instructions for signaling an active blood vessel sleeve fitted for the outside of at least a portion of a blood vessel. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to signal an active blood vessel sleeve fitted for the outside of at least a portion of at least one blood vessel. In addition to the foregoing, other system aspects are described in the claims, drawings, and text forming a part of the present disclosure.

In one or more various aspects, related systems include but are not limited to circuitry and/or programming for effecting the herein-referenced device aspects; the circuitry and/or programming can be virtually any combination of hardware, software, and/or firmware configured to effect the herein-referenced device aspects depending upon the design choices of the system designer.

In addition to the foregoing, various other embodiments are set forth and described in the text (e.g., claims and/or detailed description) and/or drawings of the present description.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE DRAWINGS

With reference now to FIG. 1, shown is an example of an environment in which one or more blood vessel sleeve technologies may be implemented.

With reference now to FIG. 3, shown are examples of embodiments of blood vessel sleeves, which may serve as a context for introducing one or more devices, methods, and systems described herein.

With reference now to FIG. 4, shown are examples of embodiments of blood vessel sleeves, which may serve as a context for introducing one or more devices, methods, and systems described herein.

With reference now to FIG. 5, shown are examples of embodiments of blood vessel sleeves, which may serve as a context for introducing one or more devices, methods, and systems described herein.

Figure 6:
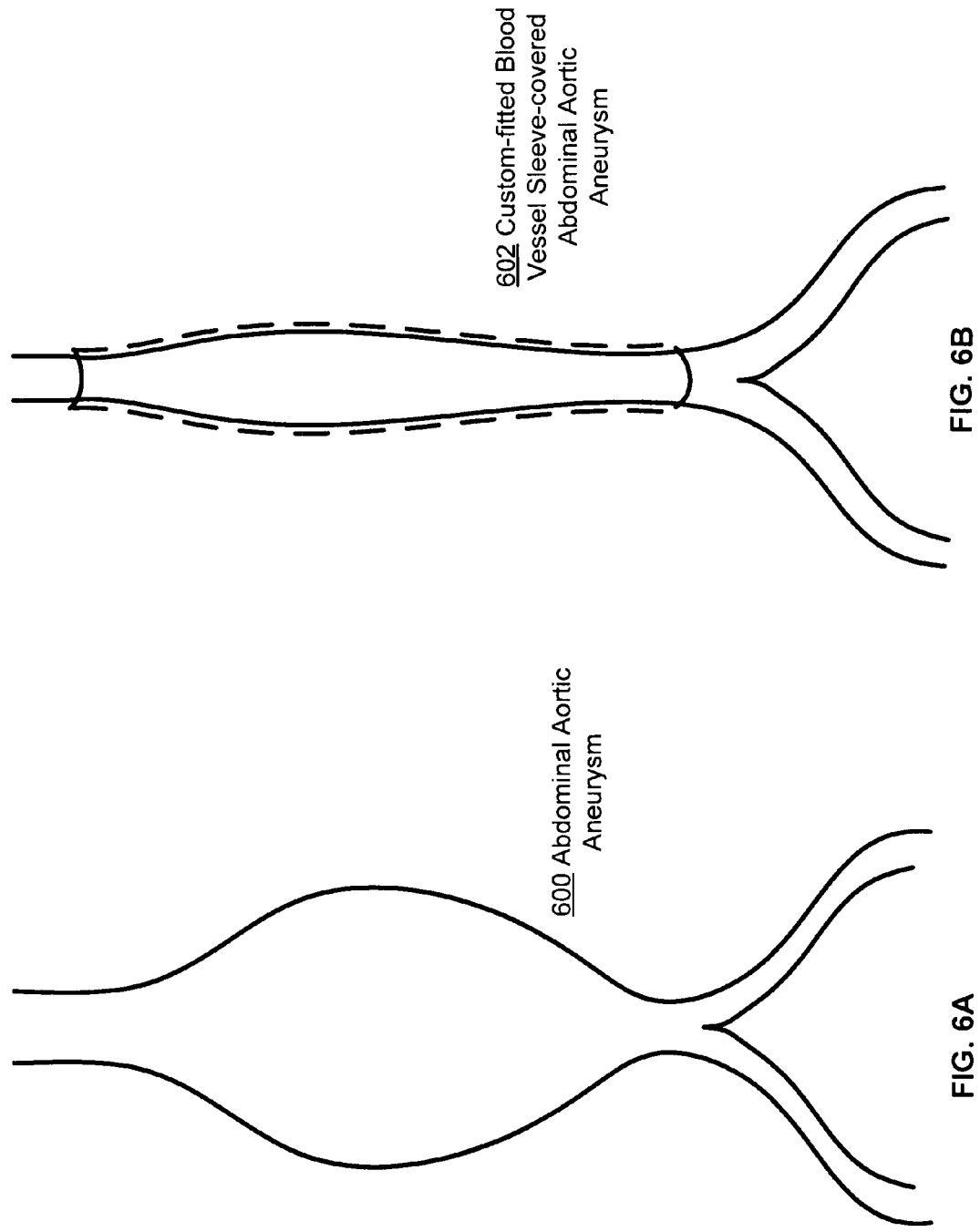

With reference now to FIG. 6, shown are examples of embodiments of blood vessel sleeves, which may serve as a context for introducing one or more devices, methods, and systems described herein.

With reference now to FIG. 7, shown are examples of embodiments of blood vessel sleeves, which may serve as a context for introducing one or more devices, methods, and systems described herein.

With reference now to FIG. 8, shown are examples of embodiments of blood vessel sleeves, which may serve as a context for introducing one or more devices, methods, and systems described herein.

Figure 9:
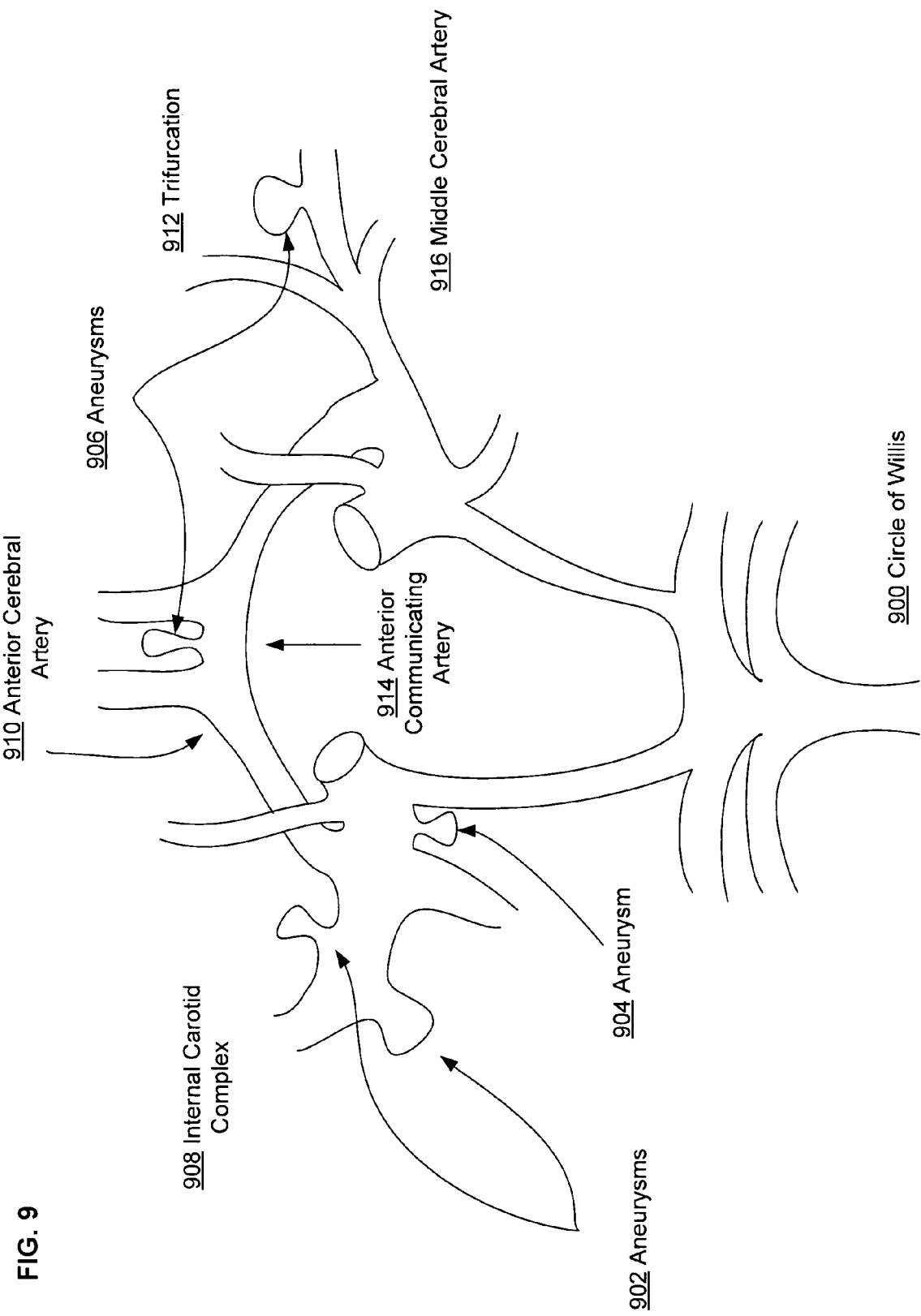

With reference now to FIG. 9, shown are examples of blood vessel anatomy, which may serve as a context for introducing one or more devices, methods, and systems described herein.

Figure 10:
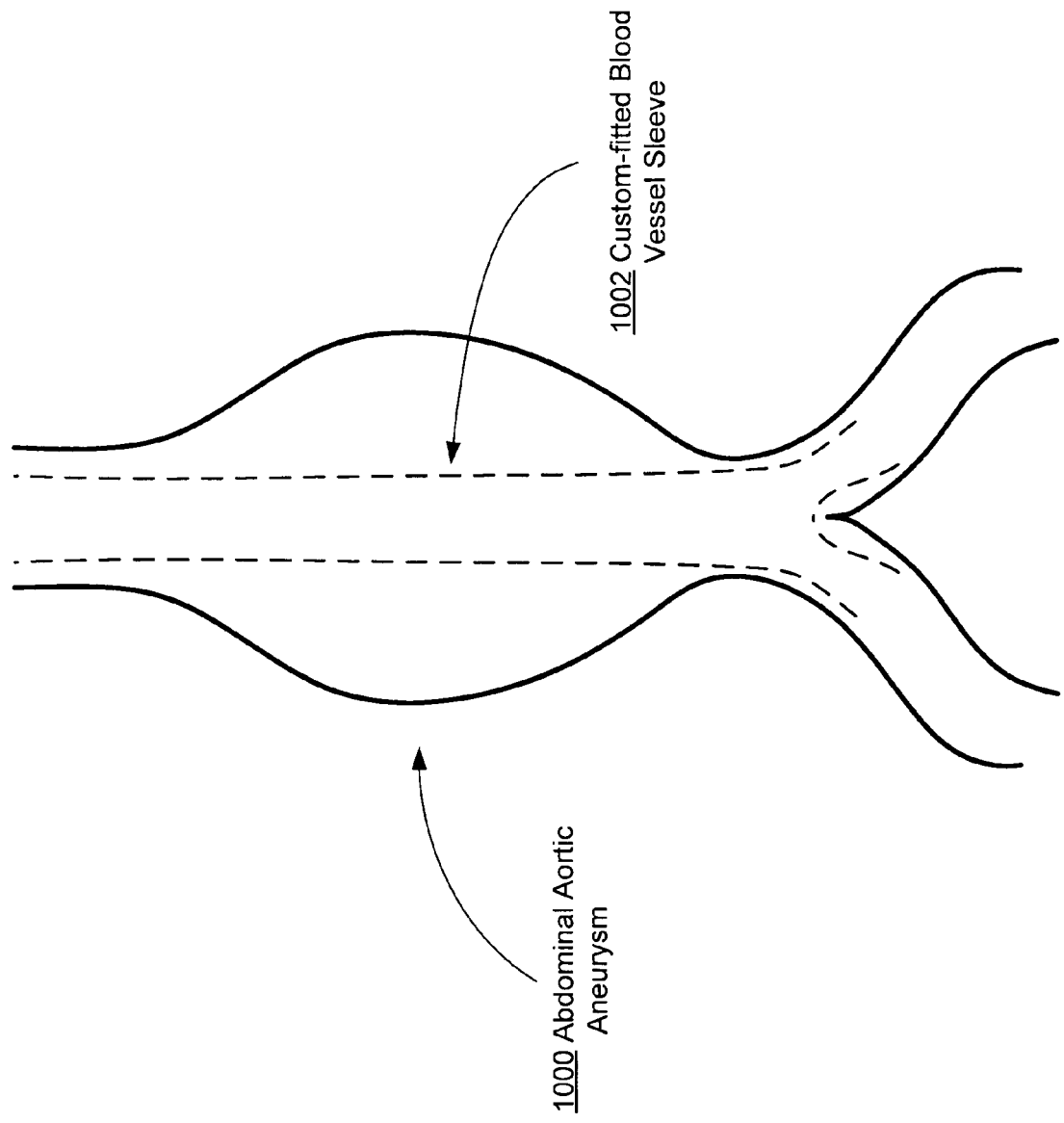

With reference now to FIG. 10, shown are examples of embodiments of blood vessel sleeves, which may serve as a context for introducing one or more devices, methods, and systems described herein.

Figure 11:
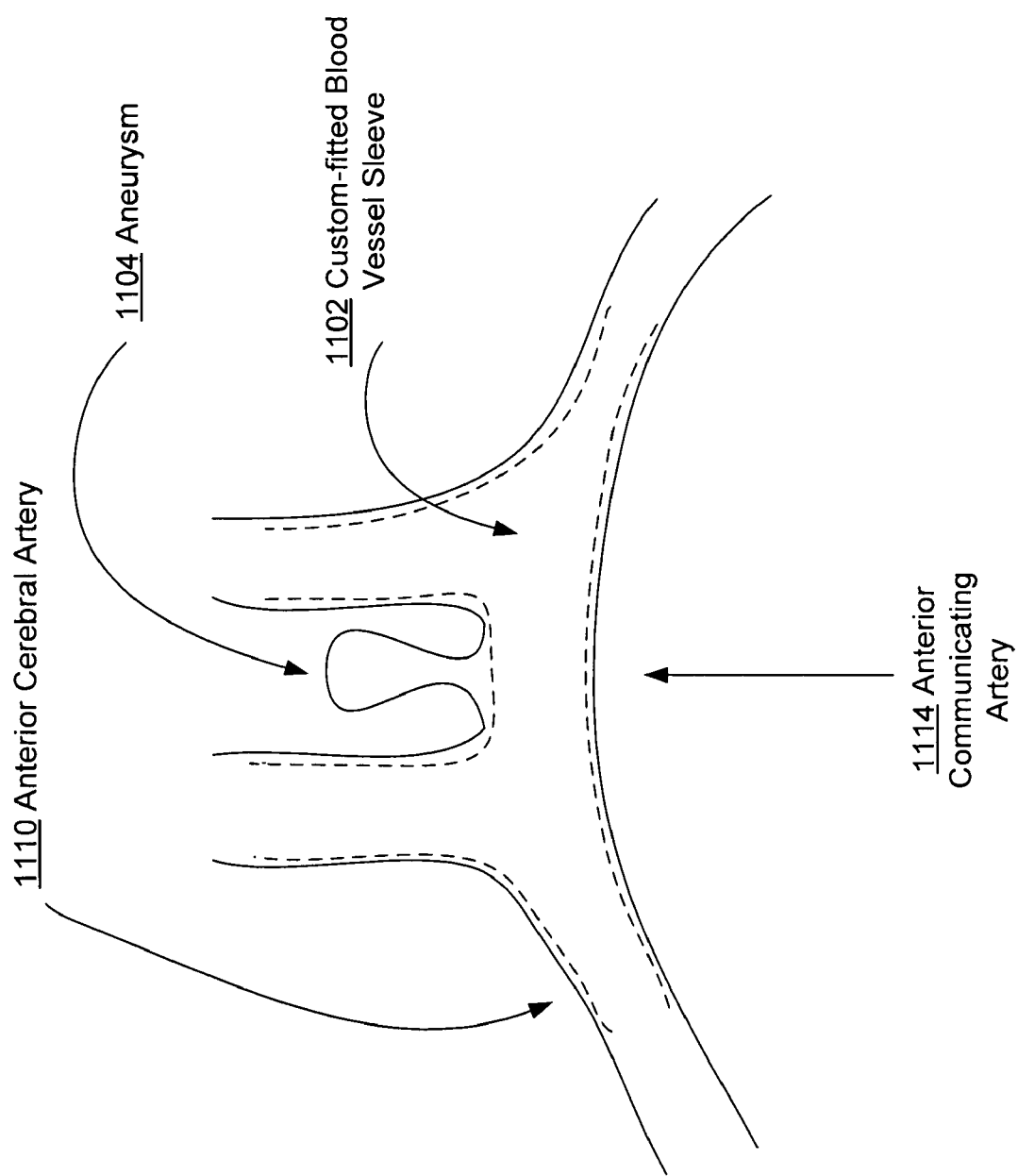

With reference now to FIG. 11, shown are examples of embodiments of blood vessel sleeves, which may serve as a context for introducing one or more devices, methods, and systems described herein.

Figure 12:
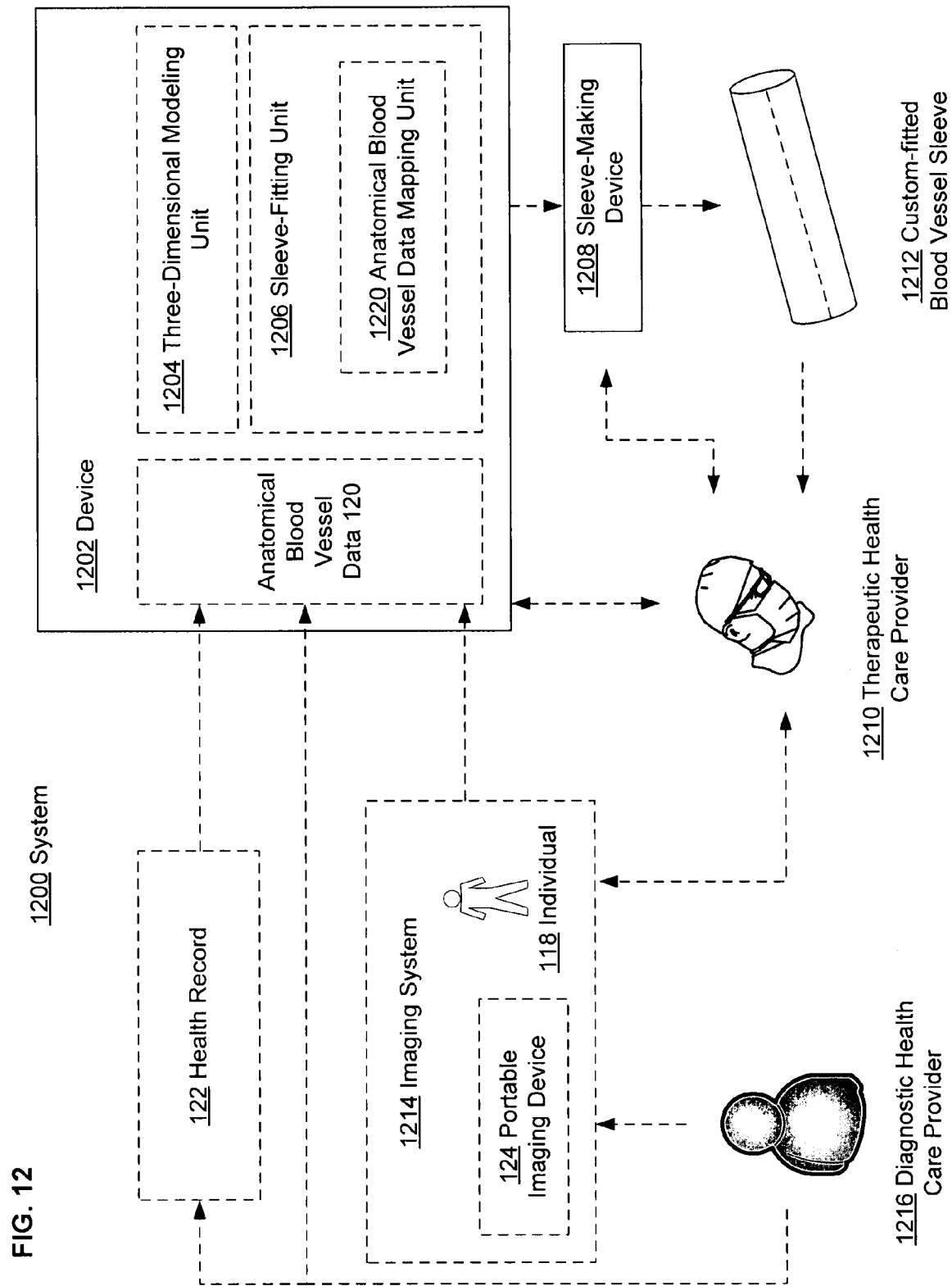

With reference now to FIG. 12, shown is an example of an environment in which one or more blood vessel sleeve technologies may be implemented.

Figure 13:
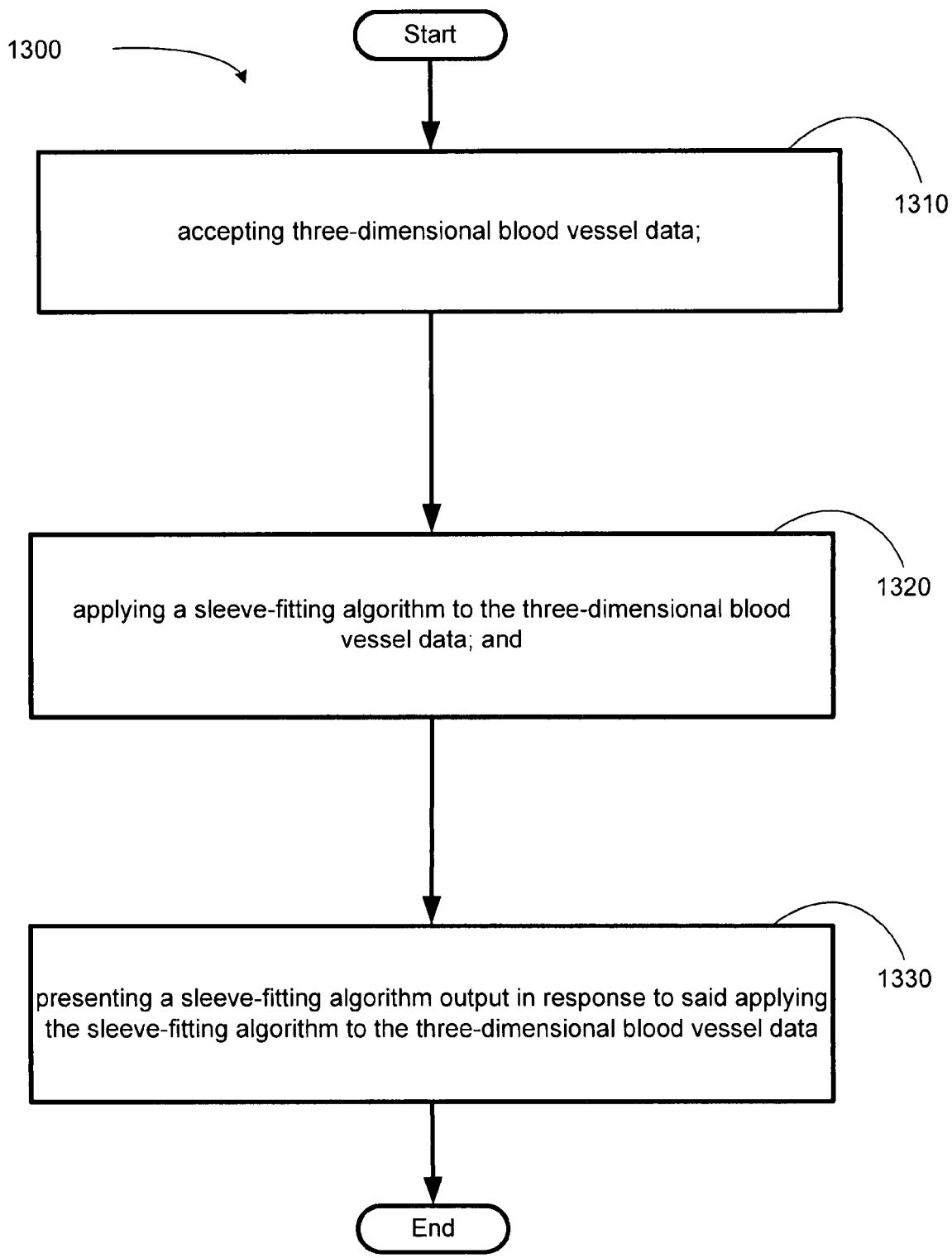

FIG. 13 illustrates an operational flow representing example operations related to methods and systems for specifying a blood vessel sleeve.

Figure 14:
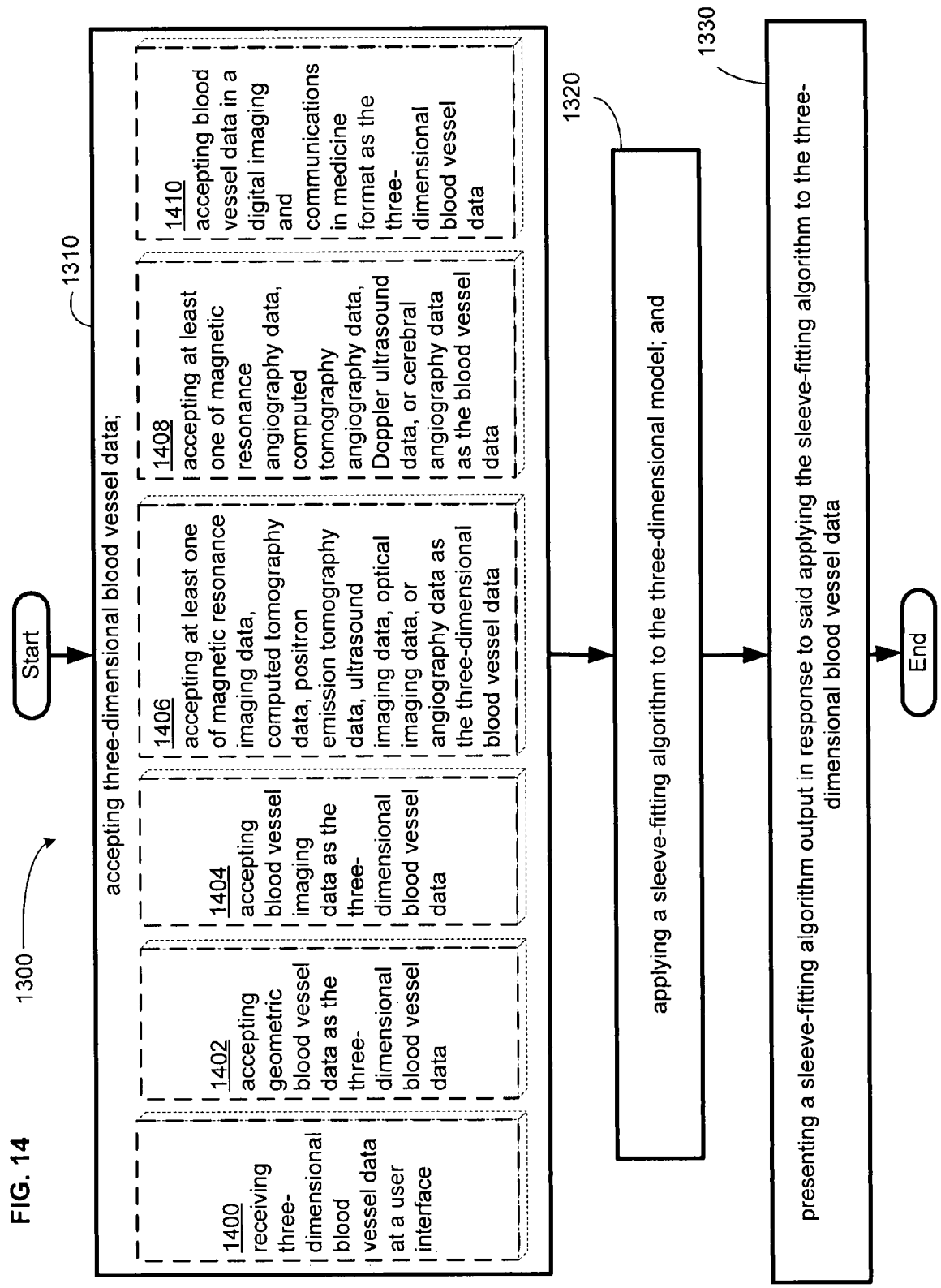

FIG. 14 illustrates an alternative embodiment of the example operational flow of FIG. 13.

Figure 15:
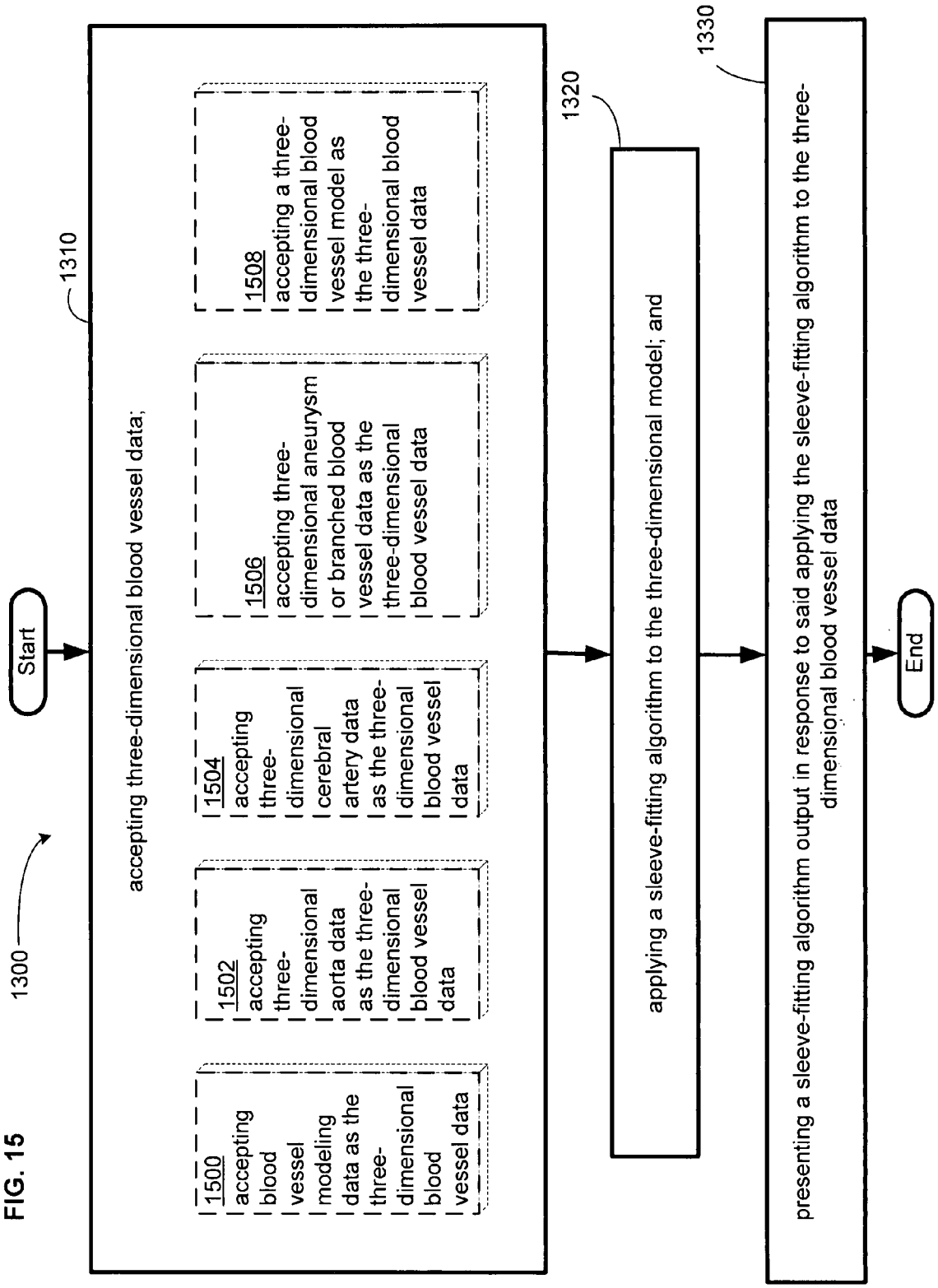

FIG. 15 illustrates an alternative embodiment of the example operational flow of FIG. 13.

Figure 16:
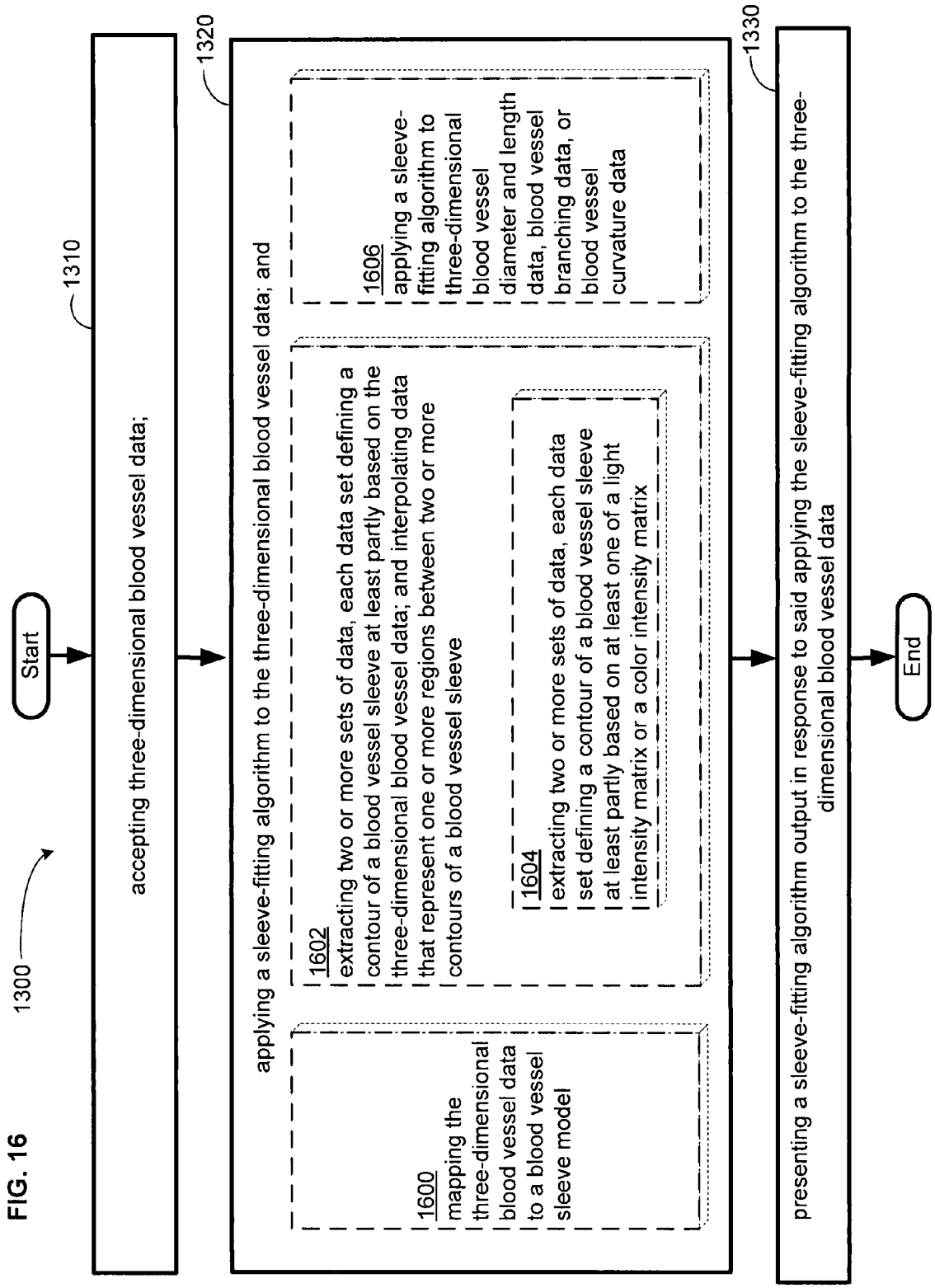

FIG. 16 illustrates an alternative embodiment of the example operational flow of FIG. 13.

Figure 17:
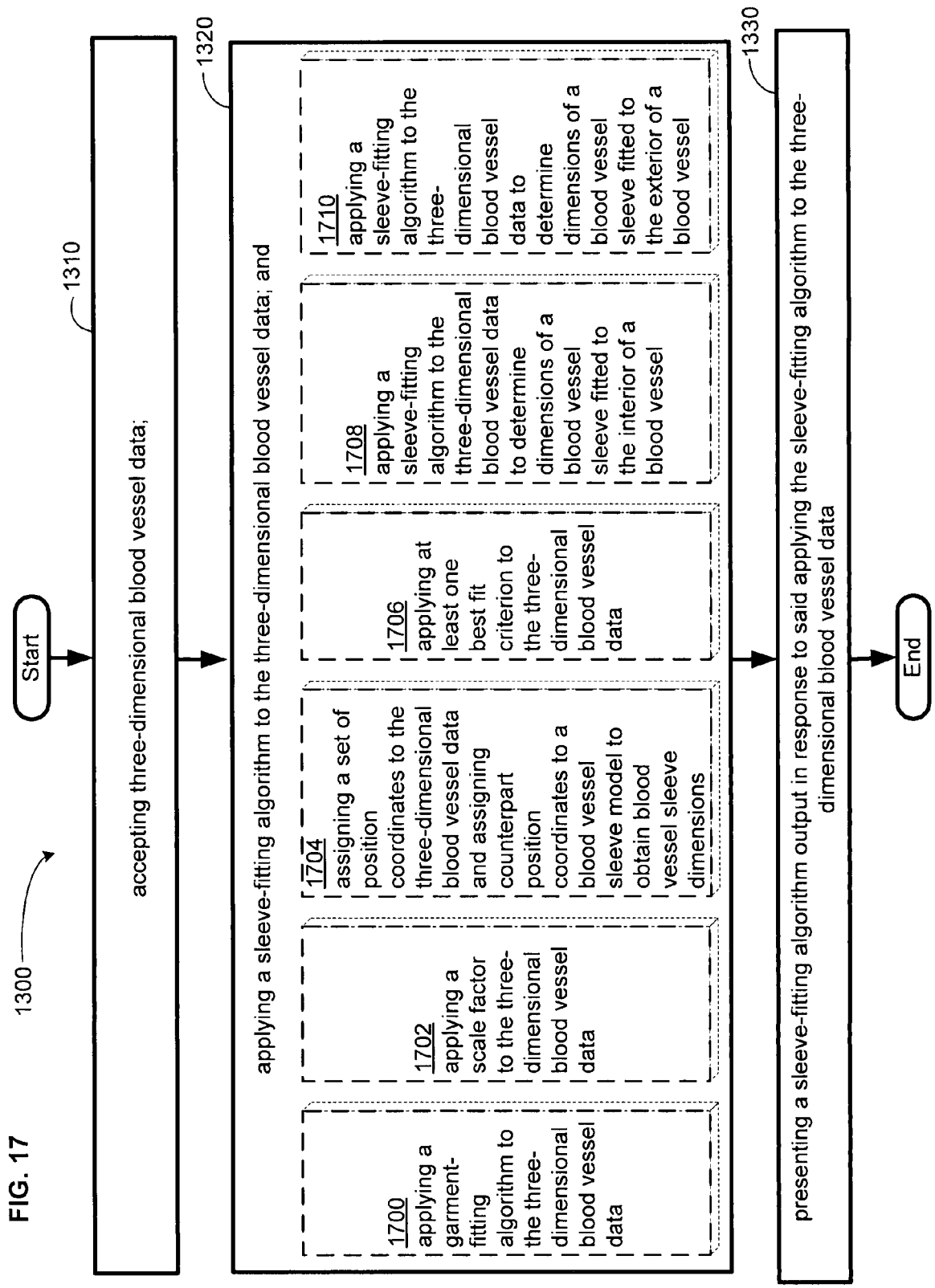

FIG. 17 illustrates an alternative embodiment of the example operational flow of FIG. 13.

Figure 18:
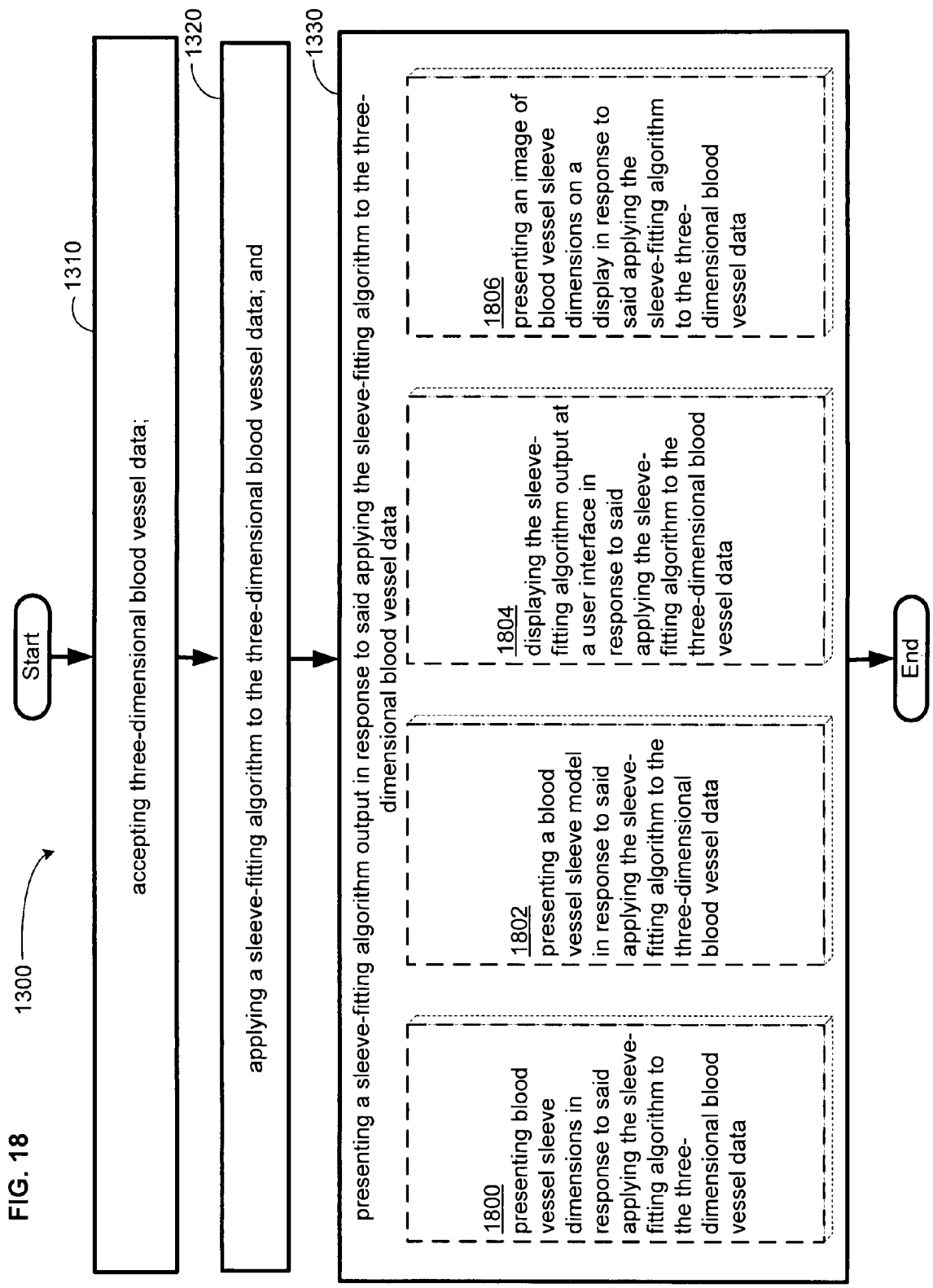

FIG. 18 illustrates an alternative embodiment of the example operational flow of FIG. 13.

Figure 19:
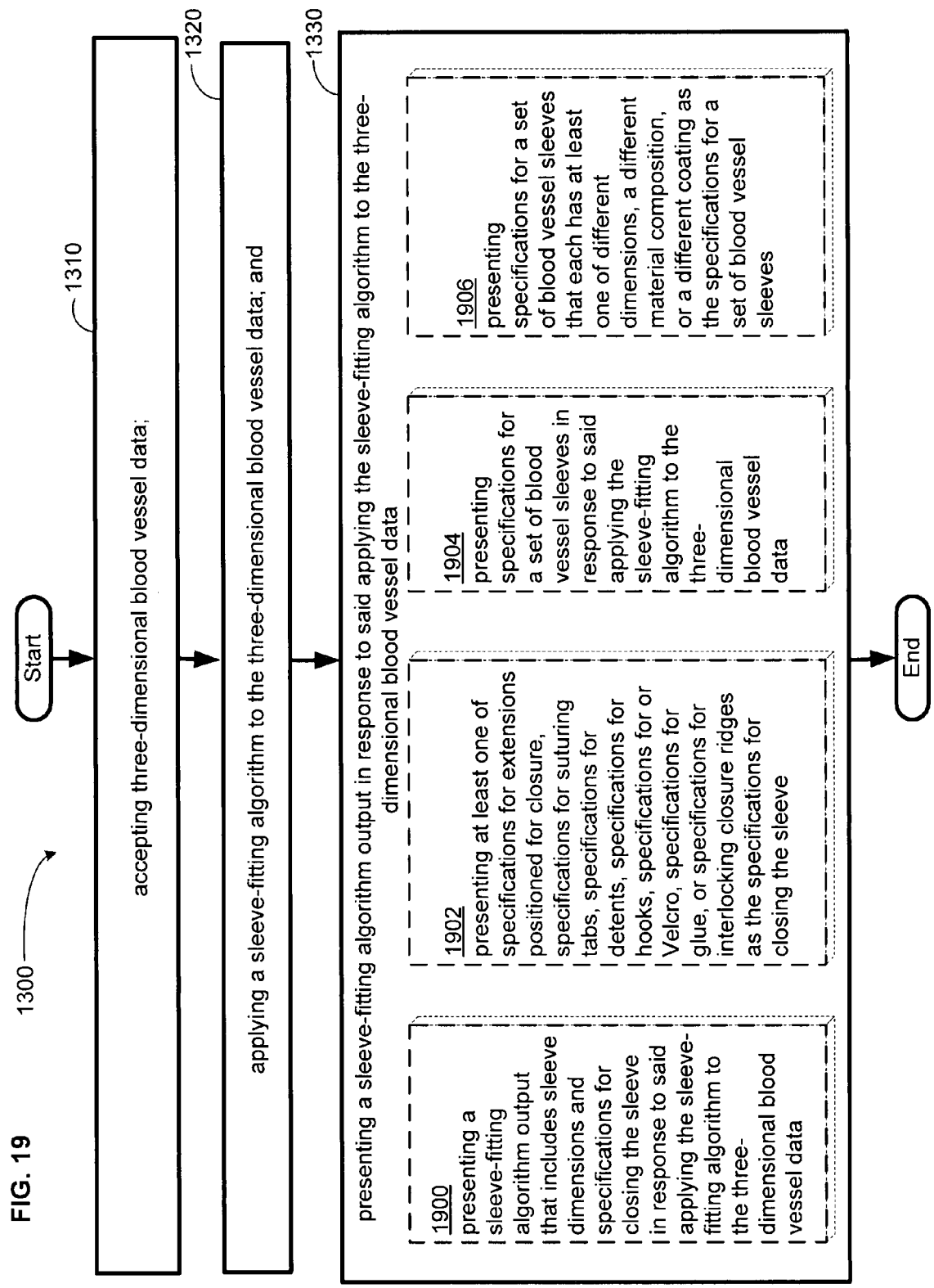

FIG. 19 illustrates an alternative embodiment of the example operational flow of FIG. 13.

Figure 20:
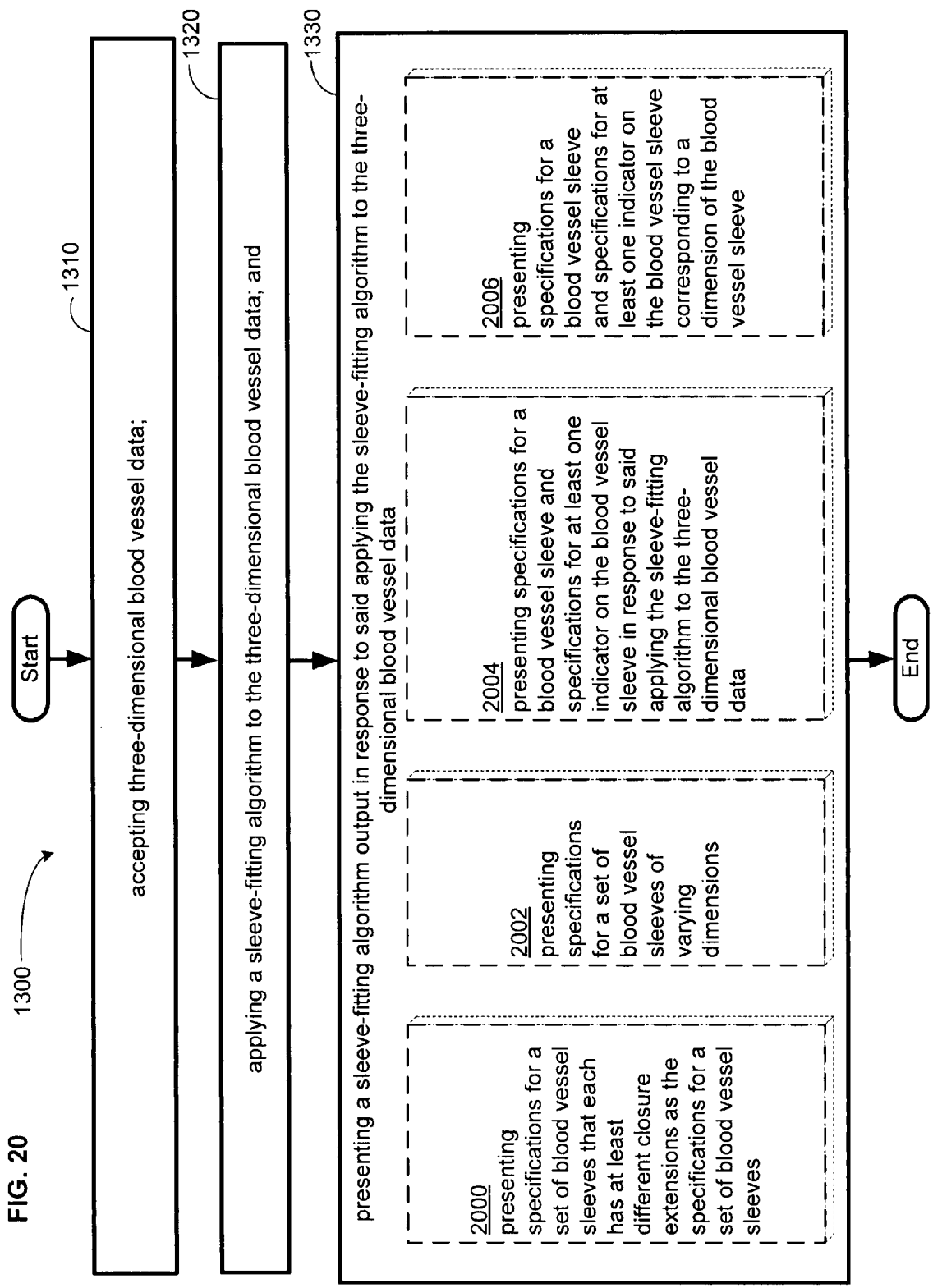

FIG. 20 illustrates an alternative embodiment of the example operational flow of FIG. 13.

Figure 21:
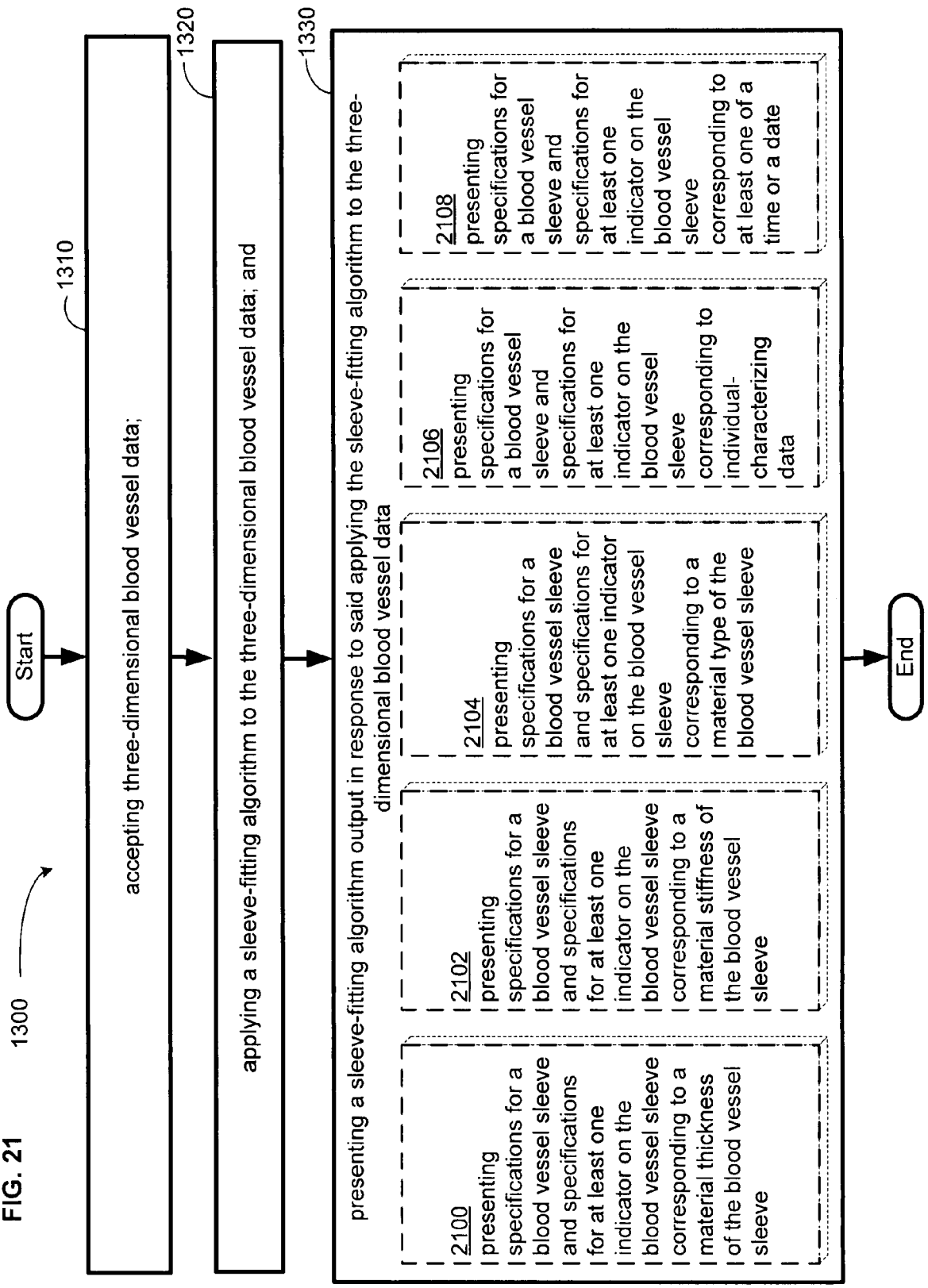

FIG. 21 illustrates an alternative embodiment of the example operational flow of FIG. 13.

Figure 22:
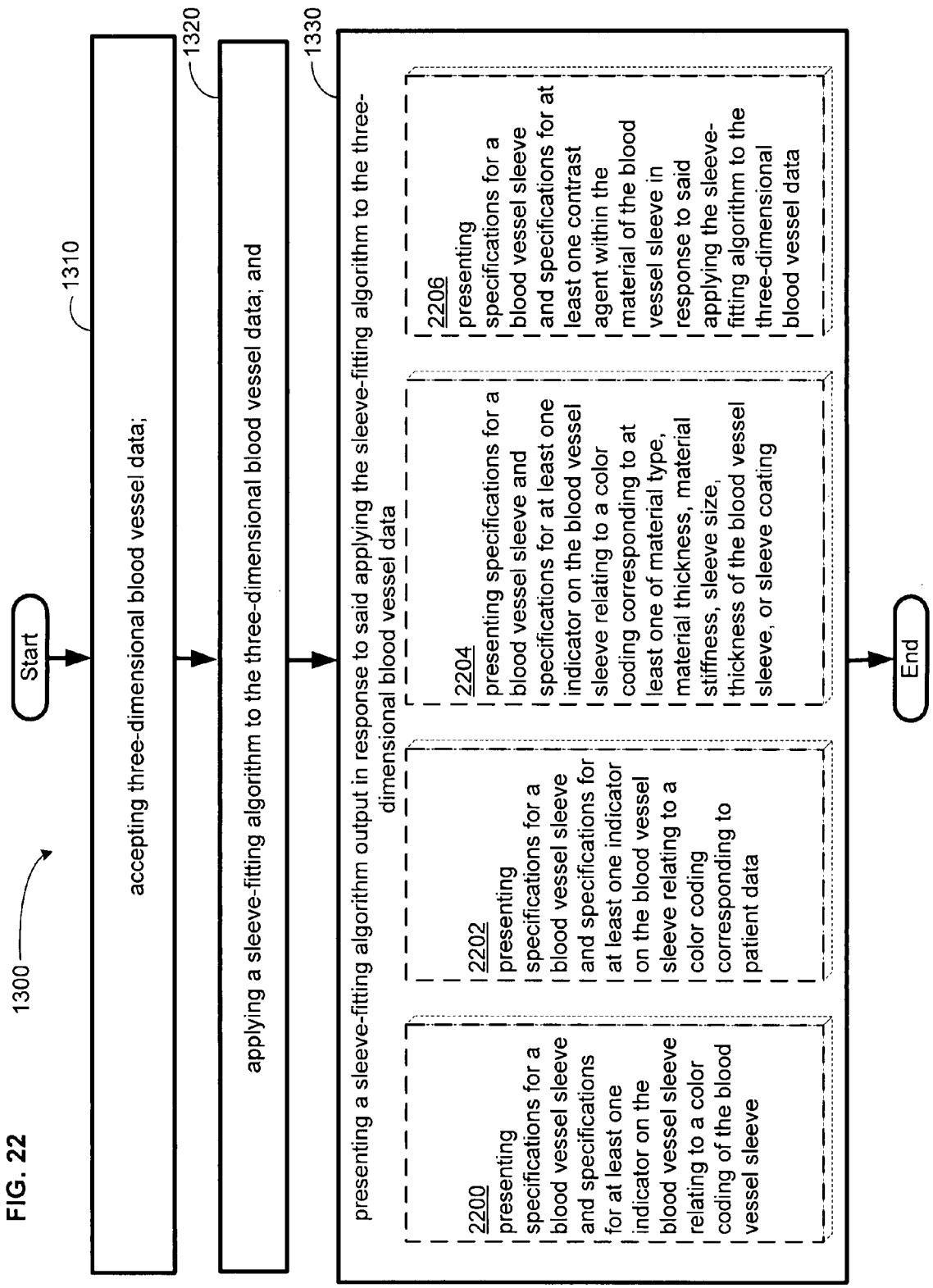

FIG. 22 illustrates an alternative embodiment of the example operational flow of FIG. 13.

Figure 23:
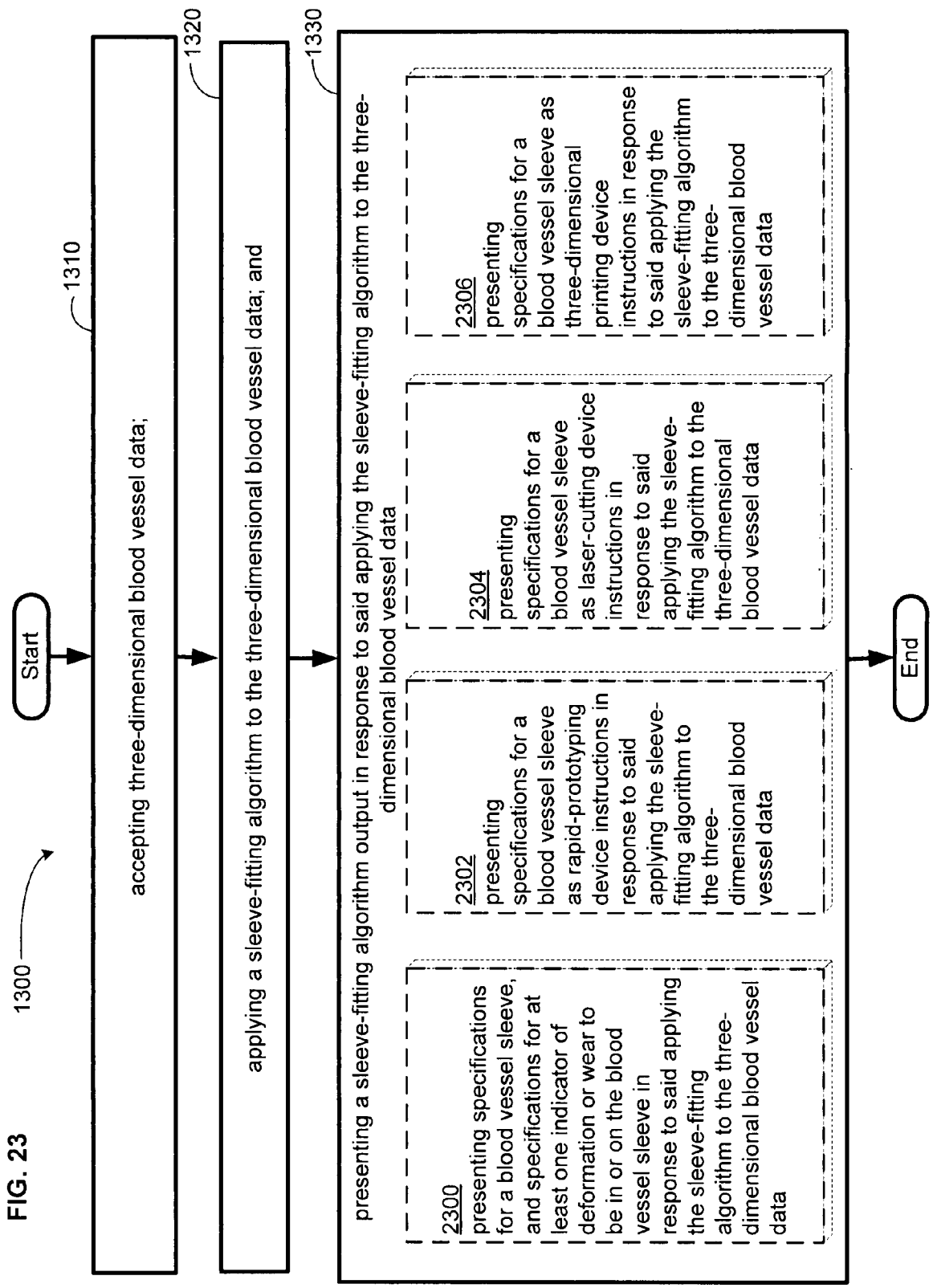

FIG. 23 illustrates an alternative embodiment of the example operational flow of FIG. 13.

Figure 24:
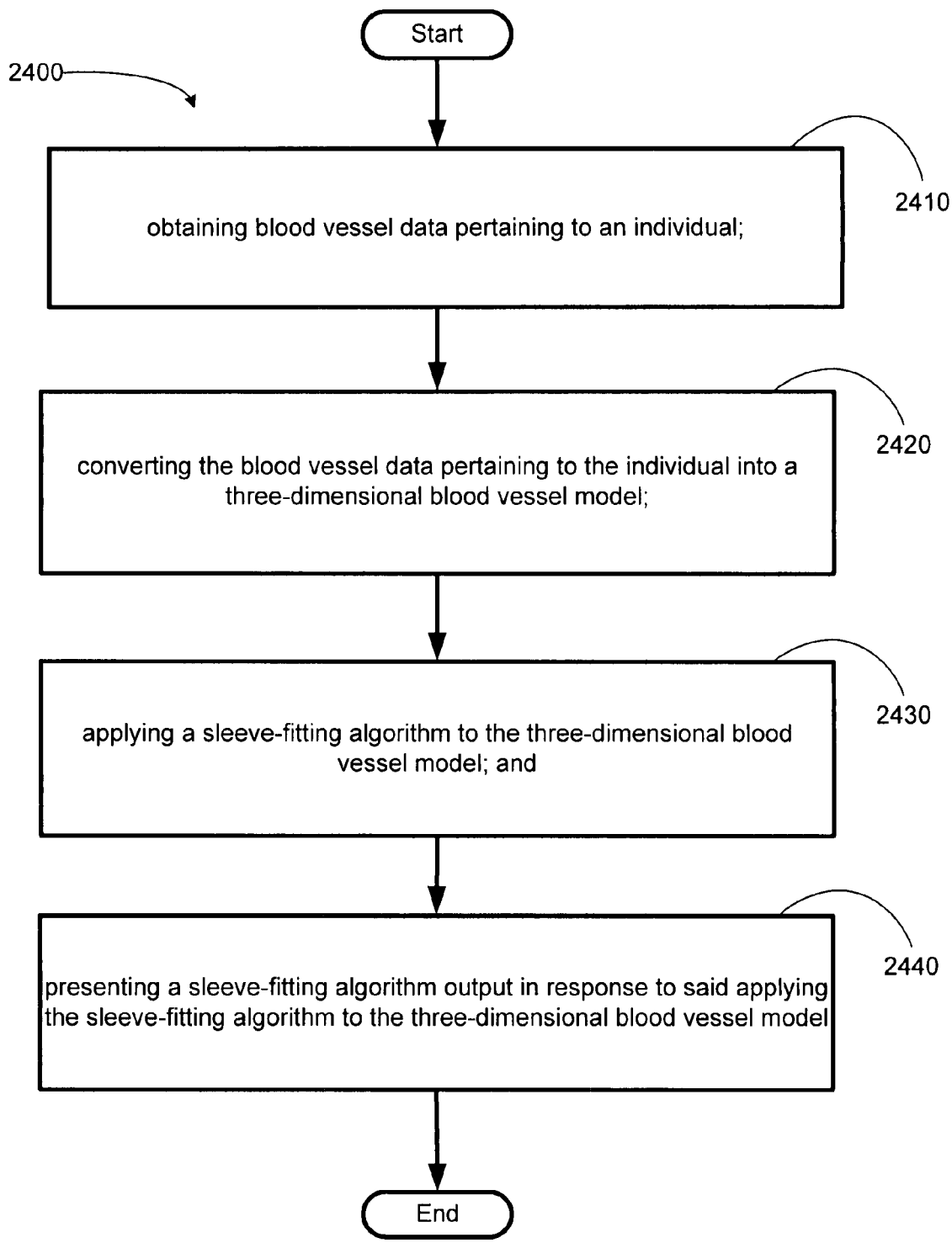

FIG. 24 illustrates another operational flow representing example operations related to methods and systems for specifying a blood vessel sleeve.

Figure 25:
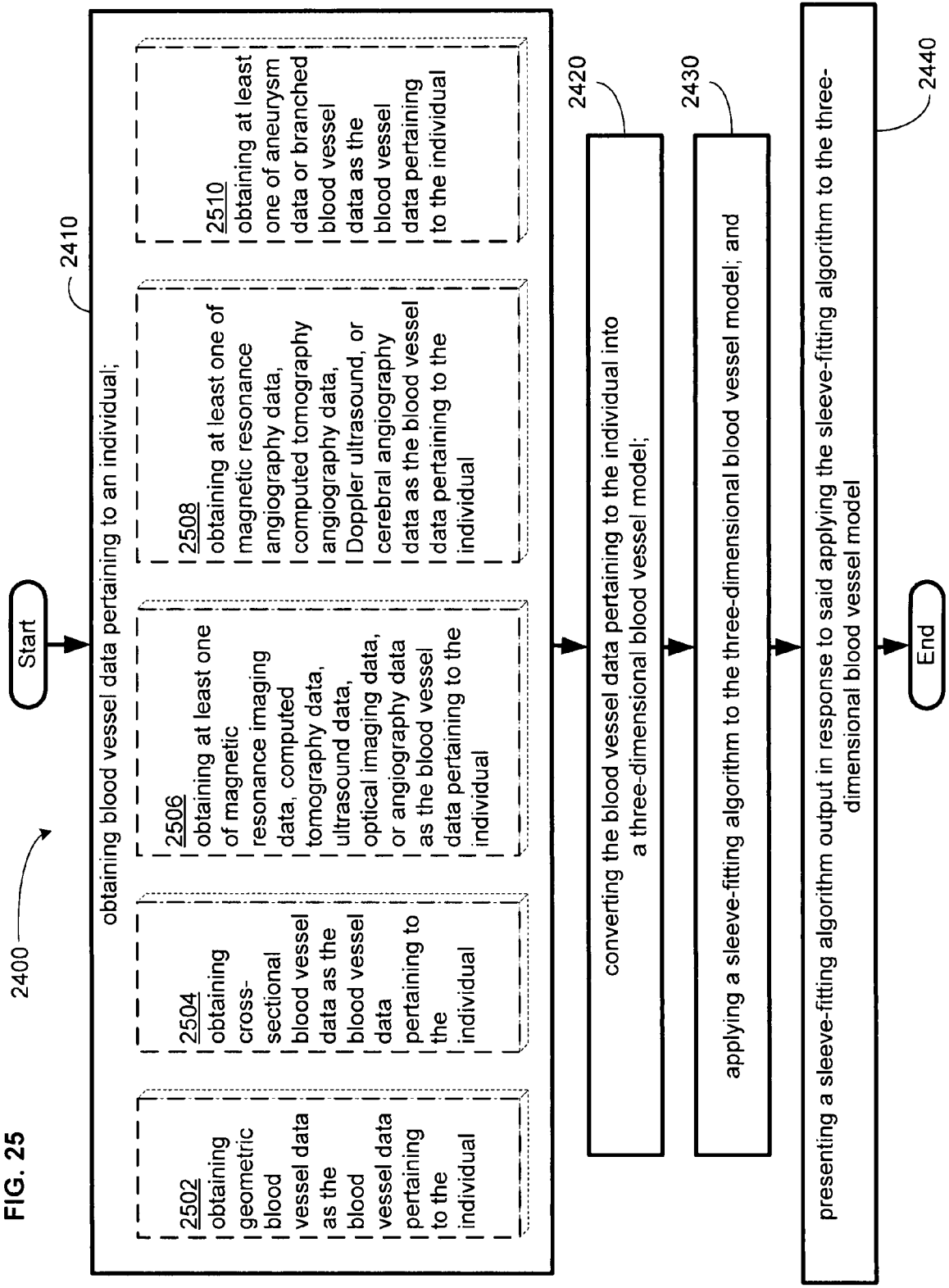

FIG. 25 illustrates an alternative embodiment of the example operational flow of FIG. 24.

Figure 26:
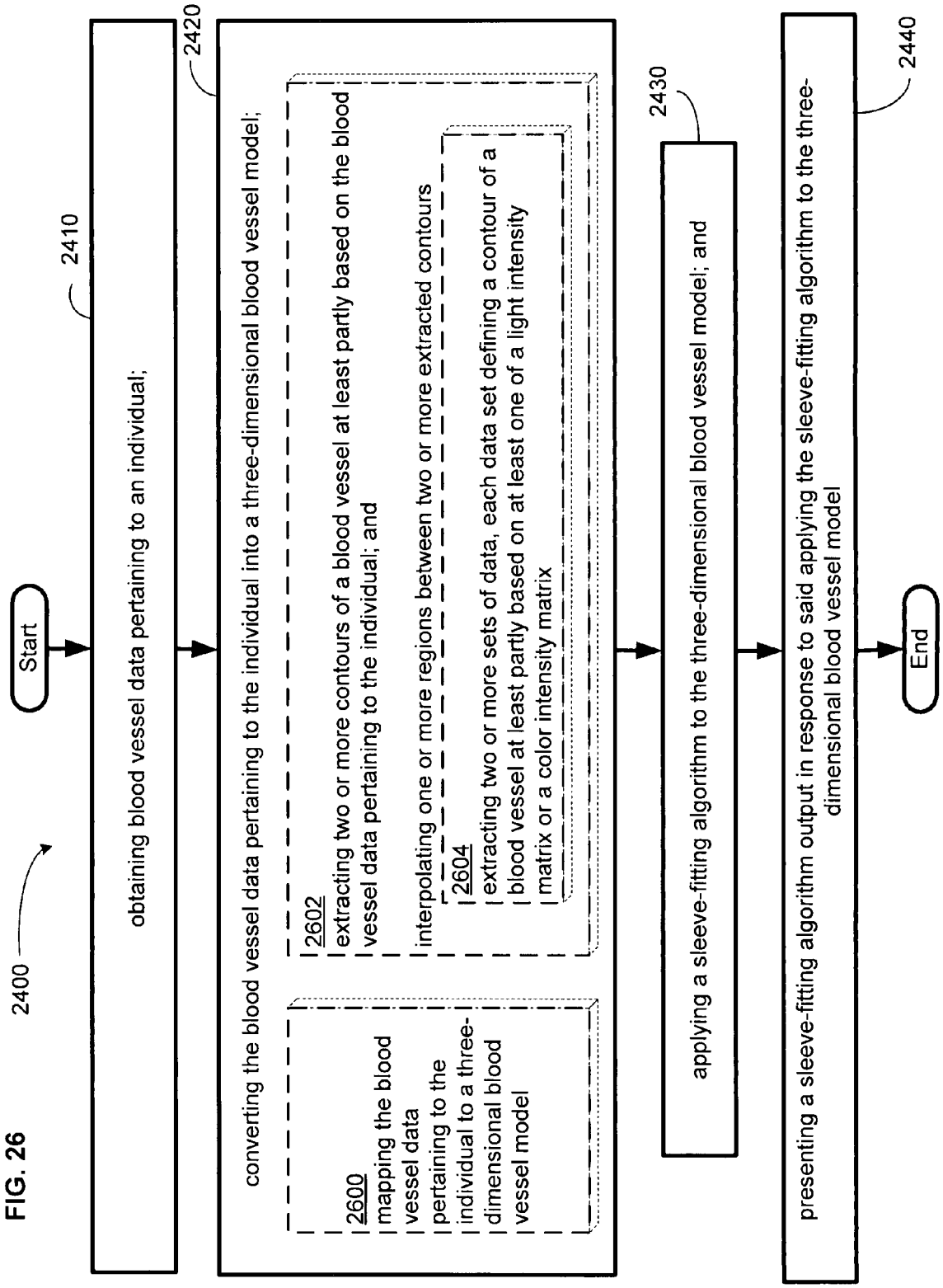

FIG. 26 illustrates an alternative embodiment of the example operational flow of FIG. 24.

Figure 27:
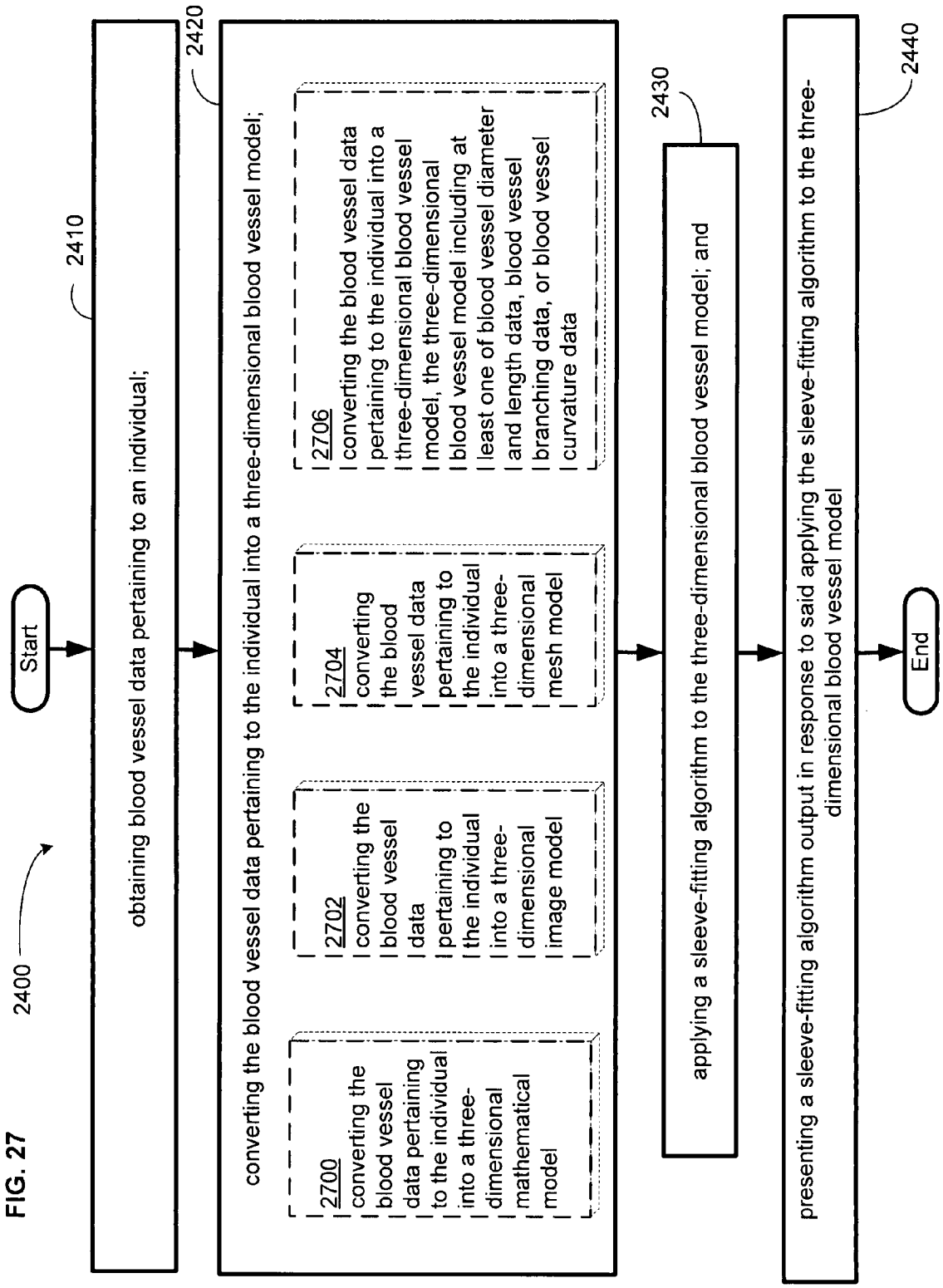

FIG. 27 illustrates an alternative embodiment of the example operational flow of FIG. 24.

Figure 28:
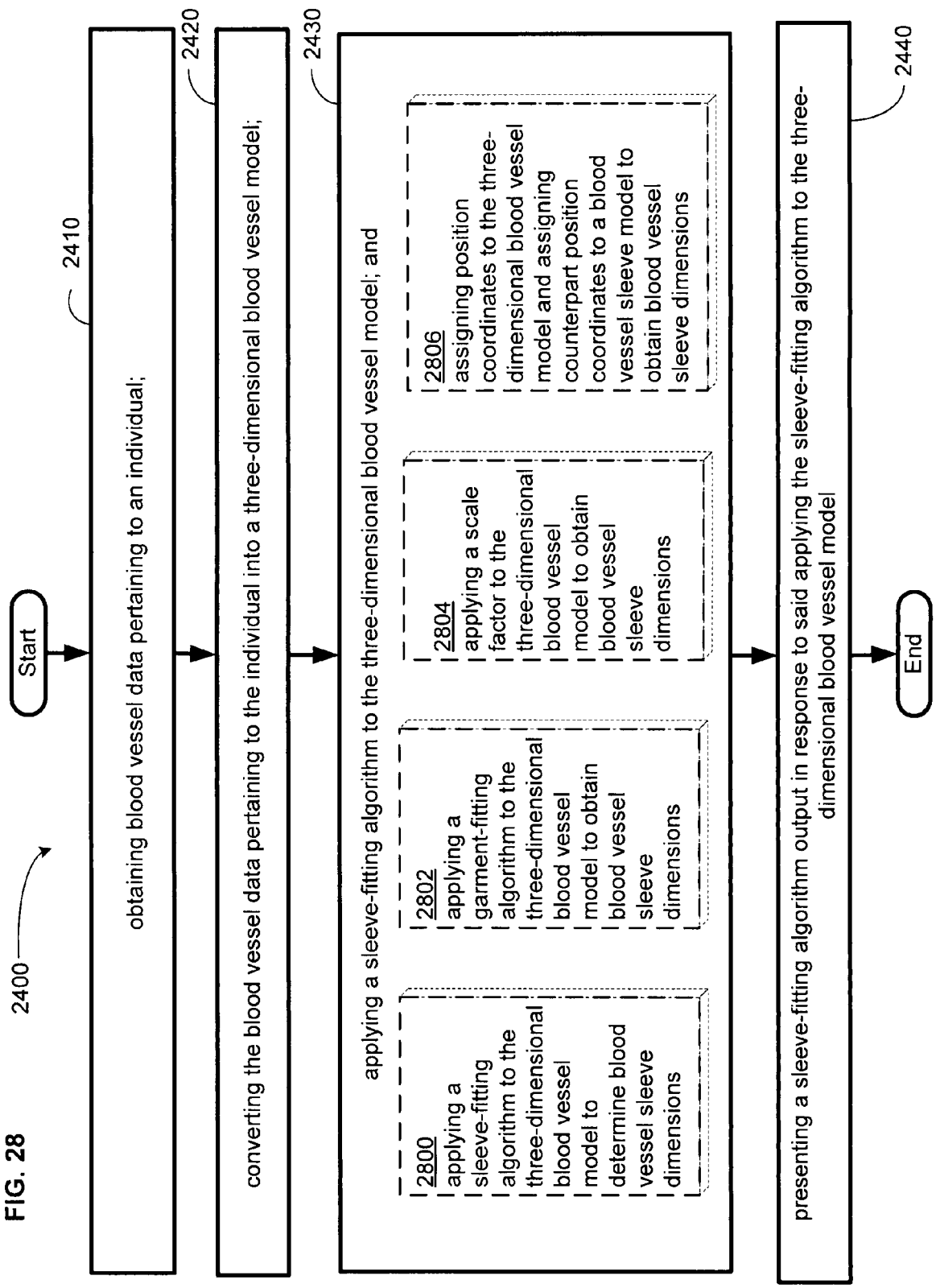

FIG. 28 illustrates an alternative embodiment of the example operational flow of FIG. 24.

Figure 29:
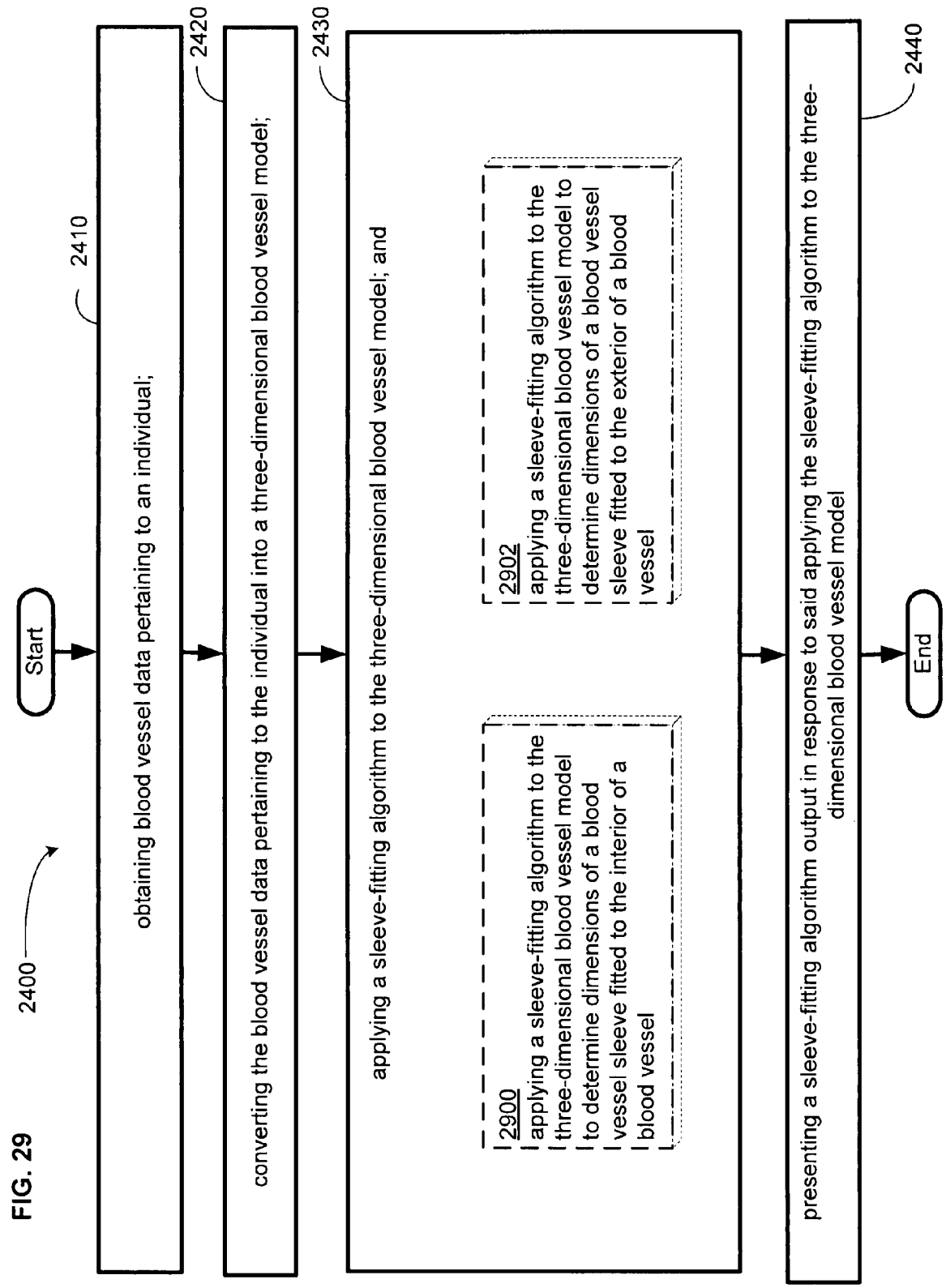

FIG. 29 illustrates an alternative embodiment of the example operational flow of FIG. 24.

Figure 30:
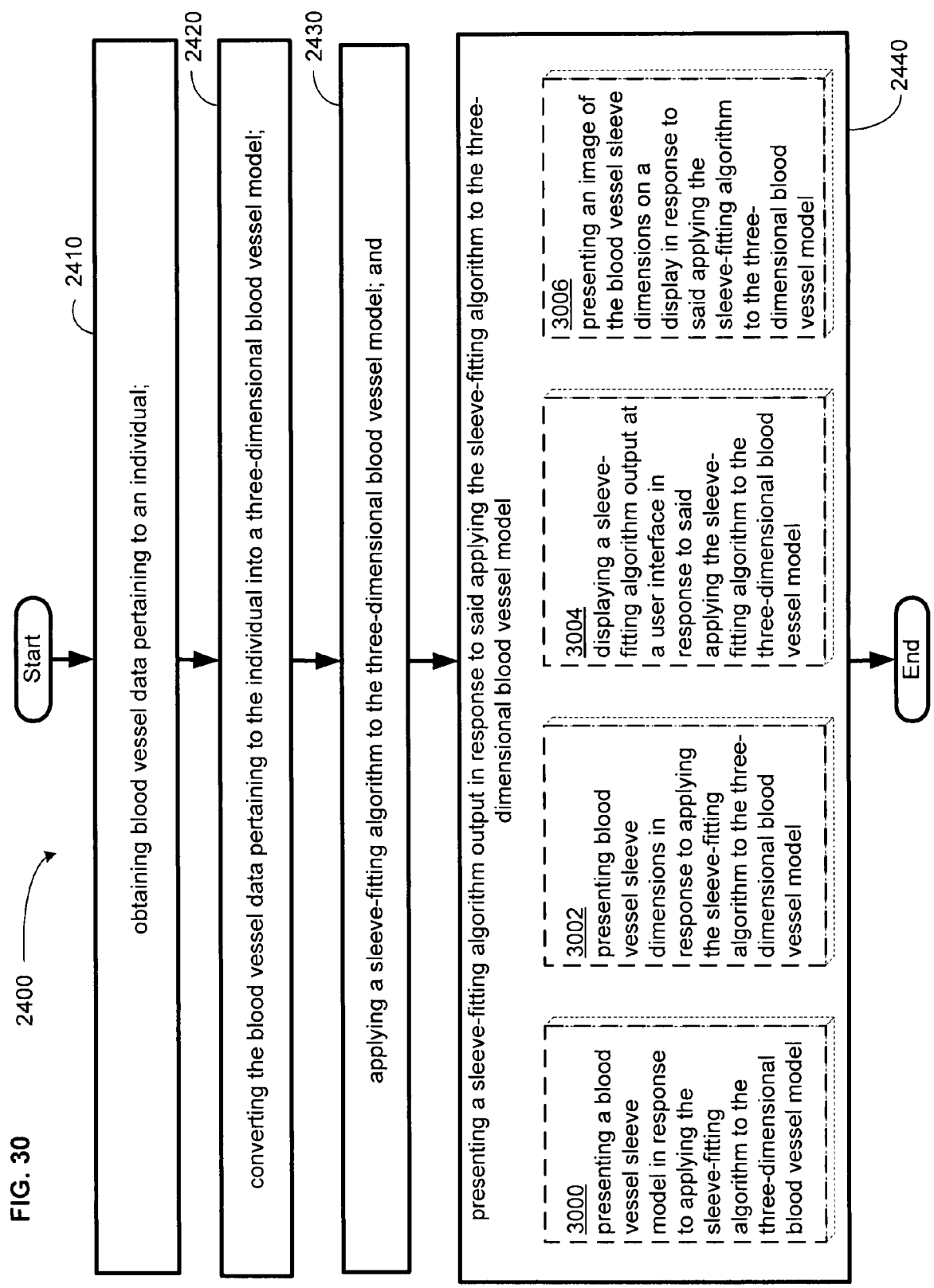

FIG. 30 illustrates an alternative embodiment of the example operational flow of FIG. 24.

Figure 31:
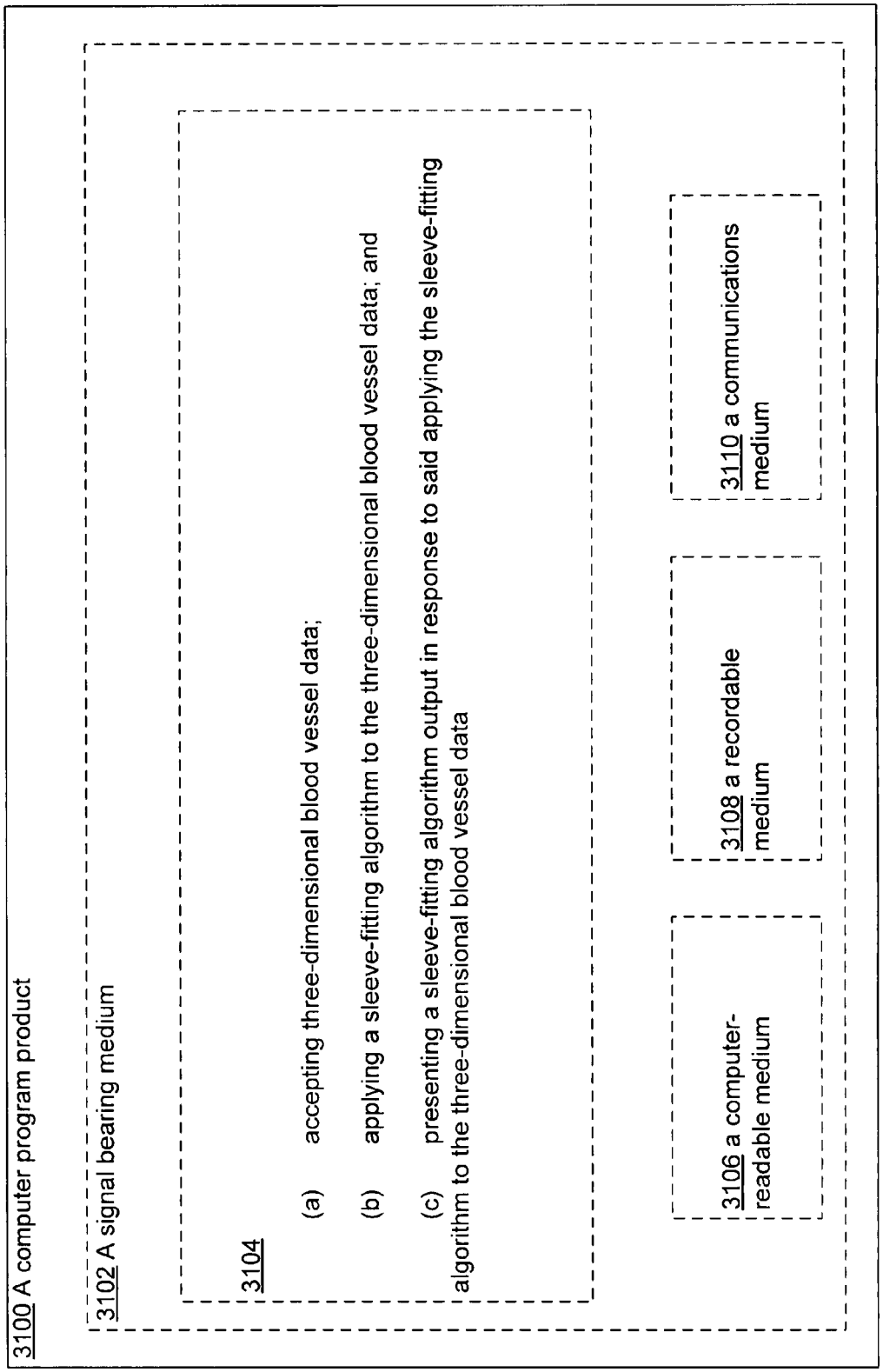

FIG. 31 illustrates a partial view of an example computer program product that includes a computer program for executing a computer process on a computing device.

FIG. 32 illustrates an example device in which embodiments may be implemented.

Figure 33:
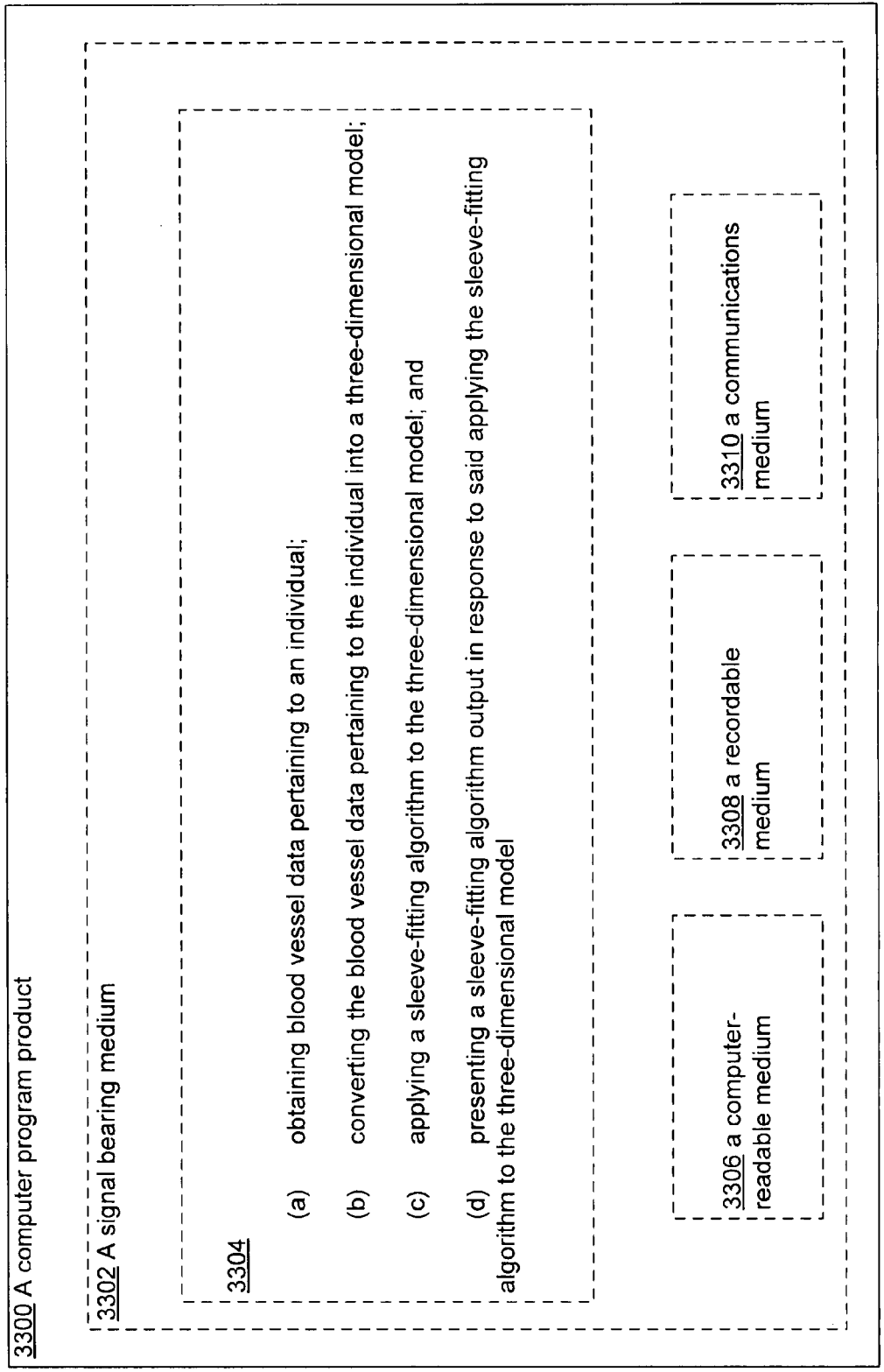

FIG. 33 illustrates a partial view of an example computer program product that includes a computer program for executing a computer process on a computing device.

FIG. 34 illustrates an example device in which embodiments may be implemented.

FIG. 35 illustrates an operational flow representing example operations related to methods and systems for making a blood vessel sleeve.

Figure 36:
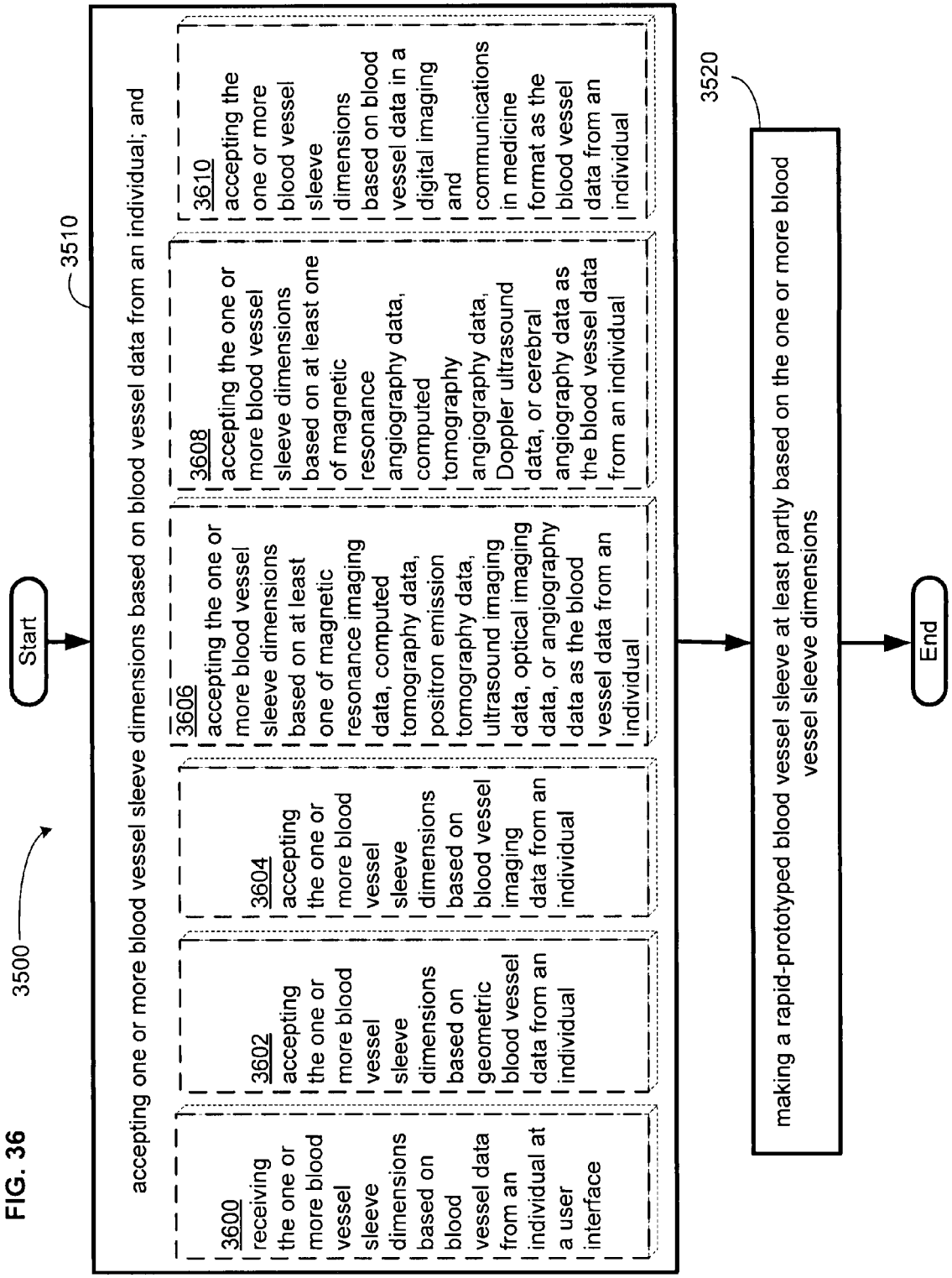

FIG. 36 illustrates an alternative embodiment of the example operational flow of FIG. 35.

Figure 37:
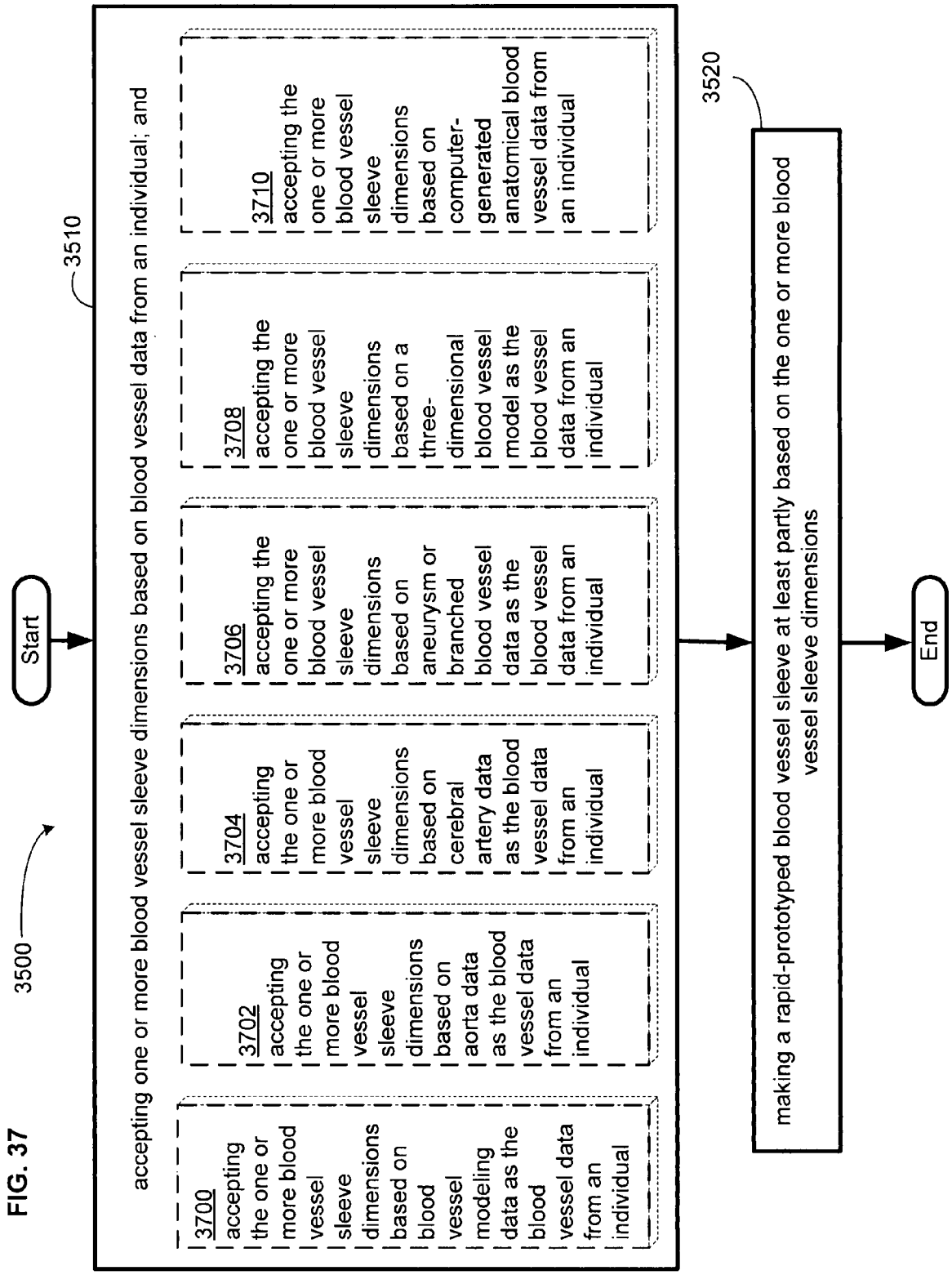

FIG. 37 illustrates an alternative embodiment of the example operational flow of FIG. 35.

Figure 38:
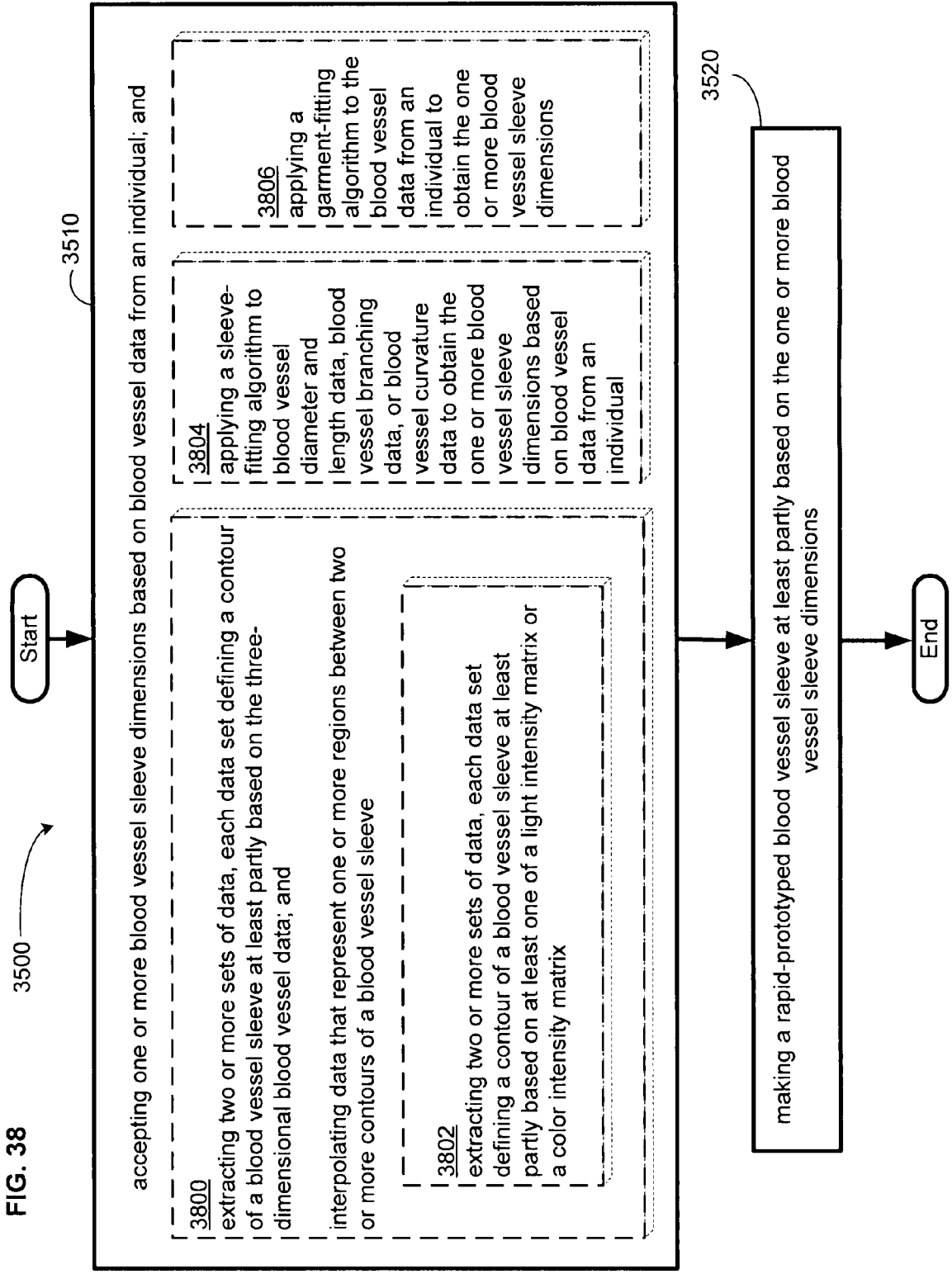

FIG. 38 illustrates an alternative embodiment of the example operational flow of FIG. 35.

Figure 39:
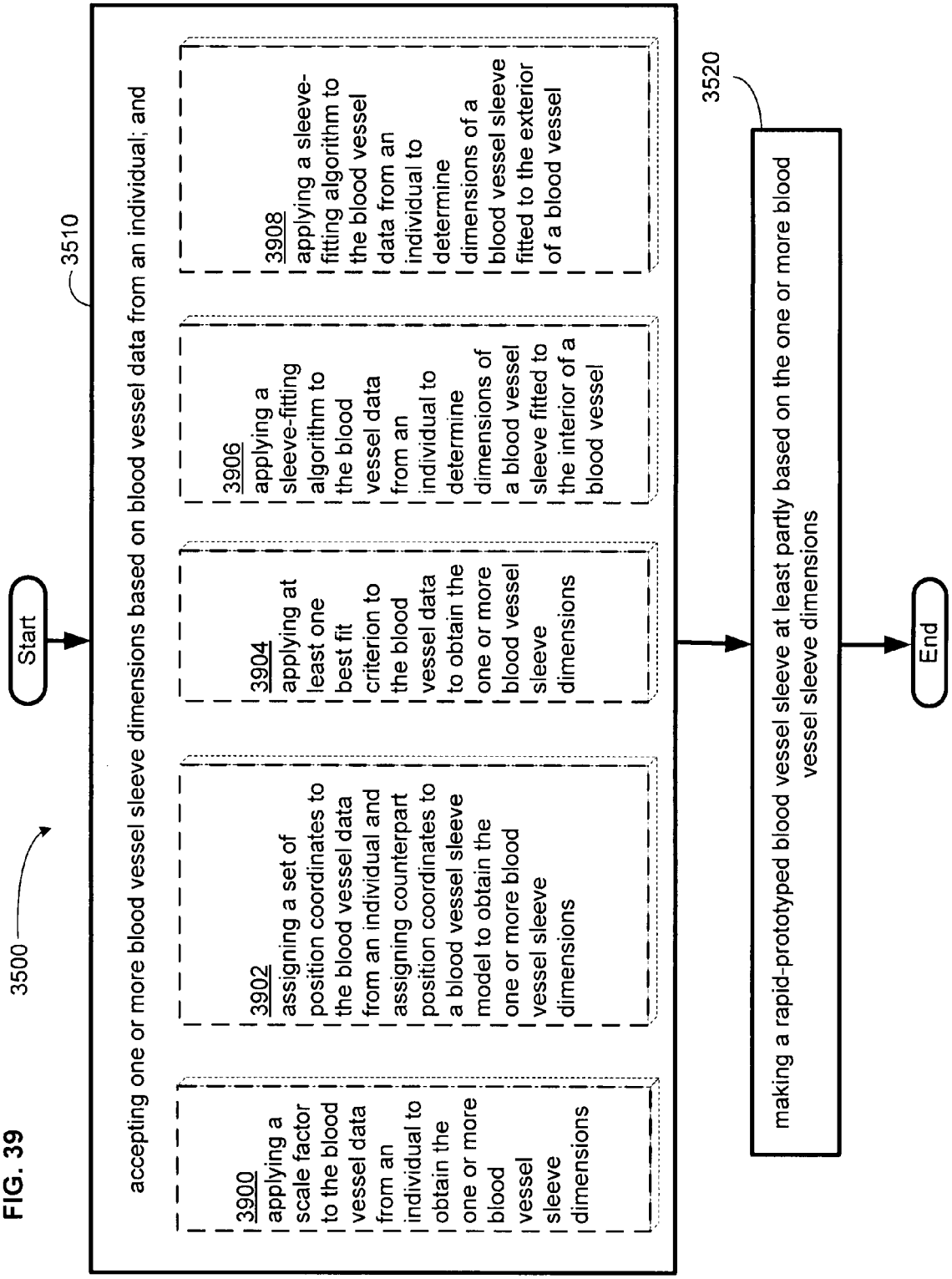

FIG. 39 illustrates an alternative embodiment of the example operational flow of FIG. 35.

Figure 40:
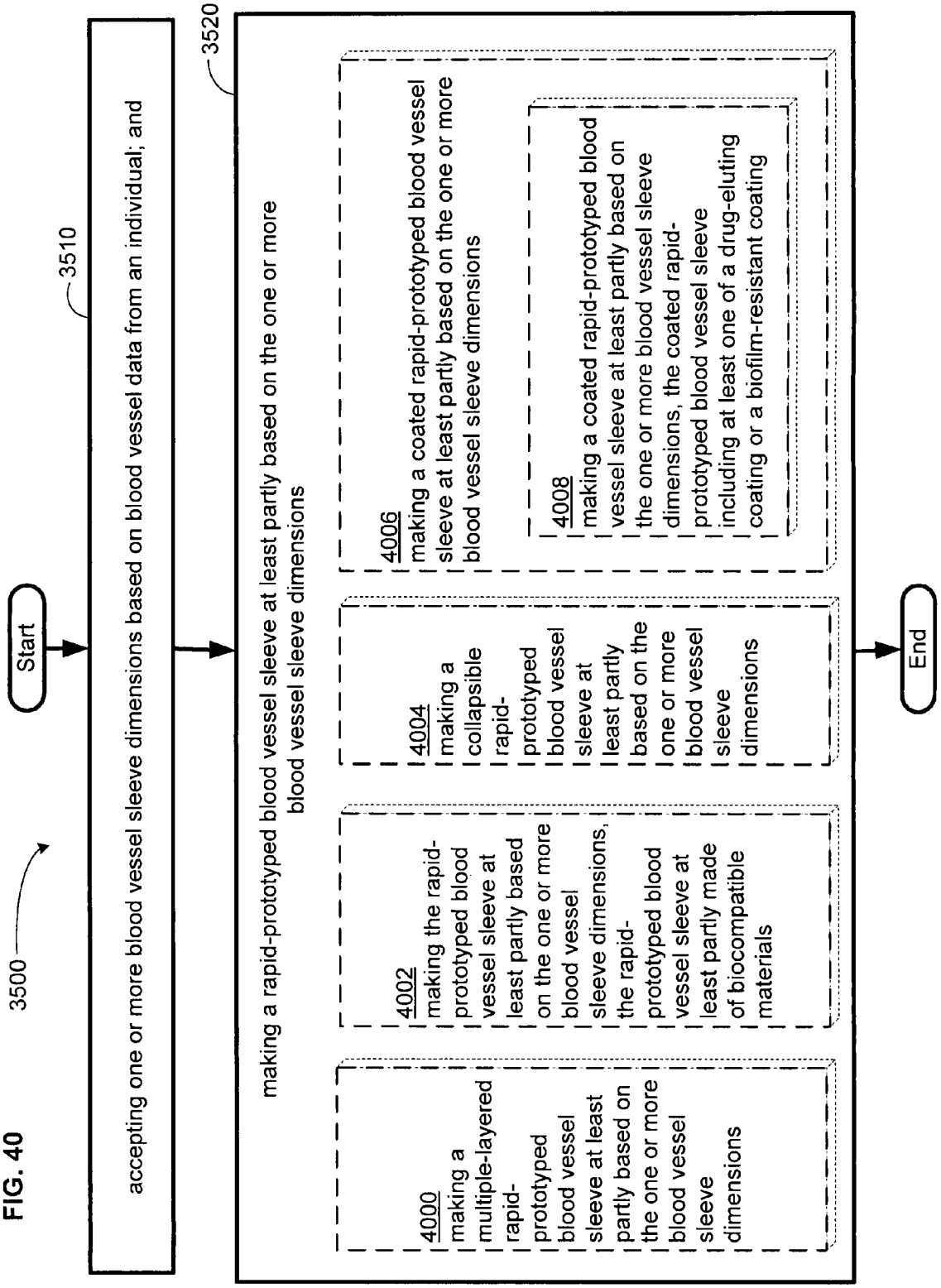

FIG. 40 illustrates an alternative embodiment of the example operational flow of FIG. 35.

Figure 41:
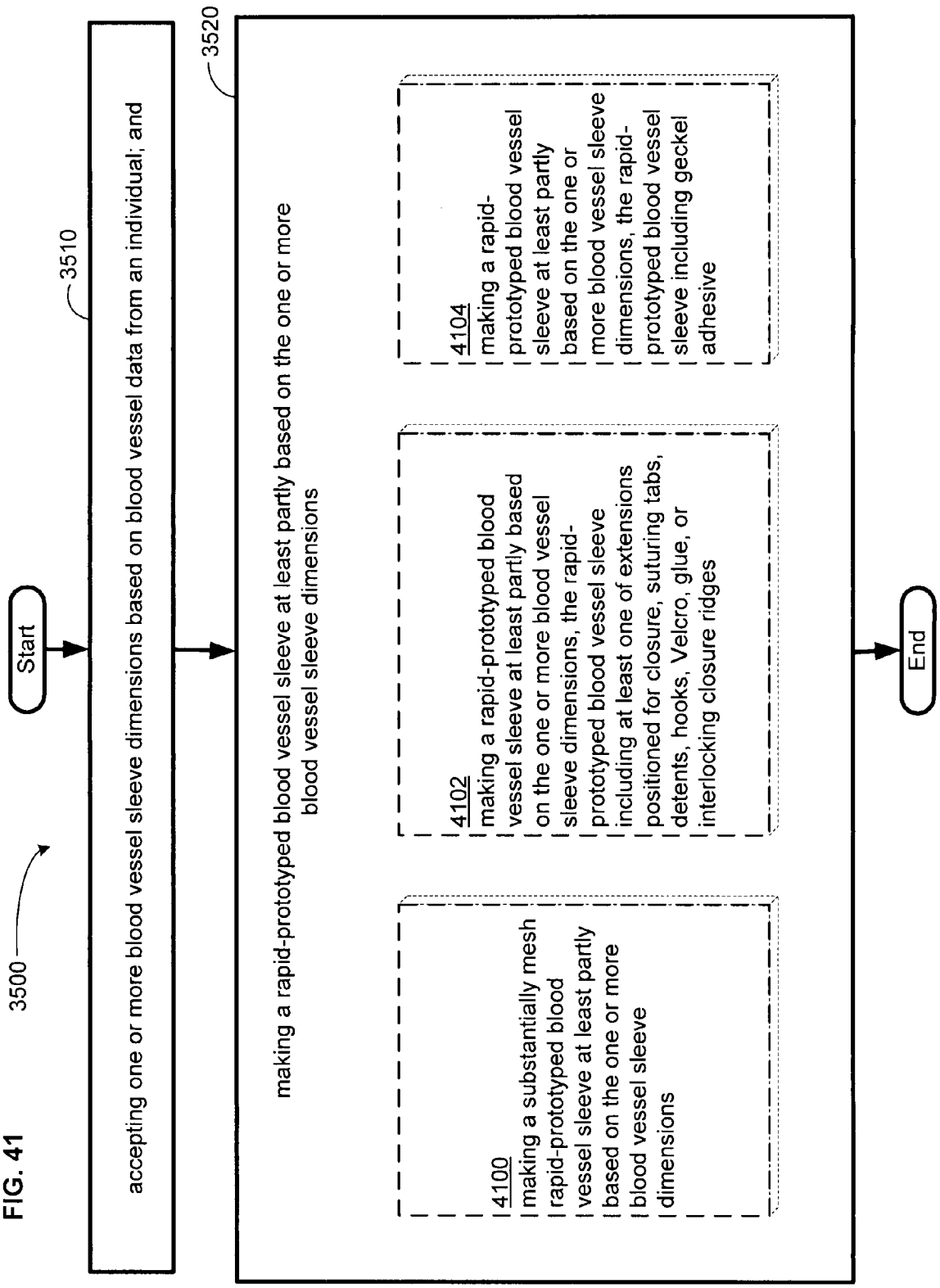

FIG. 41 illustrates an alternative embodiment of the example operational flow of FIG. 35.

Figure 42:
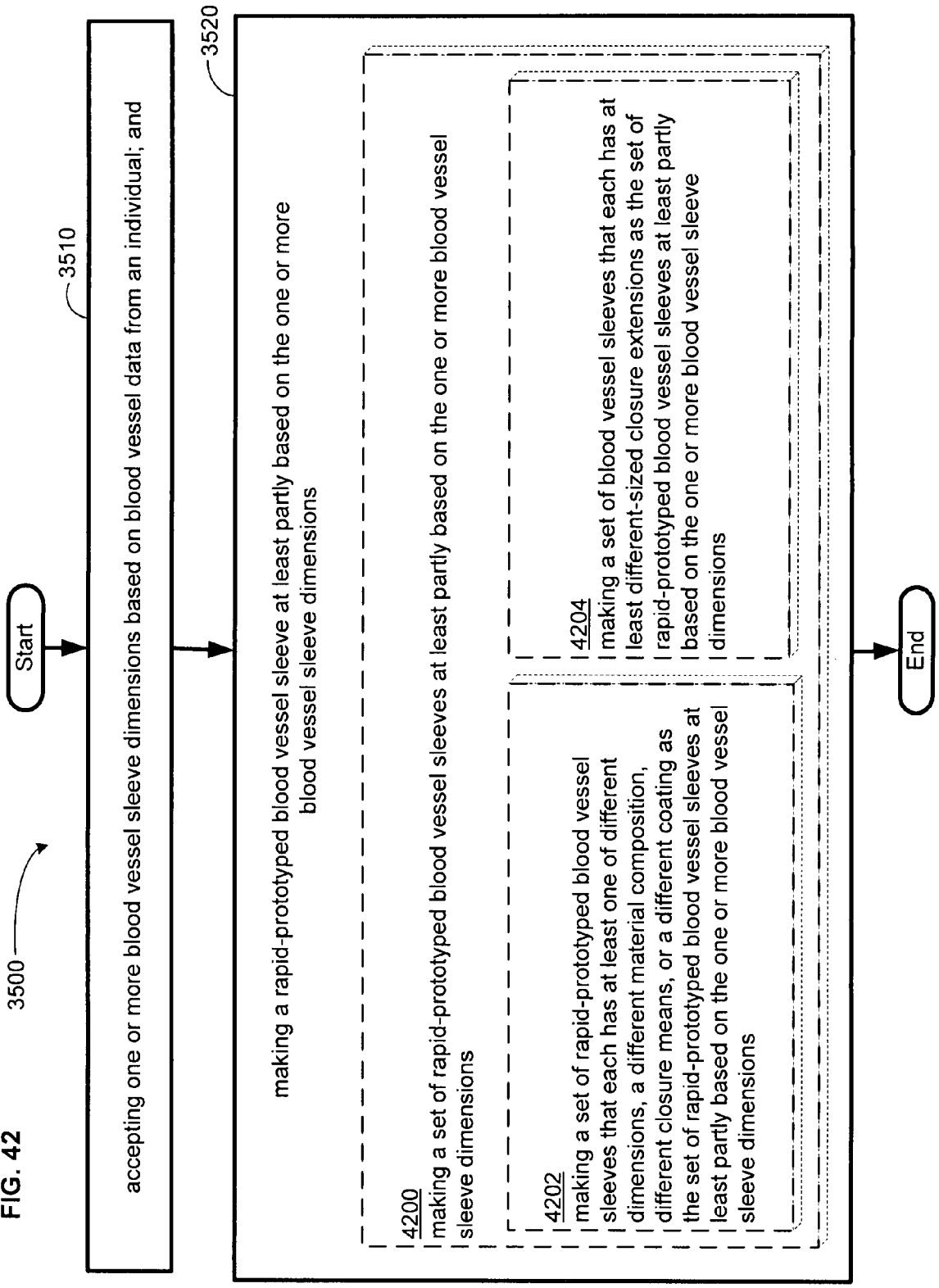

FIG. 42 illustrates an alternative embodiment of the example operational flow of FIG. 35.

Figure 43:
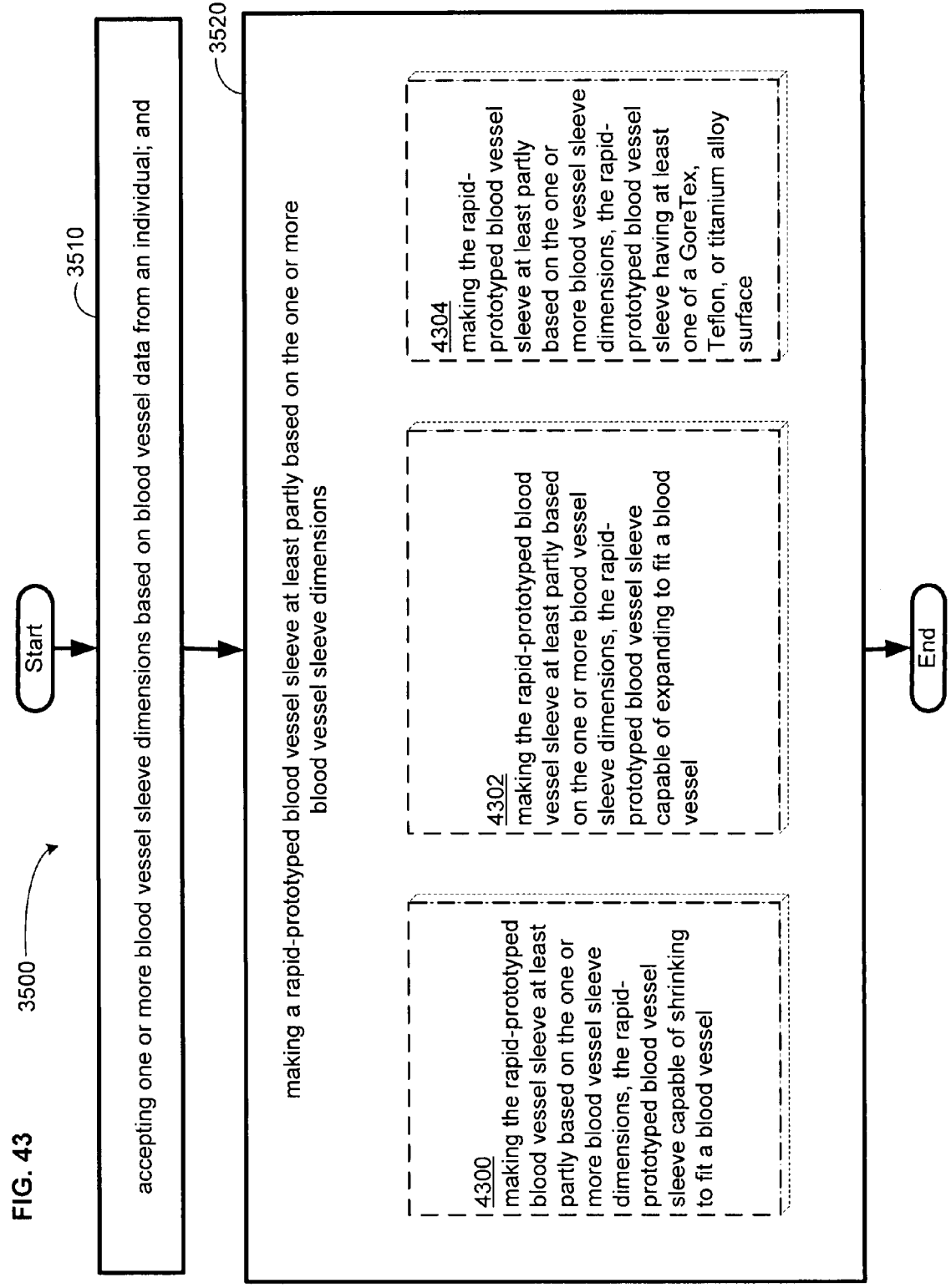

FIG. 43 illustrates an alternative embodiment of the example operational flow of FIG. 35.

Figure 44:
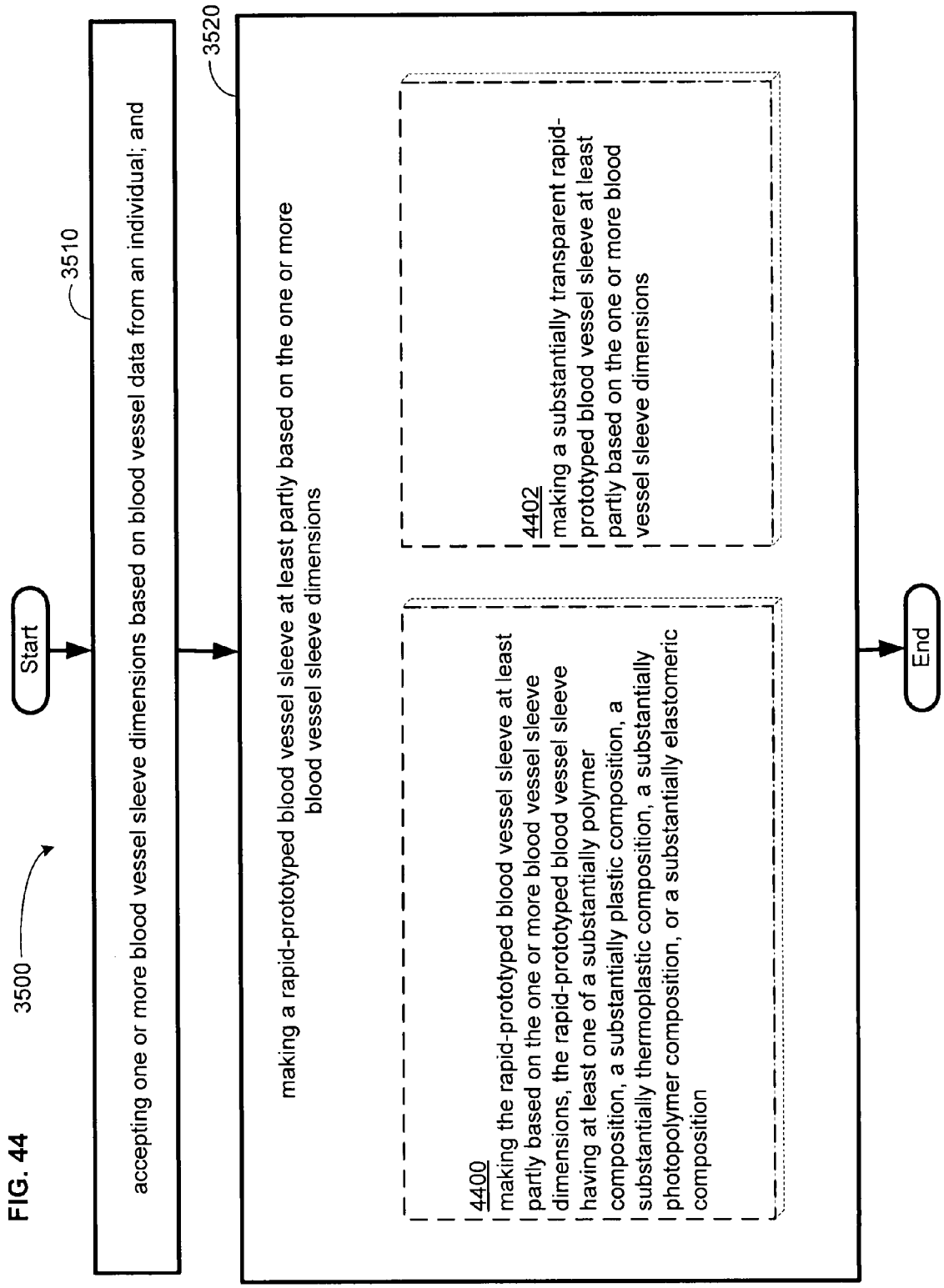

FIG. 44 illustrates an alternative embodiment of the example operational flow of FIG. 35.

Figure 45:
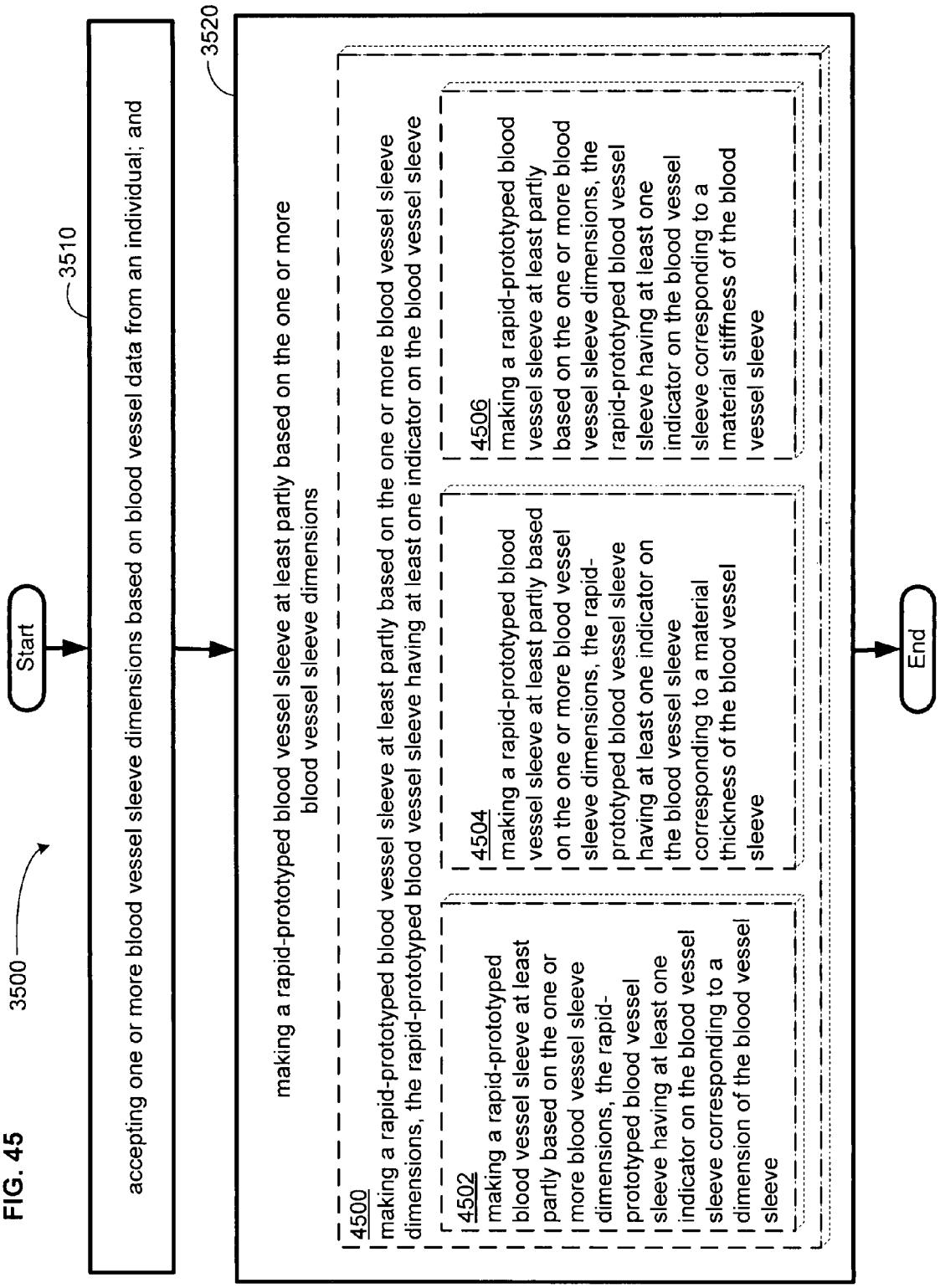

FIG. 45 illustrates an alternative embodiment of the example operational flow of FIG. 35.

Figure 46:
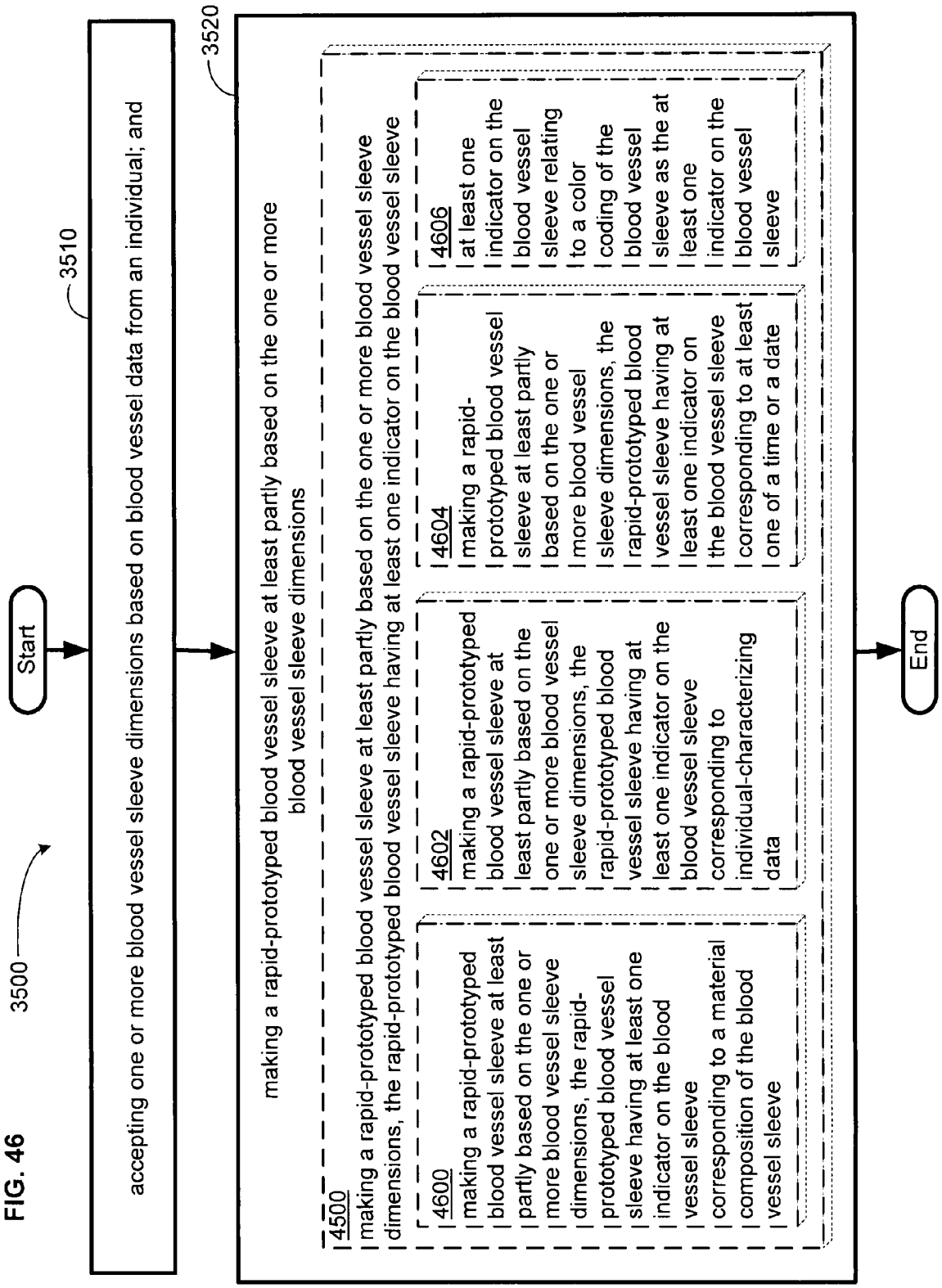

FIG. 46 illustrates an alternative embodiment of the example operational flow of FIG. 35.

Figure 47:
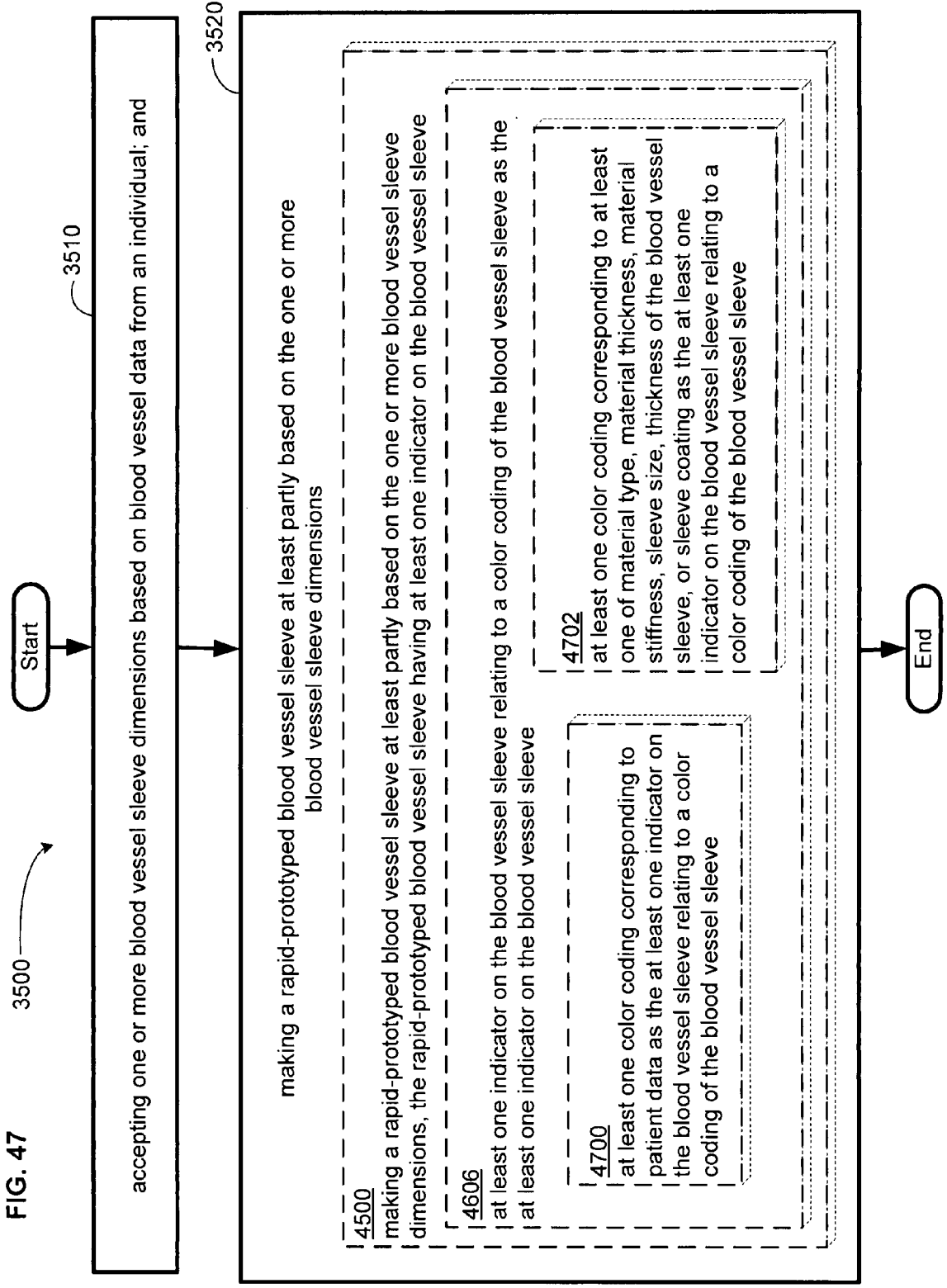

FIG. 47 illustrates an alternative embodiment of the example operational flow of FIG. 35.

Figure 48:
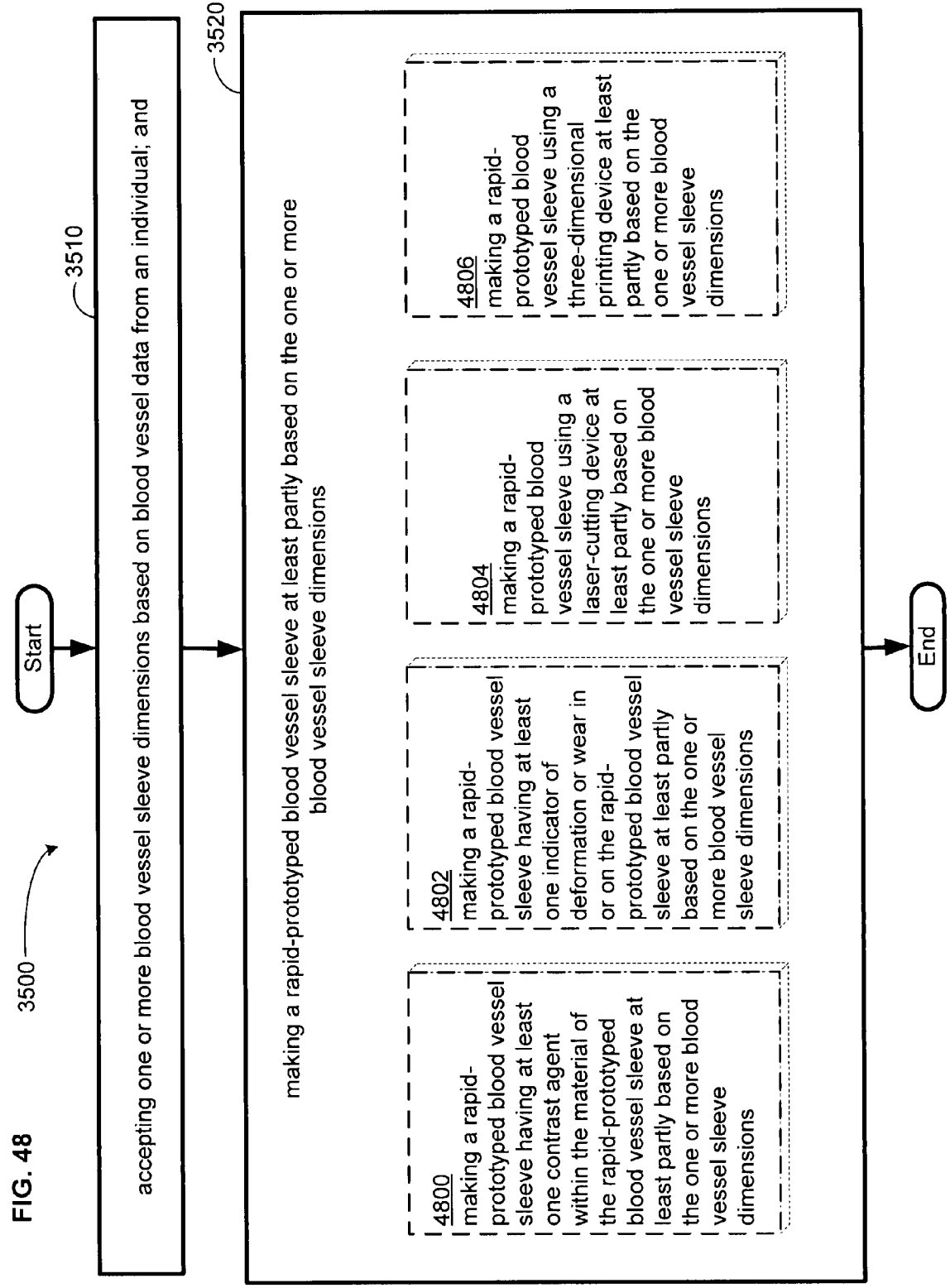

FIG. 48 illustrates an alternative embodiment of the example operational flow of FIG. 35.

Figure 49:
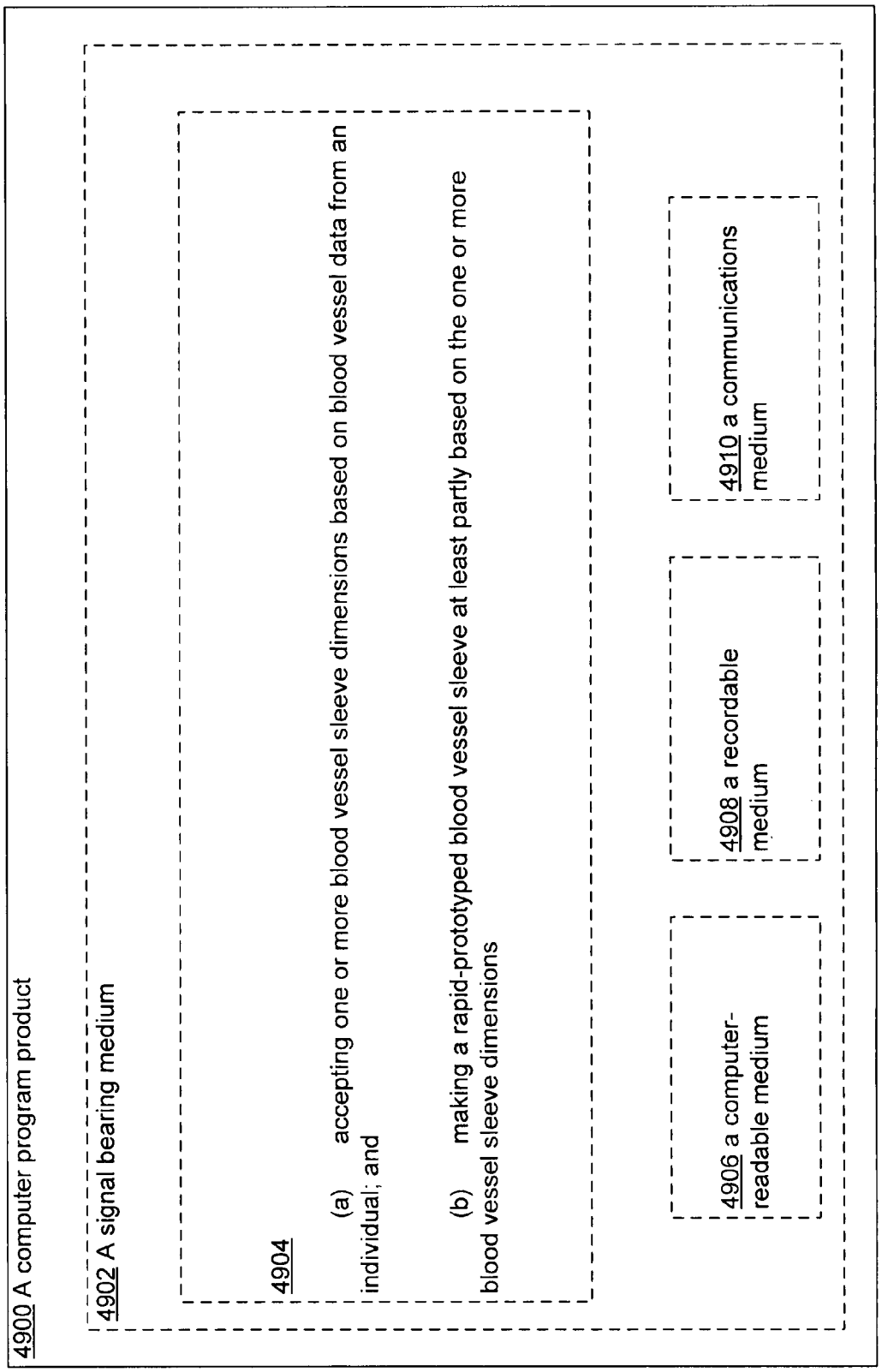

FIG. 49 illustrates a partial view of an example computer program product that includes a computer program for executing a computer process on a computing device.

FIG. 50 illustrates an example device in which embodiments may be implemented.

Figure 51:
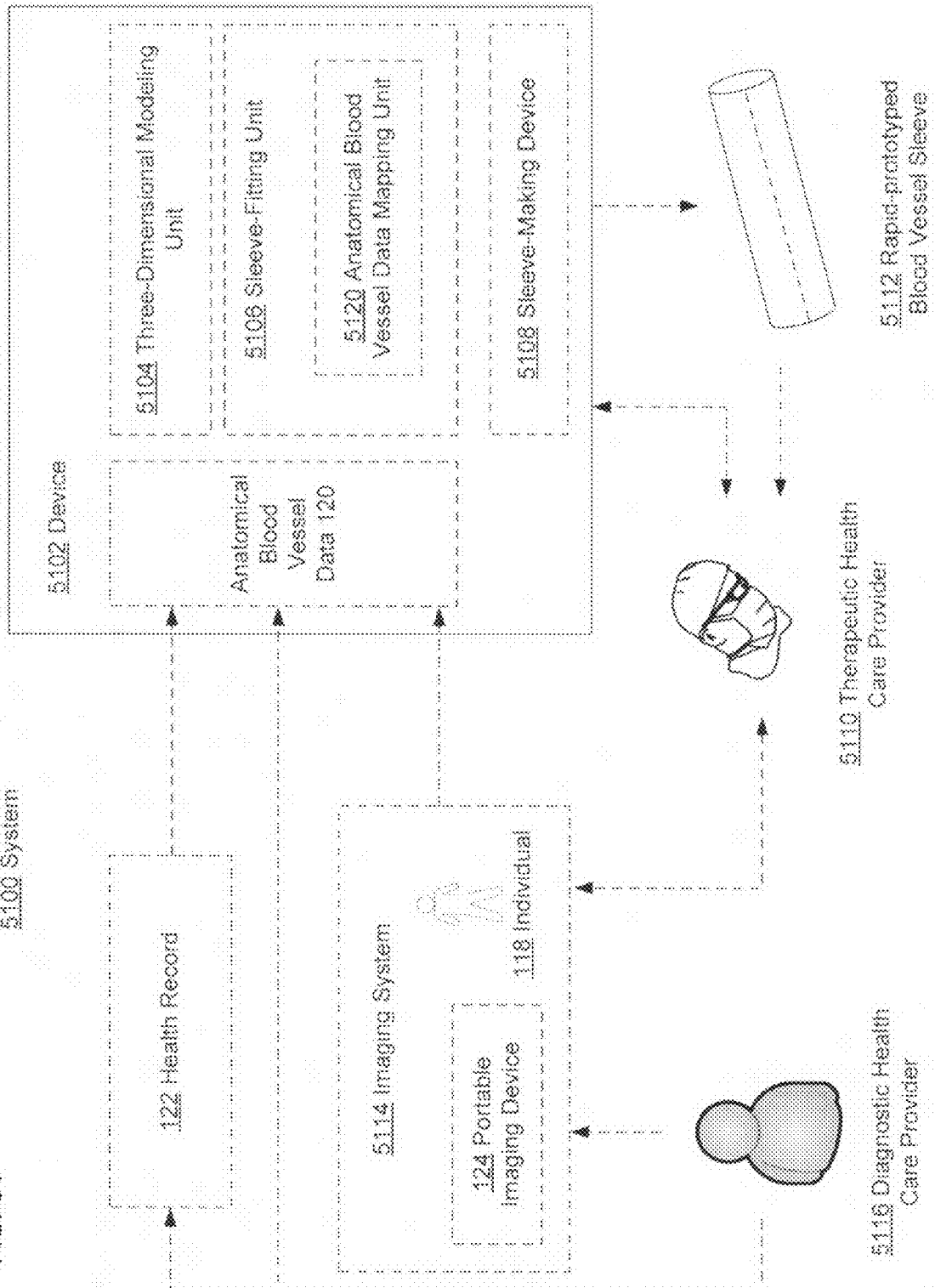

With reference now to FIG. 51, shown is an example of an environment in which one or more blood vessel sleeve technologies may be implemented.

Figure 52:
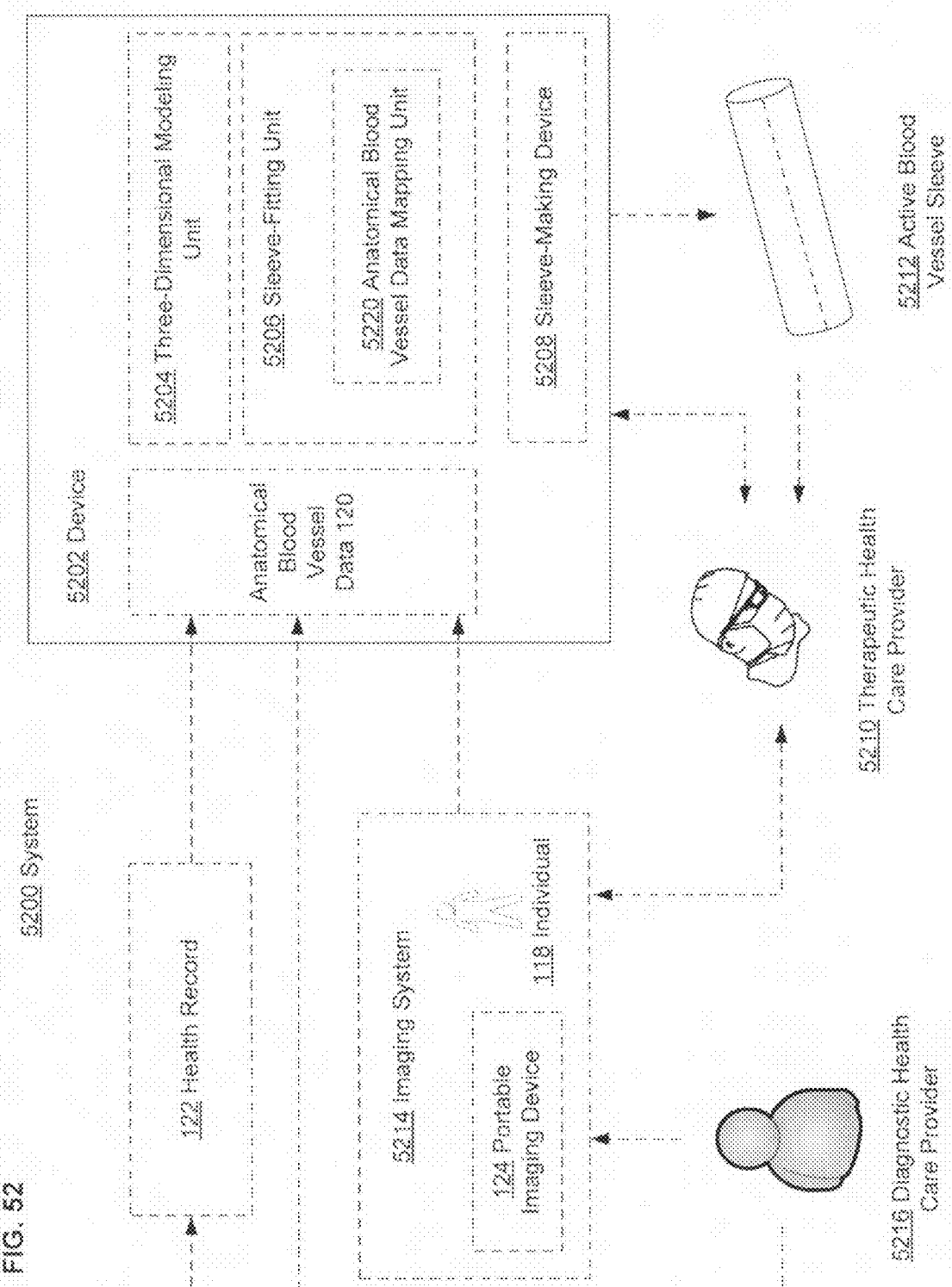

With reference now to FIG. 52, shown are examples of embodiments of blood vessel sleeves, which may serve as a context for introducing one or more devices, methods, and systems described herein.

With reference now to FIG. 53, shown are examples of embodiments of blood vessel sleeves, which may serve as a context for introducing one or more devices, methods, and systems described herein.

Figure 54:
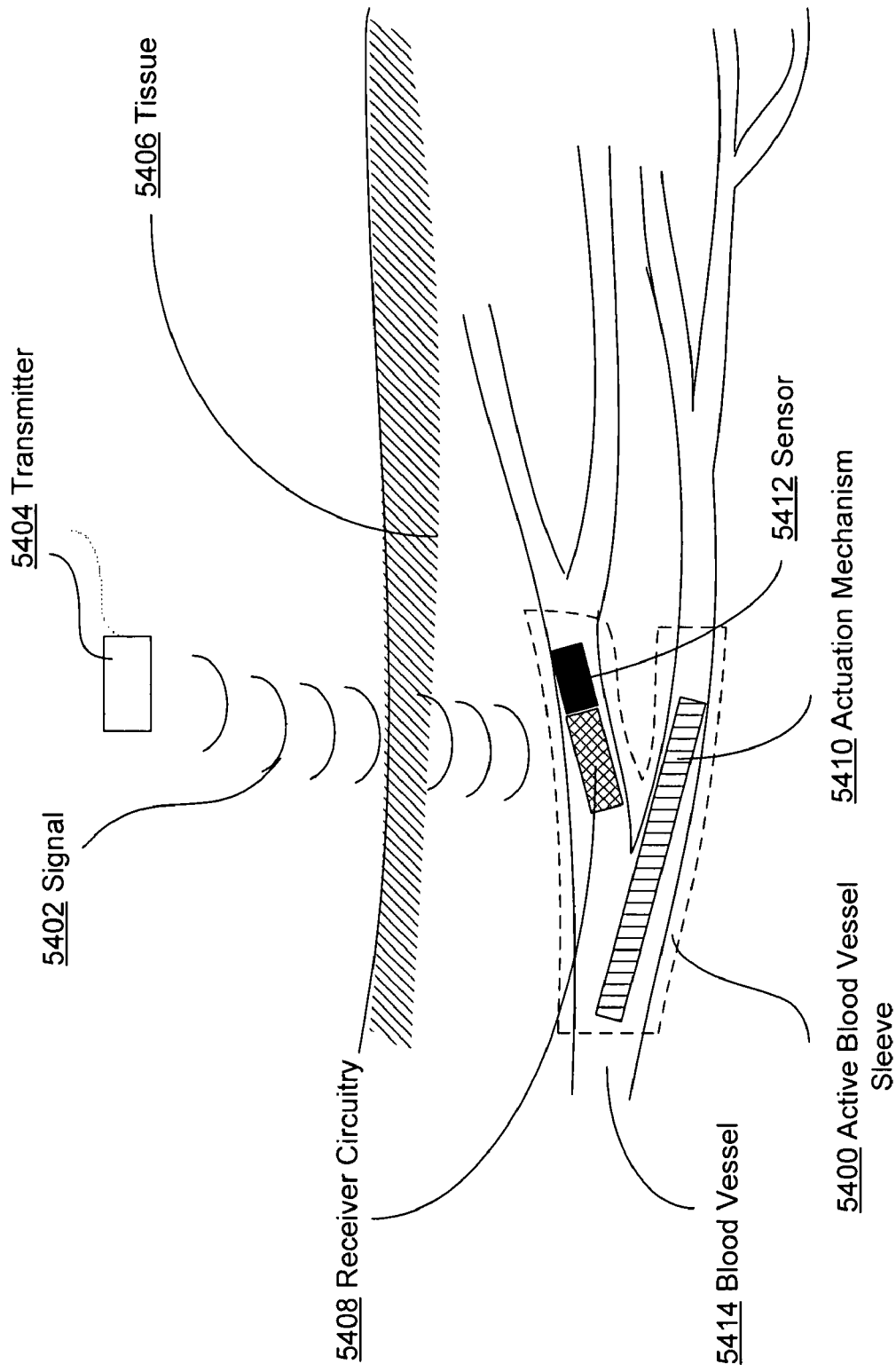

With reference now to FIG. 54, shown are examples of embodiments of blood vessel sleeves, which may serve as a context for introducing one or more devices, methods, and systems described herein.

Figure 55:
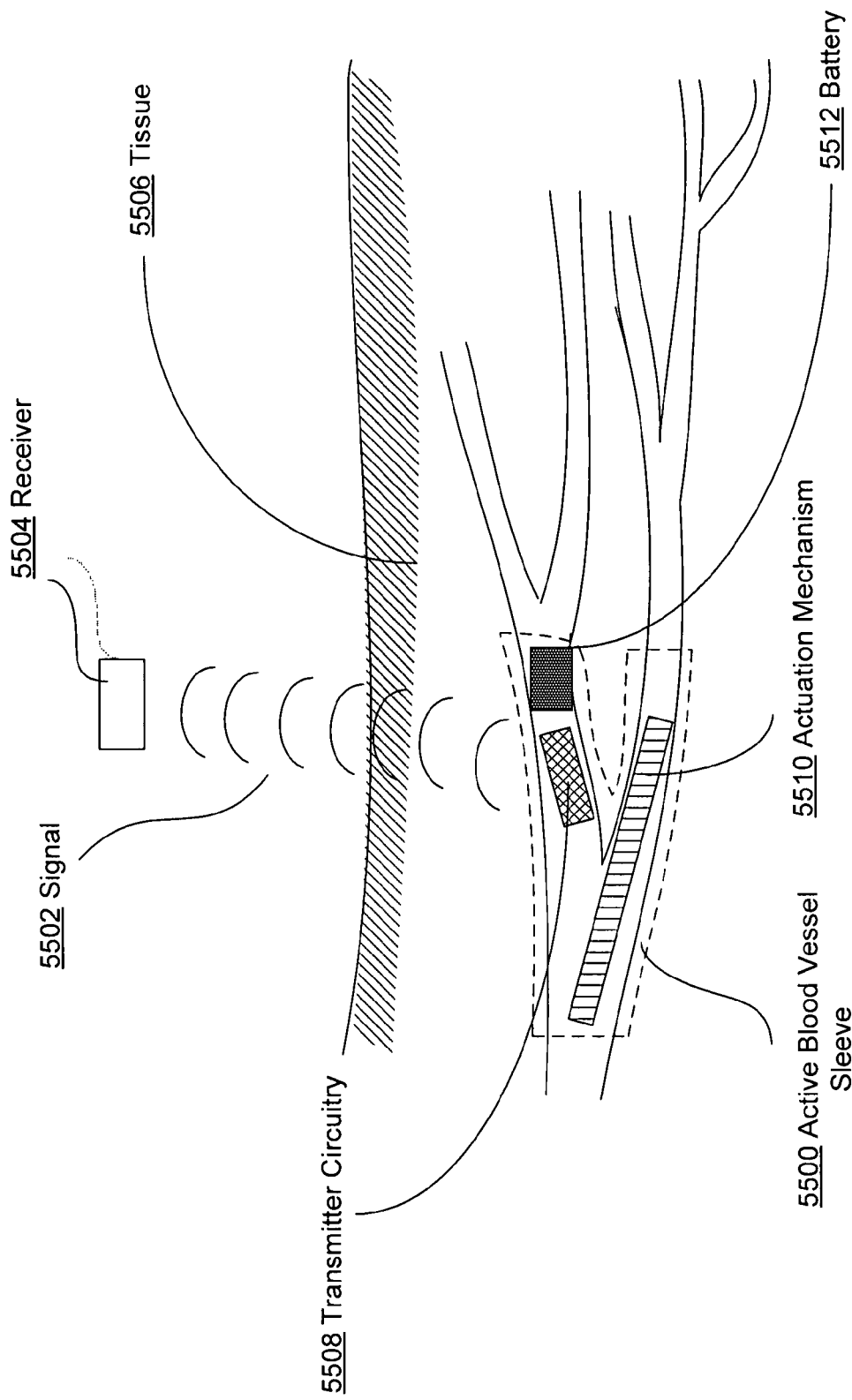

With reference now to FIG. 55, shown are examples of embodiments of blood vessel sleeves, which may serve as a context for introducing one or more devices, methods, and systems described herein.

Figure 56:
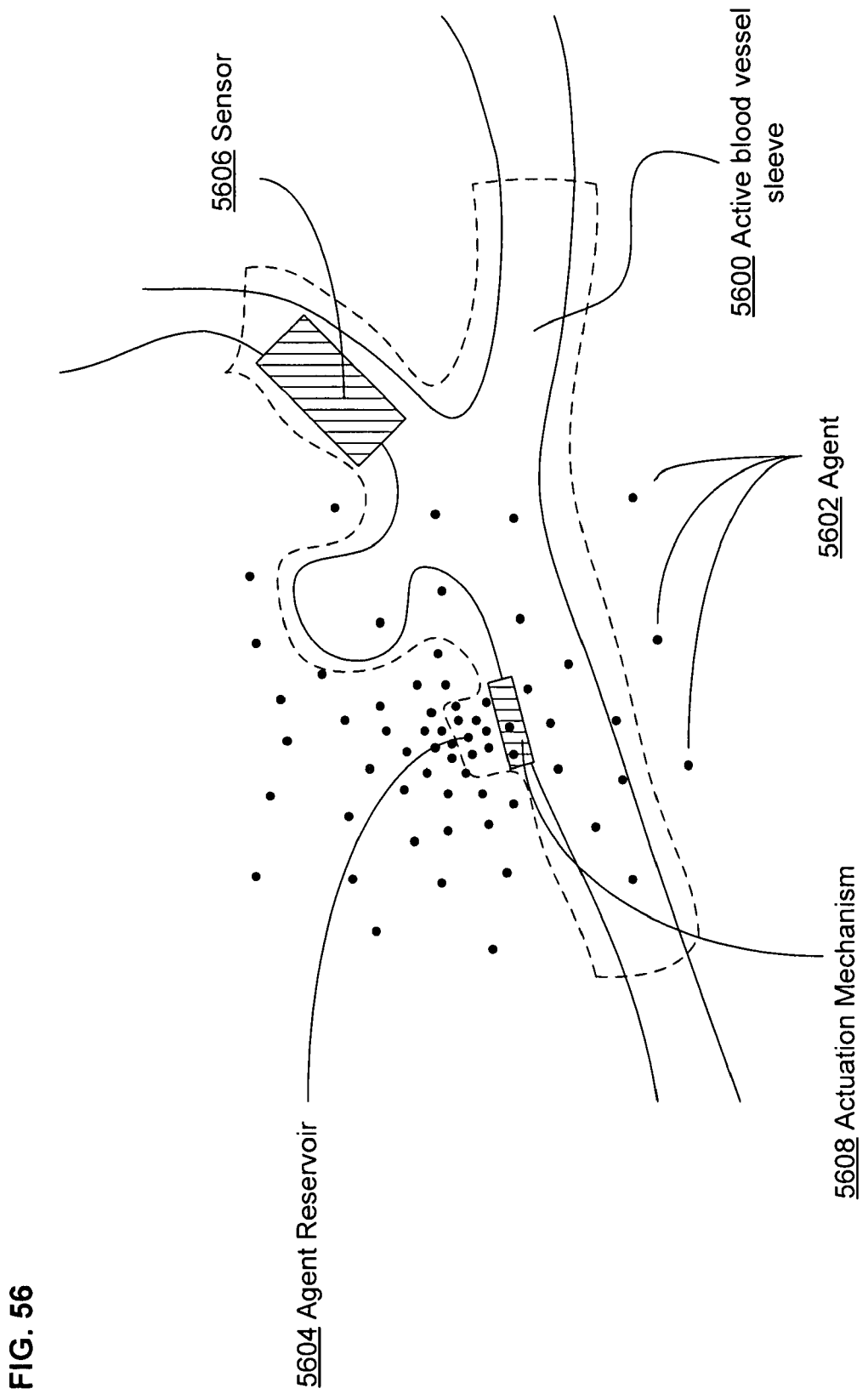

With reference now to FIG. 56, shown are examples of embodiments of blood vessel sleeves, which may serve as a context for introducing one or more devices, methods, and systems described herein.

Figure 57:
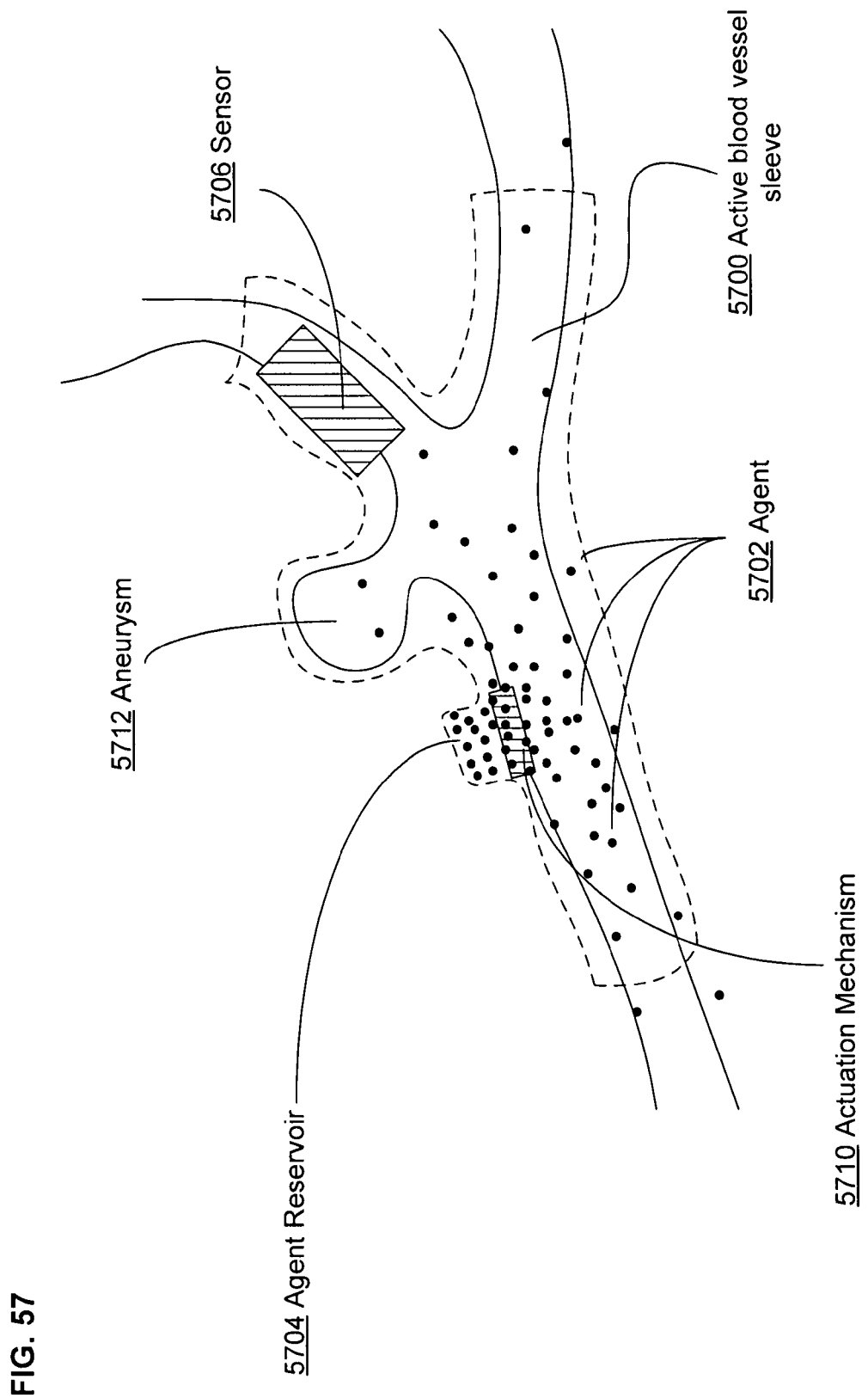

With reference now to FIG. 57, shown are examples of embodiments of blood vessel sleeves, which may serve as a context for introducing one or more devices, methods, and systems described herein.

Figure 58:
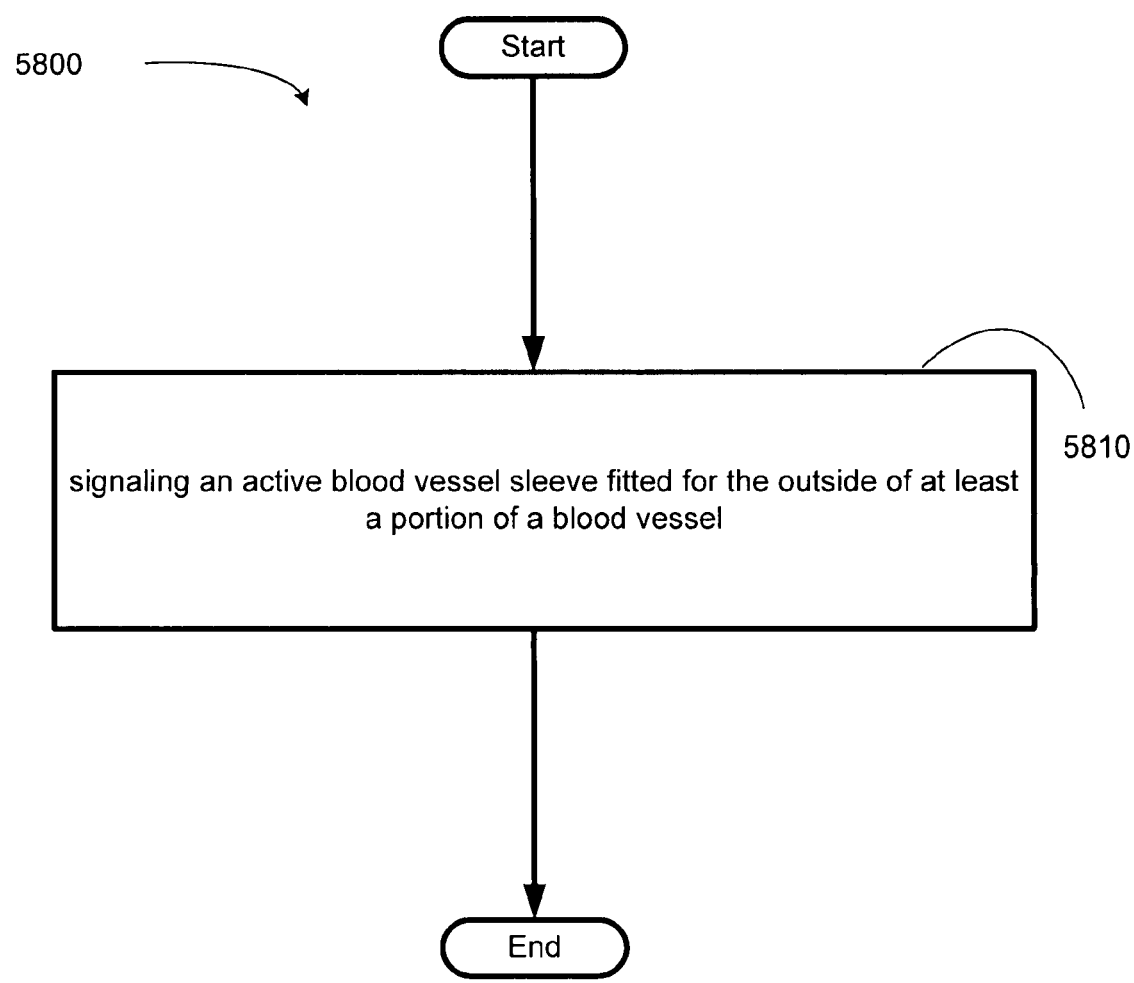

FIG. 58 illustrates an operational flow representing example operations related to methods and systems for making a blood vessel sleeve.

Figure 59:
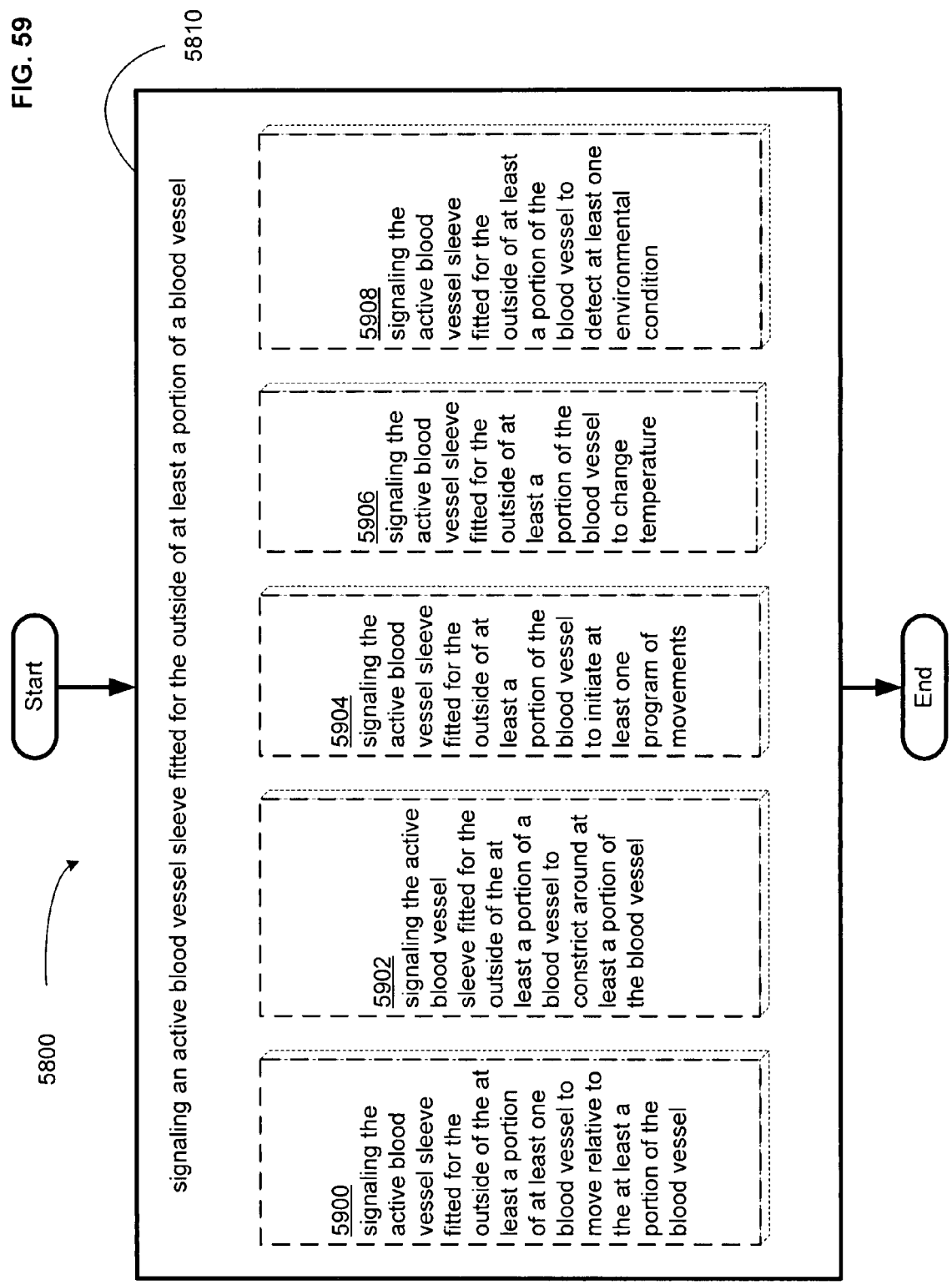

FIG. 59 illustrates an alternative embodiment of the example operational flow of FIG. 58.

Figure 60:
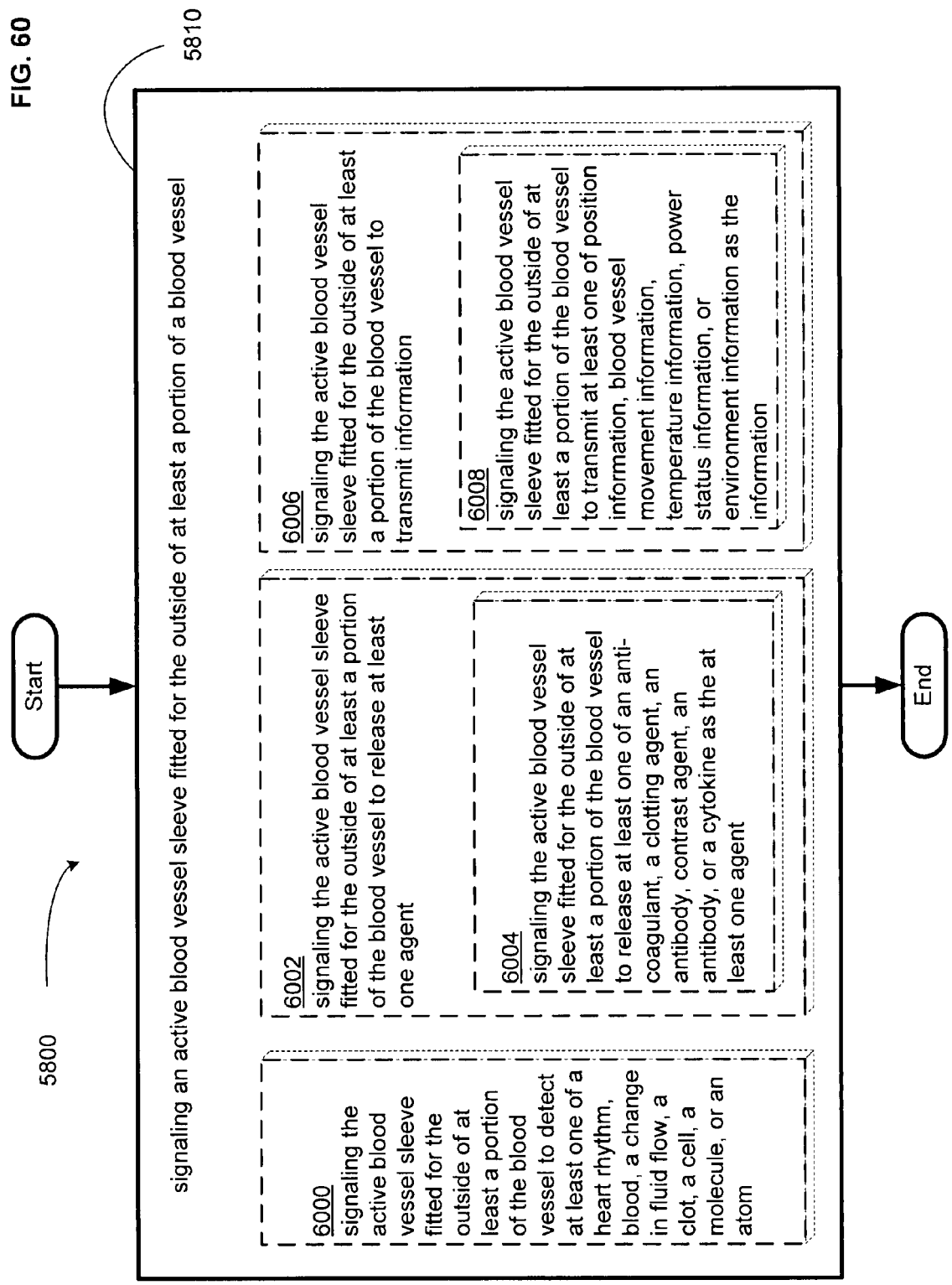

FIG. 60 illustrates an alternative embodiment of the example operational flow of FIG. 58.

Figure 61:
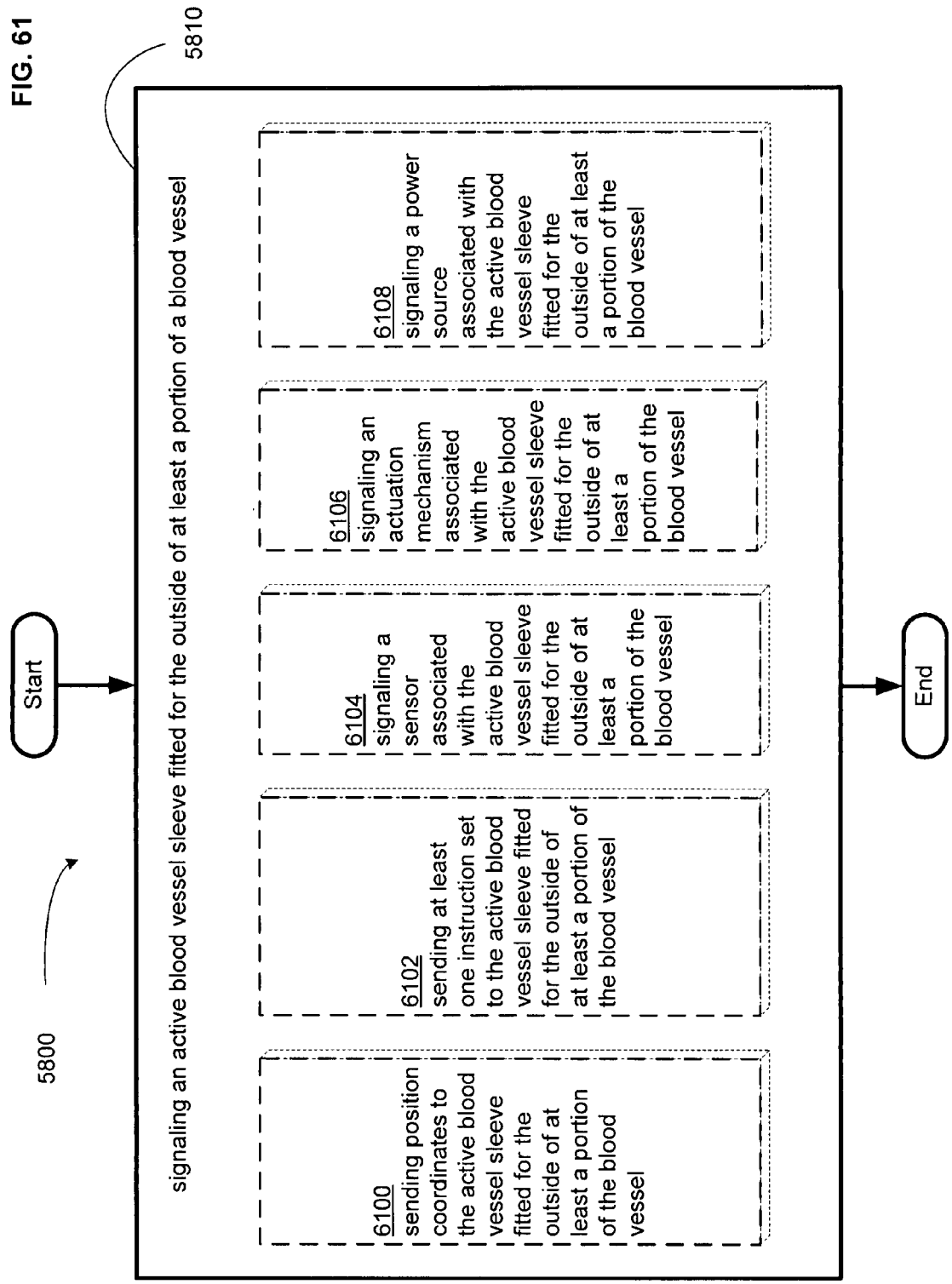

FIG. 61 illustrates an alternative embodiment of the example operational flow of FIG. 58.

Figure 62:
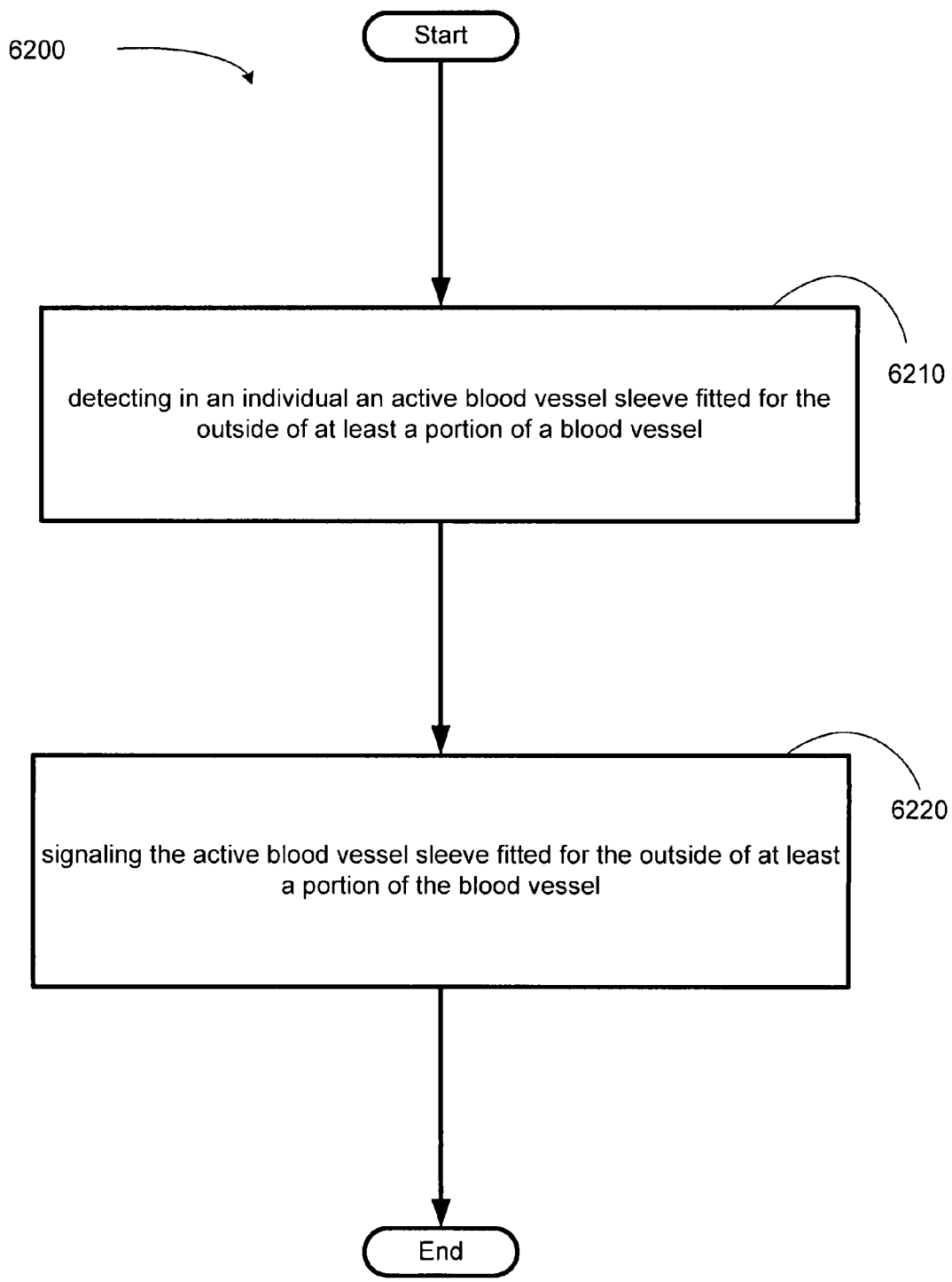

FIG. 62 illustrates an operational flow representing example operations related to methods and systems for making a blood vessel sleeve.

Figure 63:
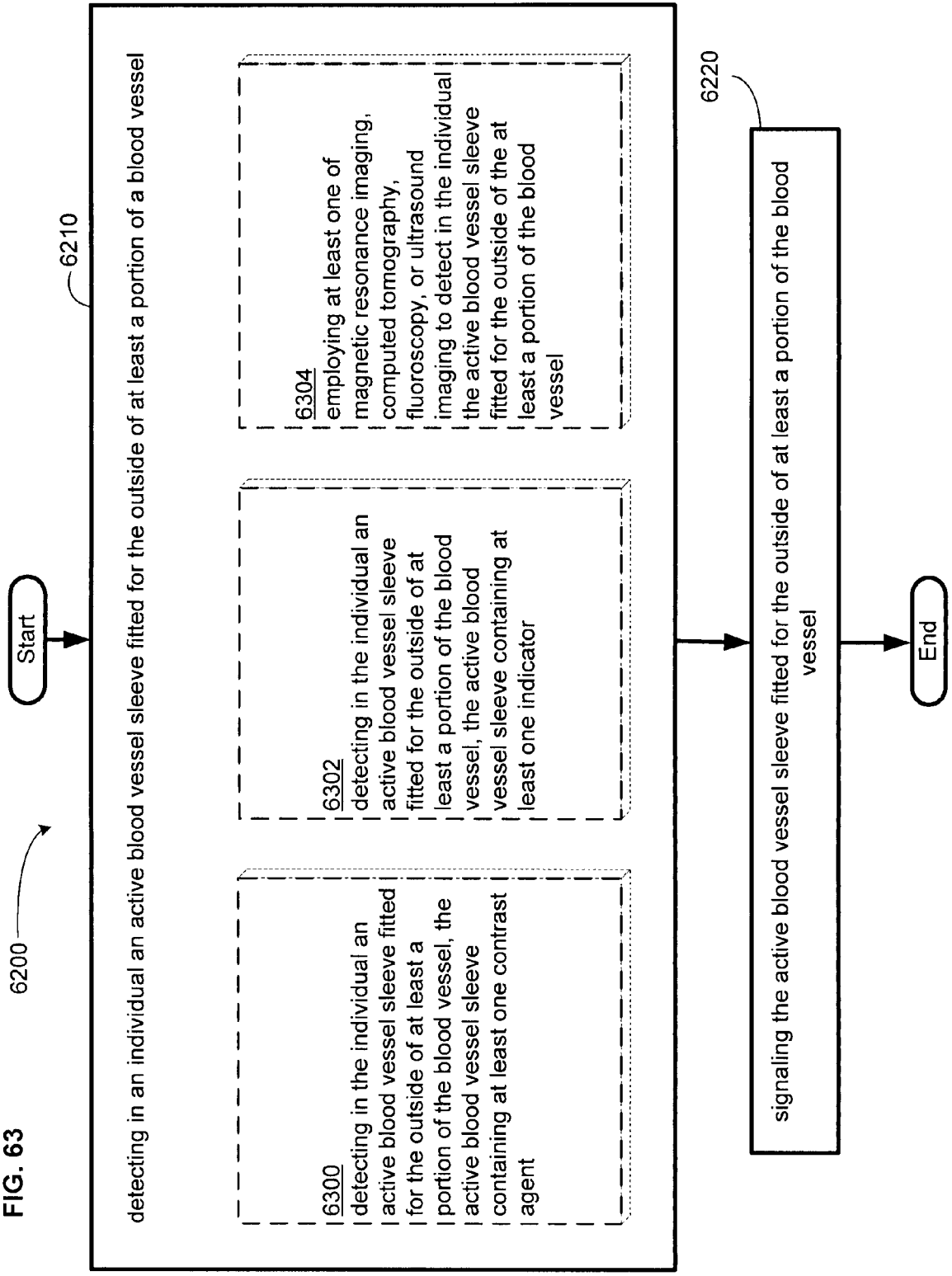

FIG. 63 illustrates an alternative embodiment of the example operational flow of FIG. 62.

Figure 64:
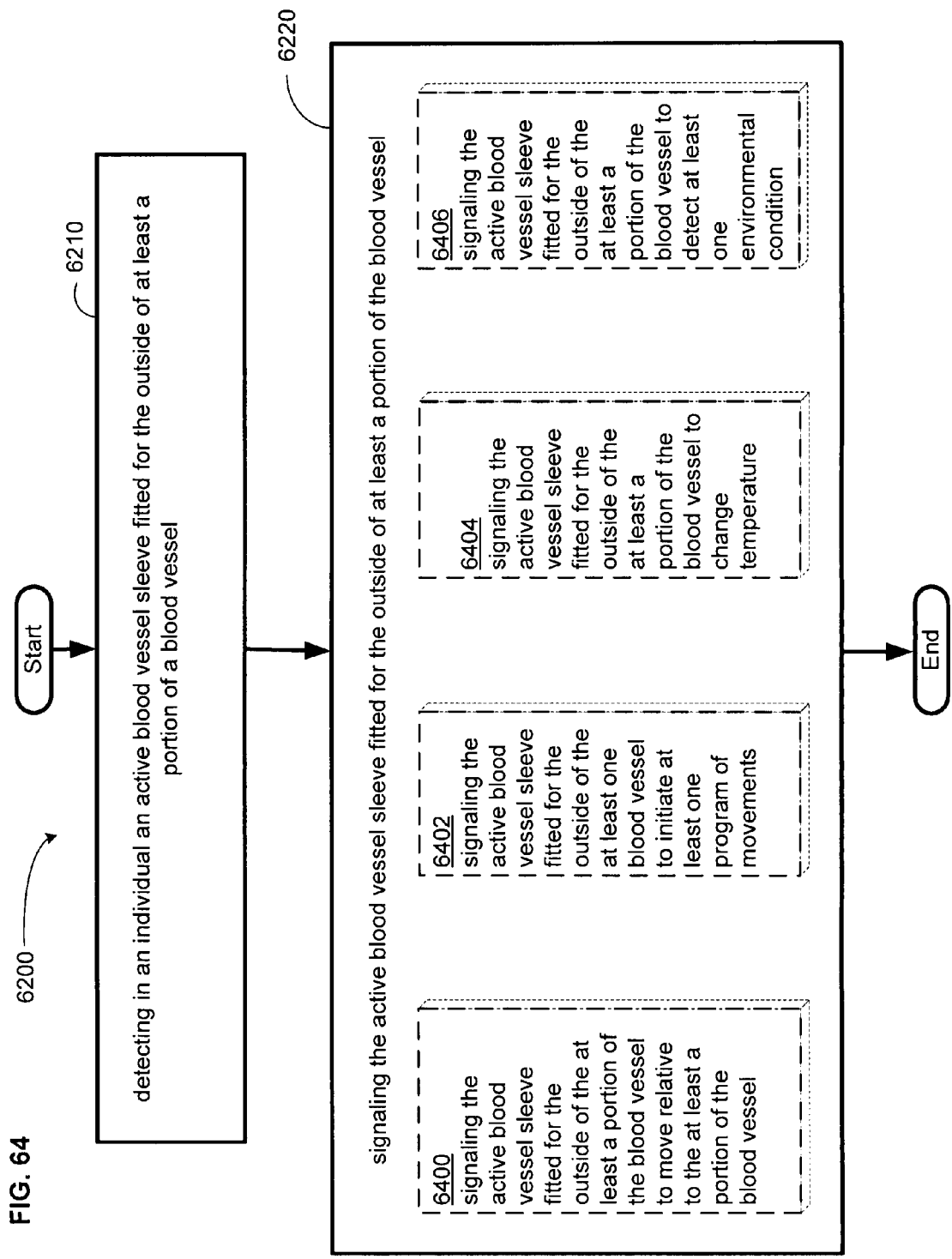

FIG. 64 illustrates an alternative embodiment of the example operational flow of FIG. 62.

Figure 65:
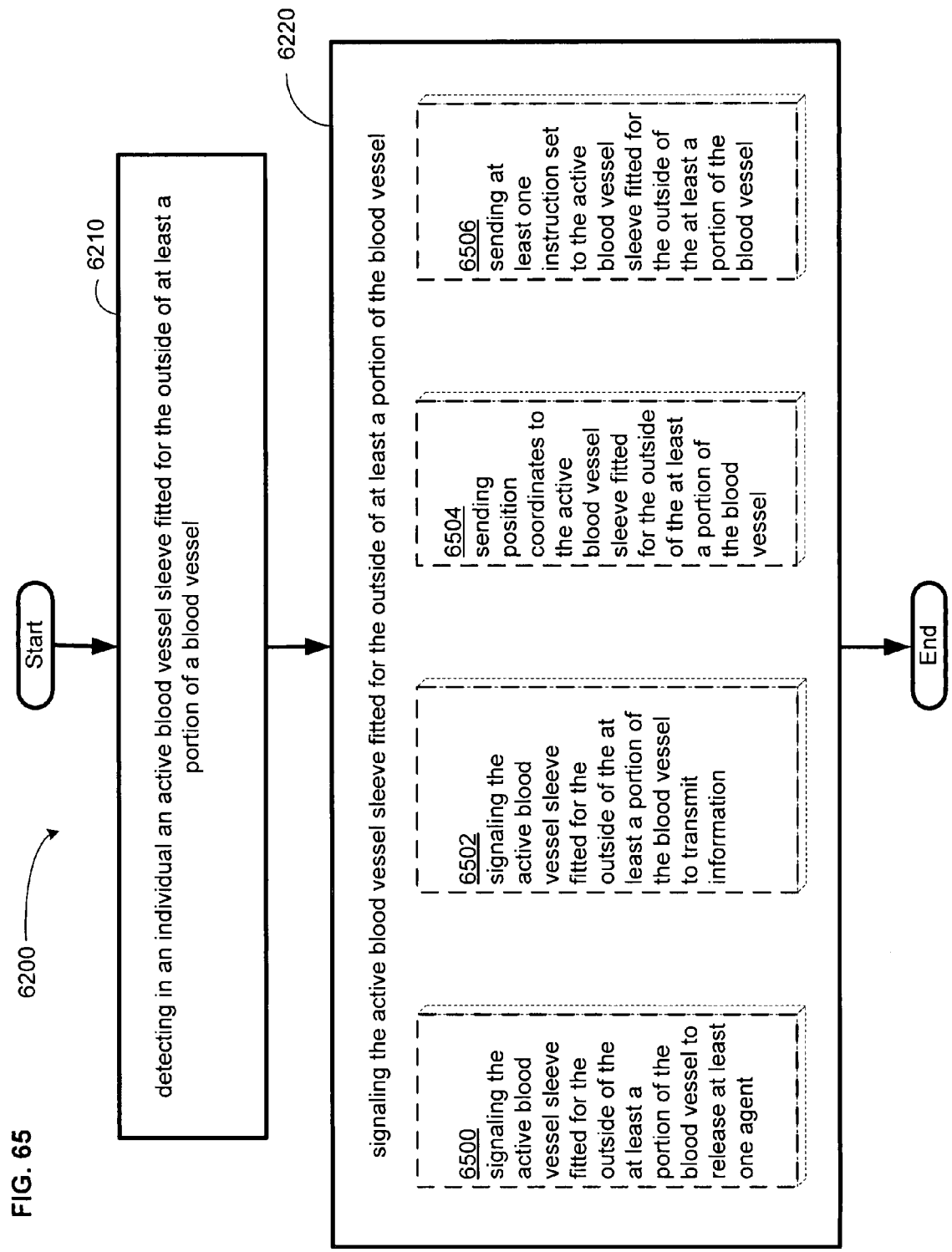

FIG. 65 illustrates an alternative embodiment of the example operational flow of FIG. 62.

Figure 66:
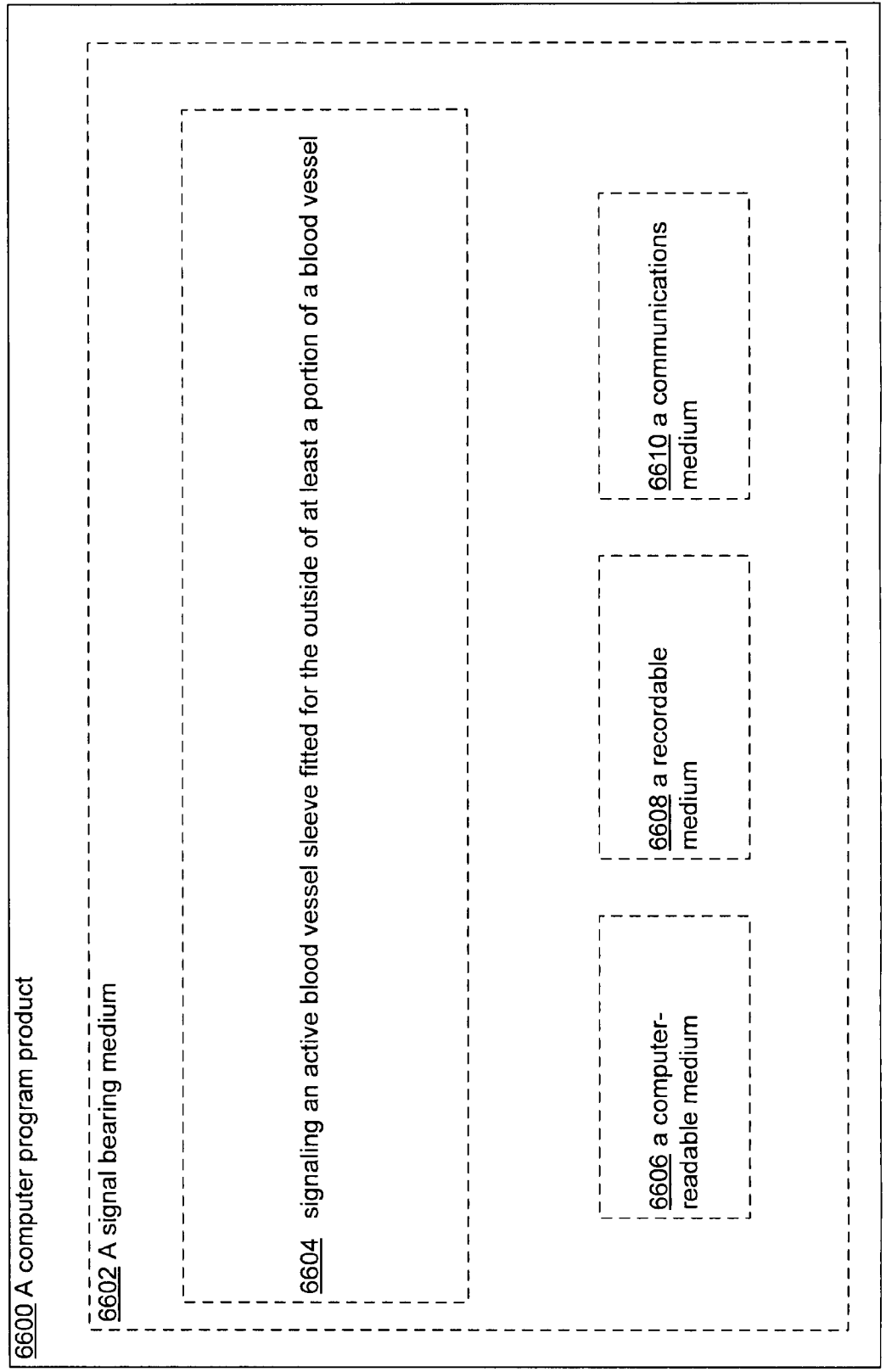

FIG. 66 illustrates a partial view of an example computer program product that includes a computer program for executing a computer process on a computing device.

FIG. 67 illustrates an example device in which embodiments may be implemented.

The use of the same symbols in different drawings typically indicates similar or identical items.

DETAILED DESCRIPTION

Figure 1:
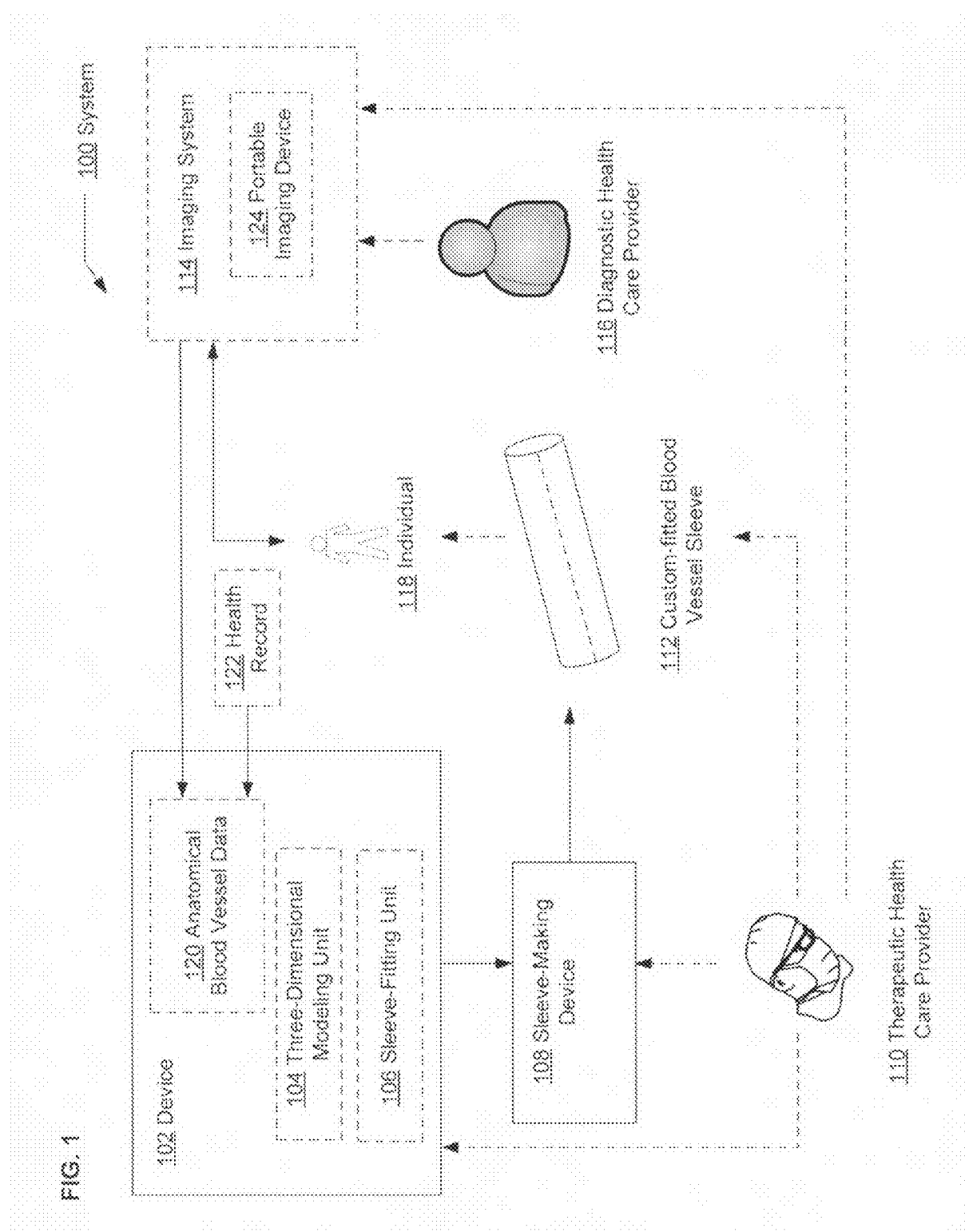

FIG. 1 illustrates an example system 100 in which embodiments may be implemented. The system 100 includes at least one device 102. The at least one device 102 may contain, for example, a three-dimensional modeling unit 104 and a sleeve-fitting unit 106. Imaging system 114 may generate anatomical blood vessel data 120 from an individual 118, or anatomical blood vessel data 120 from an individual 118 may be obtained from a health record 122 that is external to the device 102. Imaging system 114 may be operated by diagnostic health care provider 116 and/or therapeutic health care provider 110 to obtain anatomical blood vessel data 120 from an individual 118.

Therapeutic health care provider 110 may interact with the device 102 to determine blood vessel sleeve specifications based on anatomical blood vessel data 120 from an individual 118. Therapeutic health care provider 110 may also interact with sleeve-making device 108 to obtain custom-fitted blood vessel sleeve 112 based on anatomical blood vessel data 120 from an individual 118. Therapeutic health care provider 110 may then employ the custom-fitted blood vessel sleeve 112 to address a blood vessel of individual 118 in an open surgical procedure, in a laparoscopic surgery procedure, through a catheter insertion procedure, or the like.

In some embodiments, the imaging system 114 and the device 102 may be combined in a single device, or the imaging system 114, the device 102, and the sleeve-making device 108 may be combined in a single device. In some embodiments the imaging system 114 may be a portable imaging device 124 that can communicate with the at least one device 102, on which the sleeve-fitting unit 106 is operable, via a wireless network for example. In some embodiments, the sleeve-making device 108 may be operable remotely through the device 102 via, for example, a network connection.

In FIG. 1, the at least one device 102 is illustrated as possibly being included within a system 100. Any kind of computing device may be used in connection with the three-dimensional modeling unit 104 and/or sleeve-fitting unit 106, such as, for example, a workstation, a desktop computer, a mobile computer, a networked computer, a collection of servers and/or databases, cellular phone, personal entertainment device, or a tablet PC.

Additionally, not all of the three-dimensional modeling unit 104 and/or sleeve-fitting unit 106 need be implemented on a single computing device. For example, the three-dimensional modeling unit 104 may be implemented and/or operable on a remote computer, while the sleeve-fitting unit 106 and/or sleeve-making device 108 is implemented and/or stored on a local computer. Further, aspects of the three-dimensional modeling unit 104, sleeve-fitting unit 106, imaging system 114, and/or sleeve-making device 108 may be implemented in different combinations and implementations than that shown in FIG. 1. For example, functionality of the sleeve-making device 108 may be incorporated into the device 102. In some embodiments, the at least one device 102 may process anatomical blood vessel data 120 from an individual 118 according to anatomical profiles available as updates through a health records network.

The anatomical blood vessel data 120 from an individual 118 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
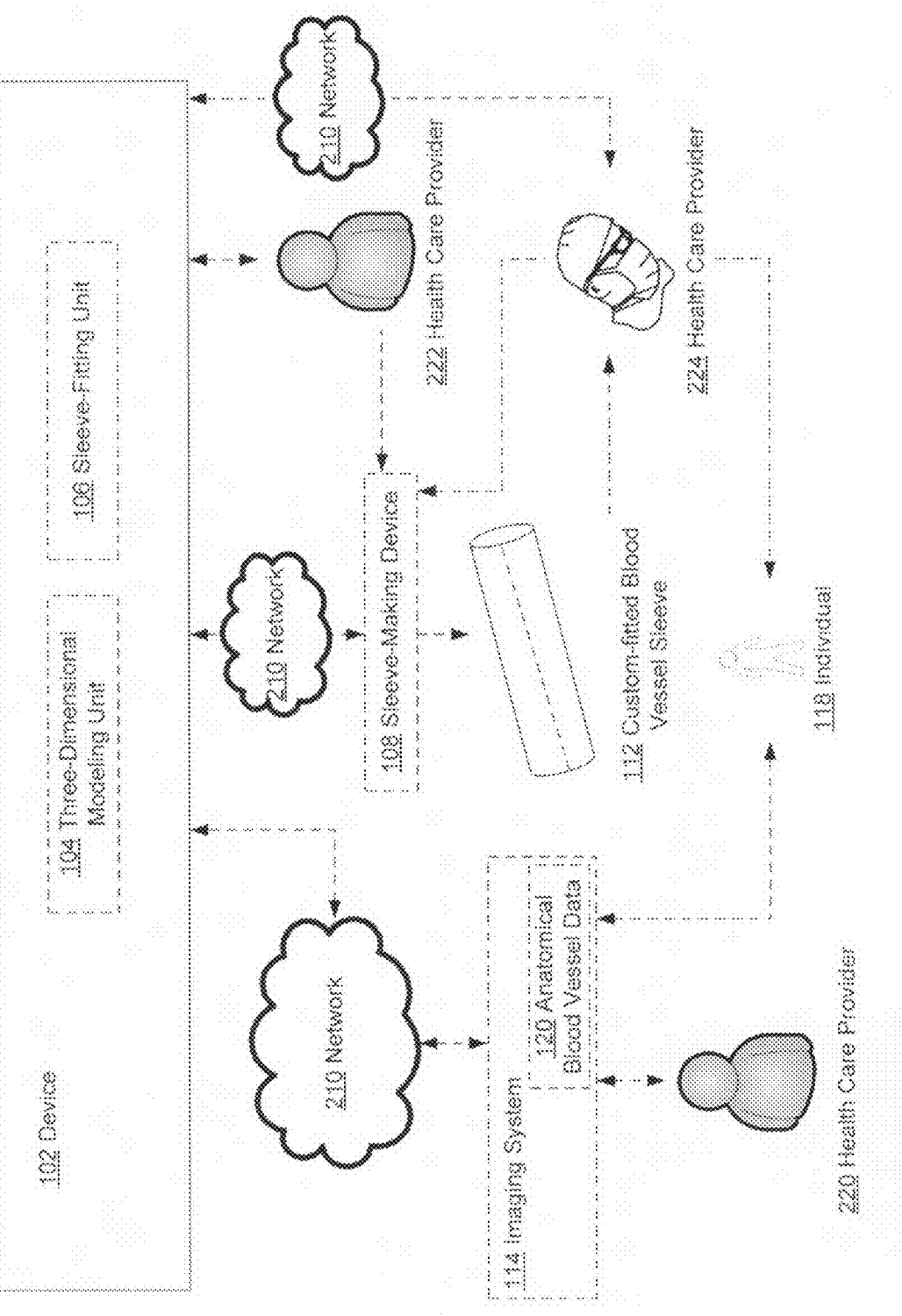
FIG. 2 illustrates certain alternative embodiments of the exemplary environment of FIG. 1.

FIG. 2 illustrates certain alternative embodiments of the system 100 of FIG. 1. In FIG. 2, a health care provider 220 may interact with imaging system 114 to obtain anatomical blood vessel data 120 from an individual 118. The anatomical blood vessel data 120 from an individual 118 may be sent through a network 210 to three-dimensional modeling unit 104 and/or sleeve-fitting unit 106 operable on at least one device 102. The three-dimensional modeling unit 104 and/or sleeve-fitting unit 106 may be implemented on the at least one device 102, or elsewhere within the system 100 but separate from the at least one device 102. The at least one device 102 may be in communication remotely over a network 210 or locally with the sleeve-making device 108, health care provider 222, and/or health care provider 224. A health care provider may interact with the at least one device 102, three-dimensional modeling unit 104, sleeve-fitting unit 106, and/or sleeve-making device 108 through, for example, a user interface. Of course, it should be understood that there may be other health care providers other than the specifically-illustrated health care provider 220, health care provider 222, and/or health care provider 224, for example, each with access to at least a portion of system 100.

In this way, the sleeve-making device 108 may generate a custom-fitted blood vessel sleeve 112, perhaps remotely via a network 210 as if the health care provider 220, health care provider 222, and/or health care provider 224 were interacting locally with the at least one device 102 and/or sleeve-making device 108.

As referenced herein, the at least one device 102, three-dimensional modeling unit 104, and/or sleeve-fitting unit 106 may be used to perform various data querying, recall, and/or manipulation techniques with respect to the anatomical blood vessel data 120, in order to, for example, construct a model of a portion of a blood vessel or determine specifications of a blood vessel sleeve for use in treating a portion of a blood vessel. For example, where the anatomical blood vessel data 120 is organized, keyed to, and/or otherwise accessible using one or more reference health condition attributes or profiles, various Boolean, statistical, and/or semi-boolean searching techniques may be performed to match anatomical blood vessel data 120 with reference health data, attributes, or profiles.

Many examples of databases and database structures may be used in connection with the at least one device 102, three-dimensional modeling unit 104, and/or sleeve-fitting unit 106. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more of reference blood vessel attribute may be performed, or Boolean operations using a reference health attribute may be performed. For example, weighted Boolean operations may be performed in which different weights or priorities are assigned to one or more of the reference health attributes, perhaps relative to one another. For example, a number-weighted, exclusive-OR operation may be performed to request specific weightings of desired (or undesired) anatomical blood vessel data 120 to be included or excluded.

FIG. 3 illustrates an exemplary embodiment related to a custom-fitted blood vessel sleeve. In FIG. 3 and in following figures that include various examples of custom-fitted blood vessel sleeves, discussion and explanation may be provided with respect to the above-described system environments of FIGS. 1-2, and/or with respect to other examples and contexts. However, it should be understood that the exemplary embodiments may be executed in a number of other environments and contexts, and/or in modified versions of FIGS. 1-2. Also, although the various exemplary embodiments are presented in the context of the system environments of FIGS. 1-2, it should be understood that the various exemplary embodiments may be produced by other systems than those which are illustrated.

With respect to FIG. 3A, blood vessel 300 from an individual 118 is shown, the blood vessel 300 having a portion bearing a berry aneurysm 302. With respect to FIG. 3B, shown is a custom-fitted blood vessel sleeve 306 based on anatomical blood vessel data from an individual 118. For example, shown is custom-fitted blood vessel sleeve 306 that may be placed around the blood vessel 300 to support and/or confine the berry aneurysm 302. FIG. 3B thus shows a blood vessel sleeve that is custom-fitted for at least one aneurysm on at least one blood vessel at least partly based on anatomical blood vessel data 120 from the individual 118.

Aneurysms may involve arteries or veins and have various causes. They are commonly further classified by shape, structure, and location. A saccular aneurysm may resemble a small bubble that appears on the side of a blood vessel. The innermost layer of an artery, in direct contact with the flowing blood, is the tunica intima, commonly called the intima. Adjacent to this layer is the tunica media, known as the media and composed of smooth muscle cells and elastic tissue. The outermost layer is the tunica adventitia or tunica externa. This layer is composed of tougher connective tissue. A saccular aneurysm develops when fibers in the outer layer separate allowing the pressure of the blood to force the two inner layers to balloon through. A saccular aneurysm with a narrow neck connecting the bubble-like pouch to the main blood vessel is known as a berry aneurysm.

A fusiform aneurysm may be a bulging around the entire circumference of the vessel without protrusion of the inner layers. It may be shaped like a football or spindle.

Aneurysms can result from hypertension in conjunction with atherosclerosis that weakens the tunica adventitia, from congenital weakness of the adventitial layer (as in Marfan syndrome), and/or from infection.

Rupture and blood clotting are two health risks involved with aneurysms. Rupture typically leads to a drop in blood pressure, rapid heart rate, and/or lightheadedness. The risk of death is high except for the case of rupture of blood vessels in the extremities. Risk factors for an aneurysm are diabetes, obesity, hypertension, tobacco smoking, and alcoholism.

Also known as intracranial aneurysm or brain aneurysm, cerebral aneurysms make up a large proportion of aneurysm incidence. A common location of cerebral aneurysms is on the arteries at the base of the brain, known as the Circle of Willis. Approximately 85% of cerebral aneurysms develop in the anterior part of the Circle of Willis, and involve the internal carotid arteries and their major branches that supply the anterior and middle sections of the brain. The most common sites include the anterior communicating artery (30-35%), the bifurcation of the internal carotid and posterior communicating artery (30-35%), the bifurcation of the middle cerebral artery (20%), the bifurcation of the basilar artery, and the remaining posterior circulation arteries (5%). The custom-fitted blood vessel sleeve 306 may accordingly be a blood vessel sleeve that is custom-fitted for at least one cerebral artery at least partly based on anatomical cerebral artery data from the individual 118 (see FIG. 9).

Eventual rupture of a cerebral aneurysm may be called an aneurysmal subarachnoid hemorrhage, in which blood flows into the subarachnoid space of the brain and forms clots. One complication of aneurysmal subarachnoid hemorrhage is the development of vasospasm. Approximately 1 to 2 weeks following the initial hemorrhage, an individual 118 may experience spasm of the cerebral arteries, which may result in stroke. The etiology of vasospasm is thought to be secondary to an inflammatory process that occurs as the blood in the subarachnoid space is resorbed.

Vasospasm may be monitored in a variety of ways. Non-invasive methods include transcranial Doppler, which is a method of measuring the velocity of blood in the cerebral arteries using ultrasound. As the vessels narrow due to vasospasm, the velocity of blood increases. The amount of blood reaching the brain can also be measured by computed tomography scanning (CT scanning), magnetic resonance imaging (MRI), or nuclear perfusion scanning.

Non-intracranial aneurysms commonly arise distal to the origin of the renal arteries at the infrarenal abdominal aorta, a condition often caused by atherosclerosis. The thoracic aorta may also be involved. One common form of thoracic aortic aneurysm involves widening of the proximal aorta and the aortic root, leading to aortic insufficiency. Common aortic aneurysms may include abdominal aortic aneurysm and aneurysm of the aortic arch.

The human aorta is a relatively low-resistance circuit for circulating blood. The lower extremities have higher arterial resistance, and the repeated trauma of a reflected arterial wave on the distal aorta may injure a weakened aortic wall and contribute to aneurysmal degeneration. Systemic hypertension compounds the injury, accelerates the expansion of known aneurysms, and may contribute to their formation. The custom-fitted blood vessel sleeve 306 may accordingly be a blood vessel sleeve that is custom-fitted for at least one aorta at least partly based on anatomical aorta data from the individual 118.

Aneurysms occur in the legs also, particularly in the deep vessels (e.g., the popliteal vessels in the knee). Arterial aneurysms are much more common, but venous aneurysms also occur (e.g., the popliteal venous aneurysm). Blood clots from popliteal arterial aneurysms can travel downstream and suffocate tissue. Only if the resulting pain and/or numbness are ignored over a significant period of time will such extreme results as amputation be needed. Clotting in popliteal venous aneurysms are much more serious as the clot can embolize and travel to the heart, or through the heart to the lungs (i.e., a pulmonary embolism).

The occurrence and expansion of an aneurysm in a given segment of the arterial tree involves local hemodynamic factors and factors intrinsic to the arterial segment itself. Hemodynamically, the coupling of aneurysmal dilation and increased wall stress is approximated by the Law of Laplace. Specifically, the Law of Laplace states that the (arterial) wall tension is proportional to the pressure times the radius of the arterial conduit (T=P×R). As diameter increases, wall tension increases, which contributes to increasing diameter. As tension increases, risk of rupture increases. Increased pressure (systemic hypertension) and increased aneurysm size aggravate wall tension and therefore increase the risk of rupture. In addition, the vessel wall is supplied by the blood within its lumen in humans. Therefore in a developing aneurysm, the most ischemic portion of the aneurysm is at the farthest end, resulting in weakening of the vessel wall there and aiding further expansion of the aneurysm. Thus all aneurysms will eventually, if left to complete their evolution, rupture without intervention.

Treatment of cerebral aneurysm may include surgical intervention (i.e., invasive surgery) called clipping, in which a craniotomy is performed, followed by placement of a titanium clip around the aneurysm neck. Another treatment method, coil embolization, involves the insertion of a catheter through the groin with a small microcatheter navigated to the aneurysm itself through the cerebral arteries. Coils known as Guglielmi Detachable Coils (GDCs) are then deployed into the aneurysm, filling it from within and thus preventing blood from entering the aneurysm itself by forming a large clot on the coils.

For aortic aneurysms or aneurysms that happen in the vessels that supply blood to the arms, legs, and head, surgery may involve inserting a covered metallic stent graft through the arteries of the leg to be deployed across the inside of the weakened section of the blood vessel.

A false or pseudoaneurysm does not primarily involve distortion of a blood vessel, but instead is composed of a collection of blood leaking out of an artery or vein into a region next to the blood vessel and confined by the surrounding tissue. This blood-filled cavity may eventually either clot enough to seal the leak or it may rupture the tissue enclosing it and disperse into nearby tissues. Pseudoaneurysms may be caused by trauma that punctures the artery, and are a known complication of percutaneous arterial procedures such as arteriography, arterial grafting, or use of an artery for injection, such as by drug abusers repeatedly searching with a needle for a usable vein. Like true aneurysms, pseudoaneurysms may be felt as an abnormal pulsatile mass on palpation.

In FIG. 3B, the custom-fitted blood vessel sleeve 306 is shown with a custom-fitted blood vessel sleeve aperture 314 that may accommodate a blood vessel branch 304 associated with blood vessel 300. The custom-fitted blood vessel sleeve 306 further can have dimensions that accommodate a berry aneurysm 302 or other aneurysm. Appropriate dimensions for the custom-fitted blood vessel sleeve 306 may be obtained by the device 102, imaging system 114, and/or sleeve-fitting unit 106 operable on the device 102 or otherwise associated with system 100. Alternatively, specifications for the custom-fitted blood vessel sleeve 306 may be obtained via an integrated system containing imaging system 114, three-dimensional modeling unit 104, sleeve-fitting unit 106, and sleeve-making device 108. Accordingly, a custom-fitted blood vessel sleeve 306 may accommodate various blood vessel dimensions and features, including blood vessel diameter, blood vessel branching, blood vessel curvature 308, aneurysm dimensions, or other anatomical variation in an individual 118.

In order to be placed on a blood vessel, the custom-fitted blood vessel sleeve 306 may include a custom-fitted blood vessel sleeve opening 312, by which the custom-fitted blood vessel sleeve 306 may be passed over a longitudinal axis of the blood vessel 300, for example, and any blood vessel branch 304 that may be present. The custom-fitted blood vessel sleeve 306 may also include at least one closure means, as discussed below, such that after passing over the longitudinal axis of the blood vessel 300, the sleeve may be closed to resume, for example, a closed cylinder configuration.

With respect to FIG. 3C, shown is the custom-fitted blood vessel sleeve 306 in place around blood vessel 300 and berry aneurysm 302. In the case of an aneurysm, for example, that is in proximity to a blood vessel branch 304, the custom-fitted blood vessel sleeve 306 may incorporate a custom-fitted blood vessel sleeve aperture 314 through which the blood vessel branch 304 may pass, as shown in FIG. 3C.

Placement of custom-fitted blood vessel sleeve 306 on an aneurysm-affected portion of a blood vessel 300 may serve to inhibit, prevent, and/or mitigate rupture of the aneurysm-affected portion of the blood vessel 300. Further, the custom-fitted blood vessel sleeve 306 may be designed with specifications such that when the custom-fitted blood vessel sleeve 306 is placed on the blood vessel 300, the aneurysm is compressed in diameter and thereby supported, for example, circumferentially by the custom-fitted blood vessel sleeve 306. In this scenario, the circumference of the aneurysm-affected portion of the blood vessel 300 may be reduced, with an attendant reduction in blood vessel wall tension according to the Law of Laplace, as discussed above.

Such reduction in wall tension afforded by a custom-fitted blood vessel sleeve 306 may address an aneurysm-affected portion of a blood vessel 300, an atherosclerosis-affected portion of a blood vessel 300, and/or other condition involving compromised blood vessel wall integrity.

FIG. 4 illustrates an exemplary embodiment related to a custom-fitted blood vessel sleeve. With respect to FIG. 4A, blood vessel 400 from an individual 118 is shown, the blood vessel 400 having a fusiform aneurysm 402 and a blood vessel branch 404.

With respect to FIG. 4B, shown is a custom-fitted blood vessel sleeve 406 that is based on anatomical blood vessel data 120 from an individual 118. In this example, the custom-fitted blood vessel sleeve 406 may include an integrated custom-fitted blood vessel branch sleeve portion 408 that may be placed around a portion of the blood vessel branch 404, typically in conjunction with placing the custom-fitted blood vessel sleeve 406 around a portion of blood vessel 400 and/or fusiform aneurysm 402. The custom-fitted blood vessel sleeve 406 may accordingly be a blood vessel sleeve that is custom-fitted for at least one branched blood vessel at least partly based on anatomical blood vessel data from the individual 118.

With respect to FIG. 4C, shown is the custom-fitted blood vessel sleeve 406 in place around blood vessel 400, fusiform aneurysm 402, and blood vessel branch 404.

FIG. 5 illustrates an exemplary embodiment related to a custom-fitted blood vessel sleeve. With respect to FIGS. 5A-5E, a set of custom-fitted blood vessel sleeves 506 of varying size is depicted. This size gradation is further depicted in FIG. 5F, wherein oblique cross-sections 502 are presented for each of the custom-fitted blood vessel sleeves of FIGS. 5A-5E. The oblique cross-sections 502 are shown as lines of varying length, beginning with 5a and increasing through 5E, corresponding to cross-sections of FIGS. 5A through 5E, respectively.

FIG. 6 illustrates an exemplary embodiment related to a custom-fitted blood vessel sleeve. With respect to FIG. 6A, an abdominal aortic aneurysm 600 is shown. FIG. 6B depicts a custom-fitted blood vessel sleeve-covered abdominal aortic aneurysm 602. As shown in FIG. 6B, the custom-fitted blood vessel sleeve may be of a smaller diameter, for example, than the aneurysm around which it is placed. In effect, placement of a custom-fitted blood vessel sleeve in this way may constrict the blood vessel and return it to a diameter that is closer to or the same as its diameter prior to occurrence of the aneurysm. In this way the custom-fitted blood vessel sleeve may provide support for the blood vessel wall and act to prevent rupture of the aneurysm.

Accordingly, a custom-fitted blood vessel sleeve may be a blood vessel sleeve that is custom-fitted for the exterior of a blood vessel at least partly based on anatomical blood vessel data 120 from the individual 118. Alternatively, a custom-fitted blood vessel sleeve may be a blood vessel sleeve that is custom-fitted for the interior of a blood vessel at least partly based on anatomical blood vessel data 120 from the individual 118. Such a sleeve fitted to the interior of a blood vessel is shown in FIG. 10 and FIG. 11.

FIG. 7 illustrates an exemplary embodiment related to a custom-fitted blood vessel sleeve. With respect to FIG. 7A, an oblique view of a cross-section of a custom-fitted blood vessel sleeve 700 is shown. The custom-fitted blood vessel sleeve 700 may be composed of single or multiple layers to confer desired properties of stiffness, applicability to a blood vessel 300, expansion or contraction capability, durability, ease of manufacture, drug delivery capability, or the like. The custom-fitted blood vessel sleeve 700 may accordingly be a multiple-layered blood vessel sleeve that is custom-fitted for the blood vessel at least partly based on anatomical blood vessel data 120 from the individual 118. As used herein, the word "multiple" refers to "at least two or more." FIG. 7A shows a custom-fitted blood vessel sleeve 700 having a lumen 708, a custom-fitted blood vessel sleeve opening 701, an external layer 702, a middle layer 704, and an internal layer 706. In some embodiments, the custom-fitted blood vessel sleeve opening 701 may consist of a perforation that allows a therapeutic health care provider 110, for example, to open the custom-fitted blood vessel sleeve 700 immediately prior to placement on a blood vessel. Alternatively, no opening or perforation may be present, and a therapeutic health care provider 110 may cut the custom-fitted blood vessel sleeve 700 to create an opening for placement over a blood vessel.

In another embodiment, the custom-fitted blood vessel sleeve 700 may be a substantially transparent blood vessel sleeve that is custom-fitted for at least one blood vessel at least partly based on anatomical blood vessel data 120 from the individual 118. In this embodiment, the transparent nature of the blood vessel sleeve may allow a surgeon or other therapeutic health care provider 110 to visually examine the fit of the blood vessel sleeve more closely, and also to visually examine the status of the blood vessel sleeve and blood vessel at various times after the initial placement, if necessary. Such a substantially transparent sleeve may be particularly useful in cases where a problem has developed in the area of the sleeve, such as hemorrhaging, embolism, and/or stenosis of the blood vessel.

The custom-fitted blood vessel sleeve 700 may be manufactured from many kinds of materials appropriate for use in the human body, known to those of skill in the art. For example, the custom-fitted blood vessel sleeve 700 may be a blood vessel sleeve that is custom-fitted for the blood vessel at least partly based on anatomical blood vessel data 120 from the individual 118, the blood vessel sleeve at least partly made of a biocompatible material. Biocompatible material may include, for example, a polymer, a metal and/or metal alloy, a ceramic, a natural material, a pyrolytic carbon material, and/or composites thereof, or the like. Biocompatible material may also include biomimetic material and/or material with surface functionalization via protein deposition or self-assembling peptide scaffold deposition. Additionally, methods known in the art to render biocompatible chemically inert or reactive surfaces may be used, including, for example, plasma processing and/or the use of polyanhydrides. Another method for detoxification of solid freeform fabrication materials is found in U.S. Pat. No. 6,996,245 B2 entitled "Detoxification of solid freeform fabrication materials." This process involves chemical extraction and has been used to detoxify, for example, a custom hearing aid shell produced by stereolithography from an acrylate photopolymer resin.

Polyvinyl chloride is one commonly used polymer in medical devices, and other biocompatible polymers commonly used are silicone, polyurethane, polycarbonates, polyester and polyethylene, biodegradable polymers, bioactive polymers, hydrogels, molecular imprinted polymers, conductive polymers, and biopolymers. Such polymers may be applied to meshes, foams, sponges or hydrogels, for example, to form a custom-fitted blood vessel sleeve 700. Bioactive polymers may serve secondary functions such as stimulating or inhibiting tissue growth, and/or promoting adhesion.

Titanium, stainless steel, and chromium steel are examples of metals used in medical implants. Metal alloys are also commonly used to obtain desired strength, malleability, and/or fabrication properties. Composites comprised of artificial growth factors, natural materials, carbon fibers, and/or polymers are also useful as biocompatible material.

Biocompatible nanomaterial may also be used. Some such materials known to those of skill in the art may provide rejection-resistant implants. Tissue engineering using polymer scaffolds for cell hosting may also provide a biocompatible material for use with a custom-fitted blood vessel sleeve 700.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve having at least one of a substantially polymer composition, a substantially plastic composition, a substantially thermoplastic composition, a substantially photopolymer composition, or a substantially elastomeric composition.

In some embodiments, an internal layer 706 may comprise a surface that is suitable for contact with the collagen and smooth muscle cells of the tunica adventitia (i.e., the outer layer of the blood vessel) or the tunica intima (i.e., the inner layer of the blood vessel). Such a suitable surface may contain collagen binding agents such as proteins, peptides, aptamers, or the like such that adhesion of the sleeve to the blood vessel is enhanced. Other agents may be profitably integrated into the internal layer 706 such as cell growth factors to promote blood vessel wall strength, anti-coagulating agents to mitigate thrombotic events, or the like.

In another embodiment, an external layer 702 may be adjacent to the inner layer of the blood vessel, as in stent-like placements of a blood vessel sleeve within a blood vessel. In these cases, the external layer 702 and/or other layers of the sleeve may contain active agents that inhibit or prevent stenosis of the vessel. For example, compounds such as antibodies that block blood cell adhesion are known to inhibit restenosis in stent placement situations (see U.S. patent publication 2002/0006401 A1 "Modulation of vascular healing by inhibition of leukocyte adhesion function").

Other active agents may also be employed to repair blood vessel weakening or injury, including, for example, vascular endothelial growth factor (VEGF), fibroblast growth factor 2, and/or sonic hedgehog protein or the like.

In another embodiment, a middle layer 704 may comprise a material that is a shape-forming material to provide a desired degree of structural stiffness or flexibility for the custom-fitted blood vessel sleeve 700.

In another embodiment, the custom-fitted blood vessel sleeve 700 may be a collapsible blood vessel sleeve that is custom-fitted for at least one blood vessel at least partly based on anatomical blood vessel data 120 from the individual 118. As shown in FIG. 7B, FIG. 8A, and FIG. 8B, the custom-fitted blood vessel sleeve 709 and/or 800 may be structured to expand or collapse via pleats, a folding mesh structure, or other mechanical means known in the art. Alternatively, materials may be used in the manufacture of the custom-fitted blood vessel sleeve 700 that have known expansion and/or contraction properties in the human body that are known to those of skill in the art. FIG. 7B depicts a custom-fitted blood vessel sleeve 709 with pleat 710 and pleat 712 surrounding a lumen 714, and having an outer diameter 716 in a folded state. Also depicted is an unpleated portion 717 of the sleeve. Collapsibility afforded by mechanisms such as pleats may facilitate insertion or placement of the custom-fitted blood vessel sleeve 709 into the region proximal to the blood vessel 300 prior to placement of the custom-fitted blood vessel sleeve 709 around the blood vessel 300. In one embodiment, pleat 710 may serve as a location for a therapeutic health care provider 110 to cut the custom-fitted blood vessel sleeve 709 longitudinally to create a custom-fitted blood vessel sleeve opening 701 for placement of the sleeve over a blood vessel. In such an embodiment, the custom-fitted blood vessel sleeve 709 may be made without a custom-fitted blood vessel sleeve opening 701.

FIG. 8 illustrates an exemplary embodiment related to a custom-fitted blood vessel sleeve. With respect to FIG. 8A, an oblique view of a cross-section of a custom-fitted blood vessel sleeve 800 is shown. Custom-fitted blood vessel sleeve 800 is shown with lumen 804 and pleats 802. In this and similar embodiments, the pleated region may extend for only a portion of the longitudinal length of the sleeve, for example to accommodate the portion of the blood vessel from which an aneurysm protrudes. In this case, the pleated portion of the custom-fitted blood vessel sleeve 800 may be specified to expand to a certain degree to fit the aneurysm, while remainder portions of the custom-fitted blood vessel sleeve 800 are unpleated (see also FIG. 7B and unpleated portion 717), and may be tailored to the dimensions of the unaffected blood vessel adjacent to the aneurysm.

With respect to FIG. 8B, a custom-fitted blood vessel sleeve cross-section 818 is shown. In this embodiment, an alternative pleated design is shown having pleats 824, pleat 820, lumen 822, inner diameter 826, and outer diameter 828. As in the above similar embodiments, the pleated region may extend for only a portion of the longitudinal length of the sleeve, for example to accommodate the portion of the blood vessel from which an aneurysm protrudes.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve at least partly made of a smart material. Smart materials may have one or more properties that can be significantly altered in a controlled fashion by external stimuli, such as stress, temperature, moisture, pH, electric or magnetic fields. There are a number of types of smart material, some of which are already common in the art. Some examples are piezoelectric materials that produce a voltage when stress is applied; this effect also applies in the reverse manner wherein a voltage across the sample will produce stress within the sample. Suitably specified structures made from these materials can therefore be made that bend, expand, or contract when a voltage is applied.

Another example of smart materials is thermoresponsive materials (e.g., either shape memory alloys, shape memory polymers, and/or other shape memory material), which are materials that can hold different shapes at various temperatures. Magnetic shape memory alloys are materials that change their shape in response to a significant change in a magnetic field. pH-sensitive polymers are materials that expand or contract when the pH of the surrounding media changes. Chromogenic systems change color in response to electrical, optical or thermal changes. These include electrochromic materials, which change their colour or opacity on the application of a voltage (e.g. liquid crystal displays), thermochromic materials change in color depending on their temperature, and photochromic materials, which change colour in response to light, for example, light sensitive sunglasses that darken when exposed to bright sunlight.

Such use of smart materials in the formation of a custom-fitted blood vessel sleeve 700 may enhance the ease of application of the sleeve to the blood vessel in terms of, for example, having a flexible sleeve during the placement procedure for opening and closing of the sleeve, followed by a manipulation that may make the sleeve more rigid as a way of enhancing the support function of the sleeve around the blood vessel.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve having at least one coating. Such a coating may be placed on an internal surface or an external surface of the custom-fitted blood vessel sleeve 700, for example the surfaces of an internal layer 706 and/or an external layer 702. A coating may comprise a coating known in the art such as one or more thrombus-resistant coatings, one or more anti-coagulant coatings, one or more biocompatibility coatings, one or more biodegradable coatings, one or more durability coatings, one or more small molecule delivery coatings, and/or one or more macromolecule delivery coatings. Examples of coatings further may include coatings that release pharmaceutically active compounds over time (e.g., drug-eluting coatings such as known drug-eluting polymers), and/or adhesive coatings (e.g., biocompatible epoxyamine adhesives described in U.S. Pat. No. 6,780,510).

Other coatings may include, for example, coatings that resist build up of cellular or biomolecular debris, or microbial debris such as fungal or bacterial growth. Some known microbial resistant coatings include silver particles in a polymer matrix that are present in the matrix material preferably at a concentration of 1 ppm to 1,000 ppm, more preferably 100 ppm to 800 ppm, especially 250 ppm to 750 ppm, and most preferably 500 pm to 700 ppm relative to the total weight of the matrix material. Such a coating is described, for example, in U.S. patent publication 2007/0051366 entitled "Medical Devices With Germ-Reducing Surfaces." Such coatings may include one or more hydrophilic surfaces, one or more hydrophobic surfaces, and/or one or more surfaces that are engineered to physically repel water or other biological molecules.

Alternatively, a sleeve surface or surface coating may be a metallic nano-powder using, for example, an inert gas condensation method. This involves vaporizing the base metal in an inert gas atmosphere, after which it is deposited as a powder and then directly processed. With this method, minimal quantities of silver are sufficient to achieve the desired antibacterial properties of the powder due to its nanostructure. The nanosilver can be used to coat the surfaces of medical devices in the production process, which helps to decrease or even avoid the use of antibiotics.

Chemical nanotechnology can also be used for coating sleeve surfaces. Such self-cleaning surfaces include those with antibacterial properties. Numerous different materials, such as metal, glass, and plastics can be coated in this way. The thin, nanoporous layer also allows a great freedom of choice in terms of the shapes that can be coated.

In another embodiment, an anti-hyperplasic agent such as, for example, poly(L-lysine)-graft-poly(ethyleneglycol) (PLL-g-PEG) adsorbed to sleeve surfaces may be used to reduce neointimal hyperplasia or other blood vessel surface hyperplasia (see Billinger et al., "Polymer stent coating for prevention of neointimal hyperplasia," J. Invasive Cardiol. 2006 September; 18(9):423-6).

In some embodiments, a coating may be applied in a perioperative procedure, for example, as described in U.S. patent publication US 2005/0037133 A1, entitled "Method for applying drug coating to a medical device in surgeon room."

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve having at least one of a polytetrafluoroethylene surface, a barbed surface, a metal surface, a silicon surface, or a hydrogel surface. Alternatively, the custom-fitted blood vessel sleeve 700 may be a blood vessel sleeve that is custom-fitted for the blood vessel at least partly based on anatomical blood vessel data 120 from the individual 118, the blood vessel sleeve having at least one of a GoreTex, Teflon, or titanium alloy surface.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve having a substantially mesh structure. Such a mesh structure is common in stent manufacture, allowing for expandability of the stent to a maximum limit.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve capable of shrinking to fit the blood vessel. Such a blood vessel sleeve may be made of a material with known shrinking or contraction properties in an aqueous environment such as is found in and around the vasculature, so that placement of the sleeve on a portion of a blood vessel will be accompanied by wetting of the sleeve material and shrinking of the material by a known amount, to fit the blood vessel. Examples of materials known to shrink upon insertion into an aqueous body environment include fabrics, especially when exposed to hot water. Other materials may shrink upon the attainment of body temperature, such as certain rubber materials as described in U.S. Pat. No. 6,221,447. Alternatively, elastic materials such as elastomeric polymers may be used to form the custom-fitted blood vessel sleeve 700. Such elastic materials, once tailored to closely fit the blood vessel 300, may have the added benefit of expanding and contracting with the blood vessel wall as the blood vessel diameter changes in response to temperature, vasoconstrictors, vasodilators, or other agents or situations that cause constriction and/or dilation of blood vessels. It should be understood that portions of a custom-fitted blood vessel sleeve 700 that are fitted to an aneurysm portion of a blood vessel may be specified to have limited expansion parameters so as to prevent rupture of the aneurysm. Accordingly, a portion of a custom-fitted blood vessel sleeve 700 may be made of stretchable material, whereas another portion of the custom-fitted blood vessel sleeve 700 may be made of non-stretchable material or material with limited expansion parameters.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve capable of expanding to fit the blood vessel. Materials known to expand in aqueous environments may also be used to make a custom-fitted blood vessel sleeve 700. Such materials include water-swellable materials (e.g., starch, gelatin, chitin, gum Arabic, xanthan, cross-linked albumin, cross-linked hyaluronan, and/or alginate. Other examples of water-swellable materials include collagen, cellulose derivatives, cross-linked poly(vinyl alcohol) and copolymers, cross-linked poly(vinylpirrolidone) and copolymers, poly(hydroxyethyl methacrylate), poly(ethylene glycol) and copolymers, polyacrylate, polyacrylate-co-starch, polyacrylate-co-polyacrylamide, polyacrylamide. Other water-swellable materials known to one of skill in the art may be used. For example, the hydrophilic polyurethanes and the like of U.S. Pat. No. 4,872,867; the water-swellable plastic polymers of U.S. Pat. Nos. 5,163,952 and 5,258,020; the solid absorbents of U.S. Pat. No. 5,554,180, such as copolymers of cellulose and starch, agar and polymeric acids; the water-swellable matrix materials of U.S. Pat. No. 4,460,642; and/or the water-swellable layers of U.S. Pat. Nos. 4,496,535 and 4,872,867 may be used. As described above, elastic materials such as elastomeric polymers may be used to form the custom-fitted blood vessel sleeve 700. Such elastic materials, once tailored to closely fit the blood vessel 300, may have the added benefit of expanding and contracting with the blood vessel wall as the blood vessel diameter changes in response to temperature, vasoconstrictors, vasodilators, or other agents or situations that cause constriction and/or dilation of blood vessels.

In another embodiment, the custom-fitted blood vessel sleeve 700 may be a blood vessel sleeve that is custom-fitted for a blood vessel at least partly based on anatomical blood vessel data from an individual, the blood vessel sleeve being made up of two or more modules. For example, a custom-fitted blood vessel sleeve 700 may be specified to fit a blood vessel trifurcation with an aneurysm at a blood vessel branch area, in which the custom-fitted blood vessel sleeve 700 is made up of sub-parts or modules that can be assembled, for example, during a surgical procedure to form a complete custom-fitted blood vessel sleeve 700.

In another embodiment, the custom-fitted blood vessel sleeve 700 may be a blood vessel sleeve that is custom-fitted for the blood vessel at least partly based on computer-generated anatomical blood vessel data 120 from the individual 118. Frequently, an individual 118 with a vascular health issue will be subject to evaluation by, for example, a diagnostic health care provider 116 such as a radiologist operating medical imaging equipment that provides computer-generated anatomical blood vessel data 120. Such medical imaging may include magnetic resonance imaging (MRI scanning), computed tomography or computed axial tomography (CT scanning), positron emission tomography (PET scanning), and/or angiography. For example, a CT scan of an individual's head may provide a large series of two-dimensional images of a cross-section of the head where digital geometry processing is used to generate a three-dimensional image based on the large series of two-dimensional images. CT scanning typically produces a volume of data pertaining to the individual 118 that can be manipulated through a process known as windowing to produce an image of various internal structures based on their ability to block an x-ray beam. Other methods of visualizing blood vessel anatomy may also be used. Such a three-dimensional image, for example, provided by a CT scan process may provide anatomical blood vessel data 120, e.g., dimensions, from which a custom-fitted blood vessel sleeve may be specified.

In another embodiment, the custom-fitted blood vessel sleeve 700 may be a blood vessel sleeve that is custom-fitted for the blood vessel at least partly based on a three-dimensional anatomical model of the blood vessel from the individual 118. As noted above, an imaging system 114 often provides two-dimensional geometric images of a cross-section of an individual's anatomy (e.g., two-dimensional anatomical blood vessel data 120) and/or three-dimensional anatomical blood vessel data 120. Such anatomical blood vessel data 120 may be converted into a three-dimensional anatomical model by a three-dimensional modeling unit 104 operable on a device 102, or by software known in the art operable on a remote device. Examples of such software include amira 4 software from Mercury Computer Systems, which describes the amira 4 software as automatic and interactive segmentation tools that support rapid processing of 3D image data. Mercury Computer Systems further states that graphics hardware is efficiently utilized to display large datasets at interactive speed with unmatched image quality.

Amira 4-supported file formats include, for example, Digital Imaging and Communications in Medicine (DICOM), which is a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, servers, workstations, printers, and network hardware from multiple manufacturers into a picture-archiving and communication system. The different devices come with DICOM conformance statements which clearly state the DICOM classes they support. DICOM has been widely adopted by hospitals and is making inroads in smaller applications like dentists' and doctors' offices. Other amira 4-supported file formats include, for example, JPEG image format, BMP image format, Raw data, TIFF image format, HTML, VRML, Catia4, and Catia5.

Amira 4 features include, for example, data manipulation and filtering, surface rendering, volume rendering, and data analysis to quantify densities, distances, areas, and volumes. Other features include, for example, advanced polygonal models, time-dependent data, fusion and alignment of multiple datasets, flow simulation within a 3D model, image segmentation, and surface reconstruction. The software supports reconstruction and analysis of vascular, dendritic, and fracture networks. The amira Skeletonization Pack combines specific micro-detailed image mosaics management with advanced automatic and semi-automatic tools for reconstruction of a 3D vessel network from confocal microscopy or synchrotron image acquisition.

Another three-dimensional modeling program that is commercially available is 3D-Doctor, made by Able Software Corp. 3D-Doctor is described as an advanced 3D modeling, image processing and measurement software for MRI, CT, PET, microscopy, scientific, and industrial imaging applications. 3D-Doctor is capable of exporting polygonal mesh three-dimensional models to STL (ASCII and Binary), DXF, IGES, 3DS, OBJ, VRML, PLY, XYZ and other formats for surgical planning, simulation, quantitative analysis, finite element analysis (FEA) and rapid prototyping applications. Using the program, one can calculate 3D volume and make other 3D measurements for quantitative analysis. 3D-doctor is approved by the FDA's 510k clearance for medical imaging and 3D visualization applications. 3D-Doctor supports both grayscale and color images stored in DICOM, TIFF, Interfile, GIF, JPEG, PNG, BMP, PGM, RAW or other image file formats. 3D-Doctor can create 3D surface models and volume rendering from 2D cross-section images in real time on a computer.

Accordingly, in another embodiment, the custom-fitted blood vessel sleeve 700 may be a blood vessel sleeve that is custom-fitted for the blood vessel at least partly based on a three-dimensional anatomical model of the blood vessel data from the individual, the three-dimensional anatomical model of the blood vessel from the individual at least partly derived from at least one of computed tomography data, magnetic resonance imaging data, positron emission tomography data, ultrasound imaging data, optical imaging data, or angiography data.

In a further embodiment, the custom-fitted blood vessel sleeve 700 may be a blood vessel sleeve that is custom-fitted for the blood vessel at least partly based on a three-dimensional anatomical model of the blood vessel from the individual, the three-dimensional anatomical model of the blood vessel from the individual at least partly derived from at least one of computed tomography angiography data, magnetic resonance angiography data, or Doppler ultrasound data.

Computed tomography angiography (CTA) is a medical imaging technique that uses x-rays to visualize blood flow in arterial and venous vessels throughout the body, from arteries serving the brain to those bringing blood to the lungs, kidneys, and arms and legs. CTA combines the use of x-rays with computerized analysis of the images. Beams of x-rays are passed from a rotating device through the area of interest in the patient's body from several different angles to create cross-sectional images, which then are assembled by computer into a three-dimensional picture of the area being studied. Compared to catheter angiography, which involves placing a sizable catheter and injecting contrast material into a large artery or vein, CTA is a much less invasive and more patient-friendly procedure-contrast material is injected into a small peripheral vein by using a small needle or catheter.

Magnetic resonance angiography (MRA) is an MRI study of the blood vessels. It utilizes MRI technology to provide detailed images of blood vessels without using any contrast material, although a paramagnetic contrast material such as gadolinium is often given to make the MRI images even clearer. MRA may also use a technique known as flow-related enhancement (e.g., 2D and 3D time-of-flight sequences), in which most of the signal on an image is due to blood which has recently moved into that plane. MRA may also use fast low angle shot magnetic resonance imaging (FLASH MRI).

For example, the Human Arterial Tree Project, which has a website at http://www.cfm.brown.edu/crunch/ATREE/index.html, has applied high performance computing to create three-dimensional models of portions of human arterial anatomy, such as arterial branches and the heart. The Project has developed a series of software tools that allows for the reconstruction of arterial geometry for use with the software program Nektar, a research code that is based on the spectral/hp element method developed by Karniadakis and Sherwin. It employs an unstructured finite element mesh with a spectral expansion within each element. Resolution can be increased by increasing the polynomial order (p-type refinement) of the element or by increasing the number of elements (h-type refinement). Discretization for complex geometries is efficient and achieves global spectral accuracy. A stiffly stable time stepping scheme is utilized with temporal accuracy up to third-order. Nektar is freeware and is being used by several research teams around the world.

Geometric data may be acquired, for example, by MRA and/or CT, possibly combined with injection of a contrast agent into the arteries. These are widely used approaches for accurate and non-invasive acquisition of arterial geometric structure. For example, the Human Arterial Tree Project used images of cross-sectional slices acquired by a GE LX Signa Echospeed version 9.1 MRI scanner. Acquired images can then be used to extract the contours of arteries of interest, for example, from an unrefined or refined color intensity matrix. For example, a sub-region of the artery can be interpolated onto a finer mesh where the actual contour extraction is performed. This permits sub-pixel resolution to better capture the arterial geometry. Arterial walls can be constructed by interpolating data that represent the region between extracted contours. Due to the relatively low resolution of CT and MRA images, a rough surface of the arterial wall may first be obtained, followed by a computational, alternative bi-directional smoothing process in which each contour is smoothed in the azimuthal and axial directions. This data can then be input into a series of scripts and imported into, for example, Gridjen, a commercially available mesh generator (Pointwise, Inc., Fort Worth, Tex.), to create a three-dimensional mesh representation of a portion of a blood vessel.

Elements created by mesh-generating programs such as Gridgen have flat faces. Representation of curved boundaries can be achieved by projection of element faces on the blood vessel walls. Parametric representation of arterial walls, saved in plot3D format and used for mesh generation, allows for consistent mapping of a grid from computational to physical space. Such a process has been used by the Human Arterial Tree Project to create a three-dimensional geometric model of the internal carotid artery (ICA) and an associated aneurysm. The model was constructed from 3D CTA data from a patient at Rhode Island Hospital. The model captures the curved surfaces of the blood vessels and bifurcation of the ICA into anterior communicating artery 914 and anterior cerebral artery 910.

Such a computed three-dimensional anatomical model may be used by the device 102 as a basis for custom-fitting a blood vessel sleeve to a blood vessel. As in the use of garment-fitting algorithms in which body dimensions are used to model a person to fit clothing to the person, sleeve-fitting algorithms may be used to fit a blood vessel sleeve to a blood vessel. For example, the device 102 and/or sleeve-fitting unit 106 can extract two or more sets of anatomical blood vessel data 120, each data set defining a contour of a blood vessel at least partly based on blood vessel data pertaining to an individual 118; and the sleeve-fitting unit 106 can interpolate data representing one or more regions between two or more extracted contours to define dimensions of a sleeve in the region between the two or more extracted contours. This process can then be repeated by the sleeve-fitting unit 106 until the dimensions of an entire sleeve are specified.

In another embodiment, the device 102 and/or sleeve-fitting unit 106 may scale a three-dimensional mesh model of a blood vessel by creating a transform matrix based on scale factors. The device 102 and/or sleeve-fitting unit 106 can multiply each point in the mesh model by the transform matrix. The use of matrix transformations to rotate, translate, and scale points in a three-dimensional space are well known in the apparel arts, as described in U.S. Pat. No. 5,850,222. In this way, a sleeve may be modeled after the blood vessel according to precise specifications.

In another embodiment, the device 102 and/or sleeve-fitting unit 106 can extract two or more sets of anatomical blood vessel data 120 that correspond to contours of a blood vessel at least partly based on at least one of a light intensity matrix or a color intensity matrix.

Fitting a sleeve to a blood vessel may be accomplished by mapping dimensions of a sleeve to the dimensions of a three-dimensional model of a blood vessel. In this way, the sleeve may be specified to fit the blood vessel as loosely or as tightly as deemed appropriate by a therapeutic health care provider 110, for example. Fitting a sleeve to a three-dimensional model can allow for a therapeutic health care provider 110 to closely fit a sleeve to the particular curvature, diameter and length, branching, and/or aneurysm dimensions of a blood vessel.

In another embodiment, a device 102 and/or sleeve-fitting unit 106 can apply a scaling factor to a three-dimensional model of a blood vessel such that sleeve dimensions or specifications are produced that are closely tailored to the blood vessel dimensions within a range of tolerance levels, for example, a percentage of the blood vessel dimensions.

Alternatively, the device 102 and/or sleeve-fitting unit 106 can assign a set of position coordinates to a three-dimensional model and assign counterpart position coordinates to a blood vessel sleeve model to produce blood vessel sleeve dimensions that fit the blood vessel.

In an alternate embodiment, the device 102 and/or sleeve-fitting unit 106 can produce sleeve specifications based on best fit criteria. In one embodiment, the best fit criteria may include specified cross-sectional dimensions. In another embodiment, the specified cross-sectional dimensions may be based on actual cross-sectional-dimensions represented by the blood vessel data. In yet another embodiment, the specified cross-sectional dimensions may be based on actual cross-sectional dimensions represented by the blood vessel data and based on tolerance criteria, e.g., 1%, 2%, 5%, or 10% variation in sleeve dimension relative to actual cross-sectional dimensions.

Various garment-fitting algorithms may be adapted to use in custom-fitting a blood vessel sleeve. For example, known garment-fitting methods such as those disclosed in U.S. Pat. Nos. 5,163,007, 5,850,222, and/or U.S. patent publication US 2004/0093105 may be employed by the sleeve-fitting unit 106 to produce custom blood vessel sleeve specifications.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve further having one or more closure means. Such closure means will ensure that the blood vessel sleeve will stay in place around the blood vessel after placement to perform its function of, for example, supporting the weakened wall of a blood vessel with an aneurysm. Examples of closure means structure include extensions positioned for closure, suturing tabs, detents, hooks, Velcro, interlocking closure ridges, glue, or the like.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve further having one or more of extensions positioned for closure, suturing tabs, detents, hooks, Velcro, glue, or interlocking closure ridges.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve being one of a set of blood vessel sleeves. Such a set of blood vessel sleeves may be made perioperatively for use by a health care provider 110 who may want the option of having a series of different-sized sleeves for use on a patient's blood vessel during a surgery to address, for example, an aneurysm.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve being one of a set of blood vessel sleeves that each has at least one of different dimensions, a different material composition, or a different coating. Again, such a set of blood vessel sleeves may be made perioperatively for use by a therapeutic health care provider 110 who may want the option of having sleeves of varying composition, dimensions, and/or coating. The therapeutic health care provider 110 may, upon viewing surgically the actual blood vessel to be addressed, make a judgment on the spot to select a certain size or kind of sleeve depending on potential differences between the results of medical imaging and first hand observation of the blood vessel.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve being one of a set of blood vessel sleeves that each has at least different closure extensions.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve being one of a set of blood vessel sleeves of progressively increasing or progressively decreasing size.

In another embodiment, the custom-fitted blood vessel sleeve 700 may be a blood vessel sleeve that is custom-fitted for the blood vessel at least partly based on anatomical blood vessel data 120 from the individual 118, the blood vessel sleeve further having an indicator on the blood vessel sleeve. Such an indicator may aid the therapeutic health care provider 110 in, for example, tracking the blood vessel sleeve during surgery. An indicator may include a text label or numerical information, or an indicator may be a symbol or code that represents other information. Alternatively, the indicator may be a radio-frequency identification device (RFID) that contains information about the sleeve and/or the patient receiving the sleeve.

In another embodiment, the indicator on the custom-fitted blood vessel sleeve 700 may be an indicator corresponding to a size of the blood vessel sleeve. For example, where a series of different-sized sleeves is produced by rapid-prototyping, an indicator of size will aid the therapeutic health care provider 110 in choosing the correct sleeve. Similarly, the indicator on the custom-fitted blood vessel sleeve 700 may be an indicator corresponding to a material thickness of the blood vessel sleeve. Alternatively, the indicator on the custom-fitted blood vessel sleeve 700 may be an indicator corresponding to a material stiffness of the blood vessel sleeve. Or, the indicator on the custom-fitted blood vessel sleeve 700 may be an indicator corresponding to a material type of the blood vessel sleeve.

In another embodiment, the indicator on the custom-fitted blood vessel sleeve 700 may be an indicator corresponding to individual-characterizing data. Examples of individual-characterizing data may include name, social security number, and/or medical history information. Alternatively, the indicator on the custom-fitted blood vessel sleeve 700 may be an indicator corresponding to at least one of a time or a date.

In another embodiment, the indicator on the custom-fitted blood vessel sleeve 700 may be an indicator relating to a color coding of the blood vessel sleeve. As a rapid-recognition feature, color coding would allow a therapeutic health care provider 110 to quickly identify a particular feature of a custom-fitted blood vessel sleeve 112. In another embodiment, the color coding of the custom-fitted blood vessel sleeve 700 may be a color coding corresponding to patient data. In another embodiment, the color coding of the custom-fitted blood vessel sleeve 700 may be a color coding corresponding to at least one of material type, material thickness, material stiffness, sleeve size, thickness of the blood vessel sleeve, or sleeve coating.

In another embodiment, a custom-fitted blood vessel sleeve 112 may include a blood vessel sleeve that is custom-fitted for the blood vessel at least partly based on anatomical blood vessel data 120 from the individual 118, the blood vessel sleeve further having at least one contrast agent within the material of the blood vessel sleeve. Doping, impregnating, embedding, or otherwise placing a contrast agent within the material composition of a custom-fitted blood vessel sleeve 112 may enhance medical imaging of the sleeve subsequent to its placement on or within a blood vessel in an individual 118. This may be useful for short-term and/or long-term follow-up of the functioning of the custom-fitted blood vessel sleeve 112 in the individual 118. For example, a sleeve containing a paramagnetic material such as gadolinium or $Mn^{++}$ will appear in MRI-scanned images, and a sleeve containing iodine will appear in CT-scanned images. A custom-fitted blood vessel sleeve 112 may contain, for example, multiple contrast agents to facilitate detection of the sleeve by a number of different imaging methods.

In another embodiment, a custom-fitted blood vessel sleeve 112 may include a blood vessel sleeve that is custom-fitted for the blood vessel at least partly based on anatomical blood vessel data 120 from the individual 118, the blood vessel sleeve further having at least one indicator of deformation or wear. For example, the custom-fitted blood vessel sleeve 112 may have visible grid or otherwise detectable grid of perpendicular lines on its surface, such that upon deformation or wearing of the sleeve, the right angles of the grid change to acute or obtuse angles in the area of wear or deformation. The degree and/or rate of wear and/or deformation may thus be apparent from an imaging or inspection of the indicator of deformation or wear after a period of time.

A custom-fitted blood vessel sleeve 112 may be made by rapid-prototyping in a perioperative scenario in which, for example, a therapeutic health care provider 110 obtains anatomical blood vessel data 120 from an individual 118 via an imaging system 114; using a device 102, three-dimensional modeling unit 104, and/or sleeve-fitting unit 106, the therapeutic health care provider 110 may then operate a sleeve-making device 108 to produce a custom-fitted blood vessel sleeve 112. This production of a custom-fitted blood vessel sleeve 112 may be carried out by a rapid-prototyping device, by, for example, automated two-dimensional laser-cutting of fabric or three-dimensional printing.

Accordingly, custom-fitted blood vessel sleeve 700 may be a blood vessel sleeve that is custom-fitted for the blood vessel at least partly based on anatomical blood vessel data 120 from the individual 118, the blood vessel sleeve further consisting essentially of laser-cutting device output. Alternatively, the custom-fitted blood vessel sleeve 700 may be a blood vessel sleeve that is custom-fitted for the blood vessel at least partly based on anatomical blood vessel data 120 from the individual 118, the blood vessel sleeve further consisting essentially of three-dimensional printer output.

Rapid-prototyping may include additive fabrication, three-dimensional printing, solid freeform fabrication, and/or layered manufacturing. With rapid-prototyping, objects can be formed with any geometric complexity or intricacy without the need for elaborate machine setup or final assembly; and objects can be made from multiple materials, as composites, and/or materials can be varied in a controlled fashion at any location in an object.

Examples of known rapid-prototyping devices and methods may include use of a stereolithography apparatus, which uses a UV laser to trace a cross-section of the product model layer by layer across the top of a vat of liquid polymer. This then hardens a thin layer of the material. As each layer is traced, the object is lowered slightly for the laser to trace the next cross-section of the object in the polymer, solidifying that layer and bonding it to the previous layer. This is done layer by layer until the object is formed. Another method is selective laser sintering, which uses a laser to fuse (i.e., sinter) a thin layer of powdered material into a solid object. After each layer is completed, a thin layer of the powdered material is spread across the top for the fusing of the next layer. This is a good method for fine detail and thin-walled parts.

Another rapid-prototyping method is fused deposition modeling, which uses a temperature-controlled head to extrude and deposit thermoplastic material based on computer-aided drafting (CAD) cross-section slices. The material starts in a semi-liquid state, bonds to the previous solid layer, and then hardens. Another method is solid ground curing, which prints each CAD cross-section slice on a glass photomask using a electrostatic process like a photocopier. An ultraviolet light shines through the mask onto a thin layer of polymer, hardening the exposed resin. Residual liquid resin is vacuumed off and a liquid wax is spread onto any spaces. This layer is cooled to a solid and then milled to thickness. Repeating the process with the next layer builds up the part.

Laminated object manufacturing starts with a thin layer (4 to 8 millimeters) of sheet material and uses a laser to cut a first CAD pattern based on a cross-section. A blank sheet backed with a dry adhesive is then rolled across the cut layer and heat-bonded. The cutting process begins again on that sheet. This process builds parts with relatively thick walls.

Inkjet Technology deposits tiny droplets of hot liquid thermoplastic in a desired pattern, layer by layer. Droplets of material may generate a support structure that is later melted away, dissolved or physically removed.

Direct shell production casting produces ceramic casting molds for metal casting using a layered printing process depositing a liquid binder onto a layer of ceramic powder. After the mold is "printed," it is then fired. These molds will handle any metal and are more accurate than those made from sand casting.

Direct metal deposition uses a CNC laser to fuse layers of metal powder. The resulting prototypes made from H13 tool steel, aluminum and other metals are suitable for use in production.

Precision metal deposition, or PMD, flat wire metal deposition technology uses an energy source such as a laser, to fuse a solid metal flat wire to a substrate.

3D Printing is a term that describes several similar technologies for machines that often operate in an office-like setting. An inkjet system may be used to print glue onto layers of loose ceramic (alumina) powder to build casting molds or appearance models. A liquid binder material with powdered metal may also be printed.

Rapid-prototyping can produce sleeves made of, for example, thermoplastics and eutectic metals (fused deposition modeling), photopolymer (stereolithography and multi-jet modeling), paper (laminated object manufacturing), Titanium alloys (electron beam melting), and various polymers and other materials (3D Printing).

Automated fitting systems and rapid-prototyping systems have been developed in the textile and apparel industry. For example, the clothing industry has developed body scanners that perform body imaging functions that are similar to the medical imaging functions of medical imaging devices. According to the clothing industry, because an image of the body is captured during the scanning process, the location and description of the measurements can be altered as needed in mere seconds. Also, the measurements obtained using this technology have the potential of being more precise and reproducible than measurements obtained through the physical measurement process. Further, with the availability of an infinite number of linear and non-linear measurements the possibility exists for garments to be created to mold to the 3 dimensional shapes of unique human bodies. Finally, body-scanning technology allows measurements to be obtained in a digital format that can integrate automatically into apparel CAD systems without the human intervention that takes additional time and can introduce error. These benefits from the apparel industry may be applied to the specification and manufacture of custom-fitting blood vessel sleeves as well.

Textile or apparel systems for clothing specification and/or rapid production include the following examples. Assyst/Bullmer, Inc. has an array of products that have been developed to support rapid product creation. Product functions include pattern making and grading; sketching, design, and draping; automated pattern making; automated marker making; data conversion and exchange; sewing plan generation; cut order planning; plotting, milling, and routing; automated material handling; automated fabric spreading; and automated material cutting.

Cad.assyst from Assyst/Bullmer, Inc. is an apparel pattern development and modification software program. It includes software for pattern design, grading, and marker making/nesting. The system enables one to digitize patterns into the system, or create pattern pieces directly on a display, grade them, and create markers. With this program, many pattern pieces can be worked on simultaneously, without restrictions. One feature is pattern dependency that allows any changes made on a source pattern to also occur on the patterns created from it. Macros can be easily created for repetitive tasks, such as the addition of seam allowances, the creation of facings, and the placement of buttons and buttonholes. Piece and grading information can be imported from Gerber, Lectra, PAD, or any other program that can export using the AAMA .dxf file format. Such a system may be developed for specifying a custom blood vessel sleeve, such that a sleeve pattern may be created based on anatomical blood vessel data 120 from an individual 118. Such a blood vessel sleeve pattern may be manipulated in an electronic system to achieve desired measurements and/or manufacturing specifications.

One can grade using standard x/y and distance grading within rule tables. Or one can perform visual, direct modifications to pattern shapes on individual sizes. Modifications are automatically recorded in the grade table and there are no size display limitations. Piece grading is automatically recalculated whenever a piece is modified, scaled, mirrored, rotated, or split. Using the flexible measure grading function, one can measure and compare the graded lines and curves of multiple pieces. Accordingly, a blood vessel sleeve pattern based on anatomical blood vessel data 120 from an individual 118 may be graded according to the judgment of a therapeutic health care provider 110 or other health care provider.

With cad.assyst, a seam allowance feature supports all pattern design and production process requirements. Any change of the piece design contour will automatically adjust the seam and hem lines. Seams can be hidden while modifying or grading pieces. Also, the pleat functionality supports all known pleat variations in the apparel industry. One can modify pattern pieces with open or closed pleats. Accordingly, seam and/or pleat characteristics of a custom-fitted blood vessel sleeve 800 may be specified and/or manufactured according to the above known functions of the apparel industry.

A dart feature allows one to reposition and make modifications to the piece contour whether the dart is open or closed. Hatching allows one to develop sewing plans, which can be sent to individual production facilities and to external information systems. A stitch-counting feature supports the development of pattern data for flat-form knitting. This function calculates for each size the x/y number of knits with recognition of the shrinkage factor. The information is exported in an interface file and can be transferred to known stitching machines. A grade line allows grading of any created curve or line in the pattern piece. Such grading may be useful in making a set of custom-fitted blood vessel sleeves of varying dimensions for use by a therapeutic health care provider 110 or other health care provider in an operative setting or a perioperative setting. In such an instance, as discussed above, a health care provider 224 may select an appropriate custom-fitted blood vessel sleeve 406 from among a set of custom-fitted blood vessel sleeves 506, according to an actual view of a blood vessel to be addressed or other anatomical features of an area proximate to an affected blood vessel. For example, to minimize frictional contact of a custom-fitted blood vessel sleeve 406 with a nearby organ, blood vessel, or other structure, a therapeutic health care provider 110 or other health care provider may select a custom-fitted blood vessel sleeve that is, for example, thinner along one axis, shorter along one axis, and/or composed of a different material in a certain portion of the sleeve.

Smart.pattern is a program that is a modification tool rather than a construction tool. The purpose of this software is to automate work done repeatedly by creating macros that are organized by type of activity. Compound macros can also be created to work together. The system has 500 pre-defined modules that can be used to easily create a background macro. After training, a user can create her own modules for activities not initially covered. Leonardo is a program for managing made-to-measure or custom products. The system is made up of three parts that recreate a specific pattern based on defined measurements. This program affords faster specification of garments made from different combinations of body measurements. Such a system may be applied to modifying custom-fitted blood vessel sleeve patterns once created based on anatomical blood vessel data 120 from an individual 118.

Gerber Technology's PDS 2000 allows the user to move multiple lines at once, in the same direction, or in reverse, as desired. The system can also remember where pieces were on the screen when they were saved so that they can return to that position when recalled. Multiple pieces can be selected at one time using the marquis function. Pieces can also come into the work area in a full-scale view. This allows patterns to be created or refined in less time. Accordingly multiple custom-fitted blood vessel sleeves may be specified concurrently.

APDS 3D is software from Asahi that allows a virtual try-on of garments created in PDS 2000. This system comes with a variety of dress forms—men's, ladies', children's, Juniors, and with legs—all of which can be altered by the user, to some degree. An ease table is built into the system, which allows fabric drape to be demonstrated based on Kawabata values. Essentially, this software allows the user to drape 2D patterns on-screen and make pattern revisions, check new designs and graded patterns on a virtual drape model, and input fabric design to create a virtual sample. Such a system adapted for use with a custom-fitted blood vessel sleeve specification system can model a custom-fitted blood vessel sleeve over a virtual blood vessel to simulate fit of the custom-fitted blood vessel sleeve.

INVESTRONICA SISTEMAS has introduced a 3D system from an alliance with Toyobo called Dressing Sim FDK. This system acts as a virtual try-on of garments created through the Pattern Generation System (PGS). The user will import a body form, import a pattern created in PGS, and import pattern characteristics. After lining each garment piece up to the body, it can be evaluated from each side of the body. Once properly aligned, the garment will be virtually seamed together. Fabric variations can be applied to simulate fabric drape and relaxed to conform to the body. As above for the APDS 3D software, such a system adapted for use with a custom-fitted blood vessel sleeve specification system can model custom-fitted blood vessel sleeve patterns over a virtual blood vessel to simulate fit of the custom-fitted blood vessel sleeve.

Another product is the 3D-Design system, which has 50 to 60 body shapes to cover a wide range of ages, sizes, and shapes of people. The user will also have the ability to change the measurements of the key dimensions, as desired. INVESTRONICA handles the issue of ease in their Body Garment 3D Design system by allowing the user to define the specific amount of ease desired in specific locations. Once the ease layer has been defined, the designer will be able to draw design lines on the 3 dimensional form. These lines will then be used to identify pattern shapes that will be flattened to 2D for export into their PGS system. Such a system adapted for use with a custom-fitted blood vessel sleeve specification system can model a custom-fitted blood vessel sleeve, including layers in the case of multiple-layered sleeves.

3D Sample software allows a two-dimensional set of patterns to be placed on a 3D form that is the correct size for a virtual try-on of the virtually sewn garment. The user can also create a technical drawing of the garment, export it to Adobe Illustrator and/or a pattern file. If the garment is too small to fit correctly, body parts will show through. Such a virtual try-on system can also be adapted to a custom-fitted blood vessel sleeve specification system such that a sleeve fitted to a blood vessel can be visualized in order to, for example, select the correct size of sleeve.

Many CAD systems used in apparel pattern-making have some method that enables pattern alterations based on individual measurements. Many, including those from Gerber Technologies, Lectra Systems, Investronica, and Assyst, have three preparational activities in common that allow automatic alterations to be made. These preparational activities allow the automatic alteration of existing garment patterns. This set of activities requires a knowledge of garment design, grading, and garment construction, as well as an understanding of computer programming. Developers have been working to integrate measurements extracted from three-dimensional body scanners in the garment specification process. Such expertise can be adapted for use with a custom-fitted blood vessel sleeve specification system to model a custom-fitted blood vessel sleeve.

In one embodiment, an alteration rule table can be created, as is done with the Gerber Accumark system. Such an alteration rule table can be created according to how the structural lines of the garment should move based on the difference between actual body measurements of the subject and the physical measurement upon which the sizing grade was based at key locations. Key measurement locations for a fitted shift, for example, include the bust, waist, hip, backwaist length, and waist height. Alteration rules can be created much like grade rules in that the grading movement may be significant to the orientation of the pattern piece on the computer screen. As adapted to a custom-fitted blood vessel sleeve specification system, blood vessel measurements such as diameter, curvature, branching, aneurysm dimensions, or the like can be applied to an alteration rule table according to how the structural lines of the sleeve should move based on known movement of the blood vessel during systole and diastole, or based on simulated movement of the blood vessel during various blood circulation events.

Once a garment is graded and prepared for alteration, the accuracy of the alteration decisions can be evaluated. To do this, the garment is often compared to a three-dimensionally scanned body of a test subject. This can be done by extracting the key measurements needed for each garment, and physically inserting those measurements within the size code tables in, for example, the Gerber Accumark System. A customized marker can be made for each garment using the grade rule, alteration, and size code tables developed. The garments can then be fit-tested on a test subject. A similar process may be performed by the sleeve-fitting unit 106 in comparing a custom-fitted sleeve, custom-fitted sleeve pattern, or standard sleeve pattern to a three-dimensionally scanned blood vessel of an individual 118. The sleeve-fitting unit 106 may then extract the key measurements needed for the custom-fitted blood vessel sleeve and insert the extracted measurements within a size table. A customized marker can then be made for each sleeve using grade rule, alteration, and size code tables.

Similarly, a custom-fitted blood vessel sleeve may be specified based custom-fitting techniques, grade rules, and/or alteration rules such as those that have been developed and used in the field of garment specification, described above. Just as clothing makers can specify a tailored joining of a body tube of a specific proportion for an individual 118 with sleeve tubes of a specific proportion for the individual, a device 102 and/or sleeve-fitting unit 106 can join, for example, a sleeve portion corresponding to the specific anatomy of a blood vessel 400 with a sleeve portion corresponding to the specific anatomy of a blood vessel branch 404 together with the juncture where the two meet and any specific aneurysm anatomy that may be present on the blood vessel 400 and/or blood vessel branch 404.

Similarly, a custom-fitted blood vessel sleeve 406 may be specified that is capable of fitting a complex blood vessel junction. For example, FIG. 9 illustrates the blood vessel anatomy of the Circle of Willis 900, a complex of arteries in the area of the inferior surface of the brain surrounding the pituitary gland where aneurysms are commonly found, and where a custom-fitted blood vessel sleeve 406 may be employed.

For example, a custom-fitted blood vessel sleeve 406 may be fitted to aneurysms 902 that are in proximity to each other on the internal carotid complex 908. Alternatively, a custom-fitted blood vessel sleeve 406 may be specified to fit aneurysms 906 near a trifurcation 912 in the region of the middle cerebral artery 916, or a four-way junction such as that near the anterior communicating artery 914 and the anterior cerebral artery 910. Alternatively, a custom-fitted blood vessel sleeve 406 may be specified to fit an aneurysm 904 near a five-way junction at the internal carotid complex 908. Accordingly, blood vessel sleeves may be specified to fit any blood vessel and/or aneurysm anatomy.

Further, known garment-fitting algorithms may be employed to alter a stock or standard blood vessel sleeve pattern to fit an individual's anatomy, based on specific anatomical blood vessel data 120 for the individual 118.

FIG. 10 illustrates the blood vessel anatomy of the abdominal aorta, similar to FIG. 6. In the embodiment of FIG. 10, a custom-fitted blood vessel sleeve 1002 has been placed on the interior aspect of the abdominal aorta to funnel bloodflow through the region affected by the abdominal aortic aneurysm 1000. Additionally, a distal portion of the custom-fitted blood vessel sleeve 1002 may be bifurcated to match the anatomy of the abdominal aorta at the junction of the aorta with the right and left common iliac arteries. Such an interior custom-fitted blood vessel sleeve 1002 may be placed within an affected blood vessel via a catheterization procedure, for example, via a femoral artery of the leg. In such cases, a collapsible custom-fitted blood vessel sleeve 1002 may be conveniently inserted into a catheter, guided to the affected portion of the abdominal aorta, and then expanded to fit, for example, the affected portion of the abdominal aorta.

FIG. 11 illustrates a portion of the blood vessel anatomy of the Circle of Willis, where a custom-fitted blood vessel sleeve 406 may be employed. In FIG. 11, a custom-fitted blood vessel sleeve 1102 has been placed on the interior aspect of the junction of the anterior communicating artery 1114 and the anterior cerebral artery 1110. Shown in FIG. 11 is an aneurysm 1104 at the junction; the custom-fitted blood vessel sleeve 1102 can be seen to block blood flow into the aneurysm 1104 from the inside of the anterior communicating artery 1114. Further, the branched nature of the custom-fitted blood vessel sleeve 1102 in this example may serve an anchoring function to help keep the custom-fitted blood vessel sleeve 1102 in place, in proximity to the affected portion of the anterior communicating artery 1114.

FIG. 12 illustrates an example system 1200 in which embodiments may be implemented. The system 1200 includes at least one device 1202. The at least one device 1202 may contain, for example, an anatomical blood vessel data mapping unit 1220, a three-dimensional modeling unit 1204, and/or a sleeve-fitting unit 1206. Imaging system 1214 may generate anatomical blood vessel data 120 from an individual 118, or anatomical blood vessel data 120 from an individual 118 may be obtained from a health record 122 that is external to the device 1202. Imaging system 1214 may be operated by diagnostic health care provider 1216 and/or therapeutic health care provider 1210 to obtain anatomical blood vessel data 120 from an individual 118.

Therapeutic health care provider 1210 may interact with the device 1202 to determine blood vessel sleeve specifications based on anatomical blood vessel data 120 from an individual 118. Therapeutic health care provider 1210 may also interact with sleeve-making device 1208 to obtain custom-fitted blood vessel sleeve 1212 based on anatomical blood vessel data 120 from an individual 118. Therapeutic health care provider 1210 may then employ the custom-fitted blood vessel sleeve 1212 to address a blood vessel of individual 118 in an open surgical procedure, in a laparoscopic surgery procedure, through a catheter insertion procedure, or the like.

In some embodiments, the imaging system 1214 and the device 1202 may be combined in a single device, or the imaging system 1214, the device 1202, and the sleeve-making device 1208 may be combined in a single device. In some embodiments the imaging system 1214 may be a portable imaging device 124 that can communicate with the at least one device 1202, on which the sleeve-fitting unit 1206 is operable, via a wireless network for example. In some embodiments, the sleeve-making device 1208 may be operable remotely through the device 1202 via, for example, a network connection.

In FIG. 12, the at least one device 1202 is illustrated as possibly being included within a system 1200. Any kind of computing device may be used in connection with the anatomical mapping unit 1220, three-dimensional modeling unit 1204 and/or sleeve-fitting unit 1206, such as, for example, a workstation, a desktop computer, a mobile computer, a networked computer, a collection of servers and/or databases, cellular phone, personal entertainment device, or a tablet PC.

Additionally, not all of the anatomical mapping unit 1220, three-dimensional modeling unit 104 and/or sleeve-fitting unit 106 need be implemented on a single computing device. For example, the anatomical mapping unit 1220 and/or three-dimensional modeling unit 1204 may be implemented and/or operable on a remote computer, while the sleeve-fitting unit 1206 and/or sleeve-making device 1208 is implemented and/or stored on a local computer. Further, aspects of the anatomical mapping unit 1220, three-dimensional modeling unit 1204, sleeve-fitting unit 1206, imaging system 1214, and/or sleeve-making device 1208 may be implemented in different combinations and implementations than that shown in FIG. 1. For example, functionality of the sleeve-making device 1208 may be incorporated into the device 1202. In some embodiments, the at least one device 1202 may process anatomical blood vessel data 120 from an individual 118 according to anatomical profiles available as updates through a health records network.

The anatomical blood vessel data 120 from an individual 118 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

FIG. 13 illustrates an operational flow 1300 representing example operations relating to methods and systems for specifying a blood vessel sleeve. In FIG. 13 and in following figures that include various examples of operational flows, discussion, and explanation may be provided with respect to the above-described examples of FIGS. 1-12, and/or with respect to other examples and contexts. However, it should be understood that the operational flows may be executed in a number of other environment and contexts, and/or in modified versions of FIGS. 1-12. Also, although the various operational flows are presented in the sequence(s) illustrated, it should be understood that the various operations may be performed in other orders than those which are illustrated, or may be performed concurrently.

After a start operation, operation 1310 shows accepting three-dimensional blood vessel data. The three-dimensional data may be accepted from an imaging system 114, portable imaging device 124, and/or from a three-dimensional modeling unit 104.

For example, the three-dimensional modeling unit 1204 of the device 1202 may receive anatomical blood vessel data 120, such as, for example, one or more health records 122 relating to an individual 118 and/or an individual 118's data from an imaging system 1214. For example, this may include a three-dimensional construct of two-dimensional image data from an individual's blood vessel, for example, from a CT scan. Alternatively, the three-dimensional blood vessel data may refer to a series of two-dimensional section images that together make up three-dimensional blood vessel data.

Operation 1320 depicts applying a sleeve-fitting algorithm to the three-dimensional blood vessel data. For example, the sleeve-fitting unit 1206, anatomical blood vessel data mapping unit 1220, and/or device 1202 may apply a scaling function to the three-dimensional blood vessel data to obtain specifications for a blood vessel sleeve that may, for example, fit a branched section of an artery that is afflicted with an aneurysm. Such a scaling function may not merely extrapolate from an available three-dimensional model of a blood vessel, but the scaling function may be used to, for example, constrict a portion of the blood vessel that is afflicted with an aneurysm (see FIG. 6B), while leaving another portion of the blood vessel unconstricted.

Operation 1330 depicts presenting a sleeve-fitting algorithm output in response to said applying the sleeve-fitting algorithm to the three-dimensional blood vessel data. For example, the sleeve-fitting unit 1206, anatomical blood vessel data mapping unit 1220, and/or device 1202 may send blood vessel sleeve dimensions as the sleeve-fitting algorithm output. Such blood vessel sleeve dimensions may be sent to a therapeutic health care provider 1210, or, for example, directly to a sleeve-making device 1208. Alternatively, the sleeve-fitting algorithm output may be stored in at least one memory in, for example, the device 1202. In this regard, it should be understood that the sleeve-fitting algorithm output may first be encoded and/or represented in digital form (i.e., as digital data), prior to the assignment to the at least one memory. For example, a digitally-encoded representation of the sleeve-fitting algorithm output may be stored in a local memory, or may be transmitted for storage in a remote memory.

Thus, an operation may be performed related either to a local or remote storage of the digital data, or to another type of transmission of the digital data. Of course, operations also may be performed related to accessing, querying, recalling, or otherwise obtaining the digital data from a memory, including, for example, receiving a transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

FIG. 14 illustrates alternative embodiments of the example operational flow 1300 of FIG. 13. FIG. 14 illustrates example embodiments where the accepting operation 1310 may include at least one additional operation. Additional operations may include operation 1400, 1402, 1404, 1406, 1408, and/or operation 1410.

Operation 1400 depicts receiving three-dimensional blood vessel data at a user interface. For example, diagnostic health care provider 1216, therapeutic health care provider 1210, health care provider 220, and/or health care provider 222 may access a user interface to receive three-dimensional blood vessel data from, for example, an imaging system 1214, a portable imaging device 124, a three-dimensional modeling unit 1204, and/or the device 1202. Three-dimensional blood vessel data may include, as discussed below, CT scan data, MRI data, three-dimensional modeling data, or the like.

Operation 1402 depicts accepting geometric blood vessel data as the three-dimensional blood vessel data. For example, the sleeve-fitting unit 1206, anatomical blood vessel data mapping unit 1220, three-dimensional modeling unit 1204, and/or device 1202 may accept, for example, a set of contiguous two-dimensional cross-sections of an individual's blood vessel anatomy, which, taken together, constitute three-dimensional blood vessel data. Such cross-sections are typical of, for example, CT scan output and MRI scan output.

Operation 1404 depicts accepting blood vessel imaging data as the three-dimensional blood vessel data. For example, the sleeve-fitting unit 1206, anatomical blood vessel data mapping unit 1220, three-dimensional modeling unit 1204, and/or device 1202 may accept, for example, three-dimensional data from any blood vessel imaging procedure, such as magnetic resonance imaging, angiography, ultrasound, radiography, optical imaging, or the like.

Operation 1406 depicts accepting at least one of magnetic resonance imaging data, computed tomography data, positron emission tomography data, ultrasound imaging data, optical imaging data, or angiography data as the three-dimensional blood vessel data. For example, the sleeve-fitting unit 1206, anatomical blood vessel data mapping unit 1220, three-dimensional modeling unit 1204, and/or device 1202 may accept, for example, anatomical blood vessel data 120 from an individual 118 from an imaging system 1214 and/or a health record 122 in the form of MRI scanner output or CT scanner output.

Operation 1408 depicts accepting at least one of magnetic resonance angiography data, computed tomography angiography data, Doppler ultrasound data, or cerebral angiography data as the blood vessel data. For example, the sleeve-fitting unit 1206, anatomical blood vessel data mapping unit 1220, three-dimensional modeling unit 1204, and/or device 1202 may accept, for example, anatomical blood vessel data 120 from an individual 118 from an imaging system 1214 and/or a health record 122 in the form of transcranial Doppler ultrasound data or magnetic resonance angiography data relating to a cerebral blood vessel aneurysm.

Operation 1410 depicts accepting blood vessel data in a digital imaging and communications in medicine format as the three-dimensional blood vessel data. For example, the sleeve-fitting unit 1206, anatomical blood vessel data mapping unit 1220, three-dimensional modeling unit 1204, and/or device 1202 may accept, for example, anatomical blood vessel data 120 from an individual 118 from an imaging system 1214 and/or a health record 122 in the form of CT scan data in a digital imaging and communications in medicine format (DICOM). Such a format is a standard for handling, storing, printing, and transmitting information in medical imaging. Supported modalities include, for example, angioscopy, color flow Doppler, computed radiography, duplex Doppler, digital subtraction angiography, fluorescein angiography, ultrasound, x-ray angiography, just to name a few. Of course imaging data in virtually any format may be accepted by the sleeve-fitting unit 1206, anatomical blood vessel data mapping unit 1220, three-dimensional modeling unit 1204, and/or device 1202.

FIG. 15 illustrates alternative embodiments of the example operational flow 1300 of FIG. 13. FIG. 15 illustrates example embodiments where the accepting operation 1310 may include at least one additional operation. Additional operations may include operation 1500, 1502, 1504, 1506, and/or operation 1508.

Operation 1500 depicts accepting blood vessel modeling data as the three-dimensional blood vessel data. For example, the sleeve-fitting unit 1206, anatomical blood vessel data mapping unit 1220, and/or device 1202 may accept, for example, a three-dimensional mathematical model of a blood vessel or a three-dimensional image model of a blood vessel, for example, from three-dimensional modeling unit 1204 or from health care provider 222.

Operation 1502 depicts accepting three-dimensional aorta data as the three-dimensional blood vessel data. For example, the sleeve-fitting unit 1206, three-dimensional modeling unit 1204, anatomical blood vessel data mapping unit 1220, and/or device 1202 may accept, for example, a three-dimensional model of the ascending aorta, aortic arch, descending aorta, thoracic aorta, and/or the abdominal aorta of an individual 118.

Operation 1504 depicts accepting three-dimensional cerebral artery data as the three-dimensional blood vessel data.

For example, the sleeve-fitting unit 1206, three-dimensional modeling unit 1204, anatomical blood vessel data mapping unit 1220, and/or device 1202 may accept, for example, three-dimensional blood vessel data relating to an internal carotid artery, anterior communicating artery, middle cerebral artery, or other artery of the Circle of Willis of an individual 118.

Operation 1506 depicts accepting three-dimensional aneurysm or branched blood vessel data as the three-dimensional blood vessel data. For example, the sleeve-fitting unit 1206, three-dimensional modeling unit 1204, anatomical blood vessel data mapping unit 1220, and/or device 1202 may accept, for example, three-dimensional CT scan data relating to a portion of a blood vessel with an aneurysm. For example, the aneurysm may be associated with the abdominal aorta, or close to a branch point in the Circle of Willis.

Operation 1508 depicts accepting a three-dimensional blood vessel model as the three-dimensional blood vessel data. For example, the sleeve-fitting unit 1206, three-dimensional modeling unit 1204, anatomical blood vessel data mapping unit 1220, and/or device 1202 may accept, for example, a computer-generated three-dimensional polygonal mesh model of a blood vessel of an individual 118. Other examples of a three-dimensional blood vessel model may include a wireframe model, a solid model, a computer tomography model, or the like.

FIG. 16 illustrates alternative embodiments of the example operational flow 1300 of FIG. 13. FIG. 16 illustrates example embodiments where the applying operation 1320 may include at least one additional operation. Additional operations may include operation 1600, 1602, 1604, and/or operation 1606.

Operation 1600 depicts mapping the three-dimensional blood vessel data to a blood vessel sleeve model. For example, the sleeve-fitting unit 1206, three-dimensional modeling unit 1204, anatomical blood vessel data mapping unit 1220, and/or device 1202 may map three-dimensional blood vessel data corresponding to the exterior surface of a blood vessel, for example, to a three-dimensional blood vessel sleeve model that approximates the exterior dimensions of the blood vessel. Alternatively, for example, the sleeve-fitting unit 1206, three-dimensional modeling unit 1204, anatomical blood vessel data mapping unit 1220, and/or device 1202 may map three-dimensional blood vessel data corresponding to the interior surface of a blood vessel, for example, to a three-dimensional blood vessel sleeve model that approximates the interior dimensions of the blood vessel.

Operation 1602 depicts extracting two or more sets of data, each data set defining a contour of a blood vessel sleeve at least partly based on the three-dimensional blood vessel data; and interpolating data that represent one or more regions between two or more contours of a blood vessel sleeve. For example, the sleeve-fitting unit 1206, three-dimensional modeling unit 1204, anatomical blood vessel data mapping unit 1220, and/or device 1202 may extract, from a three-dimensional model of a blood vessel, data sets defining curvature contours of a blood vessel sleeve to fit the blood vessel. The sleeve-fitting unit 1206, three-dimensional modeling unit 1204, anatomical blood vessel data mapping unit 1220, and/or device 1202 may then interpolate data that represent the blood vessel sleeve surface between the curvature contours in order to construct, for example, a three-dimensional solid model of the blood vessel sleeve.

Operation 1604 depicts extracting two or more sets of data, each data set defining a contour of a blood vessel sleeve at least partly based on at least one of a light intensity matrix or a color intensity matrix. For example, the sleeve-fitting unit 1206, three-dimensional modeling unit 1204, anatomical blood vessel data mapping unit 1220, and/or device 1202 may extract, from a set of CT scan black-and-white and/or grayscale images, data sets defining curvature contours of a blood vessel sleeve to fit a blood vessel shown in the images. Alternatively, for example, the sleeve-fitting unit 1206, three-dimensional modeling unit 1204, anatomical blood vessel data mapping unit 1220, and/or device 1202 may extract blood vessel sleeve contour data sets based on an unrefined or refined color intensity matrix. In one embodiment, the light intensity matrix and/or color intensity matrix consist of black-and-white and/or grayscale pixels corresponding to geometric blood vessel anatomical data.

Operation 1606 depicts applying a sleeve-fitting algorithm to three-dimensional blood vessel diameter and length data, blood vessel branching data, or blood vessel curvature data. For example, the sleeve-fitting unit 1206, three-dimensional modeling unit 1204, anatomical blood vessel data mapping unit 1220, and/or device 1202 may apply a sleeve-fitting algorithm to various aspects of three-dimensional blood vessel data. In one embodiment, the three-dimensional blood vessel data corresponds to the anatomy of a blood vessel branch junction affected by a nearby aneurysm. In this case, the sleeve-fitting algorithm may take into account the geometry of the branch junction, the geometry of the aneurysm, and any scale factor that a health care provider 222 may employ to change the geometry of the blood vessel through the use of the blood vessel sleeve.

FIG. 17 illustrates alternative embodiments of the example operational flow 1300 of FIG. 13. FIG. 17 illustrates example embodiments where the applying operation 1320 may include at least one additional operation. Additional operations may include operation 1700, 1702, 1704, 1706, 1708, and/or operation 1710.

Operation 1700 depicts applying a garment-fitting algorithm to the three-dimensional blood vessel data. As in the use of garment-fitting algorithms in which body dimensions are used to model a person to fit clothing to the person, sleeve-fitting algorithms may be used to fit a blood vessel sleeve to a blood vessel. For example, the sleeve-fitting unit 1206, three-dimensional modeling unit 1204, anatomical blood vessel data mapping unit 1220, and/or device 1202 can extract two or more sets of anatomical blood vessel data 120, each data set defining a contour of a blood vessel sleeve at least partly based on blood vessel data pertaining to an individual 118; and the sleeve-fitting unit 1206, for example, can interpolate data representing one or more regions between two or more extracted contours to define dimensions of a sleeve in the region between the two or more extracted contours. This process can then be repeated by the sleeve-fitting unit 1206 until the dimensions of an entire sleeve are specified. In another example, the sleeve-fitting unit 1206, three-dimensional modeling unit 1204, anatomical blood vessel data mapping unit 1220, and/or device 1202 may apply a scale factor to three-dimensional blood vessel data to specify a custom-fitted blood vessel sleeve 112 that is in some degree larger or smaller than the interior or exterior surface of a blood vessel.

Various other garment-fitting algorithms may be adapted to use in custom-fitting a blood vessel sleeve. For example, known garment-fitting methods such as those disclosed in U.S. Pat. Nos. 5,163,007, 5,850,222, and/or U.S. patent publication US 2004/0093105 may be applied by the sleeve-fitting unit 1206 and/or device 1202 to three-dimensional blood vessel data.

Operation 1702 depicts applying a scale factor to the three-dimensional blood vessel data. For example, the sleeve-fitting unit 1206, three-dimensional modeling unit 1204, anatomical blood vessel data mapping unit 1220, and/or device 1202 may scale a three-dimensional mesh model of a blood vessel by creating a transform matrix based on scale factors. The device 102 and/or sleeve-fitting unit 106 can multiply each point in the mesh model by the transform matrix. The use of matrix transformations to rotate, translate, and scale points in a three-dimensional space are well known in the apparel arts, as described in U.S. Pat. No. 5,850,222. In this way, a sleeve may be modeled after the blood vessel according to precise specifications.

Operation 1704 depicts assigning a set of position coordinates to the three-dimensional blood vessel data and assigning counterpart position coordinates to a blood vessel sleeve model to obtain blood vessel sleeve dimensions. For example, the sleeve-fitting unit 1206, three-dimensional modeling unit 1204, anatomical blood vessel data mapping unit 1220, and/or device 1202 can assign a set of position coordinates to a three-dimensional model and assign counterpart position coordinates to a blood vessel sleeve model to produce blood vessel sleeve dimensions that fit the blood vessel.

Operation 1706 depicts applying at least one best fit criterion to the three-dimensional blood vessel data. For example, the sleeve-fitting unit 1206, three-dimensional modeling unit 1204, anatomical blood vessel data mapping unit 1220, and/or device 1202 can apply a best fit criterion to three-dimensional blood vessel data. In one embodiment, the best fit criteria may include specified cross-sectional dimensions. In another embodiment, the specified cross-sectional dimensions may be based on actual cross-sectional-dimensions represented by the blood vessel data. In yet another embodiment, the specified cross-sectional dimensions may be based on actual cross-sectional dimensions represented by the blood vessel data and based on tolerance criteria, e.g., 1%, 2%, 5%, or 10% variation in sleeve dimension relative to actual cross-sectional dimensions.

Operation 1708 depicts applying a sleeve-fitting algorithm to the three-dimensional blood vessel data to determine dimensions of a blood vessel sleeve fitted to the interior of a blood vessel. For example, the sleeve-fitting unit 1206, three-dimensional modeling unit 1204, anatomical blood vessel data mapping unit 1220, and/or device 1202 can apply a sleeve-fitting algorithm to three-dimensional blood vessel data corresponding to the interior surface of a blood vessel, taking into account any branching and/or curvature that may be present. A therapeutic health care provider 1210 may wish to take advantage of blood vessel branching as a way of anchoring a blood vessel sleeve in place in the vicinity of, for example, an aneurysm. Custom-fitting a blood vessel sleeve to the interior of a blood vessel may also take into account any stenosis that may be present in the blood vessel, for example, due to atherosclerotic plaque or prior angioplasty/stent therapy.

Operation 1710 depicts applying a sleeve-fitting algorithm to the three-dimensional blood vessel data to determine dimensions of a blood vessel sleeve fitted to the exterior of a blood vessel. For example, the sleeve-fitting unit 1206, three-dimensional modeling unit 1204, anatomical blood vessel data mapping unit 1220, and/or device 1202 can apply a sleeve-fitting algorithm to three-dimensional blood vessel data corresponding to the exterior surface of a blood vessel, taking into account any branching, curvature, and/or aneurysm(s) that may be present. Applying a sleeve-fitting algorithm to the three-dimensional blood vessel data to determine dimensions of a blood vessel sleeve fitted to the exterior of a blood vessel may involve design choices on the part of a therapeutic health care provider 1210 as to the exact fit that will best address the medical issue present in the individual 118. Those of skill in the art may use their professional judgment in applying a sleeve-fitting algorithm to the three-dimensional blood vessel data to determine dimensions of a blood vessel sleeve fitted to the exterior of a blood vessel on a case-by-case basis.

FIG. 18 illustrates alternative embodiments of the example operational flow 1300 of FIG. 13. FIG. 18 illustrates example embodiments where the presenting operation 1330 may include at least one additional operation. Additional operations may include operation 1800, 1802, 1804, and/or operation 1806.

Operation 1800 depicts presenting blood vessel sleeve dimensions in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present blood vessel sleeve length, diameter, curvature, branching, or other physical dimensions that specify the geometry of the blood vessel sleeve.

Operation 1802 depicts presenting a blood vessel sleeve model in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present a solid blood vessel sleeve model that embodies the blood vessel sleeve physical dimensions. Such a blood vessel sleeve model may be computer-generated and it may be exported to a sleeve making device 1208 for manufacture of the blood vessel sleeve.

Operation 1804 depicts displaying the sleeve-fitting algorithm output at a user interface in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can send blood vessel sleeve specifications to a user interface where a therapeutic health care provider 1210 and/or health care provider 222 may view them.

Operation 1806 depicts presenting an image of blood vessel sleeve dimensions on a display in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can send an image of a custom-fitted blood vessel sleeve 1212 to a user interface where a therapeutic health care provider 1210 and/or health care provider 222 may view it. Such an image of a custom-fitted blood vessel sleeve 1212 may conveniently be superimposed over an image or model of the blood vessel it is being fitted to. Adjustments to the blood vessel sleeve image may be made at this point, for example, using a computer-aided drafting program, three-dimensional modeling program, and/or adapted garment-fitting program known in the art.

FIG. 19 illustrates alternative embodiments of the example operational flow 1300 of FIG. 13. FIG. 19 illustrates example embodiments where the presenting operation 1330 may include at least one additional operation. Additional operations may include operation 1900, 1902, 1904, and/or operation 1906.

Operation 1900 depicts presenting a sleeve-fitting algorithm output that includes sleeve dimensions and specifications for closing the sleeve in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present blood vessel sleeve dimensions as well as specifications for closing the sleeve. For example, in the case of a custom-fitted blood vessel sleeve for use on the exterior of a blood vessel, a longitudinal slit may be required to place the sleeve over the blood vessel. The slit may then be closed in order to regain a closed cylinder configuration in order to support the blood vessel from without. Any known means of closing such a cylindrical sleeve, including branched sleeves, may be employed by, for example, the sleeve-fitting unit 1206, three-dimensional modeling unit 1204, anatomical blood vessel data mapping unit 1220, and/or device 1202. Such closure means will ensure that the blood vessel sleeve will stay in place around the blood vessel after placement to perform its function of, for example, supporting the weakened wall of a blood vessel with an aneurysm. Examples of closure means structure include extensions positioned for closure, suturing tabs, detents, hooks, Velcro, interlocking closure ridges, glue, or the like.

Operation 1902 depicts presenting at least one of specifications for extensions positioned for closure, specifications for suturing tabs, specifications for detents, specifications for hooks, specifications for Velcro, specifications for glue, or specifications for interlocking closure ridges as the specifications for closing the sleeve. For example, the sleeve-fitting unit 1206, three-dimensional modeling unit 1204, anatomical blood vessel data mapping unit 1220, and/or device 1202 can present detailed specifications for closure mechanisms such as geometric dimensions of appropriately-sized suturing tabs according to the preference of, for example, a therapeutic health care provider 1210.

Operation 1904 depicts presenting specifications for a set of blood vessel sleeves in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present specifications for a set of blood vessel sleeves. Such a set of blood vessel sleeves may be made perioperatively for use by a therapeutic health care provider 1210 who may want the option of having a series of different-sized sleeves for use on a patient's blood vessel during a surgery to address, for example, an aneurysm on the blood vessel.

Operation 1906 depicts presenting specifications for a set of blood vessel sleeves that each has at least one of different dimensions, a different material composition, or a different coating as the specifications for a set of blood vessel sleeves. For example, the sleeve-fitting unit 1206, three-dimensional modeling unit 1204, anatomical blood vessel data mapping unit 1220, and/or device 1202 can present specifications for a set of blood vessel sleeves that vary according to size, material composition, coating, or combinations of these variables. Such a varied set of sleeves may provide a therapeutic health care provider 1210 with a choice of custom-fitted blood vessel sleeves to use, for example, at the time the blood vessel is visible during surgery.

FIG. 20 illustrates alternative embodiments of the example operational flow 1300 of FIG. 13. FIG. 20 illustrates example embodiments where the presenting operation 1330 may include at least one additional operation. Additional operations may include operation 2000, 2002, 2004, and/or operation 2006.

Operation 2000 depicts presenting specifications for a set of blood vessel sleeves that each has at least different closure extensions as the specifications for a set of blood vessel sleeves. For example, the sleeve-fitting unit 1206, three-dimensional modeling unit 1204, anatomical blood vessel data mapping unit 1220, and/or device 1202 can present specifications for a set of blood vessel sleeves that each has a different size of, for example, suture tabs. Such range of different sized suturing tabs may be convenient for a therapeutic health care provider 1210 in selecting a sleeve that may be placed over a blood vessel and sutured in place easily despite tortuous curvature of a blood vessel or interfering anatomy of local structures near the blood vessel.

Operation 2002 depicts presenting specifications for a set of blood vessel sleeves of varying dimensions. For example, the sleeve-fitting unit 1206, three-dimensional modeling unit 1204, anatomical blood vessel data mapping unit 1220, and/or device 1202 can present specifications for a set of blood vessel sleeves that vary in, for example, the dimensions of the portion of the sleeve that directly contacts an aneurysm portion of a blood vessel. In this embodiment, the circumference of the sleeve portion directly contacting the aneurysm may, for example, vary by percentages, e.g., 5% increments, so that, for example, in a perioperative scenario a therapeutic health care provider 1210 may choose the custom-fitted blood vessel sleeve 1212 that will best address the aneurysm according to observation of the blood vessel during surgery.

Operation 2004 depicts presenting specifications for a blood vessel sleeve and specifications for at least one indicator on the blood vessel sleeve in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present specifications for a blood vessel sleeve and specifications for an indicator on the sleeve that provides information about the sleeve. Examples of the information provided by such an indicator may include size, material composition, patient information, dimensions, time and date, hospital, or the like.

Operation 2006 depicts presenting specifications for a blood vessel sleeve and specifications for at least one indicator on the blood vessel sleeve corresponding to a dimension of the blood vessel sleeve. For example, the sleeve-fitting unit 1206, three-dimensional modeling unit 1204, anatomical blood vessel data mapping unit 1220, and/or device 1202 can present specifications for a blood vessel sleeve and specifications for an indicator of the size of the sleeve, for example, in the case where a therapeutic health care provider 1210 desires to select one of a set of custom-fitted blood vessel sleeves. Such an indicator may be detectable by visual inspection of the blood vessel sleeve. In one embodiment, an indicator may be detectable after implantation via radio frequency identification technology or other known detection methods.

FIG. 21 illustrates alternative embodiments of the example operational flow 1300 of FIG. 13. FIG. 21 illustrates example embodiments where the presenting operation 1330 may include at least one additional operation. Additional operations may include operation 2100, 2102, 2104, 2106, and/or operation 2108.

Operation 2100 depicts presenting specifications for a blood vessel sleeve and specifications for at least one indicator on the blood vessel sleeve corresponding to a material thickness of the blood vessel sleeve. For example, the sleeve-fitting unit 1206, three-dimensional modeling unit 1204, anatomical blood vessel data mapping unit 1220, and/or device 1202 can present specifications for a blood vessel sleeve and specifications for an indicator that provides information as to the thickness of the blood vessel sleeve. In some embodiments, the thickness of the blood vessel sleeve may vary over the length or other dimension of the sleeve according to desired flexibility, strength, or other desired functional characteristic.

Operation 2102 depicts presenting specifications for a blood vessel sleeve and specifications for at least one indicator on the blood vessel sleeve corresponding to a material stiffness of the blood vessel sleeve. For example, the sleeve-fitting unit 1206, three-dimensional modeling unit 1204, anatomical blood vessel data mapping unit 1220, and/or device 1202 can present specifications for a blood vessel sleeve and specifications for an indicator that provides information regarding the stiffness of the material composition of the sleeve or a portion of the sleeve.

Operation 2104 depicts presenting specifications for a blood vessel sleeve and specifications for at least one indicator on the blood vessel sleeve corresponding to a material type of the blood vessel sleeve. For example, the sleeve-fitting unit 1206, three-dimensional modeling unit 1204, anatomical blood vessel data mapping unit 1220, and/or device 1202 can present specifications for a blood vessel sleeve and specifications for an indicator of the type of material that the sleeve is made of. In one embodiment, a set of blood vessel sleeves may be made of different materials for selection by a therapeutic health care provider 1210. An indicator of material type can serve to distinguish the different sleeves to aid in the selection by the therapeutic health care provider 1210.

Operation 2106 depicts presenting specifications for a blood vessel sleeve and specifications for at least one indicator on the blood vessel sleeve corresponding to individual-characterizing data. For example, the sleeve-fitting unit 1206, three-dimensional modeling unit 1204, anatomical blood vessel data mapping unit 1220, and/or device 1202 can present specifications for a blood vessel sleeve and specifications for an indicator on the blood vessel sleeve corresponding to, for example, the individual's name. Alternatively, detailed information as to the individual's medical condition may be encoded on the blood vessel sleeve as the indicator of individual-characterizing data.

Operation 2108 depicts presenting specifications for a blood vessel sleeve and specifications for at least one indicator on the blood vessel sleeve corresponding to at least one of a time or a date. For example, the sleeve-fitting unit 1206, three-dimensional modeling unit 1204, anatomical blood vessel data mapping unit 1220, and/or device 1202 can present specifications for a blood vessel sleeve and specifications for an indicator of the time and/or date of surgery, and/or the time and/or date of manufacture of the blood vessel sleeve.

FIG. 22 illustrates alternative embodiments of the example operational flow 1300 of FIG. 13. FIG. 22 illustrates example embodiments where the presenting operation 1330 may include at least one additional operation. Additional operations may include operation 2200, 2202, 2204, and/or operation 2206.

Operation 2200 depicts presenting specifications for a blood vessel sleeve and specifications for at least one indicator on the blood vessel sleeve relating to a color coding of the blood vessel sleeve. For example, the sleeve-fitting unit 1206, three-dimensional modeling unit 1204, anatomical blood vessel data mapping unit 1220, and/or device 1202 can present specifications for a blood vessel sleeve and specifications for a color indicator for use with the blood vessel sleeve to provide information relating to various characteristics of the sleeve and/or the individual receiving the sleeve.

Operation 2202 depicts presenting specifications for a blood vessel sleeve and specifications for at least one indicator on the blood vessel sleeve relating to a color coding corresponding to patient data. For example, the sleeve-fitting unit 1206, three-dimensional modeling unit 1204, anatomical blood vessel data mapping unit 1220, and/or device 1202 can present specifications for a blood vessel sleeve and specifications for a color indicator of patient data. As a rapid-recognition feature, color coding can allow a therapeutic health care provider 110 to quickly identify a particular feature of a custom-fitted blood vessel sleeve 112. In another embodiment, the color coding of the custom-fitted blood vessel sleeve 700 may be a color coding corresponding to patient data such as name, medical history, or the like.

Operation 2204 depicts presenting specifications for a blood vessel sleeve and specifications for at least one indicator on the blood vessel sleeve relating to a color coding corresponding to at least one of material type, material thickness, material stiffness, sleeve size, thickness of the blood vessel sleeve, or sleeve coating. For example, the sleeve-fitting unit 1206, three-dimensional modeling unit 1204, anatomical blood vessel data mapping unit 1220, and/or device 1202 can present specifications for a blood vessel sleeve and specifications for a color indicator of various characteristics of the blood vessel sleeve, including, for example, physical dimensions, composition, surface coating, or the like.

Operation 2206 depicts presenting specifications for a blood vessel sleeve and specifications for at least one contrast agent within the material of the blood vessel sleeve in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present specifications for a blood vessel sleeve and specifications for a contrast agent to be used within the blood vessel sleeve to aid in visualization of the sleeve post-implantation. As discussed above, doping, impregnating, embedding, or otherwise placing a contrast agent within the material composition of a custom-fitted blood vessel sleeve 112 may enhance medical imaging of the sleeve subsequent to its placement on or within a blood vessel in an individual 118. This may be useful for short-term and/or long-term follow-up of the functioning of the custom-fitted blood vessel sleeve 112 in the individual 118. For example, a sleeve containing a paramagnetic material such as gadolinium or $Mn^{++}$ will appear in MRI-scanned images, and a sleeve containing iodine will appear in CT-scanned images. A custom-fitted blood vessel sleeve 112 may contain, for example, multiple contrast agents to facilitate detection of the sleeve by a number of different imaging methods.

FIG. 23 illustrates alternative embodiments of the example operational flow 1300 of FIG. 13. FIG. 23 illustrates example embodiments where the presenting operation 1330 may include at least one additional operation. Additional operations may include operation 2300, 2302, 2304, and/or operation 2306.

Operation 2300 depicts presenting specifications for a blood vessel sleeve, and specifications for at least one indicator of deformation or wear to be in or on the blood vessel sleeve in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can present specifications for a blood vessel sleeve and specifications for an indicator of deformation or wearing of the sleeve. In one embodiment, as discussed above, a custom-fitted blood vessel sleeve 112 may have a visible grid or otherwise detectable grid of perpendicular lines on its surface, such that upon deformation or wearing of the sleeve, the right angles of the grid change to acute or obtuse angles in the area of wear or deformation. The degree and/or rate of wear and/or deformation may thus be apparent from an imaging or inspection of the indicator of deformation or wear after a period of time.

Operation 2302 depicts presenting specifications for a blood vessel sleeve as rapid-prototyping device instructions in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can send specifications for a blood vessel sleeve as rapid-prototyping instructions to a rapid-prototyping device for making a blood vessel sleeve. In one embodiment, specifications for a blood vessel sleeve may be sent to an automated laser-cutter for rapid-prototyping-style manufacture. In another embodiment, specifications for a blood vessel sleeve may be sent to a three-dimensional printing device for rapid-prototyping-style manufacture. Alternatively, specifications for a blood vessel sleeve may be converted to any rapid-prototyping device instruction set known in the art for use with any rapid-prototyping device known in the art.

Operation 2304 depicts presenting specifications for a blood vessel sleeve as laser-cutting device instructions in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can send specifications for a blood vessel sleeve as rapid-prototyping instructions to an automated two-dimensional laser-cutting device in order to make a blood vessel sleeve out of a substantially two-dimensional piece of material.

Operation 2306 depicts presenting specifications for a blood vessel sleeve as three-dimensional printing device instructions in response to said applying the sleeve-fitting algorithm to the three-dimensional blood vessel data. For example, the sleeve-fitting unit 1206, three-dimensional modeling unit 1204, anatomical blood vessel data mapping unit 1220, and/or device 1202 can send specifications for a blood vessel sleeve as three-dimensional printing device instructions to a three-dimensional printing device in order to make a three-dimensional blood vessel sleeve. Specifications for a blood vessel sleeve as three-dimensional printing device instructions may be sent to any of the three-dimensional printing devices discussed above, or to other three-dimensional printing devices known in the art.

FIG. 24 illustrates an operational flow 2400 representing example operations relating to methods and systems for specifying a blood vessel sleeve. In FIG. 24 and in following figures that include various examples of operational flows, discussion, and explanation may be provided with respect to the above-described examples of FIGS. 1-12, and/or with respect to other examples and contexts. However, it should be understood that the operational flows may be executed in a number of other environment and contexts, and/or in modified versions of FIGS. 1-12. Also, although the various operational flows are presented in the sequence(s) illustrated, it should be understood that the various operations may be performed in other orders than those which are illustrated, or may be performed concurrently.

After a start operation, operation 2410 shows obtaining blood vessel data pertaining to an individual. The blood vessel data may be accepted from an imaging system 1214, portable imaging device 124, and/or from a three-dimensional modeling unit 1204.

For example, the three-dimensional modeling unit 1204 of the device 1202 may receive anatomical blood vessel data 120, such as, for example, one or more health records 122 relating to an individual 118 and/or an individual 118's data from an imaging system 1214. For example, this may include a three-dimensional construct of two-dimensional image data from an individual's blood vessel, for example, from a CT scan. Alternatively, the blood vessel data may refer to a series of two-dimensional MRI scan images.

Operation 2420 depicts converting the blood vessel data pertaining to the individual into a three-dimensional blood vessel model. For example, the sleeve-fitting unit 1206, anatomical blood vessel data mapping unit 1220, and/or device 1202 may apply a mapping function to the blood vessel data to create three-dimensional model of an imaged blood vessel, for example, a branched section of an artery that is afflicted with an aneurysm. As discussed above, known three-dimensional modeling techniques may be used to construct a three-dimensional model using blood vessel data pertaining to an individual.

Operation 2430 depicts applying a sleeve-fitting algorithm to the three-dimensional blood vessel model. For example, the sleeve-fitting unit 1206, anatomical blood vessel data mapping unit 1220, and/or device 1202 may apply a sleeve-fitting algorithm to the three-dimensional model of a blood vessel to produce, for example, blood vessel sleeve dimensions. A sleeve-fitting algorithm may include a mapping function that maps points on the three-dimensional blood vessel model to points on a model of a blood vessel sleeve. Alternatively, a sleeve-fitting algorithm may use a scale factor to scale the dimensions of the three-dimensional blood vessel model to give dimensions of a blood vessel sleeve. Other known sleeve-fitting algorithms known in the apparel industry and as described herein may also be applied by sleeve-fitting unit 1206, anatomical blood vessel data mapping unit 1220, and/or device 1202.

Operation 2440 depicts presenting a sleeve-fitting algorithm output in response to said applying the sleeve-fitting algorithm to the three-dimensional blood vessel model. For example, sleeve-fitting unit 1206, anatomical blood vessel data mapping unit 1220, and/or device 1202 may send blood vessel sleeve dimensions to a therapeutic health care provider 1210, or, for example, directly to a sleeve-making device 1208. Alternatively, the sleeve-fitting algorithm output may be stored in at least one memory in, for example, the device 1202. In this regard, it should be understood that the sleeve-fitting algorithm output may first be encoded and/or represented in digital form (i.e., as digital data), prior to the assignment to the at least one memory. For example, a digitally-encoded representation of the sleeve-fitting algorithm output may be stored in a local memory, or may be transmitted for storage in a remote memory.

Thus, an operation may be performed related either to a local or remote storage of the digital data, or to another type of transmission of the digital data. Of course, operations also may be performed related to accessing, querying, recalling, or otherwise obtaining the digital data from a memory, including, for example, receiving a transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

FIG. 25 illustrates alternative embodiments of the example operational flow 2400 of FIG. 24. FIG. 25 illustrates example embodiments where the obtaining operation 2410 may include at least one additional operation. Additional operations may include operation 2502, 2504, 2506, 2508, and/or operation 2510.

Operation 2502 depicts obtaining geometric blood vessel data as the blood vessel data pertaining to the individual. For example, the three-dimensional modeling unit 1204, sleeve-fitting unit 1206, anatomical blood vessel data mapping unit 1220, and/or device 1202 may receive two-dimensional cross-sections of an individual's blood vessel anatomy. Such cross-sections are typical of, for example, CT scan output and MRI scan output.

Operation 2504 depicts obtaining cross-sectional blood vessel data as the blood vessel data pertaining to the individual. For example, the three-dimensional modeling unit 1204, sleeve-fitting unit 1206, anatomical blood vessel data mapping unit 1220, and/or device 1202 may receive a set of contiguous two-dimensional cross-sections of an individual's blood vessel anatomy, which, taken together, can be mapped to a three-dimensional blood vessel model.

Operation 2506 depicts obtaining at least one of magnetic resonance imaging data, computed tomography data, ultrasound data, optical imaging data, or angiography data as the blood vessel data pertaining to the individual. For example, the three-dimensional modeling unit 1204, sleeve-fitting unit 1206, anatomical blood vessel data mapping unit 1220, and/or device 1202 may receive, for example, anatomical blood vessel data 120 from an individual 118 from an imaging system 1214 and/or a health record 122 in the form of angiography data or ultrasound device output.

Operation 2508 depicts obtaining at least one of magnetic resonance angiography data, computed tomography angiography data, Doppler ultrasound, or cerebral angiography data as the blood vessel data pertaining to the individual. For example, the three-dimensional modeling unit 1204, sleeve-fitting unit 1206, anatomical blood vessel data mapping unit 1220, and/or device 1202 may receive, for example, anatomical blood vessel data 120 from an individual 118 from an imaging system 1214 and/or a health record 122 in the form of magnetic resonance angiography data or cerebral angiography data.

Operation 2510 depicts obtaining at least one of aneurysm data or branched blood vessel data as the blood vessel data pertaining to the individual. For example, the sleeve-fitting unit 1206, three-dimensional modeling unit 1204, anatomical blood vessel data mapping unit 1220, and/or device 1202 may receive, for example, three-dimensional CT scan data relating to a portion of a blood vessel with an aneurysm. For example, the aneurysm may be associated with the abdominal aorta, or close to a branch point in the Circle of Willis.

FIG. 26 illustrates alternative embodiments of the example operational flow 2400 of FIG. 24. FIG. 26 illustrates example embodiments where the converting operation 2420 may include at least one additional operation. Additional operations may include operation 2600, 2602, and/or operation 2604.

Operation 2600 depicts mapping the blood vessel data pertaining to the individual to a three-dimensional blood vessel model. For example, the sleeve-fitting unit 1206, three-dimensional modeling unit 1204, anatomical blood vessel data mapping unit 1220, and/or device 1202 may map blood vessel data to a three-dimensional blood vessel model that approximates the exterior dimensions of the blood vessel. Alternatively, for example, the sleeve-fitting unit 1206, three-dimensional modeling unit 1204, anatomical blood vessel data mapping unit 1220, and/or device 1202 may map blood vessel data corresponding to the interior surface of a blood vessel, for example, to a three-dimensional blood vessel model that approximates the interior dimensions of the blood vessel.

Operation 2602 depicts extracting two or more sets of data, each data set defining a contour of a blood vessel at least partly based on the blood vessel data pertaining to the individual; and interpolating data that represent one or more regions between two or more contours. For example, the sleeve-fitting unit 1206, three-dimensional modeling unit 1204, anatomical blood vessel data mapping unit 1220, and/or device 1202 may extract, from blood vessel image data, data sets defining curvature contours of a blood vessel. The sleeve-fitting unit 1206, three-dimensional modeling unit 1204, anatomical blood vessel data mapping unit 1220, and/or device 1202 may then interpolate data that represent the blood vessel surface between the curvature contours in order to construct, for example, a three-dimensional solid model of the blood vessel.

Operation 2604 depicts extracting two or more sets of data, each data set defining a contour of a blood vessel at least partly based on at least one of a light intensity matrix or a color intensity matrix. For example, the sleeve-fitting unit 1206, three-dimensional modeling unit 1204, anatomical blood vessel data mapping unit 1220, and/or device 1202 may extract, from a set of CT scan black-and-white and/or grayscale images, data sets defining curvature contours of a blood vessel shown in the images. Alternatively, for example, the sleeve-fitting unit 1206, three-dimensional modeling unit 1204, anatomical blood vessel data mapping unit 1220, and/or device 1202 may extract blood vessel contour data sets based on an unrefined or refined color intensity matrix. In one embodiment, the light intensity matrix and/or color intensity matrix consist of black-and-white and/or grayscale pixels corresponding to geometric blood vessel anatomical data.

FIG. 27 illustrates alternative embodiments of the example operational flow 2400 of FIG. 24. FIG. 27 illustrates example embodiments where the converting operation 2420 may include at least one additional operation. Additional operations may include operation 2700, 2702, 2704, and/or operation 2706.

Operation 2700 depicts converting the blood vessel data pertaining to the individual into a three-dimensional mathematical model. For example, the sleeve-fitting unit 1206, anatomical blood vessel data mapping unit 1220, and/or device 1202 may convert, for example, blood vessel data from a health record 122, an imaging system 1214, and/or health care provider 222, into a three-dimensional mathematical model of a blood vessel. Converting blood vessel data into a mathematical model may be done, for example, by applying equations known in the art that assign points in two-dimensional space to a three-dimensional matrix. As discussed above, publicly computer programs are available that can perform such mathematical transformations.

Operation 2702 depicts converting the blood vessel data pertaining to the individual into a three-dimensional image model. For example, the sleeve-fitting unit 1206, three-dimensional modeling unit 1204, anatomical blood vessel data mapping unit 1220, and/or device 1202 may convert, for example, CT scan image data pertaining to an individual 118 into a computer-generated three-dimensional polygonal wireframe model of a blood vessel of the individual 118. Other examples of a three-dimensional blood vessel image models may include a surface mesh model, a solid model, a computer tomography model, or the like.

Operation 2704 depicts converting the blood vessel data pertaining to the individual into a three-dimensional mesh model. For example, the sleeve-fitting unit 1206, three-dimensional modeling unit 1204, anatomical blood vessel data mapping unit 1220, and/or device 1202 may convert, for example, MRI scan image data pertaining to an individual 118 into a computer-generated three-dimensional mesh model of a blood vessel of the individual 118. Other examples of a three-dimensional mesh model may include a surface mesh model, a triangulated surface mesh model, a dynamic mesh model, or the like.

Operation 2706 depicts converting the blood vessel data pertaining to the individual into a three-dimensional blood vessel model, the three-dimensional blood vessel model including at least one of blood vessel diameter and length data, blood vessel branching data, or blood vessel curvature data. For example, the sleeve-fitting unit 1206, three-dimensional modeling unit 1204, anatomical blood vessel data mapping unit 1220, and/or device 1202 may convert blood vessel data into a three-dimensional blood vessel model that captures various aspects of the anatomy of the modeled blood vessel. In one embodiment, the three-dimensional blood vessel model contains data corresponding to the anatomy of a blood vessel branch junction affected by a nearby aneurysm. In this case, the three-dimensional blood vessel model may embody the geometry of the branch junction, the geometry of the aneurysm, and the anatomy of proximal portions of the blood vessel.

FIG. 28 illustrates alternative embodiments of the example operational flow 2400 of FIG. 24. FIG. 28 illustrates example embodiments where the applying operation 2430 may include at least one additional operation. Additional operations may include operation 2800, 2802, 2804, and/or operation 2806.

Operation 2800 depicts applying a sleeve-fitting algorithm to the three-dimensional blood vessel model to determine blood vessel sleeve dimensions. For example, the sleeve-fitting unit 1206, three-dimensional modeling unit 1204, anatomical blood vessel data mapping unit 1220, and/or device 1202 may apply a sleeve-fitting algorithm to various aspects of three-dimensional blood vessel model. In one embodiment, the three-dimensional blood vessel model corresponds to the anatomy of a portion of the abdominal aorta affected by an aneurysm. In this case, the sleeve-fitting algorithm may take into account the geometry of the aorta proximal to the aneurysm, the geometry of the aneurysm itself, and any scale factor that a health care provider 222 may wish to employ to change the geometry of the abdominal aorta through the use of the blood vessel sleeve.

Operation 2802 depicts applying a garment-fitting algorithm to the three-dimensional blood vessel model to obtain blood vessel sleeve dimensions. As in the use of garment-fitting algorithms in which body dimensions are used to model a person to fit clothing to the person, a sleeve-fitting algorithm or garment-fitting algorithm may be used to fit a blood vessel sleeve to a blood vessel. For example, based on the three-dimensional blood vessel model, the sleeve-fitting unit 1206, three-dimensional modeling unit 1204, anatomical blood vessel data mapping unit 1220, and/or device 1202 can extract two or more sets of blood vessel sleeve data, each data set defining a contour of a blood vessel sleeve at least partly based on blood vessel data pertaining to an individual 118. The sleeve-fitting unit 1206, for example, can then interpolate data representing one or more regions between two or more extracted contours to define dimensions of a sleeve in the region between the two or more extracted contours. This process can then be repeated by the sleeve-fitting unit 1206 until the dimensions of an entire sleeve are specified. In another example, the sleeve-fitting unit 1206, three-dimensional modeling unit 1204, anatomical blood vessel data mapping unit 1220, and/or device 1202 may apply a scale factor to a three-dimensional blood vessel model to specify a custom-fitted blood vessel sleeve 112 that is in some degree larger or smaller than an interior or exterior surface of the three-dimensional blood vessel model, and by extension, a surface of the corresponding blood vessel.

Various other garment-fitting algorithms may be adapted to use in custom-fitting a blood vessel sleeve. For example, known garment-fitting methods such as those disclosed in U.S. Pat. Nos. 5,163,007, 5,850,222, and/or U.S. patent publication US 2004/0093105 may be applied by the sleeve-fitting unit 1206 and/or device 1202 to a three-dimensional blood vessel model.

Operation 2804 depicts applying a scale factor to the three-dimensional blood vessel model to obtain blood vessel sleeve dimensions. For example, the sleeve-fitting unit 1206, three-dimensional modeling unit 1204, anatomical blood vessel data mapping unit 1220, and/or device 1202 may scale a three-dimensional mesh model of a blood vessel by creating a transform matrix based on scale factors. The device 102 and/or sleeve-fitting unit 106 can multiply each point in the mesh model by the transform matrix. The use of matrix transformations to rotate, translate, and scale points in a three-dimensional space are well known in the apparel arts, as described in U.S. Pat. No. 5,850,222. In this way, a sleeve may be modeled after the blood vessel according to precise specifications.

Operation 2806 depicts assigning position coordinates to the three-dimensional blood vessel model and assigning counterpart position coordinates to a blood vessel sleeve model to obtain blood vessel sleeve dimensions. For example, the sleeve-fitting unit 1206, three-dimensional modeling unit 1204, anatomical blood vessel data mapping unit 1220, and/or device 1202 can assign a set of position coordinates within a three-dimensional blood vessel model to counterpart position coordinates on a blood vessel sleeve model to produce blood vessel sleeve dimensions that fit the blood vessel.

FIG. 29 illustrates alternative embodiments of the example operational flow 2400 of FIG. 24. FIG. 29 illustrates example embodiments where the applying operation 2430 may include at least one additional operation. Additional operations may include operation 2900, and/or operation 2902.

Operation 2902 depicts applying a sleeve-fitting algorithm to the three-dimensional blood vessel model to determine dimensions of a blood vessel sleeve fitted to the interior of a blood vessel. For example, the sleeve-fitting unit 1206, three-dimensional modeling unit 1204, anatomical blood vessel data mapping unit 1220, and/or device 1202 can apply a sleeve-fitting algorithm to a three-dimensional blood vessel model corresponding to the interior surface of a blood vessel, taking into account any branching and/or curvature that may be present. A therapeutic health care provider 1210 may wish to take advantage of blood vessel branching as a way of anchoring a blood vessel sleeve in place in the vicinity of, for example, an aneurysm. Custom-fitting a blood vessel sleeve to the interior of a blood vessel may also take into account any stenosis that may be present in the blood vessel, for example, due to atherosclerotic plaque or prior angioplasty/stent therapy.

Operation 2902 depicts applying a sleeve-fitting algorithm to the three-dimensional blood vessel model to determine dimensions of a blood vessel sleeve fitted to the exterior of a blood vessel. For example, the sleeve-fitting unit 1206, three-dimensional modeling unit 1204, anatomical blood vessel data mapping unit 1220, and/or device 1202 can apply a sleeve-fitting algorithm to a three-dimensional blood vessel model corresponding to the exterior surface of a blood vessel, taking into account any branching, curvature, and/or aneurysm(s) that may be present. Applying a sleeve-fitting algorithm to the three-dimensional blood vessel model to determine dimensions of a blood vessel sleeve fitted to the exterior of a blood vessel may involve design choices on the part of a therapeutic health care provider 1210 as to the exact fit that will best address the medical issue present in the individual 118. Those of skill in the art may use their professional judgment in applying a sleeve-fitting algorithm to the three-dimensional blood vessel model to determine dimensions of a blood vessel sleeve fitted to the exterior of a blood vessel.

FIG. 30 illustrates alternative embodiments of the example operational flow 2400 of FIG. 24. FIG. 30 illustrates example embodiments where the presenting operation 2440 may include at least one additional operation. Additional operations may include operation 3000, 3002, 3004, and/or operation 3006.

Operation 3000 depicts presenting a blood vessel sleeve model in response to applying the sleeve-fitting algorithm to the three-dimensional blood vessel model. For example, the sleeve-fitting unit 1206, three-dimensional modeling unit 1204, anatomical blood vessel data mapping unit 1220, and/or device 1202 can present a solid blood vessel sleeve model that embodies the blood vessel sleeve physical dimensions. Such a blood vessel sleeve model may be computer-generated and it may be exported to a sleeve making device 1208 for manufacture of the blood vessel sleeve.

Operation 3002 depicts presenting blood vessel sleeve dimensions in response to applying the sleeve-fitting algorithm to the three-dimensional blood vessel model. For example, the sleeve-fitting unit 1206, three-dimensional modeling unit 1204, anatomical blood vessel data mapping unit 1220, and/or device 1202 can present blood vessel sleeve length, diameter, curvature, branching, or other physical dimensions that specify the geometry of the blood vessel sleeve, based on the three-dimensional blood vessel sleeve model.

Operation 3004 depicts displaying a sleeve-fitting algorithm output at a user interface in response to said applying the sleeve-fitting algorithm to the three-dimensional blood vessel model. For example, the sleeve-fitting unit 1206, three-dimensional modeling unit 1204, anatomical blood vessel data mapping unit 1220, and/or device 1202 can send blood vessel sleeve specifications to a user interface where a therapeutic health care provider 1210 and/or health care provider 222 may view them.

Operation 3006 depicts presenting an image of blood vessel sleeve dimensions on a display in response to said applying the sleeve-fitting algorithm to the three-dimensional blood vessel model. For example, the sleeve-fitting unit 1206, three-dimensional modeling unit 1204, anatomical blood vessel data mapping unit 1220, and/or device 1202 can send an image of a custom-fitted blood vessel sleeve 1212 to a user interface where a therapeutic health care provider 1210 and/or health care provider 222 may view it. Such an image of a custom-fitted blood vessel sleeve 1212 may conveniently be superimposed over an image or model of the blood vessel it is being fitted to. Adjustments to the blood vessel sleeve image may be made at this point, for example, using a computer-aided drafting program, three-dimensional modeling program, and/or adapted garment-fitting program known in the art.

FIG. 31 illustrates a partial view of an example computer program product 3100 that includes a computer program 3104 for executing a computer process on a computing device. An embodiment of the example computer program product 3100 is provided using a signal bearing medium 3102, and may include at one or more instructions for accepting three-dimensional blood vessel data; one or more instructions for applying a sleeve-fitting algorithm to the three-dimensional blood vessel data; and one or more instructions for presenting a sleeve-fitting algorithm output in response to said applying the sleeve-fitting algorithm to the three-dimensional blood vessel data. The one or more instructions may be, for example, computer executable and/or logic-implemented instructions. In one implementation, the signal-bearing medium 3102 may include a computer-readable medium 3106. In one implementation, the signal bearing medium 3102 may include a recordable medium 3108. In one implementation, the signal bearing medium 3102 may include a communications medium 3110.

FIG. 32 illustrates an example system 3200 in which embodiments may be implemented. The system 3200 includes a computing system environment. The system 3200 also illustrates the health care provider 222 using a device 3204, which is optionally shown as being in communication with a computing device 3202 by way of an optional coupling 3206. The optional coupling 3206 may represent a local, wide-area, or peer-to-peer network, or may represent a bus that is internal to a computing device (e.g., in example embodiments in which the computing device 3202 is contained in whole or in part within the device 3204). A storage medium 3208 may be any computer storage media.

The computing device 3202 includes computer-executable instructions 3210 that when executed on the computing device 3202 cause the computing device 3202 to accept three-dimensional blood vessel data; to apply a sleeve-fitting algorithm to the three-dimensional blood vessel data; and to present a sleeve-fitting algorithm output in response to said applying the sleeve-fitting algorithm to the three-dimensional blood vessel data. As referenced above and as shown in FIG. 32, in some examples, the computing device 3202 may optionally be contained in whole or in part within the device 3204.

In FIG. 32, then, the system 3200 includes at least one computing device (e.g., 3202 and/or 3204). The computer-executable instructions 3210 may be executed on one or more of the at least one computing device. For example, the computing device 3202 may implement the computer-executable instructions 3210 and output a result to (and/or receive data from) the device 3204. Since the computing device 3202 may be wholly or partially contained within the device 3204, the device 3204 also may be said to execute some or all of the computer-executable instructions 3210, in order to be caused to perform or implement, for example, various ones of the techniques described herein, or other techniques.

The device 3204 may include, for example, a portable computing device, workstation, or desktop computing device. In another example embodiment, the computing device 3202 is operable to communicate with the device 3204 associated with the health care provider 222 to receive information about input from the health care provider 222 or other sources for performing the data conversion, sleeve-fitting, and presenting the sleeve-fitting algorithm output.

FIG. 33 illustrates a partial view of an example computer program product 3300 that includes a computer program 3304 for executing a computer process on a computing device. An embodiment of the example computer program product 3300 is provided using a signal bearing medium 3302, and may include at one or more instructions for obtaining blood vessel data pertaining to an individual; one or more instructions for converting the blood vessel data pertaining to the individual into a three-dimensional blood vessel model; one or more instructions for applying a sleeve-fitting algorithm to the three-dimensional blood vessel model; and one or more instructions for presenting a sleeve-fitting algorithm output in response to said applying the sleeve-fitting algorithm to the three-dimensional blood vessel model. The one or more instructions may be, for example, computer executable and/or logic-implemented instructions. In one implementation, the signal-bearing medium 3302 may include a computer-readable medium 3306. In one implementation, the signal bearing medium 3302 may include a recordable medium 3308. In one implementation, the signal bearing medium 3302 may include a communications medium 3310.

FIG. 34 illustrates an example system 3400 in which embodiments may be implemented. The system 3400 includes a computing system environment. The system 3400 also illustrates the health care provider 222 using a device 3404, which is optionally shown as being in communication with a computing device 3402 by way of an optional coupling 3406. The optional coupling 3406 may represent a local, wide-area, or peer-to-peer network, or may represent a bus that is internal to a computing device (e.g., in example embodiments in which the computing device 3402 is contained in whole or in part within the device 3404). A storage medium 3408 may be any computer storage media.

The computing device 3402 includes computer-executable instructions 3410 that when executed on the computing device 3402 cause the computing device 3402 to obtain blood vessel data pertaining to an individual; to convert the blood vessel data pertaining to the individual into a three-dimensional model; to apply a sleeve-fitting algorithm to the three-dimensional model; and to present a sleeve-fitting algorithm output in response to said applying the sleeve-fitting algorithm to the three-dimensional model. As referenced above and as shown in FIG. 34, in some examples, the computing device 3402 may optionally be contained in whole or in part within the device 3404.

In FIG. 34, then, the system 3400 includes at least one computing device (e.g., 3402 and/or 3404). The computer-executable instructions 3410 may be executed on one or more of the at least one computing device. For example, the computing device 3402 may implement the computer-executable instructions 3410 and output a result to (and/or receive data from) the device 3404. Since the computing device 3402 may be wholly or partially contained within the device 3404, the device 3404 also may be said to execute some or all of the computer-executable instructions 3410, in order to be caused to perform or implement, for example, various ones of the techniques described herein, or other techniques.

The device 3404 may include, for example, a portable computing device, workstation, or desktop computing device. In another example embodiment, the computing device 3402 is operable to communicate with the device 3404 associated with the health care provider 222 to receive information about input from the health care provider 222 or other sources for performing the data conversion, sleeve-fitting, and presenting the sleeve-fitting algorithm output.

FIG. 51 illustrates an example system 5100 in which embodiments may be implemented. The system 5100 includes at least one device 5102. The at least one device 5102 may contain, for example, an anatomical blood vessel data mapping unit 120, a three-dimensional modeling unit 5104, and/or a sleeve-fitting unit 5106. Imaging system 5114 may generate anatomical blood vessel data 120 from an individual 118, or anatomical blood vessel data 120 from an individual 118 may be obtained from a health record 122 that is external to the device 5102. Imaging system 5114 may be operated by diagnostic health care provider 5116 and/or therapeutic health care provider 5110 to obtain anatomical blood vessel data 120 from an individual 118.

Therapeutic health care provider 5110 may interact with the device 5102 to determine blood vessel sleeve specifications based on anatomical blood vessel data 120 from an individual 118. Therapeutic health care provider 5110 may also interact with sleeve-making device 5108 to obtain rapid-prototyped blood vessel sleeve 5112 based on anatomical blood vessel data 120 from an individual 118. Therapeutic health care provider 5110 may then employ the rapid-prototyped blood vessel sleeve 5112 to address a blood vessel of individual 118 in an open surgical procedure, in a laparoscopic surgery procedure, through a catheter insertion procedure, or the like.

In some embodiments, the imaging system 5114 and the device 5102 may be combined in a single device, or the imaging system 5114, the device 5102, and/or the sleeve-making device 5108 may be combined in a single device. In some embodiments the imaging system 5114 may be a portable imaging device 124 that can communicate with the at least one device 5102, on which the sleeve-fitting unit 5106 is operable, via a wireless network for example. In some embodiments, the sleeve-making device 5108 may be operable remotely through the device 5102 via, for example, a network connection.

In FIG. 51, the at least one device 5102 is illustrated as possibly being included within a system 5100. Any kind of computing device may be used in connection with the anatomical blood vessel mapping unit 5120, three-dimensional modeling unit 5104 and/or sleeve-fitting unit 5106, such as, for example, a workstation, a desktop computer, a mobile computer, a networked computer, a collection of servers and/or databases, cellular phone, personal entertainment device, or a tablet PC.

Additionally, not all of the anatomical blood vessel mapping unit 5120, three-dimensional modeling unit 5104 and/or sleeve-fitting unit 5106 need be implemented on a single computing device. For example, the anatomical blood vessel mapping unit 5120 and/or three-dimensional modeling unit 5104 may be implemented and/or operable on a remote computer, while the sleeve-fitting unit 5106 and/or sleeve-making device 5108 is implemented and/or stored on a local computer. Further, aspects of the anatomical blood vessel mapping unit 5120, three-dimensional modeling unit 5104, sleeve-fitting unit 5106, imaging system 5114, and/or sleeve-making device 5108 may be implemented in different combinations and implementations than that shown in FIG. 51. For example, functionality of the sleeve-making device 5108 may be incorporated into the device 5102. In some embodiments, the at least one device 5102 may process anatomical blood vessel data 120 from an individual 118 according to anatomical profiles available as updates through a health records network.

The anatomical blood vessel data 120 from an individual 118 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

FIG. 35 illustrates an operational flow 3500 representing example operations relating to methods and systems for making a blood vessel sleeve. In FIG. 35 and in following figures that include various examples of operational flows, discussion, and explanation may be provided with respect to the above-described examples of FIGS. 1-34, and/or with respect to other examples and contexts. However, it should be understood that the operational flows may be executed in a number of other environment and contexts, and/or in modified versions of FIGS. 1-34. Also, although the various operational flows are presented in the sequence(s) illustrated, it should be understood that the various operations may be performed in other orders than those which are illustrated, or may be performed concurrently.

After a start operation, operation 3510 shows accepting one or more blood vessel sleeve dimensions based on blood vessel data from an individual. The one or more blood vessel sleeve dimensions may be calculated by the device 102, the sleeve-fitting unit 106 and/or the three-dimensional modeling unit 104 based on blood vessel data from, for example, health record 122, imaging system 5114, or portable imaging device 124.

For example, the three-dimensional modeling unit 1204 of the device 1202 may receive anatomical blood vessel data 120, such as, for example, one or more health records 122 relating to an individual 118 and/or an individual 118's data from an imaging system 1214. For example, this may include a three-dimensional construct of two-dimensional image data from an individual's blood vessel, for example, from a CT scan. Alternatively, the blood vessel data may refer to a series of two-dimensional section images that together make up three-dimensional blood vessel data. The three-dimensional modeling unit 1204, anatomical blood vessel data mapping unit 5120 (see FIG. 51), or sleeve-fitting unit 106 may calculate one or more blood vessel sleeve dimensions based on the blood vessel data from an individual.

For example, the sleeve-fitting unit 1206, anatomical blood vessel data mapping unit 1220, and/or device 1202 may apply a scaling function to the anatomical blood vessel data 120 to obtain specifications for a blood vessel sleeve that may, for example, fit a branched section of an artery that is afflicted with an aneurysm. Such a scaling function may not merely extrapolate from an available three-dimensional model of a blood vessel, but the scaling function may be used to, for example, constrict or constrain a portion of the blood vessel that is afflicted with an aneurysm (see FIG. 6B), while leaving another portion of the blood vessel unconstricted.

Operation 3520 depicts making a rapid-prototyped blood vessel sleeve at least partly based on the one or more blood vessel sleeve dimensions. For example, the sleeve-fitting unit 1206, anatomical blood vessel data mapping unit 1220, three-dimensional modeling unit 5104, and/or device 1202 may send the one or more blood vessel sleeve dimensions to a sleeve-making device 1208. Blood vessel sleeve dimensions may be sent to a therapeutic health care provider 5110, or, for example, directly to a sleeve-making device 108. Alternatively, the blood vessel sleeve dimensions may be stored in at least one memory in, for example, the device 1202. In this regard, it should be understood that the blood vessel sleeve dimensions may first be encoded and/or represented in digital form (i.e., as digital data), prior to the assignment to the at least one memory. For example, a digitally-encoded representation of the blood vessel sleeve dimensions may be stored in a local memory, or may be transmitted for storage in a remote memory. The sleeve-making device 1208 may be independent of device 1202, or alternatively, sleeve-making device 5108 may integrated with device 5102, sleeve-fitting unit 5106, anatomical blood vessel data mapping unit 5120, and/or three-dimensional modeling unit 5104.

Thus, an operation may be performed related either to a local or remote storage of the digital data, or to another type of transmission of the digital data. Of course, operations also may be performed related to accessing, querying, recalling, or otherwise obtaining the digital data from a memory, including, for example, receiving a transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

FIG. 36 illustrates alternative embodiments of the example operational flow 3500 of FIG. 35. FIG. 36 illustrates example embodiments where the accepting operation 3510 may include at least one additional operation. Additional operations may include operation 3600, 3602, 3604, 3606, 3608, and/or operation 3610.

Operation 3600 depicts receiving the one or more blood vessel sleeve dimensions based on blood vessel data from an individual at a user interface. For example, diagnostic health care provider 1216, therapeutic health care provider 1210, health care provider 220, and/or health care provider 222 may access a user interface to receive one or more blood vessel sleeve dimensions from, for example, device 5102, sleeve-fitting unit 5106, anatomical blood vessel data mapping unit 5120, and/or three-dimensional modeling unit 5104. The blood vessel sleeve dimensions may be based on blood vessel data from an individual acquired from an imaging system 1214, a portable imaging device 124, a three-dimensional modeling unit 1204, and/or the device 1202. For example, blood vessel data from an individual may include, as discussed below, CT scan data, MRI data, three-dimensional modeling data, or the like.

Operation 3602 depicts accepting the one or more blood vessel sleeve dimensions based on geometric blood vessel data from an individual. For example, the device 1202, sleeve-making device 1208, and/or sleeve-making device 5108 may accept, for example, blood vessel sleeve dimensions based on a set of contiguous two-dimensional cross-sections of an individual's blood vessel anatomy, which, taken together, constitute three-dimensional blood vessel data. Such cross-sections are typical of, for example, CT scan output and MRI scan output. A sleeve-fitting unit 1206, anatomical blood vessel data mapping unit 1220, and/or three-dimensional modeling unit 1204 may operate to determine the blood vessel sleeve dimensions.

Operation 3604 depicts accepting the one or more blood vessel sleeve dimensions based on blood vessel imaging data from an individual. For example, the device 1202, sleeve-making device 1208, and/or sleeve-making device 5108 may accept, for example, blood vessel sleeve dimensions based on blood vessel data from any blood vessel imaging procedure, such as magnetic resonance imaging, angiography, ultrasound, radiography, optical imaging, or the like. Such blood vessel sleeve dimensions may be calculated based on the blood vessel imaging data from an individual by sleeve-fitting unit 1206, anatomical blood vessel data mapping unit 1220, three-dimensional modeling unit 1204, and/or device 1202. Alternatively, the blood vessel sleeve dimensions may be accepted from a source independent of the device 1202, sleeve-making device 1208, and/or sleeve-making device 5108 such as, for example, a health care provider 222.

Operation 3606 depicts accepting the one or more blood vessel sleeve dimensions based on at least one of magnetic resonance imaging data, computed tomography data, positron emission tomography data, ultrasound imaging data, optical imaging data, or angiography data as the blood vessel data from an individual. For example, the device 1202, sleeve-making device 1208, and/or sleeve-making device 5108 may accept, for example, blood vessel sleeve dimensions based on blood vessel data from a magnetic resonance imaging procedure. Such blood vessel sleeve dimensions may be calculated based on the MRI data from an individual by sleeve-fitting unit 1206, anatomical blood vessel data mapping unit 1220, three-dimensional modeling unit 1204, and/or device 1202. Alternatively, the blood vessel sleeve dimensions may be accepted from a source independent of the device 1202, sleeve-making device 1208, and/or sleeve-making device 5108 such as, for example, therapeutic health care provider 1210.

Operation 3608 depicts accepting the one or more blood vessel sleeve dimensions based on at least one of magnetic resonance angiography data, computed tomography angiography data, Doppler ultrasound data, or cerebral angiography data as the blood vessel data from an individual. For example, the device 1202, sleeve-making device 1208, and/or sleeve-making device 5108 may accept, for example, blood vessel sleeve dimensions based on blood vessel data from a cerebral angiography procedure. Such blood vessel sleeve dimensions may be calculated based on the cerebral angiography data from an individual by sleeve-fitting unit 1206, anatomical blood vessel data mapping unit 1220, three-dimensional modeling unit 1204, and/or device 1202. Alternatively, the blood vessel sleeve dimensions may be accepted from a source independent of the device 1202, sleeve-making device 1208, and/or sleeve-making device 5108 such as, for example, therapeutic health care provider 1210.

Operation 3610 depicts accepting the one or more blood vessel sleeve dimensions based on blood vessel data in a digital imaging and communications in medicine format as the blood vessel data from an individual. For example, the device 1202, sleeve-making device 1208, and/or sleeve-making device 5108 may accept, for example, one or more blood vessel sleeve dimensions based on blood vessel data from a CT scan. Such blood vessel sleeve dimensions may be calculated based on the CT scan data from an individual by sleeve-fitting unit 1206, anatomical blood vessel data mapping unit 1220, three-dimensional modeling unit 1204, and/or device 1202. Alternatively, the blood vessel sleeve dimensions may be accepted from a source independent of the device 1202, sleeve-making device 1208, and/or sleeve-making device 5108 such as, for example, therapeutic health care provider 1210. The CT scan data and/or blood vessel sleeve dimensions may be accepted, for example, in a digital imaging and communications in medicine format (DICOM). This format is a standard for handling, storing, printing, and transmitting information in medical imaging. Supported modalities include, for example, angioscopy, color flow Doppler, computed radiography, duplex Doppler, digital subtraction angiography, fluorescein angiography, ultrasound, x-ray angiography, just to name a few. Of course imaging data including blood vessel sleeve dimensions in virtually any format may be accepted by the device 1202, sleeve-making device 1208, sleeve-making device 5108, and/or therapeutic health care provider 1210.

FIG. 37 illustrates alternative embodiments of the example operational flow 3500 of FIG. 35. FIG. 37 illustrates example embodiments where the accepting operation 3510 may include at least one additional operation. Additional operations may include operation 3700, 3702, 3704, 3706, 3708, and/or operation 3710.

Operation 3700 depicts accepting the one or more blood vessel sleeve dimensions based on blood vessel modeling data as the blood vessel data from an individual. For example, the device 1202, sleeve-making device 1208, and/or sleeve-making device 5108 may accept, for example, one or more blood vessel sleeve dimensions based on a three-dimensional mathematical model of a blood vessel or a three-dimensional image model of a blood vessel, for example, constructed by sleeve-fitting unit 1206, anatomical blood vessel data mapping unit 1220, three-dimensional modeling unit 1204, and/or device 1202. Alternatively, the blood vessel sleeve dimensions may be based on a blood vessel model from a source independent of the device 1202, sleeve-making device 1208, and/or sleeve-making device 5108 such as, for example, therapeutic health care provider 1210.

Operation 3702 depicts accepting the one or more blood vessel sleeve dimensions based on aorta data as the blood vessel data from an individual. For example, the device 1202, sleeve-making device 1208, and/or sleeve-making device 5108 may accept, for example, one or more blood vessel sleeve dimensions based on, for example, a three-dimensional model of the ascending aorta, aortic arch, descending aorta, thoracic aorta, and/or the abdominal aorta of an individual 118.

Operation 3704 depicts accepting the one or more blood vessel sleeve dimensions based on cerebral artery data as the blood vessel data from an individual. For example, the device 1202, sleeve-making device 1208, and/or sleeve-making device 5108 may accept, for example, one or more blood vessel sleeve dimensions based on, for example, the anatomy of at least one of an internal carotid artery, an anterior communicating artery, a middle cerebral artery, or other artery of the Circle of Willis of an individual 118.

Operation 3706 depicts accepting the one or more blood vessel sleeve dimensions based on aneurysm or branched blood vessel data as the blood vessel data from an individual. For example, the device 1202, sleeve-making device 1208, and/or sleeve-making device 5108 may accept, for example, one or more blood vessel sleeve dimensions based on, for example, CT scan data relating to a portion of a blood vessel with an aneurysm. For example, the aneurysm may be associated with the abdominal aorta, or the aneurysm may be close to a branch point in the Circle of Willis.

Operation 3708 depicts accepting the one or more blood vessel sleeve dimensions based on a three-dimensional blood vessel model as the blood vessel data from an individual. For example, the device 1202, sleeve-making device 1208, and/or sleeve-making device 5108 may accept, for example, one or more blood vessel sleeve dimensions based on, for example, a computer-generated three-dimensional polygonal mesh model of a blood vessel of an individual 118. Other examples of a three-dimensional blood vessel model may include a wireframe model, a solid model, a computed tomography model, or the like.

Operation 3710 depicts accepting the one or more blood vessel sleeve dimensions based on computer-generated anatomical blood vessel data from an individual. For example, the device 1202, sleeve-making device 1208, and/or sleeve-making device 5108 may accept, for example, one or more blood vessel sleeve dimensions based on, for example, a computer-generated model of a blood vessel of an individual 118. The model may be constructed by sleeve-fitting unit 1206, anatomical blood vessel data mapping unit 1220, three-dimensional modeling unit 1204, and/or device 1202. Alternatively, the blood vessel sleeve dimensions may be based on computer-generated anatomical blood vessel from a source such as, for example, therapeutic health care provider 1210, imaging system 5114, health record 122, and/or imaging system 114.

FIG. 38 illustrates alternative embodiments of the example operational flow 3500 of FIG. 35. FIG. 38 illustrates example embodiments where the accepting operation 3510 may include at least one additional operation. Additional operations may include operation 3800, 3802, 3804, and/or operation 3806.

Operation 3800 depicts extracting two or more sets of data, each data set defining a contour of a blood vessel sleeve at least partly based on the blood vessel data from an individual;

and interpolating data that represent one or more regions between two or more contours of a blood vessel sleeve. For example, the sleeve-fitting unit 1206, three-dimensional modeling unit 1204, anatomical blood vessel data mapping unit 1220, and/or device 1202 may extract, from a three-dimensional model of a blood vessel, data sets defining curvature contours of a blood vessel sleeve to fit the blood vessel. The sleeve-fitting unit 1206, three-dimensional modeling unit 1204, anatomical blood vessel data mapping unit 1220, and/or device 1202 may then interpolate data that represent the blood vessel sleeve surface between the curvature contours in order to construct, for example, a three-dimensional solid model of the blood vessel sleeve.

Operation 3802 depicts extracting two or more sets of data, each data set defining a contour of a blood vessel sleeve at least partly based on at least one of a light intensity matrix or a color intensity matrix. For example, the sleeve-fitting unit 1206, three-dimensional modeling unit 1204, anatomical blood vessel data mapping unit 1220, and/or device 1202 may extract, from a set of CT scan black-and-white and/or grayscale images, data sets defining curvature contours of a blood vessel sleeve (i.e., blood vessel sleeve dimensions) to fit a blood vessel shown in the images. Alternatively, for example, the sleeve-fitting unit 1206, three-dimensional modeling unit 1204, anatomical blood vessel data mapping unit 1220, and/or device 1202 may extract blood vessel sleeve contour data sets based on an unrefined or refined color intensity matrix. In one embodiment, the light intensity matrix and/or color intensity matrix consist of black-and-white and/or grayscale pixels corresponding to geometric blood vessel anatomical data.

Operation 3804 depicts applying a sleeve-fitting algorithm to blood vessel diameter and length data, blood vessel branching data, or blood vessel curvature data to obtain the one or more blood vessel sleeve dimensions based on blood vessel data from an individual. For example, the sleeve-fitting unit 1206, three-dimensional modeling unit 1204, anatomical blood vessel data mapping unit 1220, and/or device 1202 may apply a sleeve-fitting algorithm to various aspects of blood vessel data from an individual to obtain the one or more blood vessel sleeve dimensions. In one embodiment, the blood vessel data may correspond to the anatomy of a blood vessel branch junction affected by a nearby aneurysm. In this case, the sleeve-fitting algorithm may take into account the geometry of the branch junction, the geometry of the aneurysm, and any scale factor that a health care provider 222 may employ to change the geometry of the blood vessel through the use of the blood vessel sleeve.

Operation 3806 depicts applying a garment-fitting algorithm to the blood vessel data from an individual to obtain the one or more blood vessel sleeve dimensions. As discussed above, as in the use of garment-fitting algorithms in which body dimensions are used to model a person to fit clothing to the person, sleeve-fitting algorithms may be used to fit a blood vessel sleeve to a blood vessel. For example, the sleeve-fitting unit 1206, three-dimensional modeling unit 1204, anatomical blood vessel data mapping unit 1220, and/or device 1202 can extract two or more sets of anatomical blood vessel data 120, each data set defining a contour of a blood vessel sleeve at least partly based on blood vessel data pertaining to an individual 118; and the sleeve-fitting unit 1206, for example, can interpolate data representing one or more regions between two or more extracted contours to define dimensions of a sleeve in the region between the two or more extracted contours. This process can then be repeated by the sleeve-fitting unit 1206 until the dimensions of an entire sleeve are specified. In another example, the sleeve-fitting unit 5106, three-dimensional modeling unit 5104, anatomical blood vessel data mapping unit 5120, and/or device 5102 may apply a scale factor to three-dimensional blood vessel data to specify a rapid-prototyped blood vessel sleeve 5112 that is in some degree larger or smaller than the interior or exterior surface of a blood vessel.

Various other garment-fitting algorithms may be adapted to use in custom-fitting a blood vessel sleeve. For example, known garment-fitting methods such as those disclosed in U.S. Pat. Nos. 5,163,007, 5,850,222, and/or U.S. patent publication US 2004/0093105 may be applied to blood vessel data by the sleeve-fitting unit 1206 and/or device 1202 in order to obtain blood vessel sleeve dimensions.

FIG. 39 illustrates alternative embodiments of the example operational flow 3500 of FIG. 35. FIG. 39 illustrates example embodiments where the accepting operation 3510 may include at least one additional operation. Additional operations may include operation 3900, 3902, 3904, 3906, and/or operation 3908.

Operation 3900 depicts applying a scale factor to the blood vessel data from an individual to obtain the one or more blood vessel sleeve dimensions. For example, the sleeve-fitting unit 5106, three-dimensional modeling unit 5104, anatomical blood vessel data mapping unit 5120, and/or device 5102 may scale a three-dimensional mesh model of a blood vessel by creating a transform matrix based on scale factors. The device 102 and/or sleeve-fitting unit 106, for example, can multiply each point in the mesh model by the transform matrix. The use of matrix transformations to rotate, translate, and scale points in a three-dimensional space are well known in the apparel arts, as described in U.S. Pat. No. 5,850,222. In this way, a sleeve may be modeled after the blood vessel according to precise specifications.

Operation 3902 depicts assigning a set of position coordinates to the blood vessel data from an individual and assigning counterpart position coordinates to a blood vessel sleeve model to obtain the one or more blood vessel sleeve dimensions. For example, the sleeve-fitting unit 5106, three-dimensional modeling unit 5104, anatomical blood vessel data mapping unit 5120, and/or device 5102 can assign a set of position coordinates to a blood vessel model and assign counterpart position coordinates to a blood vessel sleeve model to produce blood vessel sleeve dimensions that fit the blood vessel.

Operation 3904 depicts applying at least one best fit criterion to the blood vessel data to obtain the one or more blood vessel sleeve dimensions. For example, the sleeve-fitting unit 1206, three-dimensional modeling unit 1204, anatomical blood vessel data mapping unit 1220, and/or device 1202 can apply a best fit criterion to blood vessel data from an individual. In one embodiment, the best fit criteria may include specified cross-sectional dimensions. In another embodiment, the specified cross-sectional dimensions may be based on actual cross-sectional-dimensions represented by the blood vessel data. In yet another embodiment, the specified cross-sectional dimensions may be based on actual cross-sectional dimensions represented by the blood vessel data and based on tolerance criteria, e.g., 1%, 2%, 5%, or 10% variation in sleeve dimension relative to actual cross-sectional dimensions.

Operation 3906 depicts applying a sleeve-fitting algorithm to the blood vessel data from an individual to determine dimensions of a blood vessel sleeve fitted to the interior of a blood vessel. For example, the sleeve-fitting unit 5106, three-dimensional modeling unit 5104, anatomical blood vessel data mapping unit 5120, and/or device 5102 can apply a sleeve-fitting algorithm to blood vessel data from an individual corresponding to the interior surface of a blood vessel, taking into account any branching and/or curvature that may be present. A therapeutic health care provider 1210 may wish to take advantage of blood vessel branching as a way of anchoring a blood vessel sleeve in place in the vicinity of, for example, an aneurysm. Custom-fitting a blood vessel sleeve to the interior of a blood vessel may also take into account any stenosis that may be present in the blood vessel, for example, due to atherosclerotic plaque or prior angioplasty/stent therapy.

Operation 3908 depicts applying a sleeve-fitting algorithm to the blood vessel data from an individual to determine dimensions of a blood vessel sleeve fitted to the exterior of a blood vessel. For example, the sleeve-fitting unit 5106, three-dimensional modeling unit 5104, anatomical blood vessel data mapping unit 5120, and/or device 5102 can apply a sleeve-fitting algorithm to blood vessel data from an individual corresponding to the exterior surface of a blood vessel, taking into account any branching, curvature, and/or aneurysm(s) that may be present. Applying a sleeve-fitting algorithm to the blood vessel data to determine dimensions of a blood vessel sleeve fitted to the exterior of a blood vessel may involve design choices on the part of a therapeutic health care provider 5110 as to the exact fit that will best address the medical issue present in the individual 118. Those of skill in the art may use their professional judgment to determine dimensions of a blood vessel sleeve fitted to the exterior of a blood vessel on a case-by-case basis.

FIG. 40 illustrates alternative embodiments of the example operational flow 3500 of FIG. 35. FIG. 40 illustrates example embodiments where the making operation 3510 may include at least one additional operation. Additional operations may include operation 4000, 4002, 4004, 4006, and/or operation 4008.

Operation 4000 depicts making a multiple-layered rapid-prototyped blood vessel sleeve at least partly based on the one or more blood vessel sleeve dimensions. The sleeve-making device 5108 and/or device 5102 may make a multiple-layered, rapid-prototyped blood vessel sleeve 5112 based on one or more blood vessel sleeve dimensions. For example, the blood vessel sleeve may have a first layer that serves to provide support and structural strength for a blood vessel, and the blood vessel sleeve may also have a second layer that provides a tissue scaffolding function for areas of the sleeve that are in contact with the blood vessel. Such a tissue scaffolding or matrix layer may provide an hospitable environment in which smooth muscle cells, epithelial cells, or other cells of the blood vessel may proliferate. Proliferation agents may also be used in such a tissue scaffolding layer to promote thickening of a blood vessel wall affected by an aneurysm. Examples of proliferation agents include tissue growth factors (TGFs), fibroblast growth factors (FGFs), colchicine, and thrombin. Alternatively or in addition, a known apoptotic agent or blood vessel cell anti-proliferation agent may be used in a tissue scaffolding layer of the sleeve to effect a decrease in tissue area in an affected portion of the blood vessel in close proximity to a sleeve surface. Examples of agents that can counteract smooth muscle cell proliferation may include, for example, cyclosporine A, corticosteroids, and carvedilol. Also, agents that affect migration of blood vessel cells may be employed, such as prostaglandin E2, carvedilol, cAMP-mobilizing agents, and glucocorticoids.

Operation 4002 depicts making the rapid-prototyped blood vessel sleeve at least partly based on the one or more blood vessel sleeve dimensions, the rapid-prototyped blood vessel sleeve at least partly made of biocompatible materials. The sleeve-making device 5108 and/or device 5102 may make a biocompatible, rapid-prototyped blood vessel sleeve 5112 based on one or more blood vessel sleeve dimensions. As discussed above, biocompatible material may include, for example, a polymer, a metal and/or metal alloy, a ceramic, a natural material, a pyrolytic carbon material, and/or composites thereof, or the like. Biocompatible material may also include biomimetic material and/or material with surface functionalization via protein deposition or self-assembling peptide scaffold deposition. Additionally, methods known in the art to render biocompatible chemically inert or reactive surfaces may be used, including, for example, plasma processing and/or the use of polyanhydrides. Another method for detoxification of solid freeform fabrication materials is found in U.S. Pat. No. 6,996,245 entitled "Detoxification of solid freeform fabrication materials." This process involves chemical extraction and has been used to detoxify, for example, a custom hearing aid shell produced by stereolithography from an acrylate photopolymer resin.

Polyvinyl chloride is one commonly used polymer in medical devices, and other biocompatible polymers commonly used are silicone, polyurethane, polycarbonates, polyester and polyethylene, biodegradable polymers, bioactive polymers, hydrogels, molecular imprinted polymers, conductive polymers, and biopolymers. Such polymers may be applied to meshes, foams, sponges or hydrogels, for example, to form a custom-fitted blood vessel sleeve 700. Bioactive polymers may serve secondary functions such as stimulating or inhibiting tissue growth, and/or promoting adhesion.

Titanium, stainless steel, and chromium steel are examples of metals used in medical implants. Metal alloys are also commonly used to obtain desired strength, malleability, and/or fabrication properties. Composites comprised of artificial growth factors, natural materials, carbon fibers, and/or polymers are also useful as biocompatible material.

Biocompatible nanomaterial may also be used. Some such materials known to those of skill in the art may provide rejection-resistant implants. Tissue engineering using polymer scaffolds for cell hosting may also provide a biocompatible material for used in conjunction with a sleeve-making device 1208 to make a biocompatible, rapid-prototyped blood vessel sleeve 5112.

Operation 4004 depicts making a collapsible rapid-prototyped blood vessel sleeve at least partly based on the one or more blood vessel sleeve dimensions. For example, the sleeve-making device 5108 and/or device 5102 may make a collapsible, rapid-prototyped blood vessel sleeve 5112 based on one or more blood vessel sleeve dimensions. As shown in FIG. 7B, FIG. 8A, and FIG. 8B, the custom-fitted blood vessel sleeve 709 and/or 800 may be structured to expand or collapse via pleats, a folding mesh structure, or other mechanical means known in the art. Such features may be designed into a rapid-prototyping specification such that the sleeve-making device 5108 may make, for example, a collapsible, rapid-prototyped blood vessel sleeve. Alternatively, materials may be used in the rapid-prototyping of the custom-fitted blood vessel sleeve 700 that have known expansion and/or contraction properties in the human body that are known to those of skill in the art. FIG. 7B depicts a custom-fitted blood vessel sleeve 709 with pleat 710 and pleat 712 surrounding a lumen 714, and having an outer diameter 716 in a folded state. Also depicted is an unpleated portion 717 of the sleeve. Collapsibility afforded by mechanisms such as pleats may facilitate insertion or placement of the custom-fitted blood vessel sleeve 709 into the region proximal to the blood vessel 300 prior to placement of the custom-fitted blood vessel sleeve 709 around the blood vessel 300. In one embodiment, pleat 710 may serve as a location for a therapeutic health care provider 110 to cut the custom-fitted blood vessel sleeve 709 longitudinally to create a custom-fitted blood vessel sleeve opening 701 for placement of the sleeve over a blood vessel. In such an embodiment, the custom-fitted blood vessel sleeve 709 may be made without a custom-fitted blood vessel sleeve opening 701.

Operation 4006 depicts making a coated rapid-prototyped blood vessel sleeve at least partly based on the one or more blood vessel sleeve dimensions. For example, the sleeve-making device 5108 and/or device 5102 may make a coated rapid-prototyped blood vessel sleeve 5112 based on one or more blood vessel sleeve dimensions. Such a coating may be placed on an internal surface or an external surface of the rapid-prototyped blood vessel sleeve 5112, for example the surfaces of an internal layer 706 and/or an external layer 702. As discussed above, a coating may comprise a coating known in the art such as one or more thrombus-resistant coatings, one or more anti-coagulant coatings, one or more biocompatibility coatings, one or more biodegradable coatings, one or more durability coatings, one or more small molecule delivery coatings, and/or one or more macromolecule delivery coatings.

In another embodiment, an anti-hyperplasic agent such as, for example, poly(L-lysine)-graft-poly(ethyleneglycol) (PLL-g-PEG) adsorbed to sleeve surfaces may be used as a coating to reduce neointimal hyperplasia or other blood vessel surface hyperplasia (see Billinger et al., "Polymer stent coating for prevention of neointimal hyperplasia," J. Invasive Cardiol. 2006 September; 18(9):423-6).

In some embodiments, a coating may be applied in a perioperative procedure, for example, as described in U.S. patent publication 2005/0037133 A1, entitled "Method for applying drug coating to a medical device in surgeon room."

Operation 4008 depicts making a coated rapid-prototyped blood vessel sleeve at least partly based on the one or more blood vessel sleeve dimensions, the coated rapid-prototyped blood vessel sleeve including at least one of a drug-eluting coating or a biofilm-resistant coating. For example, the sleeve-making device 5108 and/or device 5102 may make a rapid-prototyped blood vessel sleeve 5112 that has a coating that can release a therapeutic agent over time, or that has a coating that inhibits the growth of microbes. Microbes may include bacteria, fungi, protists, viruses, or the like. Examples of such coatings further may include coatings that release pharmaceutically active compounds over time (e.g., drug-eluting coatings, such as known drug-eluting polymers), and/or adhesive coatings (e.g., biocompatible epoxyamine adhesives described in U.S. Pat. No. 6,780,510).

Biofilm-resistant coatings may include, for example, coatings that resist build up of cellular or biomolecular debris, or microbial debris such as fungal or bacterial growth. Some known microbial resistant coatings include silver particles in a polymer matrix that are present in the matrix material preferably at a concentration of 1 ppm to 1,000 ppm, more preferably 100 ppm to 800 ppm, especially 250 ppm to 750 ppm, and most preferably 500 pm to 700 ppm relative to the total weight of the matrix material. Such a coating is described, for example, in U.S. patent publication 2007/0051366 entitled "Medical Devices With Germ-Reducing Surfaces." Such coatings may include one or more hydrophilic surfaces, one or more hydrophobic surfaces, and/or one or more surfaces that are engineered to physically repel water or other biological molecules.

Alternatively, a sleeve surface or surface coating may be a metallic nano-powder using, for example, an inert gas condensation method. This involves vaporizing the base metal in an inert gas atmosphere, after which it is deposited as a powder and then directly processed, for example, in a rapid-prototyping procedure. With this method, minimal quantities of silver are sufficient to achieve the desired antibacterial properties of the powder due to its nanostructure. The nanosilver can be used to coat the surfaces of medical devices in a rapid-prototyping production process, which helps to decrease or even avoid the use of antibiotics.

Chemical nanotechnology can also be used for coating sleeve surfaces. Such self-cleaning surfaces include those with antibacterial properties. Numerous different materials, such as metal, glass, and plastics can be coated in this way. The thin, nanoporous layer also allows a great freedom of choice in terms of the shapes that can be coated.

FIG. 41 illustrates alternative embodiments of the example operational flow 3500 of FIG. 35. FIG. 41 illustrates example embodiments where the making operation 3510 may include at least one additional operation. Additional operations may include operation 4100, 4102, and/or operation 4104.

Operation 4100 depicts making a substantially mesh rapid-prototyped blood vessel sleeve at least partly based on the one or more blood vessel sleeve dimensions. For example, the sleeve-making device 1208 and/or device 5102 may make a substantially mesh rapid-prototyped blood vessel sleeve 5112 based on one or more blood vessel sleeve dimensions. Such a mesh structure is common in stent and stent graft manufacture, allowing for expandability of the stent to a maximum limit from a collapsed initial configuration. Upon expansion, such a mesh sleeve typically locks into the expanded configuration such that it will generally not subsequently collapse.

Operation 4102 depicts making a rapid-prototyped blood vessel sleeve at least partly based on the one or more blood vessel sleeve dimensions, the rapid-prototyped blood vessel sleeve including at least one of extensions positioned for closure, suturing tabs, detents, hooks, Velcro, glue, or interlocking closure ridges. For example, the sleeve-making device 1208 and/or device 5102 may make a rapid-prototyped blood vessel sleeve 5112 that is equipped with a way to close the sleeve around a blood vessel after placement on the blood vessel. For example, extensions positioned for closure may include tabs that overlap with a joining edge of the sleeve in such a way that a therapeutic health care provider 5110 could sew the tab to the joining edge and thereby close the sleeve, for example, along a longitudinal axis.

Operation 4104 depicts making a rapid-prototyped blood vessel sleeve at least partly based on the one or more blood vessel sleeve dimensions, the rapid-prototyped blood vessel sleeve including geckel adhesive. For example, the sleeve-making device 1208 and/or device 5102 may make a rapid-prototyped blood vessel sleeve 5112 that has areas designed to facilitate closure that are coated with geckel adhesive. Geckel adhesive is a reversible wet/dry adhesive inspired by mussels and geckos (See Lee et al., "a reversible wet/dry adhesive inspired by mussels and geckos," Nature 448:19, pp. 338-341 (2007). Geckel adhesive surfaces may be engineered to have arrays of gecko-mimetic nanoscale pillars coated with a thin mussel-mimetic polymer film. Such adhesives provide strong, reversible, water-compatible bonding.

Other adhesives may be used in conjunction with rapid-prototyped blood vessel sleeves. For example, a smart adhesive with a switch may be employed on a portion of a rapid-prototyped blood vessel sleeve. For example, adhesives are known that combine a polyacid surface with a polybase surface. The resulting electrostatic and hydrogen bonds result in tight bonding that is reversible upon acidification of the material to a pH of <2, which causes the basic groups of the polybase surface to lose their charge and therefore lose their attraction for the polyacid surface. The two surfaces may at this point be separated. If the pH is returned to a slightly acidic or neutral pH, the surfaces may once again be bonded together (See La Spina et al., "Controlling Network-Brush Interactions to Achieve Switchable Adhesion," Angew. Chem. Int'l Ed., 46 (2007)).

FIG. 42 illustrates alternative embodiments of the example operational flow 3500 of FIG. 35. FIG. 42 illustrates example embodiments where the making operation 3510 may include at least one additional operation. Additional operations may include operation 4200, 4202, and/or operation 4204.

Operation 4200 depicts making a set of rapid-prototyped blood vessel sleeves at least partly based on the one or more blood vessel sleeve dimensions. For example, the sleeve-making device 1208 and/or device 5102 may make a set of rapid-prototyped blood vessel sleeves 5112 based on one or more blood vessel sleeve dimensions. Such a set of rapid-prototyped blood vessel sleeves may be made perioperatively for use by a therapeutic health care provider 5110 who may want the option of having a series of different-sized sleeves for use on a patient's blood vessel during a surgery to address, for example, an aneurysm. A set of rapid-prototyped blood vessel sleeves may be, at a minimum, a set of two rapid-prototyped blood vessel sleeves.

Operation 4202 depicts making a set of rapid-prototyped blood vessel sleeves that each has at least one of different dimensions, a different material composition, different closure means, or a different coating as the set of rapid-prototyped blood vessel sleeves at least partly based on the one or more blood vessel sleeve dimensions. For example, the sleeve-making device 1208 and/or device 5102 may make a set of rapid-prototyped blood vessel sleeves 5112 based on one or more blood vessel sleeve dimensions. As discussed above, such a set of blood vessel sleeves may be made perioperatively for use by a therapeutic health care provider 110 who may want the option of having sleeves of varying composition, dimensions, closure means, and/or coating. The therapeutic health care provider 110 may, upon viewing surgically the actual blood vessel to be addressed, make a judgment to select a certain size or kind of sleeve depending on any differences between the results of medical imaging and first hand observation of the blood vessel.

Operation 4204 depicts making a set of blood vessel sleeves that each has at least different-sized closure extensions as the set of rapid-prototyped blood vessel sleeves at least partly based on the one or more blood vessel sleeve dimensions. For example, the sleeve-making device 1208 and/or device 5102 may make a set of rapid-prototyped blood vessel sleeves 5112 that exhibits a range of different-sized closure extensions. Such a range of different-sized closure extensions may give a therapeutic health care provider a set of options from which to select a rapid-prototyped blood vessel sleeve 5112 that is most easily closed under the specific conditions of a given surgery.

FIG. 43 illustrates alternative embodiments of the example operational flow 3500 of FIG. 35. FIG. 43 illustrates example embodiments where the making operation 3510 may include at least one additional operation. Additional operations may include operation 4300, 4302, and/or operation 4304.

Operation 4300 depicts making the rapid-prototyped blood vessel sleeve at least partly based on the one or more blood vessel sleeve dimensions, the rapid-prototyped blood vessel sleeve capable of shrinking to fit a blood vessel. For example, the sleeve-making device 1208 and/or device 5102 may make a rapid-prototyped blood vessel sleeve 5112 based on abdominal aorta sleeve dimensions, the rapid-prototyped blood vessel sleeve capable of shrinking to fit an individual's abdominal aorta. As discussed above, such a blood vessel sleeve may be made of a material with known shrinking or contraction properties in an aqueous environment such as is found in and around the vasculature, so that placement of the sleeve on a portion of a blood vessel will be accompanied by wetting of the sleeve material and shrinking of the material by a known amount, to fit the blood vessel. Examples of materials known to shrink upon insertion into an aqueous body environment include fabrics, especially when exposed to hot water. Other materials may shrink upon the attainment of body temperature, such as certain rubber materials as described in U.S. Pat. No. 6,221,447. Alternatively, elastic materials such as elastomeric polymers may be used to form the rapid-prototyped blood vessel sleeve 5112. Such elastic materials, once tailored to closely fit the blood vessel 300, may have the added benefit of expanding and contracting with the blood vessel wall as the blood vessel diameter changes in response to temperature, vasoconstrictors, vasodilators, or other agents or situations that cause constriction and/or dilation of blood vessels. It should be understood that portions of a rapid-prototyped blood vessel sleeve 5112 that are fitted to an aneurysm portion of a blood vessel may be specified to have limited expansion parameters so as to prevent rupture of the aneurysm. Accordingly, a portion of a rapid-prototyped blood vessel sleeve 5112 may be made of stretchable material, whereas another portion of the custom-fitted blood vessel sleeve 700 may be made of non-stretchable material or material with limited expansion parameters.

Operation 4302 depicts making the rapid-prototyped blood vessel sleeve at least partly based on the one or more blood vessel sleeve dimensions, the rapid-prototyped blood vessel sleeve capable of expanding to fit a blood vessel. For example, the sleeve-making device 1208 and/or device 5102 may make a rapid-prototyped blood vessel sleeve 5112 based on cerebral artery sleeve dimensions, the rapid-prototyped blood vessel sleeve capable of expanding to fit a cerebral artery. As discussed above, materials known to expand in aqueous environments may be used to make a rapid-prototyped blood vessel sleeve 5112. Such materials include water-swellable materials (e.g., starch, gelatin, chitin, gum Arabic, xanthan, cross-linked albumin, cross-linked hyaluronan, and/or alginate. Other examples of water-swellable materials include collagen, cellulose derivatives, cross-linked poly(vinyl alcohol) and copolymers, cross-linked poly(vinylpirrolidone) and copolymers, poly(hydroxyethyl methacrylate), poly(ethylene glycol) and copolymers, polyacrylate, polyacrylate-co-starch, polyacrylate-co-polyacrylamide, polyacrylamide. Other water-swellable materials known to one of skill in the art may be used. For example, the hydrophilic polyurethanes and the like of U.S. Pat. No. 4,872,867; the water-swellable plastic polymers of U.S. Pat. Nos. 5,163,952 and 5,258,020; the solid absorbents of U.S. Pat. No. 5,554,180, such as copolymers of cellulose and starch, agar and polymeric acids; the water-swellable matrix materials of U.S. Pat. No. 4,460,642; and/or the water-swellable layers of U.S. Pat. Nos. 4,496,535 and 4,872,867 may be used. As described above, elastic materials such as elastomeric polymers may be used to form the rapid-prototyped blood vessel sleeve 5112. Such elastic materials, once tailored to closely fit the blood vessel 300, may have the added benefit of expanding and contracting with the blood vessel wall as the blood vessel diameter changes in response to temperature, vasoconstrictors, vasodilators, or other agents or situations that cause constriction and/or dilation of blood vessels.

Operation 4304 depicts making the rapid-prototyped blood vessel sleeve at least partly based on the one or more blood vessel sleeve dimensions, the rapid-prototyped blood vessel sleeve having at least one of a GoreTex, Teflon, or titanium alloy surface. For example, the sleeve-making device 1208 and/or device 5102 may make a rapid-prototyped blood vessel sleeve 5112 based on aneurysm sleeve dimensions, the rapid-prototyped blood vessel sleeve having a Teflon surface. For example, a polytetrafluoroethylene surface may have desirable properties for rapid-prototyping manufacturing, such as heat resistance, and/or a polytetrafluoroethylene surface may have desirable properties as a surface coating for the sleeve in situ, such as non-stick characteristics. Further, titanium alloy surfaces are commonly used in implantable devices for their structural and biocompatibility benefits.

FIG. 44 illustrates alternative embodiments of the example operational flow 3500 of FIG. 35. FIG. 44 illustrates example embodiments where the making operation 3510 may include at least one additional operation. Additional operations may include operation 4400 and/or operation 4402.

Operation 4400 depicts making the rapid-prototyped blood vessel sleeve at least partly based on the one or more blood vessel sleeve dimensions, the rapid-prototyped blood vessel sleeve having at least one of a substantially polymer composition, a substantially plastic composition, a substantially thermoplastic composition, a substantially photopolymer composition, or a substantially elastomeric composition. For example, the sleeve-making device 1208 and/or device 5102 may make a rapid-prototyped blood vessel sleeve 5112 based on aneurysm sleeve dimensions, the rapid-prototyped blood vessel sleeve having a substantially thermoplastic composition. Such a composition is particularly suited for a rapid-prototyping process of manufacture. For example, thermoplastics are used in fused deposition modeling, as discussed above.

Operation 4402 depicts making a substantially transparent rapid-prototyped blood vessel sleeve at least partly based on the one or more blood vessel sleeve dimensions. For example, the sleeve-making device 1208 and/or device 5102 may make a substantially transparent rapid-prototyped blood vessel sleeve 5112 based on blood vessel sleeve dimensions. In this embodiment, as discussed above, the transparent nature of the blood vessel sleeve may allow a surgeon or other therapeutic health care provider 5110 to visually examine the fit of the blood vessel sleeve more closely, and also to visually examine the status of the blood vessel sleeve and blood vessel at various times after the initial placement, if necessary. Such a substantially transparent sleeve may be particularly useful in cases where a problem has developed in the area of the sleeve, such as hemorrhaging, embolism, and/or stenosis of the blood vessel.

FIG. 45 illustrates alternative embodiments of the example operational flow 3500 of FIG. 35. FIG. 45 illustrates example embodiments where the making operation 3510 may include at least one additional operation. Additional operations may include operation 4500, 4502, 4504, and/or operation 4506.

Operation 4500 depicts making a rapid-prototyped blood vessel sleeve at least partly based on the one or more blood vessel sleeve dimensions, the rapid-prototyped blood vessel sleeve having at least one indicator on the blood vessel sleeve. For example, the sleeve-making device 1208 and/or device 5102 may make a rapid-prototyped blood vessel sleeve 5112 having at least one indicator, based on blood vessel sleeve dimensions. As discussed above, such an indicator may aid the therapeutic health care provider 5110 in, for example, tracking the blood vessel sleeve during surgery. An indicator may include a text label or numerical information, or an indicator may be a symbol or code that represents other information. Alternatively, the indicator may be a radio-frequency identification device (RFID) that contains information about the sleeve and/or the patient receiving the sleeve.

Operation 4502 depicts making a rapid-prototyped blood vessel sleeve at least partly based on the one or more blood vessel sleeve dimensions, the rapid-prototyped blood vessel sleeve having at least one indicator on the blood vessel sleeve corresponding to a dimension of the blood vessel sleeve. For example, the sleeve-making device 1208 and/or device 5102 may make a rapid-prototyped blood vessel sleeve 5112 having at least one indicator corresponding to the length, circumference, and/or curvature of the rapid-prototyped blood vessel sleeve 5112. For example, where a set or series of different-sized sleeves is produced by rapid-prototyping, an indicator of size may aid the therapeutic health care provider 5110 in choosing the correct sleeve for the blood vessel upon visual inspection.

Operation 4504 depicts making a rapid-prototyped blood vessel sleeve at least partly based on the one or more blood vessel sleeve dimensions, the rapid-prototyped blood vessel sleeve having at least one indicator on the blood vessel sleeve corresponding to a material thickness of the blood vessel sleeve. For example, the sleeve-making device 1208 and/or device 5102 may make a rapid-prototyped blood vessel sleeve 5112 having at least one indicator corresponding to the thickness of, for example, a woven or non-woven fabric material of the rapid-prototyped blood vessel sleeve 5112.

Operation 4506 depicts making a rapid-prototyped blood vessel sleeve at least partly based on the one or more blood vessel sleeve dimensions, the rapid-prototyped blood vessel sleeve having at least one indicator on the blood vessel sleeve corresponding to a material stiffness of the blood vessel sleeve. For example, the sleeve-making device 1208 and/or device 5102 may make a rapid-prototyped blood vessel sleeve 5112 having at least one indicator corresponding to the stiffness of the material used to make the rapid-prototyped blood vessel sleeve 5112. Stiffness may be described in terms of flexibility, bendability, strength, rigidity, or the like.

FIG. 46 illustrates alternative embodiments of the example operational flow 3500 of FIG. 35. FIG. 46 illustrates example embodiments where the making operation 3510 may include at least one additional operation. Additional operations may include operation 4600, 4602, 4604, and/or operation 4506.

Operation 4600 depicts making a rapid-prototyped blood vessel sleeve at least partly based on the one or more blood vessel sleeve dimensions, the rapid-prototyped blood vessel sleeve having at least one indicator on the blood vessel sleeve corresponding to a material composition of the blood vessel sleeve. For example, the sleeve-making device 1208 and/or device 5102 may make a rapid-prototyped blood vessel sleeve 5112 having at least one indicator corresponding to the composition of the material used to make the rapid-prototyped blood vessel sleeve 5112. Such compositions are described above and may include metals, polymers, fabrics, and the like.

Operation 4602 depicts making a rapid-prototyped blood vessel sleeve at least partly based on the one or more blood vessel sleeve dimensions, the rapid-prototyped blood vessel sleeve having at least one indicator on the blood vessel sleeve corresponding to individual-characterizing data. For example, the sleeve-making device 1208 and/or device 5102 may make a rapid-prototyped blood vessel sleeve 5112 having at least one indicator corresponding to information about the individual for whom the rapid-prototyped blood vessel sleeve 5112 is made. Examples of individual-characterizing data may include name, address, social security number, and/or medical history information.

Operation 4604 depicts making a rapid-prototyped blood vessel sleeve at least partly based on the one or more blood vessel sleeve dimensions, the rapid-prototyped blood vessel sleeve having at least one indicator on the blood vessel sleeve corresponding to at least one of a time or a date. For example, the sleeve-making device 1208 and/or device 5102 may make a rapid-prototyped blood vessel sleeve 5112 having at least one indicator corresponding to information about the time and/or date of manufacture and/or placement of the rapid-prototyped blood vessel sleeve 5112.

Operation 4606 depicts at least one indicator on the blood vessel sleeve relating to a color coding of the blood vessel sleeve as the at least one indicator on the blood vessel sleeve. For example, the sleeve-making device 1208 and/or device 5102 may make a rapid-prototyped blood vessel sleeve 5112 having at least one color coding associated with the rapid-prototyped blood vessel sleeve 5112. As a rapid-recognition feature, color coding allows a therapeutic health care provider 5110 to quickly identify a particular feature of a rapid-prototyped blood vessel sleeve 5112.

FIG. 47 illustrates alternative embodiments of the example operational flow 3500 of FIG. 35. FIG. 47 illustrates example embodiments where the making operation 3510 may include at least one additional operation. Additional operations may include operation 4700, and/or operation 4702.

Operation 4700 depicts at least one color coding corresponding to patient data as the at least one indicator on the blood vessel sleeve relating to a color coding of the blood vessel sleeve. For example, the sleeve-making device 1208 and/or device 5102 may make a rapid-prototyped blood vessel sleeve 5112 having at least one color coding corresponding to an individual's medical condition, such as cerebral artery aneurysm, as a procedure check to confirm that the correct patient is receiving the correct procedure.

Operation 4702 depicts at least one color coding corresponding to at least one of material type, material thickness, material stiffness, sleeve size, thickness of the blood vessel sleeve, or sleeve coating as the at least one indicator on the blood vessel sleeve relating to a color coding of the blood vessel sleeve. For example, the sleeve-making device 1208 and/or device 5102 may make a rapid-prototyped blood vessel sleeve 5112 having a color coding corresponding to the dosage of drug in a drug-eluting coating of the rapid-prototyped blood vessel sleeve 5112. For example, the sleeve-making device 1208 and/or device 5102 may make a set of three rapid-prototyped blood vessel sleeves, each with a different dosage of controlled-release anti-clotting agent. The sleeves may be made according to a color code with the lowest dosage sleeve bearing, for example, the color red; a medium dosage sleeve bearing the color green; and the highest dosage sleeve bearing the color blue.

FIG. 48 illustrates alternative embodiments of the example operational flow 3500 of FIG. 35. FIG. 48 illustrates example embodiments where the making operation 3510 may include at least one additional operation. Additional operations may include operation 4800, 4802, 4804, and/or operation 4806.

Operation 4800 depicts making a rapid-prototyped blood vessel sleeve having at least one contrast agent within the material of the rapid-prototyped blood vessel sleeve at least partly based on the one or more blood vessel sleeve dimensions. For example, the sleeve-making device 1208 and/or device 5102 may make a rapid-prototyped blood vessel sleeve 5112 containing gadolinium. Doping, impregnating, embedding, or otherwise placing a contrast agent within the material composition of a rapid-prototyped blood vessel sleeve 5112 may enhance medical imaging of the sleeve subsequent to its placement on or within a blood vessel in an individual 118. This may be useful for short-term and/or long-term follow-up of the functioning of the custom-fitted blood vessel sleeve 112 in the individual 118. For example, a sleeve containing a paramagnetic material such as gadolinium or $Mn^{++}$ will exhibit an enhanced signal in MRI-scanned images, and a sleeve containing iodine will exhibit an enhanced signal in CT-scanned images. A rapid-prototyped blood vessel sleeve 5112 may contain, for example, multiple contrast agents to facilitate or enhance detection of the sleeve by a number of different imaging methods.

Operation 4802 depicts making a rapid-prototyped blood vessel sleeve having at least one indicator of deformation or wear in or on the rapid-prototyped blood vessel sleeve at least partly based on the one or more blood vessel sleeve dimensions. For example, the sleeve-making device 1208 and/or device 5102 may make a rapid-prototyped blood vessel sleeve 5112 having a grid printed on its surface as an indicator of deformation over time. For example, the rapid-prototyped blood vessel sleeve 5112 may have a visible grid or an otherwise detectable grid of perpendicular lines on its surface, such that upon deformation or wearing of the sleeve, the right angles of the grid change to acute or obtuse angles in the area of wear and/or deformation. The degree and/or rate of wear and/or deformation may thus be apparent from an imaging or inspection of the indicator of deformation or wear after a period of time. Another such indicator of wear or deformation is a pattern of parallel lines that, over time, may lose the original parallel pattern with deformation of the sleeve over time. Any geometric pattern may serve this purpose if measured at a time zero and compared to the pattern at time n.

Operation 4804 depicts making a rapid-prototyped blood vessel sleeve using a laser-cutting device at least partly based on the one or more blood vessel sleeve dimensions. For example, the sleeve-making device 1208 and/or device 5102 may comprise an automated laser-cutting device in a perioperative scenario that can provide a therapeutic health care provider 5110 with a rapid-prototyped blood vessel sleeve 5112 to use in a surgical intervention.

Operation 4806 depicts making a rapid-prototyped blood vessel sleeve using a three-dimensional printing device at least partly based on the one or more blood vessel sleeve dimensions. For example, the sleeve-making device 1208 and/or device 5102 may comprise a three-dimensional printing device in a perioperative scenario to provide a therapeutic health care provider 5110 with a rapid-prototyped blood vessel sleeve 5112 to use in a surgical intervention.

FIG. 49 illustrates a partial view of an example computer program product 4900 that includes a computer program 4904 for executing a computer process on a computing device. An embodiment of the example computer program product 4900 is provided using a signal bearing medium 4902, and may include at one or more instructions for accepting one or more blood vessel sleeve dimensions based on blood vessel data from an individual; and one or more instructions for making a rapid-prototyped blood vessel sleeve at least partly based on the one or more blood vessel sleeve dimensions. The one or more instructions may be, for example, computer executable and/or logic-implemented instructions. In one implementation, the signal-bearing medium 4902 may include a computer-readable medium 4906. In one implementation, the signal bearing medium 4902 may include a recordable medium 4908. In one implementation, the signal bearing medium 4902 may include a communications medium 4910.

FIG. 50 illustrates an example system 5000 in which embodiments may be implemented. The system 5000 includes a computing system environment. The system 5000 also illustrates the health care provider 222 using a device 5004, which is optionally shown as being in communication with a computing device 5002 by way of an optional coupling 5006. The optional coupling 5006 may represent a local, wide-area, or peer-to-peer network, or may represent a bus that is internal to a computing device (e.g., in example embodiments in which the computing device 5002 is contained in whole or in part within the device 5004). A storage medium 5008 may be any computer storage medium.

The computing device 5002 includes computer-executable instructions 5010 that when executed on the computing device 5002 cause the computing device 5002 to accept one or more blood vessel sleeve dimensions based on blood vessel data from an individual; and to make a rapid-prototyped blood vessel sleeve at least partly based on the one or more blood vessel sleeve dimensions. As referenced above and as shown in FIG. 50, in some examples, the computing device 5002 may optionally be contained in whole or in part within the device 5004.

In FIG. 50, then, the system 5000 includes at least one computing device (e.g., 5002 and/or 5004). The computer-executable instructions 5010 may be executed on one or more of the at least one computing device. For example, the computing device 5002 may implement the computer-executable instructions 5010 and output a result to (and/or receive data from) the device 5004. Since the computing device 5002 may be wholly or partially contained within the device 5004, the device 5004 also may be said to execute some or all of the computer-executable instructions 5010, in order to be caused to perform or implement, for example, various ones of the techniques described herein, or other techniques.

The device 5004 may include, for example, a portable computing device, workstation, or desktop computing device. In another example embodiment, the computing device 5002 is operable to communicate with the device 5004 associated with the health care provider 222 to receive information about input from the health care provider 222 or other sources for blood vessel sleeve dimensions based on blood vessel data from an individual. In another example embodiment, the device 5004 may include a sleeve-making device 5012, such as a three-dimensional printer, automated laser-cutting device, or other rapid-prototyping device.

FIG. 52 illustrates an example system 5200 in which embodiments may be implemented. The system 5200 includes at least one device 5202. The at least one device 5202 may contain, for example, an anatomical blood vessel data mapping unit 120, a three-dimensional modeling unit 5204, and/or a sleeve-fitting unit 5206. Imaging system 5214 may generate anatomical blood vessel data 120 from an individual 118, or anatomical blood vessel data 120 from an individual 118 may be obtained from a health record 122 that is external to the device 5202. Imaging system 5214 may be operated by diagnostic health care provider 5216 and/or therapeutic health care provider 5210 to obtain anatomical blood vessel data 120 from an individual 118.

Therapeutic health care provider 5210 may interact with the device 5202 to determine blood vessel sleeve specifications based on anatomical blood vessel data 120 from an individual 118. Therapeutic health care provider 5210 may also interact with sleeve-making device 5208 to obtain active blood vessel sleeve 5212 based on anatomical blood vessel data 120 from an individual 118. Alternatively, the active blood vessel sleeve 5212 may be made according to standard sizes. Or, an active blood vessel sleeve or set of active blood vessel sleeves may be made according to typical blood vessel dimensions, or according to an estimate of the dimensions of a portion of a blood vessel. Therapeutic health care provider 5210 may then employ the active blood vessel sleeve 5212 to address a blood vessel of individual 118 in an open surgical procedure, in a laparoscopic surgery procedure, through a catheter insertion procedure, or the like.

In some embodiments, the imaging system 5214 and the device 5202 may be combined in a single device, or the imaging system 5214, the device 5202, and/or the sleeve-making device 5208 may be combined in a single device. In some embodiments the imaging system 5214 may be a portable imaging device 124 that can communicate with the at least one device 5202, on which the sleeve-fitting unit 5206 is operable, via a wireless network for example. In some embodiments, the sleeve-making device 5208 may be operable remotely through the device 5202 via, for example, a network connection.

In FIG. 52, the at least one device 5202 is illustrated as possibly being included within a system 5200. Any kind of computing device may be used in connection with the anatomical blood vessel mapping unit 5220, three-dimensional modeling unit 5204 and/or sleeve-fitting unit 5206, such as, for example, a workstation, a desktop computer, a mobile computer, a networked computer, a collection of servers and/or databases, cellular phone, personal entertainment device, or a tablet PC.

Additionally, not all of the anatomical blood vessel mapping unit 5220, three-dimensional modeling unit 5204 and/or sleeve-fitting unit 5206 need be implemented on a single computing device. For example, the anatomical blood vessel mapping unit 5220 and/or three-dimensional modeling unit 5204 may be implemented and/or operable on a remote computer, while the sleeve-fitting unit 5206 and/or sleeve-making device 5208 is implemented and/or stored on a local computer. Further, aspects of the anatomical blood vessel mapping unit 5220, three-dimensional modeling unit 5204, sleeve-fitting unit 5206, imaging system 5214, and/or sleeve-making device 5208 may be implemented in different combinations and implementations than that shown in FIG. 52. For example, functionality of the sleeve-making device 5208 may be incorporated into the device 5202. In some embodiments, the at least one device 5202 may process anatomical blood vessel data 120 from an individual 118 according to anatomical profiles available as updates through a health records network.

An active blood vessel sleeve that is capable of altering its dimensions (e.g., changing in length, diameter, and/or curvature) may also be of utility in some applications. Mechanisms of effecting such change in other medical devices have been described in, for example, U.S. patent application 2005/0177223 "Medical devices having MEMs functionality and methods of making same."

FIG. 53 illustrates an exemplary embodiment related to an active blood vessel sleeve. In FIG. 53 and in following figures that include various examples of active blood vessel sleeves, discussion and explanation may be provided with respect to the above-described system environment of FIG. 52, and/or with respect to other examples and contexts. However, it should be understood that the exemplary embodiments may be executed in a number of other environments and contexts, and/or in modified versions of FIG. 52. Also, although the various exemplary embodiments are presented in the context of the system environment of FIG. 52, it should be understood that the various exemplary embodiments may be produced by other systems than those which are illustrated.

With respect to FIG. 53A, blood vessel 5304 from an individual 118 is shown, the blood vessel 5304 having a portion bearing a fusiform aneurysm 5306. Active blood vessel sleeve 5300 fitted to the outside of blood vessel 5304 is shown exerting inward pressure on the fusiform aneurysm 5306. With respect to FIG. 53B, shown is an active blood vessel sleeve fitted for the outside of at least a portion of at least one blood vessel 5304. For example, shown is active blood vessel sleeve 5300 that may be placed around the blood vessel 5304 to support and/or reduce the size of the aneurysm 5302. FIG. 53B thus shows an active blood vessel sleeve fitted for the outside of at least a portion of at least one aneurysm on the at least a portion of the at least one blood vessel 5304.

In another embodiment, an active blood vessel sleeve fitted for the outside of at least a portion of an aorta may be placed on an affected portion of, for example, the abdominal aorta in order to reduce the diameter of a distended portion of abdominal aorta (see, e.g., FIG. 53A).

In another embodiment, an active blood vessel sleeve fitted for the outside of at least a portion of at least one cerebral artery may be made. Such an active blood vessel sleeve may be used to address aneurysms in, for example, vessels in the Circle of Willis, as discussed above.

In another embodiment, an active blood vessel sleeve fitted for the outside of at least a portion of at least one branched blood vessel may be manufactured that will address the particular geometry of a branched blood vessel.

In another embodiment, a multiple-layered active blood vessel sleeve fitted for the outside of at least a portion of the at least one blood vessel may be made that, for example, contains more than one functional layer and/or more than one structural layer. Various functional layers may be a layer containing an environment and/or sleeve sensor, a layer containing an actuator, a layer containing a transceiver, a layer containing a transmitter, a layer containing a receiver, a layer containing a reservoir, and/or a layer containing combinations of the any of these, or like items. Examples of structural layers may include a layer that has a particular stiffness, flexibility, biocompatibility, and/or material composition, or the like.

The choice of structural element size, configuration, and/or composition appropriate for a particular blood vessel may be selected by a person of skill in the art. Structural elements may be constructed by a variety of manufacturing methods, from a variety of materials, as discussed above and as follows: Appropriate materials may include fabrics, metals, ceramics, polymers, and composite materials having suitable biocompatibility, sterilizability, mechanical, and physical properties, as will be known to those of skill in the art. Examples of materials and selection criteria are described, for example, in The Biomedical Engineering Handbook, Second Edition, Volume I, J. D. Bronzino, Ed., CRC Press LLC, pp. IV-1-43-31 (2000). Manufacturing techniques may include injection molding, extrusion, die-cutting, rapid-prototyping, self-assembly, or the like, and may depend on the choice of material, device size, and/or configuration.

Functional layers or portions of an active blood vessel sleeve, including sensing portions, active portions, and/or contraction mechanisms or structures, as well as any associated circuitry, may be fabricated on or in the structural element using various microfabrication and/or MEMS techniques, or may be constructed separately and subsequently combined with the structural element, as one or more distinct components. Examples of microfabrication techniques may include, for example, those disclosed in U.S. patent applications 2005/0221529; 2005/0121411; 2005/0126916; and Nyitrai et al.; "Preparing Stents with Masking & Etching Technology," 26th International Spring Seminar on Electronics Technology, bearing dates of May 8, 2003-5/11/2003, pp. 321-324; IEEE.

In another embodiment, a collapsible active blood vessel sleeve fitted for the outside of at least a portion of the at least one blood vessel may be produced that, for example, is structured to expand or collapse via pleats, a folding mesh structure, or other mechanical means known in the art. Alternatively, materials may be used in the manufacture of the custom-fitted blood vessel sleeve 700 that have known expansion and/or contraction properties in the human body that are known to those of skill in the art. FIG. 7B depicts a custom-fitted blood vessel sleeve 709 with pleat 710 and pleat 712 surrounding a lumen 714, and having an outer diameter 716 in a folded state. Also depicted is an unpleated portion 717 of the sleeve. Such a sleeve may also be an active blood vessel sleeve fitted for the outside of at least a portion of at least one blood vessel. Collapsibility afforded by mechanisms such as pleats may facilitate insertion or placement of the active blood vessel sleeve into the region proximal to the blood vessel 300 prior to placement of the active blood vessel sleeve around the blood vessel 300. In one embodiment, pleat 710 may serve as a location for a therapeutic health care provider 110 to cut an active blood vessel sleeve longitudinally to create an opening for placement of the sleeve over a blood vessel. In such an embodiment, the active blood vessel sleeve may be made without an opening. A collapsible active blood vessel sleeve fitted for the outside of at least a portion of at least one blood vessel may be particularly suited for use in a laparoscopic surgery situation, in which case the insertion aperture may be small, and a collapsed active blood vessel sleeve may fit through a relatively small incision and subsequently expanded for placement around a blood vessel.

In another embodiment, a substantially transparent active blood vessel sleeve fitted for the outside of at least a portion of the at least one blood vessel may be made that, as discussed above, may allow a surgeon or other therapeutic health care provider 110 to visually examine the fit of the active blood vessel sleeve more closely, and also to visually examine the status of the active blood vessel sleeve and blood vessel at various times after the initial placement, if necessary. Such a substantially transparent active blood vessel sleeve may be particularly useful in cases where a problem has developed in the blood vessel in the area of the sleeve, such as hemorrhaging, embolism, and/or stenosis of the blood vessel.

In another embodiment, an active blood vessel sleeve fitted for the outside of at least a portion of the at least one blood vessel, the active blood vessel sleeve at least partly made of a biocompatible material may be made that may include, for example, a polymer, a metal and/or metal alloy, a ceramic, a natural material, a pyrolytic carbon material, and/or composites thereof, or the like. As discussed above, biocompatible material may also include biomimetic material and/or material with surface functionalization via protein deposition or self-assembling peptide scaffold deposition. Additionally, methods known in the art to render biocompatible chemically inert or reactive surfaces may be used, including, for example, plasma processing and/or the use of polyanhydrides.

Another embodiment includes an active blood vessel sleeve fitted for the outside of at least a portion of the at least one blood vessel, the active blood vessel sleeve at least partly made of a smart material. Smart materials may have one or more properties that can be significantly altered in a controlled fashion by external stimuli, such as stress, temperature, moisture, pH, electric or magnetic fields. There are a number of types of smart material, some of which are already common in the art. Some examples are piezoelectric materials that produce a voltage when stress is applied; this effect also applies in the reverse manner wherein a voltage across the sample will produce stress within the sample. Suitably specified structures made from these materials can therefore be made that bend, expand, or contract when a voltage is applied.

Another example of smart material is thermoresponsive material (e.g., either shape memory alloy, shape memory polymer, and/or other shape memory material), which are materials that can hold different shapes at various temperatures. Magnetic shape memory alloys are materials that change their shape in response to a significant change in a magnetic field. pH-sensitive polymers are materials that expand or contract when the pH of the surrounding media changes. Chromogenic systems change color in response to electrical, optical or thermal changes. These include electrochromic materials, which change their colour or opacity on the application of a voltage (e.g. liquid crystal displays), thermochromic materials change in color depending on their temperature, and photochromic materials, which change colour in response to light, for example, light sensitive sunglasses that darken when exposed to bright sunlight.

Such use of smart materials in the formation of an active blood vessel sleeve may enhance the ease of application of the sleeve to the blood vessel in terms of, for example, having a flexible sleeve during the placement procedure for opening and closing of the sleeve, followed by a manipulation that may make the sleeve more rigid as a way of enhancing the support function of the sleeve around the blood vessel.

Such smart materials may have only a limited capacity for movement. For this reason, the active nature of the active blood vessel sleeve may be important in allowing the active blood vessel sleeve to change conformation over a wide movement range relative to the movement range of a passive blood vessel sleeve made of smart material.

Other examples of smart materials are described in "Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html; "Agile new plastics change shape with heat"; MIT Tech Talk; Nov. 22, 2006; p. 5 (1 page); and Shahinpoor et al., "Ionic polymer-metal composites: IV. Industrial and medical applications; Smart Materials and Structures; pp. 197-214; Vol. 14; Institute of Physics Publishing (2005).

Another embodiment includes an active blood vessel sleeve fitted for the outside of at least a portion of the at least one blood vessel, the active blood vessel sleeve having at least one coating. As discussed above, such a coating may be placed on an internal surface or an external surface of the active blood vessel sleeve, for example the surfaces of an internal layer and/or an external layer. A coating may comprise a coating known in the art such as one or more thrombus-resistant coatings, one or more anti-coagulant coatings, one or more biocompatibility coatings, one or more biodegradable coatings, one or more durability coatings, one or more small molecule delivery coatings, and/or one or more macromolecule delivery coatings. Examples of coatings further may include coatings that release pharmaceutically active compounds over time (e.g., drug-eluting coatings such as known drug-eluting polymers), and/or adhesive coatings (e.g., biocompatible epoxyamine adhesives described in U.S. Pat. No. 6,780,510). Other examples of coatings that may be used with active blood vessel sleeves are discussed above.

Another embodiment includes an active blood vessel sleeve fitted for the outside of at least a portion of the at least one blood vessel, the active blood vessel sleeve capable of shrinking to fit the blood vessel. Such an active blood vessel sleeve may be made of a material with known shrinking or contraction properties in an aqueous environment such as is found in and around the vasculature, so that placement of the sleeve on a portion of a blood vessel will be accompanied by wetting of the sleeve material and shrinking of the material by a known amount, to fit the blood vessel. As discussed above, examples of materials known to shrink upon insertion into an aqueous body environment include fabrics, especially when exposed to hot water. Other materials may shrink upon the attainment of body temperature, such as certain rubber materials as described in U.S. Pat. No. 6,221,447. Alternatively, elastic materials such as elastomeric polymers may be used to form the active blood vessel sleeve. Such elastic materials, once tailored to closely fit a blood vessel, may have the added benefit of expanding and contracting with the blood vessel wall as the blood vessel diameter changes in response to temperature, vasoconstrictors, vasodilators, or other agents or situations that cause constriction and/or dilation of blood vessels. It should be understood that portions of an active blood vessel sleeve that are fitted to the outside of an aneurysm portion of a blood vessel may be specified to have limited expansion parameters so as to prevent rupture of the aneurysm. Accordingly, a portion of an active blood vessel sleeve may be made of stretchable material, whereas another portion of the active blood vessel sleeve may be made of non-stretchable material or material with limited expansion parameters.

Another embodiment includes an active blood vessel sleeve fitted for the outside of at least a portion of the at least one blood vessel, the active blood vessel sleeve capable of expanding to fit the blood vessel. As discussed above, materials known to expand in aqueous environments may also be used to make an active blood vessel sleeve. Such materials include water-swellable materials (e.g., starch, gelatin, chitin, gum Arabic, xanthan, cross-linked albumin, cross-linked hyaluronan, and/or alginate. Other examples of water-swellable materials include collagen, cellulose derivatives, cross-linked poly(vinyl alcohol) and copolymers, cross-linked poly(vinylpirrolidone) and copolymers, poly(hydroxyethyl methacrylate), poly(ethylene glycol) and copolymers, polyacrylate, polyacrylate-co-starch, polyacrylate-co-polyacrylamide, polyacrylamide. Other water-swellable materials known to one of skill in the art may be used. For example, the hydrophilic polyurethanes and the like of U.S. Pat. No. 4,872,867; the water-swellable plastic polymers of U.S. Pat. Nos. 5,163,952 and 5,258,020; the solid absorbents of U.S. Pat. No. 5,554,180, such as copolymers of cellulose and starch, agar and polymeric acids; the water-swellable matrix materials of U.S. Pat. No. 4,460,642; and/or the water-swellable layers of U.S. Pat. Nos. 4,496,535 and 4,872,867 may be used. As described above, elastic materials such as elastomeric polymers may be used to form the active blood vessel sleeve. Such elastic materials may have the added benefit of expanding and contracting with the blood vessel wall as the blood vessel diameter changes in response to temperature, vasoconstrictors, vasodilators, or other agents or situations that cause constriction and/or dilation of blood vessels. An active blood vessel sleeve may be actuated to effect expansion of the sleeve in response to, for example, stenosis of the blood vessel around which the sleeve had been placed.

Another embodiment includes an active blood vessel sleeve fitted for the outside of at least a portion of the at least one blood vessel, the active blood vessel sleeve being made up of two or more modules. For example, an active blood vessel sleeve may be specified to fit a blood vessel trifurcation with an aneurysm at a blood vessel branch area, in which the active blood vessel sleeve is made up of sub-parts or modules that can be assembled, for example, during a surgical procedure to form a complete active blood vessel sleeve. In another example, the active blood vessel sleeve may be made up of a plurality of functional modules, structural modules, or combinations thereof. For example, as discussed below, a module containing an agent reservoir may be combined with a structural module that is custom-fitted to a blood vessel of an individual. Other modules may include an actuator module, a sensor module, transceiver module, receiver module, and/or a transmitter module, or the like.

Another embodiment includes an active blood vessel sleeve fitted for the outside of at least a portion of the at least one blood vessel, the active blood vessel sleeve having at least one of a polytetrafluoroethylene surface, a barbed surface, a metal surface, a silicon surface, or a hydrogel surface.

Another embodiment includes an active blood vessel sleeve fitted for the outside of at least a portion of the at least one blood vessel, the active blood vessel sleeve having at least one of a GoreTex surface, a Teflon surface, or a titanium alloy surface.

Another embodiment includes an active blood vessel sleeve fitted for the outside of at least a portion of the at least one blood vessel, the active blood vessel sleeve having at least one of a substantially polymer composition, a substantially plastic composition, a substantially thermoplastic composition, a substantially photopolymer composition, or a substantially elastomeric composition.

Another embodiment includes an active blood vessel sleeve custom-fitted for the outside of at least a portion of the at least one blood vessel at least partly based on anatomical blood vessel data from an individual. For example, an individual may be analyzed by an imaging system 5214 operated by a diagnostic health care provider 5216, resulting in anatomical blood vessel data 120. In one embodiment, anatomical blood vessel data 120 and/or health record 122 may be modeled in three dimensions by three-dimensional modeling unit 5204 to give physical dimensions of an affected blood vessel. A sleeve-fitting unit 5206 and/or anatomical blood vessel data mapping unit 5220 may then calculate active blood vessel sleeve dimensions. These active blood vessel sleeve dimensions may then be sent to a sleeve-making device 5208 that is, for example, part of device 5202. The output of sleeve-making device 5208 may be, for example, active blood vessel sleeve 5212, or a rapid-prototyped active blood vessel sleeve.

Another embodiment includes an active blood vessel sleeve fitted for the outside of at least a portion of the at least one blood vessel at least partly based on computer-generated anatomical blood vessel data from the individual. As discussed above, an individual 118 with a vascular health issue will frequently be subject to evaluation by, for example, a diagnostic health care provider 116 such as a radiologist operating medical imaging equipment that provides computer-generated anatomical blood vessel data 120. Such medical imaging may include magnetic resonance imaging (MRI scanning), computed tomography or computed axial tomography (CT scanning), positron emission tomography (PET scanning), and/or angiography, for example. For example, a CT scan of an individual's head may provide a large series of two-dimensional images of a cross-section of the head where digital geometry processing is used to generate a three-dimensional image based on the large series of two-dimensional images. CT scanning typically produces a volume of data pertaining to the individual 118 that can be manipulated through a process known as windowing to produce an image of various internal structures based on their ability to block an x-ray beam. Other methods of visualizing blood vessel anatomy may also be used. Such a three-dimensional image, for example, provided by a CT scan process may provide anatomical blood vessel data 120, e.g., dimensions, from which an active blood vessel sleeve may be specified and made.

Another embodiment includes an active blood vessel sleeve fitted for the outside of at least a portion of the at least one blood vessel at least partly based on a three-dimensional anatomical model of the blood vessel from the individual. As discussed above, an imaging system 114 often provides two-dimensional geometric images of a cross-section of an individual's anatomy (e.g., two-dimensional anatomical blood vessel data 120) and/or three-dimensional anatomical blood vessel data 120. Such anatomical blood vessel data 120 may be converted into a three-dimensional anatomical model by a three-dimensional modeling unit 104 operable on a device 102, or by software known in the art operable on a remote device or operable on device 5202. Examples of such software include amira 4 software from Mercury Computer Systems, which describes the amira 4 software as automatic and interactive segmentation tools that support rapid processing of 3D image data. Other aspects of such software are discussed above in greater detail.

Another embodiment includes an active blood vessel sleeve fitted for the outside of at least a portion of the at least one blood vessel at least partly based on a three-dimensional anatomical model of the blood vessel from the individual, the three-dimensional anatomical model of the blood vessel from the individual at least partly derived from at least one of computed tomography data, magnetic resonance imaging data, positron emission tomography data, ultrasound imaging data, optical imaging data, or angiography data.

Another embodiment includes an active blood vessel sleeve fitted for the outside of at least a portion of the at least one blood vessel at least partly based on a three-dimensional anatomical model of the blood vessel from the individual, the three-dimensional anatomical model of the blood vessel from the individual at least partly derived from at least one of computed tomography angiography data, magnetic resonance angiography data, or Doppler ultrasound data.

Another embodiment includes an active blood vessel sleeve fitted for the outside of at least a portion of the at least one blood vessel, the active blood vessel sleeve having one or more closures. Such closures will ensure that the active blood vessel sleeve will stay in place around the blood vessel after placement to perform its function of, for example, supporting the weakened wall of a blood vessel with an aneurysm. In one embodiment, the sleeve may be an active blood vessel sleeve fitted for the outside of at least a portion of the at least one blood vessel, the active blood vessel sleeve having at least one of extensions positioned for closure, suturing tabs, detents, hooks, Velcro, glue, or interlocking closure ridges.

Another embodiment includes an active blood vessel sleeve fitted for the outside of at least a portion of the at least one blood vessel, the blood vessel sleeve being one of a set of active blood vessel sleeves. Such a set of active blood vessel sleeves may be made perioperatively for use by a health care provider 110 who may want the option of having a series of different-sized sleeves for use on a patient's blood vessel during a surgery to address, for example, an aneurysm. Such a set of active blood vessel sleeve may each have a range of movement, for example minimum and maximum diameters that may factor into a therapeutic health care provider's decision as to which size active sleeve to use.

Another embodiment includes an active blood vessel sleeve fitted for the outside of at least a portion of the at least one blood vessel, the active blood vessel sleeve being one of a set of active blood vessel sleeves that each has at least one of different dimensions, a different material composition, or a different coating. Again, such a set of blood vessel sleeves may be made perioperatively for use by a therapeutic health care provider 5210 who may want the option of having sleeves of varying composition, dimensions, and/or coating. The therapeutic health care provider 5210 may, upon viewing surgically the actual blood vessel to be addressed, make a judgment on the spot to select a certain size or kind of active sleeve depending on any differences between the results of medical imaging and first hand observation of the blood vessel.

Another embodiment includes an active blood vessel sleeve fitted for the outside of at least a portion of the at least one blood vessel, the active blood vessel sleeve being one of a set of active blood vessel sleeves, the set of active blood vessel sleeves having at least an assortment of active blood vessel sleeves with different sleeve closures. Such an assortment of active blood vessel sleeves may include sleeves with different sized sleeve closures, and/or sleeves with different kinds of sleeve closure mechanisms.

Another embodiment includes an active blood vessel sleeve fitted for the outside of at least a portion of the at least one blood vessel, the active blood vessel sleeve being one of a set of active blood vessel sleeves of varying size.

Another embodiment includes an active blood vessel sleeve fitted for the outside of at least a portion of the at least one blood vessel, the active blood vessel sleeve having an indicator on the active blood vessel sleeve.

Another embodiment includes an active blood vessel sleeve fitted for the outside of at least a portion of the at least one blood vessel, the active blood vessel sleeve having an indicator corresponding to a size of the active blood vessel sleeve.

Another embodiment includes an active blood vessel sleeve fitted for the outside of at least a portion of the at least one blood vessel, the active blood vessel sleeve having an indicator corresponding to a material thickness of the active blood vessel sleeve.

Another embodiment includes an active blood vessel sleeve fitted for the outside of at least a portion of the at least one blood vessel, the active blood vessel sleeve having an indicator corresponding to a material stiffness of the active blood vessel sleeve.

Another embodiment includes an active blood vessel sleeve fitted for the outside of at least a portion of the at least one blood vessel, the active blood vessel sleeve having an indicator corresponding to a material type of the active blood vessel sleeve.

Another embodiment includes an active blood vessel sleeve fitted for the outside of at least a portion of the at least one blood vessel, the active blood vessel sleeve having an indicator corresponding to individual-characterizing data.

Another embodiment includes an active blood vessel sleeve fitted for the outside of at least a portion of the at least one blood vessel, the active blood vessel sleeve having an indicator corresponding to at least one of a time or a date.

Another embodiment includes an active blood vessel sleeve fitted for the outside of at least a portion of the at least one blood vessel, the active blood vessel sleeve having an indicator relating to a color coding of the active blood vessel sleeve.

Another embodiment includes an active blood vessel sleeve fitted for the outside of at least a portion of the at least one blood vessel, the active blood vessel sleeve having an indicator relating to a color coding corresponding to patient data.

Another embodiment includes an active blood vessel sleeve fitted for the outside of at least a portion of the at least one blood vessel, the active blood vessel sleeve having an indicator relating to a color coding corresponding to at least one of a material type, a material thickness, a material stiffness, an active blood vessel sleeve size, an active blood vessel sleeve thickness, or an active blood vessel sleeve coating.

Another embodiment includes an active blood vessel sleeve fitted for the outside of at least a portion of the at least one blood vessel, the active blood vessel sleeve having at least one contrast agent within a material of the active blood vessel sleeve. As discussed above, doping, impregnating, embedding, or otherwise placing a contrast agent within the material composition of an active blood vessel sleeve 5212 may enhance medical imaging of the sleeve subsequent to its placement on or within a blood vessel in an individual 118. This may be useful for short-term and/or long-term follow-up of the functioning of the active blood vessel sleeve 5212 in the individual 118. For example, a sleeve containing a paramagnetic material such as gadolinium or $Mn^{++}$ will appear in MRI-scanned images, and a sleeve containing iodine will appear in CT-scanned images. An active blood vessel sleeve 5212 may contain, for example, multiple contrast agents to facilitate detection of the sleeve by a number of different imaging methods.

Another embodiment includes an active blood vessel sleeve fitted for the outside of at least a portion of the at least one blood vessel, the active blood vessel sleeve having at least one indicator of deformation or wear. For example, the active blood vessel sleeve 5212 may have visible grid or otherwise detectable grid of perpendicular lines on its surface, such that upon deformation or wearing of the sleeve, the right angles of the grid change to acute or obtuse angles in the area of wear or deformation. As discussed above, the degree and/or rate of wear and/or deformation may thus be apparent from an imaging or inspection of the indicator of deformation or wear after a period of time.

Another embodiment includes an active blood vessel sleeve fitted for the outside of at least a portion of the at least one blood vessel, the active blood vessel sleeve containing at least one power source. In various embodiments as described herein, an active blood vessel sleeve may include a power source configured to provide power to at least one of the sensor 5412, and/or the actuation mechanism 5410. The power source may be at least one of a current source or a magnetic field source. The power source may be at least one of an electrochemical battery, nuclear battery, a fuel cell, a biothermal power source, a pressure-rectifying mechanism, or an acceleration rectifying mechanism. Alternatively, the power source may include at least one of a lithium iodine battery, a microbattery, a button cell battery, a thin film battery, a nanocomposite battery, an enzymatic fuel cell, a biofuel cell, or a glucose fuel cell.

One or more power sources of the same or different types may be included in the active blood vessel sleeve, without limitation. Batteries may be located on the active blood vessel sleeve, possibly a microbattery like those available from Quallion LLC (http://www.quallion.com), designed as a film (U.S. Pat. Nos. 5,338,625 and 5,705,293), and/or printable nanocomposite batteries (Pushparaj et al., "Flexible Energy Storage Devices Based on Nanocomposite Paper" Proc. Natl. Acad. Sci. USA, 10.1073, Aug. 15, 2007). Alternatively, the power source may include one or more fuel cells such as an enzymatic, microbial, or photosynthetic fuel cell or other biofuel cell (US2003/0152823A1; WO03/106966A2; or Chen et al., "A Miniature Biofuel Cell," J. Am. Chem. Soc. 2001, 123, 8630-8631), and could be of any size, including the micro- or nano-scale. The power source may be an energy-scavenging device such as a pressure-rectifying mechanism that utilizes pulsatile changes in blood pressure, for example, or an acceleration-rectifying mechanism as used in self-winding watches, or other types of flow-rectifying mechanism capable of deriving energy from other flow parameters.

In some embodiments, the power source may be an electrical power source located remote from the active blood vessel sleeve and connected to the active blood vessel sleeve by a wire, or the power source may be an optical power source located remote from the active blood vessel sleeve and connected to the active blood vessel sleeve by an optical connector, such as a glass fiber or bundle of fibers. In some embodiments, the power source may be a power receiver capable of receiving power from an external source, for example, an acoustic source or electromagnetic source (e.g., infrared energy, or inductively coupled, as described in U.S. Pat. No. 6,170,485 or U.S. patent application 2005/0228259). Thus the active blood vessel sleeve may be an active blood vessel sleeve fitted for the outside of at least a portion of the at least one blood vessel, the active blood vessel sleeve capable of receiving power from at least one remote power source.

Other examples of remote power sources may include at least one of an ultra-low-power radio-frequency system, a radio frequency to direct current conversion system, a resonant coupling system, an evanescent wave coupling system, witricity, or an electromagnetic induction system.

In some embodiments, the active blood vessel sleeve may include a power transmitter capable of transmitting power from the active blood vessel sleeve to a secondary location. The power transmitter may be capable of transmitting at least one of acoustic power, electrical power, or optical power. The secondary location may be, for example, another device within the body, either in a blood vessel or elsewhere, that includes a power receiver and structures for using, storing and/or re-transmitting the received power.

FIG. 54 illustrates an exemplary embodiment related to an active blood vessel sleeve. In FIG. 54 and in following figures that include various examples of active blood vessel sleeves, discussion and explanation may be provided with respect to the above-described system environment of FIG. 52, and/or with respect to other examples and contexts. However, it should be understood that the exemplary embodiments may be executed in a number of other environments and contexts, and/or in modified versions of FIG. 52. Also, although the various exemplary embodiments are presented in the context of the system environment of FIG. 52, it should be understood that the various exemplary embodiments may be produced by other systems than those which are illustrated.

With respect to FIG. 54, an active blood vessel sleeve 5400 may include receiver circuitry 5408 capable of receiving a signal 5402 from a transmitter 5404, the receiver circuitry 5408 capable of signaling actuation mechanism 5410. Alternatively, actuation circuitry may be present to signal actuation mechanism 5410, or the actuation mechanism may receive a signal 5402 directly. Such a signal 5402 may contain instructions for a degree of movement to be effected by actuation mechanism 5410, for example. The signal 5402 may be capable of penetrating tissue 5406 to various depths in order to be received by active blood vessel sleeve 5400.

Active blood vessel sleeve 5400 may also contain one or more sensors 5412. In this embodiment, the active blood vessel sleeve may be an active blood vessel sleeve fitted for the outside of at least a portion of the at least one blood vessel, the active blood vessel sleeve having at least one sensor. Examples of sensors that may be included in the active blood vessel sleeve include at least one of a pressure sensor, a temperature sensor, a flow sensor, a viscosity sensor, a shear sensor (e.g., for measuring the effective shear modulus of the fluid at a frequency or strain-rate), a pH sensor, a chemical sensor (for determining the presence or concentration of a chemical compound or species), an optical sensor, an acoustic sensor, a biosensor, an electrical sensor, a magnetic sensor, and/or a time sensor. Such sensors may detect stresses to the blood vessel sleeve that may require adjustment in a physical parameter of the sleeve, such as diameter. Alternatively, a sensor may detect blood in the area of the sleeve, indicative of rupture or leaking of blood through the blood vessel wall. Such detection may trigger release of an agent, such as a coagulant or anti-coagulant, as discussed below.

In this and other embodiments disclosed herein, a condition of interest may include a variety of conditions, including but not limited to, an embolism, a plaque, a thrombus, an aneurysm, a stenosis, a puncture, a perforation, a rupture, a dissection, a tear, an inflammation, or a branching point in the blood vessel, the branching point including at least two branches of the blood vessel. The term "condition", as used herein, may refer to normally occurring anatomic features, man-made or other foreign structures, features, or conditions, disease states or injuries that may be present in a blood vessel by chance or purpose, and various detectable or measurable characteristics or parameters that indicate the presence of such conditions or features.

Sensor 5412 may be an optical sensor, an imaging device, or various other types of sensors, as are known to those of skill in the art. Upon detection of a parameter, actuation mechanism 5410 may perform ablation of the blood vessel wall; for example, actuation mechanism 5410 may be an optical device that generates light to perform, for example, laser ablation of a plaque, or it may be an acoustic device for performing ultrasonic ablation of a plaque.

As discussed above, an active blood vessel sleeve may include a power source configured to provide power to at least one sensor. An active blood vessel sleeve may include one or multiple sensors of the same or different types. Examples of a variety of sensor which may be used in embodiments as described herein are provided in U.S. Pat. Nos. 5,522,394; 5,873,835; 6,053,837; 6,409,674; 6,111,520; 6,278,379; 6,475,639; 6,855,115; and U.S. patent applications 2005/0277839 and 2005/0149170. U.S. Pat. No. 6,802,811 provides additional examples of sensing and/or monitoring. In some embodiments, an imaging device (e.g., a CCD array) may be operatively connected to active blood vessel sleeve.

An optical sensor may be configured to measure the optical absorption, optical emission, fluorescence, or phosphorescence of at least a portion of fluid in proximity to the active blood vessel sleeve. Such optical properties may be inherent optical properties of all or a portion of the fluid or surrounding tissue, or may be optical properties of materials added or introduced to the fluid, such as tags or markers for materials of interest. Optical sensing of materials in blood is described, for example, in KRUEGER, CURTIS; "New light on blood testing"; Oct. 20, 2006; pp. 1-2; St. Petersburg Times; printed on Dec. 24, 2006; located at http://www.sptimes.com/2006/10/20news_pf/Tampabay/New_light_on_blood_te.shtml.

A biosensor may detect materials including, but not limited to, a biological marker, an antibody, an antigen, a peptide, a polypeptide, a protein, a complex, a nucleic acid, a cell (and, in some cases, a cell of a particular type, e.g., by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, and/or a tag. A biosensor may include an antibody or other binding molecule such as a receptor or ligand. As used herein a sensor may include a single sensor or an array of sensors, and is not limited to a particular number or type of sensors. A sensor might comprise, in part or whole, a gas sensor such as an acoustic wave, chemiresistant, or piezoelectric sensor, or perhaps an electronic nose. A sensor may be very small, comprising a sensor or array that is a chemical sensor ("Chemical Detection with a Single-Walled Carbon Nanotube Capacitor," Snow, E. S., Science, Vol. 307, pp. 1942-1945 (2005)), a gas sensor (Hagleitner et al., "Smart single-chip gas sensor microsystem," Nature, Vol. 414, pp. 293-296 (2001)), and/or a nuclear magnetic resonance imager (Go Yusa, "Controlled multiple quantum coherences of nuclear spins in a nanometre-scale device," Nature, Vol. 343, pp. 1001-1005 (2005)). Further examples of sensors are provided in The Biomedical Engineering Handbook, Second Edition, Volume I, J. D. Bronzino, Ed., CRC Press LLC, pp. V-1-51-9 (2000), and U.S. Pat. No. 6,802,811.

A sensor may be configured to measure various parameters, including, but not limited to, the electrical resistivity of fluid, tissue, or other material, the density or sound speed of a material, the pH, the osmolality, or the index of refraction of the fluid at least one wavelength. The selection of a suitable sensor for a particular application or use site is considered to be within the capability of a person having skill in the art. In some embodiments, a sensor may include some signal processing or pre-processing capability integrated therewith.

The condition of interest detected by the sensor may include an anatomical feature (for example, a branching point) that indicates proximity to a treatment target, or indicates the presence of the treatment target itself. The condition of interest may include a man-made structure, such as an implantable device of some sort, potentially including another active blood vessel sleeve. Alternatively, the condition of interest may include one or more of an electrical field, magnetic field, temperature, flow condition, time, location, pressure, pH, presence or concentration of a chemical compound or species.

A sensor may sense a wide variety of physical or chemical properties. In some embodiments, detecting a condition of interest may include detecting the presence (or absence) of a material or structure of interest.

In some applications, detecting a condition of interest in or near the blood vessel may include detecting the presence of a material of interest in proximity to the blood vessel. A material of interest near a blood vessel may include, for example, an object such as a blood clot, a thrombus, an embolus, a plaque, an inflammation, a lipid, an aggregate, a cell, a specific type of cell, a cell fragment, a cellular component, a platelet, an organelle, a collection or aggregation of cells or components thereof, a pathogen, or a parasite.

Sensors in combination with logic circuitry (hardware, firmware, and/or software) may be used to detect a local condition of interest in or on the wall of the blood vessel, in the tissue that forms or surrounds the blood vessel, or in the fluid within the blood vessel. A location of interest near a blood vessel may include a location of anatomical interest (e.g., a branching point or nearby vessels), a location near an organ, a tumor, an injury, a diseased or damaged region (e.g., a fistula or aneurysm), an area of scar tissue, an inflammation, a blockage or constriction formed by a bacterial plaque, a blood clot, or a vasospasm, for example. Locations of interest may be identified by the detection of chemical markers or fingerprints, by altered mechanical, optical, thermal, electrical or acoustic properties, by imaging, and/or by other detection methods known to those of skill in the art. The active blood vessel sleeve may perform one or more actions with an actuation mechanism 5410 in response to detection of a location of interest. Further, tissue condition can be detected with the use of pressure pulses, as described in U.S. Pat. No. 6,170,488 and U.S. patent applications 2003/0220556 and 2004/0225325.

In another embodiment, the active blood vessel sleeve may include an active blood vessel sleeve fitted for the outside of at least a portion of the at least one blood vessel, the active blood vessel sleeve having at least one actuation mechanism 5410. The actuation mechanism 5410 may include, for example, at least one of a microactuator, a microelectromechanical actuator, a nanoelectromechanical actuator, a servo actuator, an electroactive polymer actuator, an electrostatic actuator, or a thermal actuator.

Further examples of actuation mechanisms may include polymer actuators. Most polymer actuators fall into one of four categories (1) mechanochemical gels, (2) electrochemical (wet), (3) field-activated (dry), and (4) thermally activated or phase change. A wide variety of gel actuators have been developed. These are generally chemically responsive but some can use electricity to control the amount of ionic species that, in turn, control swelling, for example. Electroactive gels have been used in the lower limbs, for example electrically-controllable mechanochemical gel fibers contracting artificial muscles. Gels are generally diffusion-limited (they typically rely on the transport of fluids and ions), so increases in speed and power require changes in the microstructure of the gel-plus-fluid delivery system. Some gels can be powered by organic solvents much in the same way that muscles are powered by nutrients. Thus, artificial muscles may be powered directly by fuels. Electrochemical polymers include both conducting polymers and ionic polymer metal composites. These are also generally diffusion-limited. Thermally responsive polymers include shape memory polymers and phase change materials such as liquid crystal elastomers. Such materials are capable of undergoing large strain changes.

Field-activated polymer muscles include electrostrictive polymers that undergo a shape change due to realignment of a crystalline phase in the presence of an electric field as well as dielectric elastomers comprising rubbery insulators that undergo a shape change due to the electrostatic forces of the charges on their compliant electrodes. The strain of electrostrictive polymers can be as high as 5%. The strain of dielectric elastomers can exceed 100%-duplicating that of natural muscle. Field-activated polymers can respond quickly and have high electromechanical coupling that can allow for overall efficiencies as high as 80%. The stiffness of dielectric elastomers is similar to that of natural muscle, but the stiffness of electrostrictive materials is more than an order of magnitude greater. Since field-activated polymers have a fast response, the force and strain of these materials could be electrically modulated to control stiffness. Actuators that already have a stiffness in a desired operating range are easier to control and more robust since such actuators can more easily respond to high-frequency shocks or disturbances that may be difficult to handle using feedback. Inherently compliant actuators can also be used in antagonistic pairs to modulate joint stiffness over a wider range than is possible with a single actuator.

Because field-activated polymers have high electromechanical coupling, they can also be operated in reverse as a generator. Thus, they can be used in a semi-active mode to provide damping or energy absorption (without the need for additional damping components). This mode of operation could also be used to recapture some of the electrical energy applied to the sleeve. It is also possible to use soft viscoelastic polymers in parallel with the actuators to add more passive damping. Dielectric elastomer actuators have already shown some promise as artificial muscles. These actuation mechanisms have been formed into cylindrical rolls that have strain, shape, and performance similar to natural skeletal muscles. These smaller actuators can be grouped to increase the stroke and force, much as individual muscles are composed of parallel fibers that in turn are made up of series of contractile units (See Herr et al., "New horizons for orthotic and prosthetic technology: artificial muscle for ambulation," Smart Structures and Materials 2004: Electroactive Polymer Actuators and Devices (EAPAD); Edited by Bar-Cohen, Yoseph. Proceedings of the SPIE, Volume 5385, pp. 1-9 (2004)).

For example, the actuation mechanism 5410 may include a heating element operatively coupled to receiver circuitry and configured to produce heating in response to receipt of a signal 5402. The heating element may be a resistive element that produces heat when current is passed through it, or it may be a magnetically active material that produces heat upon exposure to an electromagnetic field. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as gadolinium, silicate or sulfide, and antiferromagnetic materials such as canted antiferromagnetic materials (which behave similarly to ferromagnetic materials); examples of electrically active materials include ferroelectrics, piezoelectrics, and dielectrics. In some embodiments, heat may be generated through an exothermic chemical reaction. U.S. patent applications 2002/0147480 and 2005/0149170 provide examples of heating and/or cooling mechanisms and structures.

Cooling may be produced by a number of mechanisms and/or structures. For example, cooling may be produced by an endothermic reaction (such as the mixing of ammonium nitrate and water) initiated by opening of a valve or actuation of a container in response to a control signal 5402. Other methods and/or mechanisms of producing cooling may include, but are not limited to, thermoelectric (Peltier Effect) and liquid-gas-vaporization (Joule-Thomson) devices. Such cooling may facilitate contraction of the blood vessel sleeve. Once the sleeve has contracted to a desired diameter or other dimension, the active blood vessel sleeve may heat the blood vessel so as to increase permeability of the blood vessel wall to biological agents, including cells, to promote healing, for example.

In another example, heating may be used for ablation of tissue, for example where a blood vessel wall has thickened beyond acceptable limits. In addition, or alternatively, performing an action with actuation mechanism 5410 may include securing the active blood vessel sleeve 5400 into position around the blood vessel, e.g., by using various known positioning or blood vessel wall-engaging structures.

In some embodiments, the actuation mechanism 5410 may include an electromagnetic radiation source operatively coupled to receiver circuitry and configured to emit electromagnetic radiation in response to receipt of a signal 5402. Electromagnetic radiation sources may include light sources, for example, such as light emitting diodes and laser diodes, or other sources of electromagnetic energy or radiation, radio waves, microwaves, ultraviolet rays, infra-red rays, optical rays, terahertz beams, or the like.

The actuation mechanism 5410 may include an acoustic energy source (e.g., a piezoelectric element) operatively coupled to receiver circuitry and configured to emit acoustic energy in response to a signal 5402. An acoustic energy source may generate pressure pulses of various frequencies, including auditory frequencies, subsonic frequencies, and ultrasonic frequencies. A microscale acoustic transducer may be constructed, for example, as described in U.S. Pat. No. 5,569,968.

The actuation mechanism 5410 may include a pressure source operatively coupled to receiver circuitry and configured to apply pressure to the blood vessel in response to receipt of a signal 5402. Applied pressure may be positive pressure (e.g., to form a pressure fit of the active blood vessel sleeve with the blood vessel wall, or to apply pressure to a particular location, e.g., to stop bleeding). Alternatively, negative pressure may be applied (e.g., a vacuum, to adhere a portion of the blood vessel wall to the active blood vessel sleeve, for example to seal off a leak or aneurysm, or to position the device). Pressure applied to a blood vessel may influence one or both of the blood vessel walls or the contents of the blood vessel; in some cases application of pressure to a blood vessel may increase (or decrease) blood pressure in the blood vessel. A pressure source may include materials that expand through absorption of water or other materials, materials that expand or contract due to generation or consumption of gas, or materials that change conformation by chemical reactions or temperature changes, electrically-engendered Maxwell stresses, osmotic stress-generators, or the like.

Application of positive pressure to push the blood vessel walls inward, as depicted in FIGS. 53A and 53B, may be useful for repairing or compensating for an aneurysm or other structural damage or imperfection in a blood vessel wall. Expansion and/or application of negative pressure by the active blood vessel sleeve may function to open a constricted blood vessel or secure an active blood vessel sleeve in place around a blood vessel. Expansion of all or a portion of the active blood vessel sleeve may be effected by inflation of one or more chambers with liquid or gas, and/or expansion or change in configuration of a shape-change material, bimetallic structure, or the like.

In some embodiments, an active blood vessel sleeve may constrict a blood vessel until it reaches a particular dimension and then cease constricting in order to maintain the size of the sleeve at the particular dimension. At that dimension, in one embodiment, the active blood vessel sleeve may perform an action on the local blood vessel tissue or perform an action on tissue in proximity to the blood vessel, either continuously or intermittently. The particular dimension at which an active blood vessel sleeve stops constricting may be pre-selected, in which case the device may be directed to assume one or more dimensions, or a sequential change in dimensions over a certain time period. Alternatively, the ultimate dimensions may be selected as the active blood vessel sleeve is contracting around the blood vessel, based on one or more intermediate dimensions, which may be sensed by the active blood vessel sleeve. Features of the intermediate dimensions may include, but are not limited to, indicators of injury, pathology, or disease conditions to be treated by the active blood vessel sleeve, or anatomical characteristics (size, proximity to an organ or other structure, or the like) that make the location a suitable one for the device to be positioned, relative to a pathology being addressed. Features of locations of interest may include chemical, thermal, mechanical, optical, or other properties as may be sensed with various types of sensors as described elsewhere herein. A parameter may be measured at a single point in time and/or space, or a parameter may be measured over multiple dimensions (spatial, temporal, or other—e.g., frequency) to generate an image of a region that may include one or more features of interest. Signal processing to perform analysis of the signal or image may be used to detect features and/or locations of interest from a signal or image. Also, features of a location may be selected to optimize blood flow through a blood vessel. Accordingly, a blood flow sensor may be incorporated into the active blood vessel sleeve.

An actuation mechanism 5410 may be operatively coupled to receiver circuitry 5408 and configured to secure the active blood vessel sleeve in position on the blood vessel in response to a signal 5402. The actuation mechanism 5410 may include a hook or claw-like structure that may penetrate into or catch on the surface of the blood vessel, an expanding element that causes the active blood vessel sleeve to form a pressure-fit with the blood vessel, an adhesive material or glue, or other structure or material that may engage the blood vessel wall. The actuation mechanism 5410 may also include a suction-generating (negative pressure) mechanism that causes an active blood vessel sleeve to adhere to the wall of the blood vessel by suction.

The actuation mechanism 5410 may include an electric field source operatively connected to receiver circuitry 5408 and configured to apply an electric field to fluid and/or blood vessel wall, or surrounding tissue in response to a signal 5402. For example, an active blood vessel sleeve 5400 may be connected to a power source such as, for example, a capacitor, or other charge storing device, to generate a static electric field, or the power source may be a current source, such as a battery or fuel cell, capable of generating a dynamic electric field.

Alternatively, an actuation mechanism may include a magnetic field source operatively connected to receiver circuitry and configured to apply a magnetic field to fluid and/or blood vessel wall and/or surrounding tissue in response to a signal 5402. An active blood vessel sleeve adjacent to a wall of a blood vessel may include, for example, a coil connected to current source. Current from the current source flowing through the coil can produce a magnetic field. The magnetic field source need not include a coil; as known to those of skill in the art, a magnetic field may be generated by current flowing through various types of structures. Moreover, one or more fixed magnets may be included in a magnetic field source.

FIG. 55 illustrates an exemplary embodiment related to an active blood vessel sleeve. In FIG. 55 and in following figures that include various examples of active blood vessel sleeves, discussion and explanation may be provided with respect to the above-described system environment of FIG. 52, and/or with respect to other examples and contexts. However, it should be understood that the exemplary embodiments may be executed in a number of other environments and contexts, and/or in modified versions of FIG. 52. Also, although the various exemplary embodiments are presented in the context of the system environment of FIG. 52, it should be understood that the various exemplary embodiments may be produced by other systems than those which are illustrated.

With respect to FIG. 55, an active blood vessel sleeve 5500 may include transmitter circuitry 5508 capable of transmitting a signal 5502 from the active blood vessel sleeve 5500. The transmitter circuitry 5508 may transmit a signal 5502 containing information about, for example, active blood vessel sleeve position, dimensions, environment, power status, or the like. The signal 5502 may be capable of penetrating tissue 5506 to various depths in order to be received by receiver 5504. As shown in FIG. 55, the active blood vessel sleeve may include a battery 5512.

FIG. 55 depicts an active blood vessel sleeve 5500 placed around a branched blood vessel, and a remote receiver 5504, which in this example is located outside the body and tissue 5506. The active blood vessel sleeve 5500 may include transmitter circuitry 5508 operatively coupled to the active blood vessel sleeve 5500 or other structural or functional elements of the active blood vessel sleeve 5500. The transmitter circuitry 5508 may be configured to transmit a detection signal 5502 to a remote location (e.g., receiver 5504). The detection signal 5502 may be used to inform a therapeutic health care provider 5210, for example, about a condition of the subject or the active blood vessel sleeve 5500 so that suitable treatment may be provided by the health care provider, or the detection signal may contain information usable by an automated system to control operation of the active blood vessel sleeve 5500.

At least a portion of the control circuitry for active blood vessel sleeve 5500, receiver 5504, and/or transmitter 5404, may be located remote from active blood vessel sleeve 5500. Active blood vessel sleeve 5500 may include a transceiver that may include data reception and/or transmission circuitry configured to send and/or receive a wireless signal. Data may be transmitted from active blood vessel sleeve 5500 to another portion of the active blood vessel sleeve, or to a remote receiver 5504. Remote receiver 5504 may include a power source. Alternatively, a program controlling actuation mechanism 5510 may be present in the actuation mechanism 5510 itself or in another portion of the active blood vessel sleeve 5500.

FIG. 56 illustrates an exemplary embodiment related to an active blood vessel sleeve. In FIG. 56 and in following figures that include various examples of active blood vessel sleeves, discussion and explanation may be provided with respect to the above-described system environment of FIG. 52, and/or with respect to other examples and contexts. However, it should be understood that the exemplary embodiments may be executed in a number of other environments and contexts, and/or in modified versions of FIG. 52. Also, although the various exemplary embodiments are presented in the context of the system environment of FIG. 52, it should be understood that the various exemplary embodiments may be produced by other systems than those which are illustrated.

With respect to FIG. 56, an active blood vessel sleeve 5600 may include sensor 5606 capable of signaling actuation mechanism 5610. The sensor 5606 may signal actuation mechanism 5610 to open agent reservoir 5604 to release agent 5602 to the exterior of active blood vessel sleeve 5600.

In one embodiment, the actuation mechanism 5610 may be operatively connected to a sensor 5606, and configured to control the movement of the active blood vessel sleeve 5600 at least in part in response to receipt of the signal from sensor 5606 indicating detection of a condition of interest in the blood vessel.

Examples of an agent 5602 may include an adhesive, a filler, a hydrogel, an antibiotic, a pharmaceutical compound, a pharmaceutical composition, a nutrient, a hormone, a growth factor, a medication, a therapeutic compound, an enzyme, a protein, a genetic material, a cell, a fraction of a cell, a vaccine, a vitamin, a neurotransmitter, a neurotrophic agent, a neuroactive material, a cytokine, a cell-signaling material, a pro-apoptotic agent, an anti-apoptotic agent, an immunological mediator, an anti-inflammatory agent, a coagulant, an anti-coagulant, an angiogenic agent, an anti-angiogenic agent, a wound-healing agent, a salt, an ion, an antioxidant, an imaging agent, a labeling agent, a diagnostic compound, a nanomaterial, an inhibitor, or a blocker.

In some embodiments, the agent 5602 may target a treatment target, wherein an agent 5602 or sleeve movement may be determined based at least in part upon at least one sensed parameter of the treatment target. In other embodiments, an agent 5602 or sleeve movement may be determined at least in part by a treatment pattern stored in the active blood vessel sleeve 5600.

In some cases, the treatment target may include at least a portion of a wall of the blood vessel, or in some cases, the treatment target may lie beyond the wall of the blood vessel, so that delivering an agent to the treatment target may include delivering an agent 5702 (FIG. 57) to the treatment target through a wall of the blood vessel. In some cases, the treatment target may include at least a portion of the contents of the blood vessel.

The active blood vessel sleeve 5600 may include control circuitry for the actuation mechanism 5610, either on the active blood vessel sleeve 5600 itself or in a remote location, and may include a microprocessor, and/or at least one of hardware, software, and firmware. Examples of devices and/or systems for communicating within devices in the body are provided in U.S. Pat. Nos. 5,843,139; 6,409,674; or 7,125,382; U.S. patent application 2002/0198604, and Rice, "Implantable Neurostimulation Device Market Poised for Explosive Growth," Future Fab International Website; Jan. 7, 2006; pp. 1-4; printed on Oct. 6, 2006; located at http://www.future-fab.com/documents.asp?d_ID=3725.

Another embodiment includes an active blood vessel sleeve fitted for the outside of at least a portion of the at least one blood vessel, the active blood vessel sleeve having at least one agent reservoir. For example, the actuation mechanism 5610 of the active blood vessel sleeve 5600 may be configured to release an agent 5602 in response to a signal from, for example, sensor 5606. FIG. 56 depicts an active blood vessel sleeve 5600 including an agent reservoir 5604, a sensor 5606, and an actuation mechanism 5608. Upon the sensing of a condition of interest by sensor 5606, sensor 5606 may signal actuation mechanism 5608 to release agent 5602 from agent reservoir 5604 by activating actuation mechanism 5608. Actuation mechanism 5608 may include a variety of different types of release mechanisms, including, for example, a controllable valve. Various types of valves and microvalves are known to those of skill in the art, and may be used to regulate the release of an agent 5602 from agent reservoir 5604. Sensor 5606 may activate actuation mechanism 5608 by supplying an electrical signal, for example. In some embodiments, other types of signals, including magnetic signals, optical signals, acoustic signals, or other types of signals may be used. Combinations of several types of signals may be used in some embodiments. In some embodiments, sensor 5606 may signal actuation mechanism 5608 to release agent 5602 from agent reservoir 5604 in response to passage of a certain amount of time, as monitored, for example, by a timekeeping device. As shown in FIG. 56, agent 5602 may be released to the exterior aspect of the active blood vessel sleeve 5600.

In an alternative embodiment, agent 5702 (FIG. 57) may be released to the interior aspect of the active blood vessel sleeve. FIG. 57 illustrates an exemplary embodiment related to an active blood vessel sleeve. In FIG. 57 and in following figures that include various examples of active blood vessel sleeves, discussion and explanation may be provided with respect to the above-described system environment of FIG. 52, and/or with respect to other examples and contexts. However, it should be understood that the exemplary embodiments may be executed in a number of other environments and contexts, and/or in modified versions of FIG. 52. Also, although the various exemplary embodiments are presented in the context of the system environment of FIG. 52, it should be understood that the various exemplary embodiments may be produced by other systems than those which are illustrated.

With respect to FIG. 57, an active blood vessel sleeve 5700 may include sensor 5706 capable of signaling actuation mechanism 5710. The sensor 5706 may signal actuation mechanism 5710 to open agent reservoir 5704 to release agent 5702 to the interior of active blood vessel sleeve 5700.

Actuation mechanism 5508 may be a heating element, for example a resistive element connected directly to receiver circuitry, or an electrically or magnetically responsive material that may be caused to move, vibrate or heat, by an externally applied electromagnetic field, which in turn causes release of agent 5502 from agent reservoir 5504, as shown in FIG. 55. See, for example, U.S. Pat. Nos. 5,019,372 and 5,830,207, which are incorporated herein by reference. In some embodiments, an electrically or magnetically active component may be heatable by an electromagnetic control signal, and heating of the electrically or magnetically active component may cause a polymer to undergo a change in configuration. An example of a magnetically responsive polymer is described, for example, in Neto, et al., "Optical, Magnetic and Dielectric Properties of Non-Liquid Crystalline Elastomers Doped with Magnetic Colloids," Brazilian Journal of Physics; bearing a date of March 2005; pp. 184-189; Volume 35, Number 1. Other exemplary materials and structures are described in Agarwal et al., "Magnetically-driven temperature-controlled microfluidic actuators"; pp. 1-5; located at: http://www.unl.im.dendai.ac.jp/INSS2004/INSS2004_papers/OralPresentations/C2.pdf; or in U.S. Pat. No. 6,607,553. In connection with the release of materials, in some embodiments the permeability of the blood vessel wall to the released agent 5502 may be increased by the use of retractable spines that penetrate the blood vessel wall, as described in U.S. Pat. No. 6,991,617, by hollow microneedles capable of penetrating a blood vessel wall, as described in U.S. Pat. No. 6,743,211, by a chemical permeability enhancer as described in U.S. Pat. No. 6,673,363, which may be released from the active blood vessel sleeve along with the agent 5502 or from a separate reservoir or other source, or by an electrical permeability enhancer, such as a voltage source for producing electroporation, as in U.S. Pat. No. 6,512,950 or 6,022,316.

An active blood vessel sleeve 5700 may be fitted for a blood vessel that is constricted, e.g. by a vasospasm. A blood vessel is defined by blood vessel walls, which at a vasospasm site are constricted, blocking the flow of blood through the blood vessel. Active blood vessel sleeve 5700 may include sensor 5706, which can detect the presence of the vasospasm, for example, by detecting reduced flow of blood through the blood vessel, or erratic movement of the blood vessel wall. Active blood vessel sleeve 5700 also includes actuation mechanism 5710, which may be activated in response to detection of the vasospasm, to release an agent 5702 that is a vasoactive substance in order to produce relaxation of the vasospasm. Active blood vessel sleeve 5700 may also include other components not depicted in FIG. 57, but as described elsewhere herein.

FIG. 57 illustrates a further example of an active blood vessel sleeve 5700 placed in proximity to a blood vessel. A blood vessel may include an aneurysm 5712, which may be detected by sensor 5706 on active blood vessel sleeve 5700. A signal generated by sensor 5706 can cause actuation mechanism 5710 to change conformation with respect to the walls of blood vessel to support the aneurysm 5712 and prevent rupture.

In connection with detection of the presence of a material, location, or other condition(s) of interest within or near the blood vessel, the active blood vessel sleeve 5700 may be capable of removing, modifying, or destroying a material of interest or treating a location of interest. Modification or destruction of material of interest may be accomplished by the release of a suitable material (e.g., an anti-coagulant for destroying a blood clot, complement to coat a parasite for recognition by the immune system, or by the release of an anti-inflammatory, biomimetic or biologic to bind to and inactivate an inflammatory mediator such as TNFα, by the delivery of suitable energy (e.g., acoustic energy for modifying a plaque, electromagnetic energy such as light to cause a photoreaction, break bonds in a molecule, produce heating, vaporization, ablation, etc., or by delivery of heat or cold or other chemo-physical change (e.g. ambient pressure, pH, osmolality, toxic material introduction/generation) for tissue modification, as in ablation of tumor cells or plaque. For example, a pulse of acoustic energy may be used to modify an atherosclerotic plaque, or to modify a metastatic lesion in the area of the blood vessel.

In some embodiments, an active blood vessel sleeve 5700 may be a self-contained device that includes all functionalities necessary for operation of the device. In other embodiments, an active blood vessel sleeve 5400 may include an active blood vessel sleeve 5400 that may be placed on a blood vessel, and a remote portion that may include a functional portion of the active blood vessel sleeve 5400. In some embodiments, all functionalities essential for the operation of the active blood vessel sleeve 5400 may be located on the active blood vessel sleeve 5400, but certain auxiliary functions may be located in a remote portion. For example, a remote portion may provide monitoring of the operation of the active blood vessel sleeve 5400 or data collection or analysis. A remote portion may be located within the body of the subject at a distance from the active blood vessel sleeve 5400, or outside the body of the subject, as depicted in FIG. 54. The remote portion may be located near the subject (e.g., carried or worn on the subject's body or placed on a table near the subject) or distant from the subject (e.g., in a different room or building, or in a different city, state or country). Data and/or power signals may be transmitted between active blood vessel sleeve 5400 and remote portion with the use of electromagnetic or acoustic signals, or, in some embodiments, may be carried over electrical or optical links. Various types and/or combinations of types of communications methods and devices may be used, as are known to those of skill in the art. In some embodiments, transmission of information between the active blood vessel sleeve and one or more remote portions may be via multiple communication channels, in series or in parallel. In general, the remote portion may be placed in a location where there is more space available than in proximity to the blood vessel, or in a location that is more readily accessible than the area near the blood vessel. It is contemplated that a portion of any electrical circuitry portion of the active blood vessel sleeve 5400 (which may include hardware, firmware, software, or any combination thereof) may be located in a remote portion.

Methods of distributing functionalities of a system between hardware, firmware, and software located at two or more sites are well known to those of skill in the art. An electrical circuitry portion of the active blood vessel sleeve system may include, but is not limited to, electrical circuitry associated with the sensor 5412, receiver circuitry 5408, and electronics associated with the actuation mechanism 5410. While circuitry has been discussed within the context of electrical circuitry, it will be appreciated that in some embodiments other types of logic/circuitry may be used in place of or in addition to electrical circuitry, and the circuitry described herein is not limited to electrical circuitry. For example, fluid circuitry, chemo-mechanical circuitry, and other types of logic/circuitry may provide equivalent functionality and may be used in certain embodiments.

As discussed above, an active blood vessel sleeve 5400 may include an imaging marker or tag, such as a contrast agent or indicator. A remote portion may include an external imaging system or be capable of receiving information from an external imaging system. The position of the active blood vessel sleeve 5212 may be correlated with a pre-existing map, model, and/or image of the blood vessel of the subject, and/or used to construct a map, model, and/or image of the blood vessel of the subject. Movement of the active blood vessel sleeve 5212 may be controlled based at least in part upon the placement of the active blood vessel sleeve 5212 on the blood vessel of the subject. In some embodiments, the active blood vessel sleeve 5212 may include a data storage location in which a map, model, and/or image of the blood vessel of the subject may be stored. A pre-existing map, model, and/or image may be stored in the data storage location before the active blood vessel sleeve 5212 is introduced onto the blood vessel of the subject. Alternatively, a map, model, and/or image may be generated, either with the use of logic on the active blood vessel sleeve 5212 or in a remote system, on the basis of information gathered as the active blood vessel sleeve 5212 remains in place on the blood vessel of the subject. A map, model, and/or image thus generated may be stored in a memory location on the active blood vessel sleeve 5212 or elsewhere. In some embodiments, rather than storing a map, model, and/or image, other positional or locational information may be stored that may be used to control the movement of the active blood vessel sleeve. In some embodiments, it may be desired that the active blood vessel sleeve 5212 is capable of assuming a statistical distribution of blood vessel dimensions.

Circuitry components of functional aspects of an active blood vessel sleeve, such as transceiver, receiver, sensor, or actuation mechanism, may be located entirely on the active blood vessel sleeve, or may be distributed between the active blood vessel sleeve and a remote portion. The active blood vessel sleeve may include one or more sensors 5412 for measuring or detecting a condition of interest. Sensing circuitry may be associated with a sensor 5412. Circuitry associated with an active blood vessel sleeve may also include a data storage portion, which may, for example, be used to store pattern data or pattern variables for determining an actuation pattern to be carried out by actuation mechanism 5410. A data storage module may also store positional information, including, for example, the current sleeve dimensions or one or more target dimensions, or geometry of some or all of the relevant blood vessels of the subject.

In some embodiments, one or more power sources may provide power to electrical components of the active blood vessel sleeve. Some components of the active blood vessel sleeve may be operated in whole or in part under software control, and circuitry controlling active functional aspects of the active blood vessel sleeve may include hardware, software, hardware, or various combinations thereof. The active blood vessel sleeve may include components that may be primarily hardware-based, e.g., sensor 5412, actuation mechanism 5410, receiver circuitry 5408, and/or transmitter 5404. Hardware-based devices may include components that are electrical, mechanical, chemical, optical, electromechanical, electrochemical, electro-optical, and are not limited to the specific examples presented herein.

In many embodiments, circuitry may be implemented in the form of logic, for example software or digital logic circuitry. Logic modules (which may be software or hardware) may be used in the control of active blood vessel sleeves as described herein. Logic may be implemented in digital circuitry, analog circuitry, software, or combinations thereof.

In some embodiments, sensor 5412 may be capable of generating a signal indicating the presence or absence of the condition of interest, and the sensor 5412 may be configured to signal actuation mechanism 5410 of the active blood vessel sleeve 5400. Logic may be employed that uses a pre-programmed pattern which may be stored in a memory location on the active blood vessel sleeve.

Another embodiment may include a rapid-prototyped active blood vessel sleeve fitted for the outside of at least a portion of at least one blood vessel. As discussed above, rapid-prototyping may include additive fabrication, three-dimensional printing, solid freeform fabrication, and/or layered manufacturing. With rapid-prototyping, objects can be formed with any geometric complexity or intricacy without the need for elaborate machine setup or final assembly; and objects can be made from multiple materials, as composites, and/or materials can be varied in a controlled fashion at any location in an object. Various rapid-prototyping methods are discussed above, and are known in the art. In some embodiments, at least one rapid-prototyped structural portion may be combined with at least one functional portion made by conventional methods to form a complete active blood vessel sleeve fitted for the outside of a blood vessel.

FIG. 58 illustrates an operational flow 5800 representing example operations relating to methods and systems for signaling an active blood vessel sleeve fitted for the outside of at least a portion of a blood vessel. In FIG. 58 and in following figures that include various examples of operational flows, discussion, and explanation may be provided with respect to the above-described examples of FIGS. 1-57, and/or with respect to other examples and contexts. However, it should be understood that the operational flows may be executed in a number of other environment and contexts, and/or in modified versions of FIGS. 1-57. Also, although the various operational flows are presented in the sequence(s) illustrated, it should be understood that the various operations may be performed in other orders than those which are illustrated, or may be performed concurrently.

After a start operation, operation 5810 shows signaling an active blood vessel sleeve fitted for the outside of at least a portion of a blood vessel. The signaling may be performed by, for example, transmitter 5404. For example, a transmitter 5404 may send a signal to receiver circuitry 5408, such as, for example, one or more movement instructions relating to a desired position for the active blood vessel sleeve 5400. For example, this may include a signal that activates actuation mechanism 5410, for example, to move a portion of the active blood vessel sleeve 5400 a certain amount along a specified axis. Alternatively, the transmitter 5404 may send a signal 5402 to an actuation mechanism 5608, which signal 5402 tells the actuation mechanism 5608 to move in such a way as to open agent reservoir 5604.

Alternatively, a sensor 5706 may send a signal to the actuation mechanism 5710, which signal 5402 tells the actuation mechanism 5710 to move in such a way as to open agent reservoir 5704.

The signaling operation may be performed related either to a local or remote storage of analog and/or digital data, or to another type of transmission of analog and/or digital data. Of course, operations also may be performed related to accessing, querying, recalling, or otherwise obtaining analog or digital data from a memory, including, for example, transmitting analog and/or digital data from a remote memory. Accordingly, such operation(s) may involve elements including at least an operator (e.g., either human or computer) directing the operation, a transmitting computer, and/or a receiving computer (e.g., a microcomputer), and should be understood to occur within the United States as long as at least one of these elements resides in the United States.

FIG. 59 illustrates alternative embodiments of the example operational flow 5800 of FIG. 58. FIG. 59 illustrates example embodiments where the signaling operation 5810 may include at least one additional operation. Additional operations may include operation 5900, 5902, 5904, 5906, and/or operation 5908.

Operation 5900 depicts signaling the active blood vessel sleeve fitted for the outside of the at least a portion of at least one blood vessel to move relative to the at least a portion of the blood vessel. For example, transmitter 5404 may signal an active blood vessel sleeve 5400 to assume a reduced diameter relative to, for example, the diameter of the outside of blood vessel 5414. Alternatively, for example, the transmitter 5404 may transmit a signal that causes the actuation mechanism 5410 to alter the curvature of the active blood vessel sleeve 5400 relative to that of blood vessel 5414. Alternatively, for example, the transmitter 5404 may transmit a signal that causes the actuation mechanism 5410 to alter the dimensions of a portion of the active blood vessel sleeve 5400 relative to that of blood vessel 5414. In another embodiment, receiver circuitry 5408 may relay a signal from transmitter 5404 to actuation mechanism 5410, triggering a movement of the blood vessel sleeve 5400.

Operation 5902 depicts signaling the active blood vessel sleeve fitted for the outside of the at least a portion of a blood vessel to constrict around at least a portion of the blood vessel. For example, transmitter 5404 may signal a portion of an active blood vessel sleeve 5400 to assume a reduced diameter relative to, for example, the diameter of an aneurysm affecting the outside of blood vessel 5414. Such constriction may serve to support the wall of the aneurysm and prevent rupture of the blood vessel due to blood vessel wall weakening and/or increased blood vessel wall stress.

Operation 5904 depicts signaling the active blood vessel sleeve fitted for the outside of at least a portion of the blood vessel to initiate at least one program of movements. For example, transmitter 5404 may signal a portion of an active blood vessel sleeve 5400 to initiate a program of movements. For example, the transmitter 5404 may signal an actuation mechanism 5410 to assume a reduced diameter relative to a first diameter, followed by a subsequent movement to assume, for example, a third diameter that is further reduced relative to the reduced diameter. The movements may programmed to occur substantially consecutively in time, or a time delay may be programmed such that subsequent movements are triggered according to a schedule defined by, for example, a therapeutic health care provider 5210. Such programmed movement provides for a gradual assumption of ultimate blood vessel sleeve dimensions over time. Alternatively, a sensor 5412 can signal an actuation mechanism 5410 to initiate a program of movements based on a sensed parameter, such as hemorrhage, turbulence, or molecular signature or marker.

Operation 5906 depicts signaling the active blood vessel sleeve fitted for the outside of at least a portion of the blood vessel to change temperature. For example, transmitter 5404 may signal a portion of an active blood vessel sleeve 5400 to cool, which may aid vasoconstriction of blood vessel 5414. Alternatively, transmitter 5404, receiver circuitry 5408, and/or sensor 5412 may signal a temperature increase in a material of the active blood vessel sleeve 5400. Such an increase in temperature may aid in healing of, for example, blood vessel tissue.

Operation 5908 depicts signaling the active blood vessel sleeve fitted for the outside of at least a portion of the blood vessel to detect at least one environmental condition. For example, transmitter 5404 may signal sensor 5412 directly or through receiver circuitry 5408 on active blood vessel sleeve 5400 to detect one or more environmental parameters such as current blood vessel sleeve dimensions, blood vessel wall stress during systole and/or diastole, blood vessel sleeve power reserves, or the like. Alternatively, transmitter 5404, receiver circuitry 5408, and/or sensor 5412 may signal detection of altered blood flow dynamics through a portion of blood vessel 5414.

FIG. 60 illustrates alternative embodiments of the example operational flow 5800 of FIG. 58. FIG. 60 illustrates example embodiments where the signaling operation 5810 may include at least one additional operation. Additional operations may include operation 6000, 6002, 6004, 6006, and/or operation 6008.

Operation 6000 depicts signaling the active blood vessel sleeve fitted for the outside of at least a portion of the blood vessel to detect at least one of a heart rhythm, blood, a change in fluid flow, a clot, a cell, a molecule, or an atom. For example, transmitter 5404, receiver circuitry 5408, and/or sensor 5412 may signal active blood vessel sleeve 5400 to detect, for example, an arrhythmia such as atrial or ventricular fibrillation. Such detection may be based on blood pressure through a portion of the blood vessel 5414 over time. In another embodiment, transmitter 5404, receiver circuitry 5408, and/or sensor 5412 may signal active blood vessel sleeve 5400 to detect, for example, a blood clot. Such detection may be based on altered blood flow to the blood vessel 5414. In another embodiment, transmitter 5404, receiver circuitry 5408, and/or sensor 5412 may signal active blood vessel sleeve 5400 to detect, for example, lipoprotein(a) levels in the blood. High levels of lipoprotein(a) may be predictive for risk of stroke, risk of coronary heart disease, cerebrovascular disease, atherosclerosis, and/or thrombosis, for example.

In another embodiment, transmitter 5404, receiver circuitry 5408, and/or sensor 5412 may signal active blood vessel sleeve 5400 to detect, for example, a change in a fluid flow dynamic that is indicative of a rupture, leakage, turbulence, or over-constriction leading to decline in laminar flow through a blood vessel 5414.

Operation 6002 depicts signaling the active blood vessel sleeve fitted for the outside of at least a portion of the blood vessel to release at least one agent. For example, transmitter 5404, receiver circuitry 5408, and/or sensor 5412 may signal active blood vessel sleeve 5600 and/or actuation mechanism 5608 to release, for example, an agent to inhibit blood coagulation, in instances of stroke detection or elevated risk of stroke. Other agents that may be released may include, for example, an angiogenic agent, an anti-angiogenic agent, a proliferation agent, a transforming agent, or the like. Agents may be released to the external surface of the active blood vessel sleeve 5600 as in FIG. 56, and/or to the internal surface of the active blood vessel sleeve 5700 as in FIG. 57.

Operation 6004 depicts signaling the active blood vessel sleeve fitted for the outside of at least a portion of the blood vessel to release at least one of an anti-coagulant, a clotting agent, an antibody, contrast agent, or a cytokine as the at least one agent. For example, transmitter 5404, receiver circuitry 5408, and/or sensor 5412 may signal active blood vessel sleeve 5600 and/or actuation mechanism 5608 to release, for example, a therapeutic antibody and/or cytokine that is beneficial to, for example, the tunica adventitia. Agents may be released to the external surface of the active blood vessel sleeve 5600 as in FIG. 56, and/or to the internal surface of the active blood vessel sleeve 5700 as in FIG. 57.

Operation 6006 depicts signaling the active blood vessel sleeve fitted for the outside of at least a portion of the blood vessel to transmit information. For example, transmitter 5404, receiver circuitry 5408, and/or sensor 5412 may signal active blood vessel sleeve 5600 and/or transmitter circuitry 5508 to send, for example, information about current active blood vessel sleeve dimensions to, for example, an external receiver 5504.

Operation 6008 depicts signaling the active blood vessel sleeve fitted for the outside of at least a portion of the blood vessel to transmit at least one of position information, blood vessel movement information, temperature information, power status information, or environment information as the information. For example, transmitter 5404, receiver circuitry 5408, and/or sensor 5412 may signal active blood vessel sleeve 5600 and/or transmitter circuitry 5508 to send, for example, information about pulse in a portion of the blood vessel to, for example, an external receiver 5504. Alternatively, the active blood vessel sleeve 5600 and/or transmitter circuitry 5508 may be signaled to send information relating to remaining battery charge or charge consumption rate to, for example, a receiver 5504. In another embodiment, the active blood vessel sleeve 5600 and/or transmitter circuitry 5508 may transmit information about apolipoprotein E levels in the area of the active blood vessel sleeve 5600. Such information may be of interest in cases of Alzheimer's disease onset and/or familial risk of Alzheimer's disease, and/or cardiovascular disease.

FIG. 61 illustrates alternative embodiments of the example operational flow 5800 of FIG. 58. FIG. 61 illustrates example embodiments where the signaling operation 5810 may include at least one additional operation. Additional operations may include operation 6100, 6102, 6104, 6106, and/or operation 6108.

Operation 6100 depicts sending position coordinates to the active blood vessel sleeve fitted for the outside of at least a portion of the blood vessel. For example, transmitter 5404, receiver circuitry 5408, and/or sensor 5412 may send position coordinates to the active blood vessel sleeve 5400, for example, to specify a movement to arrive at a new dimension or position. Methods for assigning position coordinates are known in the art, for example in U.S. Pat. Nos. 6,569,104; 6,056,692; and 4,111,191.

Operation 6102 depicts sending at least one instruction set to the active blood vessel sleeve fitted for the outside of at least a portion of the blood vessel. For example, transmitter 5404, receiver circuitry 5408, and/or sensor 5412 may send an instruction set to the active blood vessel sleeve 5400, for example, to specify a movement, detection, transmission or other function. Examples of an instruction set may include arithmetic instructions such as add and subtract; logic instructions such as "and," "or," and "not"; data instructions such as move, input, output, load, and store; and/or control flow instructions such as goto, if . . . goto, call, and return.

Operation 6104 depicts signaling a sensor associated with the active blood vessel sleeve fitted for the outside of at least a portion of the blood vessel. For example, transmitter 5404, receiver circuitry 5408, and/or active blood vessel sleeve 5400 may signal a sensor 5606, for example, to initiate the release an agent 5602. Such a sensor may include a power sensor, an environment sensor, a fluid dynamics sensor, a pressure sensor, a position sensor, a temperature sensor, or the like.

Operation 6106 depicts signaling an actuation mechanism associated with the active blood vessel sleeve fitted for the outside of at least a portion of the blood vessel. For example, transmitter 5404, receiver circuitry 5408, sensor 5412, and/or active blood vessel sleeve 5400 may signal an actuation mechanism 5410, for example, to effect a movement of the active blood vessel sleeve 5400. Such an actuation mechanism 5410 may include a piezoelectric mechanism, a pressure rectifying mechanism, a fluid energy converter, a magnetic actuation mechanism, a microactuator fabricated from a sputtered ferromagnetic shape memory alloy thin film, or the like.

Operation 6108 depicts signaling a power source associated with the active blood vessel sleeve fitted for the outside of at least a portion of the blood vessel. For example, transmitter 5404, receiver circuitry 5408, sensor 5412, and/or active blood vessel sleeve 5400 may signal an power source associated with the active blood vessel sleeve 5400, for example, to effect a movement of an actuation mechanism 5410. Such a power source may include a radio frequency power source, an electrochemical power source, an electromagnetic power source, a kinetic energy or fluid energy converter, or the like.

FIG. 62 illustrates an operational flow 6200 representing example operations relating to active blood vessel sleeve methods and systems. In FIG. 62 and in following figures that include various examples of operational flows, discussion, and explanation may be provided with respect to the above-described examples of FIGS. 1-61, and/or with respect to other examples and contexts. However, it should be understood that the operational flows may be executed in a number of other environment and contexts, and/or in modified versions of FIGS. 1-61. Also, although the various operational flows are presented in the sequence(s) illustrated, it should be understood that the various operations may be performed in other orders than those which are illustrated, or may be performed concurrently.

After a start operation, operation 6210 shows detecting in an individual an active blood vessel sleeve fitted for the outside of at least a portion of a blood vessel; and signaling the active blood vessel sleeve fitted for the outside of at least a portion of the blood vessel. The detecting may be performed by, for example, imaging system 5214, therapeutic health care provider 5210, diagnostic health care provider 5216, receiver 5504, or the like. For example, transmitter circuitry 5508 may send a signal to receiver 5504 indicating a status of an active blood vessel sleeve 5500. In another embodiment, an imaging system 5214 such as a CT scanner may detect an active blood vessel sleeve 5500 in an individual 118. Signaling the active blood vessel sleeve 5212 may be carried out by, for example, transmitter 5404, receiver circuitry 5408, and/or sensor 5606. Alternatively, sensor 5706 may send a signal to actuation mechanism 5710, which signal tells the actuation mechanism 5710 to move in such a way as to open agent reservoir 5704.

The signaling operation may be performed related either to a local or remote storage of analog and/or digital data, or to another type of transmission of analog and/or digital data. Of course, operations also may be performed related to accessing, querying, recalling, or otherwise obtaining analog or digital data from a memory, including, for example, transmitting analog and/or digital data from a remote memory. Accordingly, such operation(s) may involve elements including at least an operator (e.g., either human or computer) directing the operation, a transmitting computer, and/or a receiving computer (e.g., a microcomputer), and should be understood to occur within the United States as long as at least one of these elements resides in the United States.

FIG. 63 illustrates alternative embodiments of the example operational flow 6200 of FIG. 62. FIG. 63 illustrates example embodiments where the detecting operation 6210 may include at least one additional operation. Additional operations may include operation 6300, 6302, and/or operation 6304.

Operation 6300 depicts detecting in the individual an active blood vessel sleeve fitted for the outside of at least a portion of the blood vessel, the active blood vessel sleeve containing at least one contrast agent. For example, imaging system 5214, therapeutic health care provider 5210, diagnostic health care provider 5216, and/or receiver 5504 may detect in an individual 118 an active blood vessel sleeve 5400 containing, for example, gadolinium as the at least one contrast agent. As discussed above, a paramagnetic material such as gadolinium or $Mn^{++}$ is commonly used as an MRI contrast agent. Other contrast agents known in the art may be used, such as iodine for use in CT scanning, and/or hybrid nanomaterials that can be used as multimodal imaging contrast agents. Silica or organic polymer loaded with optical and/or magnetic resonance imaging contrast agents can be made that are very luminescent and/or have very high relaxivities. Such hybrid nanomaterials can be integrated into an active blood vessel sleeve 5400 and give image contrast enhancement for several imaging modalities. Such hybrid nanomaterials exhibit several orders of magnitude larger relaxivities than those of existing Gd- and Mn-based small molecule contrast agents. This allows more facile image enhancement using MRI. Exceptionally high relaxivities permit use in tissue-specific imaging of a variety of different tissue conditions, including cancers and inflammation. Such hybrid nanomaterials offer positive image enhancement as compared to negative image enhancement provided by iron oxide-based contrast agents.

Operation 6302 depicts detecting in the individual an active blood vessel sleeve fitted for the outside of at least a portion of the blood vessel, the active blood vessel sleeve containing at least one indicator. For example, imaging system 5214, therapeutic health care provider 5210, diagnostic health care provider 5216, and/or receiver 5504 may detect in an individual 118 an active blood vessel sleeve 5400 having an indicator relating to patient information, dimensions, or the like, as discussed above. For example, active blood vessel sleeve 5400 may include a radio frequency identification chip as an indicator of patient information, active blood vessel sleeve information, health care provider information, or the like.

Operation 6304 depicts employing at least one of magnetic resonance imaging, computed tomography, fluoroscopy, or ultrasound imaging to detect in the individual the active blood vessel sleeve fitted for the outside of the at least a portion of the blood vessel. For example, imaging system 5214, therapeutic health care provider 5210, and/or diagnostic health care provider 5216 may employ ultrasound imaging to detect in an individual 118 an active blood vessel sleeve 5400. In another embodiment, active blood vessel sleeve 5400 may be detected by a diagnostic health care provider 5216 employing a portable MRI device. Alternatively, an active blood vessel sleeve 5400 may be detected simply through inspection during the course of a surgical intervention.

FIG. 64 illustrates alternative embodiments of the example operational flow 6200 of FIG. 62. FIG. 64 illustrates example embodiments where the signaling operation 6220 may include at least one additional operation. Additional operations may include operation 6400, 6402, 6404, and/or operation 6406.

Operation 6400 depicts signaling the active blood vessel sleeve fitted for the outside of the at least a portion of the blood vessel to move relative to the at least a portion of the blood vessel. For example, transmitter 5404 may signal an active blood vessel sleeve 5400 to assume an altered diameter relative to, for example, the diameter of the outside of blood vessel 5414. Alternatively, for example, the transmitter 5404 may transmit a signal that causes actuation mechanism 5410 to alter the curvature of the active blood vessel sleeve 5400 relative to that of blood vessel 5414. Alternatively, for example, the transmitter 5404 may transmit a signal that causes the actuation mechanism 5410 to alter the dimensions of a portion of the active blood vessel sleeve 5400 relative to that of blood vessel 5414. In another embodiment, receiver circuitry 5408 may relay a signal from transmitter 5404 to actuation mechanism 5410, initiating a movement of the active blood vessel sleeve 5400.

Operation 6402 depicts signaling the active blood vessel sleeve fitted for the outside of the at least one blood vessel to initiate at least one program of movements. For example, transmitter 5404 and/or receiver circuitry 5408 may signal a portion of an active blood vessel sleeve 5400 to initiate a program of movements. For example, transmitter 5404 may signal an actuation mechanism 5410 to assume a reduced diameter relative to a first diameter, followed by a subsequent movement to assume, for example, a third diameter that is further reduced relative to the reduced diameter. Movements may programmed to occur substantially consecutively in time, or a time delay may be programmed such that subsequent movements are triggered according to a schedule defined by, for example, a therapeutic health care provider 5210. Such programmed movement provides for a gradual or stepped assumption of ultimate blood vessel sleeve dimensions over time. Alternatively, a sensor 5412 can signal an actuation mechanism 5410 to initiate a program of movements based on a sensed parameter, such as hemorrhage, turbulence, or molecular signature or marker. Such a program of movements may include opening of an agent reservoir 5704 for a time to release an agent 5702, followed by closing the agent reservoir 5704 to stop release of agent 5702. Subsequent openings and closings may follow according to the desires of health care provider 224.

Operation 6404 depicts signaling the active blood vessel sleeve fitted for the outside of the at least a portion of the blood vessel to change temperature. For example, transmitter 5404, sensor 5412, and/or receiver circuitry 5408 may signal a portion of an active blood vessel sleeve 5400 to cool, which may aid vasoconstriction of blood vessel 5414. Alternatively, transmitter 5404, receiver circuitry 5408, and/or sensor 5412 may signal a temperature increase in a material of the active blood vessel sleeve 5400. Such an increase in temperature may aid in healing of, for example, tissue in the region of the active blood vessel sleeve 5400.

Operation 6406 depicts signaling the active blood vessel sleeve fitted for the outside of the at least a portion of the blood vessel to detect at least one environmental condition. For example, transmitter 5404 may signal sensor 5412 directly or through receiver circuitry 5408 on active blood vessel sleeve 5400 to detect one or more environmental parameters such as current blood vessel sleeve dimensions, blood vessel wall stress during systole and/or diastole, blood vessel sleeve power status, or the like. Alternatively, transmitter 5404, receiver circuitry 5408, and/or sensor 5412 may signal detection of altered blood flow dynamics through a portion of blood vessel 5414.

FIG. 65 illustrates alternative embodiments of the example operational flow 6200 of FIG. 62. FIG. 65 illustrates example embodiments where the signaling operation 6220 may include at least one additional operation. Additional operations may include operation 6500, 6502, 6504, and/or operation 6506.

Operation 6500 depicts signaling the active blood vessel sleeve fitted for the outside of the at least a portion of the blood vessel to release at least one agent. For example, transmitter 5404, receiver circuitry 5408, and/or sensor 5412 may signal active blood vessel sleeve 5600 and/or actuation mechanism 5608 to release, for example, an agent to inhibit blood coagulation, in instances of stroke detection or elevated risk of stroke. Other agents that may be released may include, for example, an angiogenic agent, an anti-angiogenic agent, a proliferation agent, a transforming agent, or the like. Agents may be released to the external surface of the active blood vessel sleeve 5600 as in FIG. 56, and/or to the internal surface of the active blood vessel sleeve 5700 as in FIG. 57.

Operation 6502 depicts signaling the active blood vessel sleeve fitted for the outside of the at least a portion of the blood vessel to transmit information. For example, transmitter 5404, receiver circuitry 5408, and/or sensor 5412 may signal active blood vessel sleeve 5600 and/or transmitter circuitry 5508 to send, for example, information about current active blood vessel sleeve dimensions to, for example, an external receiver 5504. Other information that may be transmitted may include an environmental parameter such as salinity, sleeve movement, pH, or the like.

Operation 6504 depicts sending position coordinates to the active blood vessel sleeve fitted for the outside of the at least a portion of the blood vessel. For example, transmitter 5404, receiver circuitry 5408, and/or sensor 5412 may send position coordinates to the active blood vessel sleeve 5400, for example, to effect a movement to assume a new dimension or position. Methods for assigning position coordinates are known in the art, for example in U.S. Pat. Nos. 6,569,104; 6,056,692; and 4,111,191.

Operation 6506 depicts sending at least one instruction set to the active blood vessel sleeve fitted for the outside of the at least a portion of the blood vessel. For example, transmitter 5404, receiver circuitry 5408, and/or sensor 5412 may send an instruction set to the active blood vessel sleeve 5400, for example, to specify a movement, detection, transmission or other function. Examples of an instruction set may include arithmetic instructions such as add and subtract; logic instructions such as "and," "or," and "not"; data instructions such as move, input, output, load, and store; and/or control flow instructions such as goto, if . . . goto, call, and return.

FIG. 66 illustrates a partial view of an example computer program product 6600 that includes a computer program 6604 for executing a computer process on a computing device. An embodiment of the example computer program product 6600 is provided using a signal bearing medium 6602, and may include at one or more instructions for signaling an active blood vessel sleeve fitted for the outside of at least a portion of a blood vessel. The one or more instructions may be, for example, computer executable and/or logic-implemented instructions. In one implementation, the signal-bearing medium 6602 may include a computer-readable medium 6606. In one implementation, the signal bearing medium 6602 may include a recordable medium 6608. In one implementation, the signal bearing medium 6602 may include a communications medium 6610.

FIG. 67 illustrates an example system 6700 in which embodiments may be implemented. The system 6700 includes a computing system environment. The system 6700 also illustrates the health care provider 222 using a device 6704, which is optionally shown as being in communication with a computing device 6702 by way of an optional coupling

6706. The optional coupling 6706 may represent a local, wide-area, or peer-to-peer network, or may represent a bus that is internal to a computing device (e.g., in example embodiments in which the computing device 6702 is contained in whole or in part within the device 6704). A storage medium 6708 may be any computer storage medium.

The computing device 6702 includes computer-executable instructions 6710 that when executed on the computing device 6702 cause the computing device 6702 to signal an active blood vessel sleeve fitted for the outside of at least a portion of a blood vessel. As referenced above and as shown in FIG. 67, in some examples, the computing device 6702 may optionally be contained in whole or in part within the device 6704.

In FIG. 67, then, the system 6700 includes at least one computing device (e.g., 6702 and/or 6704). The computer-executable instructions 6710 may be executed on one or more of the at least one computing device. For example, the computing device 6702 may implement the computer-executable instructions 6710 and output a result to (and/or receive data from) the device 6704. Since the computing device 6702 may be wholly or partially contained within the device 6704, the device 6704 also may be said to execute some or all of the computer-executable instructions 6710, in order to be caused to perform or implement, for example, various ones of the techniques described herein, or other techniques.

The device 6704 may include, for example, a portable computing device, workstation, or desktop computing device. In another example embodiment, the computing device 6702 is operable to communicate with the device 6704 associated with the health care provider 222 to receive information about input from the health care provider 222 or other sources for signaling an active blood vessel sleeve fitted for the outside of at least a portion of a blood vessel.

Anatomical blood vessel data 120 from an individual 118 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Although a therapeutic health care provider 110 is shown/described herein as a single illustrated figure, those skilled in the art will appreciate that a therapeutic health care provider 110 may be representative of a human health care provider, a robotic health care provider (e.g., computational entity), and/or substantially any combination thereof (e.g., a health care provider may be assisted by one or more robotic agents). In addition, a therapeutic health care provider 110, as set forth herein, although shown as a single entity may in fact be composed of two or more entities. Those skilled in the art will appreciate that, in general, the same may be said of "sender" and/or other entity-oriented terms as such terms are used herein.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet are incorporated herein by reference, to the extent not inconsistent herewith.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

What is claimed is:

1. A system comprising:
   circuitry configured for receiving from at least one sensor of at least one blood vessel sleeve blood flow data associated with at least one blood vessel;
   circuitry configured for determining at least one irregularity at least partly by identifying at least one change over time in the blood flow data associated with at least one blood vessel; and
   circuitry configured for signaling, in response to determining the at least one irregularity, at least one actuation mechanism of the at least one blood vessel sleeve to release at least one therapeutic agent from at least one reservoir associated with the at least one blood vessel sleeve.

2. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve, and in response to at least one request, blood flow data associated with at least one blood vessel.

3. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve condition data associated with at least one blood vessel.

4. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve rhythm data associated with at least one blood vessel.

5. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve pressure data associated with at least one blood vessel.

6. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve chemical data associated with at least one blood vessel.

7. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve movement data associated with at least one blood vessel.

8. The system of claim 1, wherein the circuitry configured for receiving from at least one sensor of at least one blood vessel sleeve blood flow data associated with at least one blood vessel comprises:
   circuitry configured for receiving from at least one sensor of at least one blood vessel sleeve flow rate data associated with at least one blood vessel.

9. The system of claim 1, wherein the circuitry configured for determining at least one irregularity at least partly by identifying at least one change over time in the blood flow data associated with at least one blood vessel comprises:
   circuitry configured for determining arrhythmia at least partly by identifying at least one change over time in the blood flow data associated with at least one blood vessel.

10. The system of claim 1, wherein the circuitry configured for determining at least one irregularity at least partly by identifying at least one change over time in the blood flow data associated with at least one blood vessel comprises:
    circuitry configured for determining at least one abnormal chemical level at least partly by identifying at least one change over time in the blood flow data associated with at least one blood vessel.

11. The system of claim 1, wherein the circuitry configured for determining at least one irregularity at least partly by identifying at least one change over time in the blood flow data associated with at least one blood vessel comprises:
    circuitry configured for determining at least one blood clot at least partly by identifying at least one change over time in the blood flow data associated with at least one blood vessel.

12. The system of claim 1, wherein the circuitry configured for determining at least one irregularity at least partly by identifying at least one change over time in the blood flow data associated with at least one blood vessel comprises:
    circuitry configured for determining at least one leakage at least partly by identifying at least one change over time in the blood flow data associated with at least one blood vessel.

13. The system of claim 1, wherein the circuitry configured for receiving from at least one sensor of at least one blood vessel sleeve blood flow data associated with at least one blood vessel comprises:
    circuitry configured for receiving, from at least one sensor of at least one blood vessel sleeve configured to fit inside at least one blood vessel, blood flow data associated with at least one blood vessel.

14. The system of claim 1, wherein the circuitry configured for signaling, in response to determining the at least one irregularity, at least one actuation mechanism of the at least one blood vessel sleeve to release at least one therapeutic agent from at least one reservoir associated with the at least one blood vessel sleeve comprises:

circuitry configured for signaling, in response to determining the at least one irregularity, at least one actuation mechanism of the at least one blood vessel sleeve to move the at least one blood vessel sleeve and to release at least one therapeutic agent from at least one reservoir associated with the at least one blood vessel sleeve.

15. The system of claim 1, wherein the circuitry configured for signaling, in response to determining the at least one irregularity, at least one actuation mechanism of the at least one blood vessel sleeve to release at least one therapeutic agent from at least one reservoir associated with the at least one blood vessel sleeve comprises:

circuitry configured for signaling, in response to determining the at least one irregularity, at least one actuation mechanism of the at least one blood vessel sleeve to change diameter of the at least one blood vessel sleeve and to release at least one therapeutic agent from at least one reservoir associated with the at least one blood vessel sleeve.

16. The system of claim 1, wherein the circuitry configured for signaling, in response to determining the at least one irregularity, at least one actuation mechanism of the at least one blood vessel sleeve to release at least one therapeutic agent from at least one reservoir associated with the at least one blood vessel sleeve comprises:

circuitry configured for signaling, in response to determining the at least one irregularity, at least one actuation mechanism of the at least one blood vessel sleeve to change temperature of the at least one blood vessel sleeve and to release at least one therapeutic agent from at least one reservoir associated with the at least one blood vessel sleeve.

17. The system of claim 1, wherein the circuitry configured for signaling, in response to determining the at least one irregularity, at least one actuation mechanism of the at least one blood vessel sleeve to release at least one therapeutic agent from at least one reservoir associated with the at least one blood vessel sleeve comprises:

circuitry configured for signaling, in response to determining the at least one irregularity, at least one actuation mechanism of the at least one blood vessel sleeve to release at least one contrast agent from at least one reservoir associated with the at least one blood vessel sleeve.

18. The system of claim 1, wherein at least a portion of the circuitry is coupled to the at least one blood vessel sleeve.

19. A method comprising:

receiving from at least one sensor of at least one blood vessel sleeve blood flow data associated with at least one blood vessel;

determining at least one irregularity at least partly by identifying at least one change over time in the blood flow data associated with at least one blood vessel; and signaling, in response to determining the at least one irregularity, at least one actuation mechanism of the at least one blood vessel sleeve to release at least one therapeutic agent from at least one reservoir associated with the at least one blood vessel sleeve.

20. Non-transitory computer readable media bearing one or more instructions for facilitating operations comprising:

receiving from at least one sensor of at least one blood vessel sleeve blood flow data associated with at least one blood vessel;

determining at least one irregularity at least partly by identifying at least one change over time in the blood flow data associated with at least one blood vessel; and signaling, in response to determining the at least one irregularity, at least one actuation mechanism of the at least one blood vessel sleeve to release at least one therapeutic agent from at least one reservoir associated with the at least one blood vessel sleeve.

21. A system comprising:

means for receiving from at least one sensor of at least one blood vessel sleeve blood flow data associated with at least one blood vessel;

means for determining at least one irregularity at least partly by identifying at least one change over time in the blood flow data associated with at least one blood vessel; and means for signaling, in response to determining the at least one irregularity, at least one actuation mechanism of the at least one blood vessel sleeve to release at least one therapeutic agent from at least one reservoir associated with the at least one blood vessel sleeve.

\* \* \* \* \*